(12) United States Patent
Chen et al.

(10) Patent No.: US 6,934,639 B1
(45) Date of Patent: Aug. 23, 2005

(54) METHODS FOR DESIGNING AGENTS THAT INTERACT WITH MMP-13

(75) Inventors: James M. Chen, Bedminster, NJ (US);
Dominick Mobilio, Warren, NJ (US);
Franklin J. Moy, Arlington, MA (US);
Kevin D. Parris, Newton, MA (US);
Robert Powers, Westford, MA (US);
Zhang Bao Xu, Tewksbury, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/514,026

(22) Filed: Feb. 25, 2000

(51) Int. Cl.[7] .................. G06F 19/00; G01N 33/48; G06G 7/48; A01N 37/18; A01N 43/04

(52) U.S. Cl. .................. 702/27; 702/19; 514/2; 514/44; 703/11

(58) Field of Search .................. 702/19, 27; 703/11; 514/2, 44, 19, 351; 435/7.1; 544/131

(56) References Cited

U.S. PATENT DOCUMENTS

| 5,579,250 A | * | 11/1996 | Balaji et al. | 364/496 |
| 5,929,097 A | * | 7/1999 | Levin et al. | 514/351 |
| 6,008,243 A | | 12/1999 | Bender et al. | |

OTHER PUBLICATIONS

Becker et al., "Stromelysin–1: three–dimensional structure of the inhibited catalytic domain and of the C–truncated proenzyme," Protein Sci., 4:1966–1976 (1995).
Betz et al., "A crystal structure of the catalytic domain of human neutrophil collagenase (matrix metalloproteinase–8) complexed with a peptidomimetic hydroxamate primedside inhibitor with a distinct selectivity profile," Eur. J. Biochem., 247:356–363 (1997).
Birkedal–Hansen et al., "Matrix metalloproteinases: A Review," Crit. Rev. Oral Biol. Medm., 4:197–250 (1993).
Bode et al., "The X–ray crystal structure of the catalytic domain of human neutrophil collagenase inhibited by a substrate analogue reveals the essentials for catalysis and specificity," EMBO J., 13:1263–1269 (1994).
Borkakoti et al., "Structure of the catalytic domain of human fibroblast collagenase complexed with an inhibitor," Struct. Biol., 1:106–110 (1994).
Botos et al., "Batimastat, a potent matrix mealloproteinase inhibitor, exhibits an unexpected mode of binding," Proc. Natl. Acad. Sci. U.S.A., 93:2749–2754 (1996).
Broutin et al., "Structure of Hypoderma lineatum Collagenase: a Member of the Serine Proteinase Family," Acta Cryst., D52:380–392 (1996).
Browner et al., "Matrilysin–inhibitor complexes: common themes among metalloproteases," Biochemistry, 34:6602–6610 (1995).

Ghose et al., "Determination of Pharmacophoric Geometry for Collagenase Inhibitors Using a Novel Computational Method and Its Verification Using Molecular Dynamics, NMR, and X–ray," Crystallography, J. Am. Chem. Soc., 117:4671–4682 (1995).
Gonnella et al., "Bioactive conformation of stromelysin inhibitors determined by transferred nuclear Overhauser effects," Proc. Natl. Acad. Sci. U.S.A., 92:462–466 (1995).
Gonnella et al., "Bioactive conformation of a potent stromelysin inhibitor determined by X–nucleus filtered and multi–dimensional NMR spectroscopy," Bioorg. Med. Chem., 5:2193–2201 (1997).
Gooley et al., "NMR strucutre of the inhibited catalytic domain of human stromelysin–1," Nat. Struct. Biol., 1:111–118 (1994).
Gooley et al., "Comparison of the structure of human recombinant short form stromelysin by multidimensional heteronuclear NMR and X–ray crystallography," J. Biomol. NMR, 7:8–28 (1996).
Hajduk et al., "Discovery of Potent Nonpeptide Inhibitors of Stromelysin Using SAR by NMR," J. Am. Chem. Soc., 119:5818–5827 (1997).
Lovejoy et al., "Structure of the catalytic domain of fibroblast collagenase complexed with an inhibitor," Science, 263:375–377 (1994).
Lovejoy et al., "Structural analysis of the catalytic domain of human fibroblast collagenase," Ann. N.Y. Acad. Sci., 732:375–378 (1994).
Lovejoy et al., "Crystal Structures of Recombinant 19–kDa Human Fibroblast Collagenase Complexed to Itself," Biochemistry, 33:8207–8217 (1994).
Moy et al., "Assignments, secondary structure and dynamics of the inhibitor–free catalytic fragment of human fibroblast collagenase," J. Biomol. NMR., 10:9–19 (1997).
Moy et al., "High–resolution solution structure of the inhibitor–free catalytic fragment of human fibroblast collagenase determined by multidimensional NMR," Biochemistry, 37:1495–1504 (1998).
Moy et al., "NMR solution structure of the catalytic fragment of human fibroblast collagenase complexed with a sulfonamide derivative of a hydroxamic acid compound," Biochemistry, 38:7085–7096 (1999).
Rockwell et al., "Complementarity of Combinatorial Chemistry and Structure–Based Ligand Design: Application to the Discovery of Novel Inhibitors of Matrix Metalloproteinases," J. Am. Chem. Soc., 118:10337–10338 (1996).
Spurlino et al., "A structure of mature truncated human fibroblast collagenase," Proteins, 19:98–109 (1994).

(Continued)

*Primary Examiner*—Ardin H. Marschel
(74) *Attorney, Agent, or Firm*—Fish & Richardson P.C.

(57) ABSTRACT

The present invention relates to the three dimensional structure of human collagenase 3 (MMP-13), as well as to (i) methods of using the MMP-13 structure to rationally design or identify compounds or molecules that inhibit or activate MMP-13 activity, and (ii) compounds identified using said methods.

39 Claims, 75 Drawing Sheets-

OTHER PUBLICATIONS

Stams et al., "Structure of human neutrophil collagenase reveals large S1'specificity pocket," Nat. Struct. Biol., 1:119–123 (1994).

Van Doren et al., "Solution structure of the catalytic domain of human stromelysin complexed with a hydrophobic inhibitor," Protein Sci., 4:2487–2498 (1995).

Bottomley et al., Matrix metalloproteinase inhibitors in arthritis. J. Enzyme Inhibition, 13:79–101, 1998.

Duffy and McCarthy, Matrix metalloproteinases in cancer: Prognostic markers and targets for therapy. International Journal of Oncology, 12:1343–48, 1998.

Gomis–Ruth et al., The helping hand of collagenase-3 (MMP-13) 2.7 (ang) crystal structure of its C-terminal haemopexin-like domain. J. Mol. Biol., 264(3):556–66, 1996.

Johnson et al., Matrix metalloproteinases. Current Opinion in Chemical Biology, 2:466–71, 1998.

Lovejoy et al., Crystal structure of MMP–1 and—13 reveal the structural basis for selectivity of collagenase inhibitors. Structural Biology, 6(3):217–21, Mar. 1999.

Rasmussen and McCann, Matrix metalloproteinase Inhibition as a novel anticancer strategy: A review with special focus on batimastat and marimastat. Pharmacol. Ther., 75(1):69–75, 1997.

Rothenberg et al., New Drugs on the horizon: matrix metalloproteinase inhibitors. The Oncologist, 3:271–74, 1998.

Shingleton et al., Collagenase: a key enzyme in collagen turnover. Biochem. Cell Biol., 74:759–75, 1996.

Steinmeyer and Daufeldt, Pharmacological influence of anti-rheumatic drugs on proteoglycanases from interleukin–1 treated articular cartilage. Biochemical Pharmacology, 53:1627–35, 1997.

Whittaker and Brown, Recent advances in matrix metalloproteinase inhibitor research and development. Current Opinion in Drug Discovery & Development, 1(2):157–64, 1998.

* cited by examiner

| | | | | |
|---|---|---|---|---|
| YNVFP 5 | RTLKW 10 | SKMNL 15 | TYRIV 20 | NYTPD 25 |
| MTHSE 30 | VEKAF 35 | KKAFK 40 | VWSDV 45 | TPLNF 50 |
| TRLHD 55 | GIADI 60 | MISFG 65 | IKEHG 70 | DFYPF 75 |
| DGPSG 80 | LLAHA 85 | FPPGP 90 | NYGGD 95 | AHFDD 100 |
| DETWT 105 | SSSKG 110 | YNLFL 115 | VAAHE 120 | FGHSL 125 |
| GLDHS 130 | KDPGA 135 | LMFPI 140 | YTYTG 145 | KSHFM 150 |
| LPDDD 155 | VQGIQ 160 | SLYG 164 | | |

FIG. 1

Sequence 1: MMP-13
Sequence 2: MMP-1
Identity score: 58.9 %

VGEYNVFPRTLKWSKMNLTYRIVNYTPDMTHSEVEKAFKKAFKVWSDVTPLNFTRLHDGIADIMISFGIKEHGDFYPFDG
LTEGN   PR    WEQTHLTYRIENYTPDLPRADVDHAIEKAFQLWSNVTPLTFTKVSEGQADIMISFVRGDHRDNSPFDG

PSGLLAHAFPPGPNYGGDAHFDDDETWTS          SSKGYNLF           LVAAHEFGHSLGLDHSKDPGALMF
PIYTYTGKSHFMLPDDDVQ
PGGNLAHAFQPGPGIGGDAHFDEDERWTNNFREYNLHRVAAHELGHSLGLS HST DIGALMYPSYTFSGDVQ    LAQDD
ID
                                                                              ###

GIQSLYGPGDEDPN
GIQAIYGRSQ

FIG. 2A

Sequence 1: MMP-13
Sequence 2: MMP-8
Identity score:    61.4 %

VGEYNVFPRTLKWSKMNLTYRIVNYT PDMTH S EVEKAFKKAFKVWSDVTPLNFTRLHDGIADIMISFGIKEHGDFYPFDG
            NPKWER T NLTYRIRNYTP QLSEA    EVERAI KDAFEL WSVASPLI
FTRISQGEADINIAFYQRDHGDNSPFDG
                        **

PSGLLAHAFPPGPNYGGDAHFDDDETWTSSSKGYNLFLVAAHEFGHSLGLDHSKDPGALMF PIYTYTGKSHFMLPDDDVQ
PNGILAHAFQPGQGIGGDAHFDAEETWTNTSANYNLFLVAA HEFGHSLGLAHSSDPGALMYPNYAF RETSNYSLPQDD ID
                                                                              ###

GIQSLYGPGDEDPN
GIQAIYG

|  | | Atom | Res. | | X | Y | Z | | |
|---|---|---|---|---|---|---|---|---|---|
|  | | Type | | | | | | | |
| ATOM | 1 | N | THR | 7 | -12.675 | -13.911 | -8.815 | 1.00 | 0.83 |
| ATOM | 2 | HN | THR | 7 | -12.001 | -14.254 | -8.192 | 1.00 | 1.22 |
| ATOM | 3 | CA | THR | 7 | -14.063 | -13.649 | -8.340 | 1.00 | 0.63 |
| ATOM | 4 | HA | THR | 7 | -14.744 | -14.330 | -8.830 | 1.00 | 0.73 |
| ATOM | 5 | CB | THR | 7 | -14.132 | -13.858 | -6.825 | 1.00 | 0.61 |
| ATOM | 6 | HB | THR | 7 | -13.473 | -13.158 | -6.335 | 1.00 | 0.66 |
| ATOM | 7 | OG1 | THR | 7 | -13.730 | -15.185 | -6.514 | 1.00 | 0.71 |
| ATOM | 8 | HG1 | THR | 7 | -13.721 | -15.690 | -7.330 | 1.00 | 1.07 |
| ATOM | 9 | CG2 | THR | 7 | -15.564 | -13.628 | -6.336 | 1.00 | 0.67 |
| ATOM | 10 | HG21 | THR | 7 | -15.712 | -12.577 | -6.139 | 1.00 | 1.14 |
| ATOM | 11 | HG22 | THR | 7 | -15.728 | -14.191 | -5.429 | 1.00 | 1.32 |
| ATOM | 12 | HG23 | THR | 7 | -16.261 | -13.955 | -7.093 | 1.00 | 1.23 |
| ATOM | 13 | C | THR | 7 | -14.451 | -12.208 | -8.678 | 1.00 | 0.52 |
| ATOM | 14 | O | THR | 7 | -15.416 | -11.962 | -9.374 | 1.00 | 0.65 |
| ATOM | 15 | N | LEU | 8 | -13.704 | -11.254 | -8.195 | 1.00 | 0.47 |
| ATOM | 16 | HN | LEU | 8 | -12.927 | -11.473 | -7.639 | 1.00 | 0.61 |
| ATOM | 17 | CA | LEU | 8 | -14.027 | -9.831 | -8.495 | 1.00 | 0.42 |
| ATOM | 18 | HA | LEU | 8 | -15.098 | -9.715 | -8.575 | 1.00 | 0.43 |
| ATOM | 19 | CB | LEU | 8 | -13.495 | -8.937 | -7.370 | 1.00 | 0.52 |
| ATOM | 20 | HB1 | LEU | 8 | -13.721 | -7.905 | -7.591 | 1.00 | 0.54 |
| ATOM | 21 | HB2 | LEU | 8 | -12.424 | -9.060 | -7.292 | 1.00 | 0.58 |
| ATOM | 22 | CG | LEU | 8 | -14.151 | -9.331 | -6.042 | 1.00 | 0.60 |
| ATOM | 23 | HG | LEU | 8 | -13.958 | -10.376 | -5.844 | 1.00 | 0.60 |
| ATOM | 24 | CD1 | LEU | 8 | -13.566 | -8.484 | -4.910 | 1.00 | 0.74 |
| ATOM | 25 | HD11 | LEU | 8 | -13.899 | -8.875 | -3.960 | 1.00 | 1.22 |
| ATOM | 26 | HD12 | LEU | 8 | -13.900 | -7.462 | -5.016 | 1.00 | 1.26 |
| ATOM | 27 | HD13 | LEU | 8 | -12.488 | -8.518 | -4.956 | 1.00 | 1.31 |
| ATOM | 28 | CD2 | LEU | 8 | -15.664 | -9.096 | -6.117 | 1.00 | 0.61 |
| ATOM | 29 | HD21 | LEU | 8 | -15.871 | -8.278 | -6.791 | 1.00 | 1.13 |
| ATOM | 30 | HD22 | LEU | 8 | -16.040 | -8.856 | -5.134 | 1.00 | 1.18 |
| ATOM | 31 | HD23 | LEU | 8 | -16.149 | -9.991 | -6.478 | 1.00 | 1.26 |
| ATOM | 32 | C | LEU | 8 | -13.374 | -9.438 | -9.822 | 1.00 | 0.40 |
| ATOM | 33 | O | LEU | 8 | -12.218 | -9.722 | -10.064 | 1.00 | 0.45 |
| ATOM | 34 | N | LYS | 9 | -14.109 | -8.795 | -10.687 | 1.00 | 0.36 |
| ATOM | 35 | HN | LYS | 9 | -15.042 | -8.581 | -10.474 | 1.00 | 0.36 |
| ATOM | 36 | CA | LYS | 9 | -13.536 | -8.393 | -12.002 | 1.00 | 0.37 |
| ATOM | 37 | HA | LYS | 9 | -12.521 | -8.050 | -11.862 | 1.00 | 0.39 |
| ATOM | 38 | CB | LYS | 9 | -13.539 | -9.599 | -12.944 | 1.00 | 0.50 |
| ATOM | 39 | HB1 | LYS | 9 | -12.851 | -10.344 | -12.573 | 1.00 | 0.60 |

FIG. 4A-1

| | | | | | | | |
|---|---|---|---|---|---|---|---|
| ATOM | 40 | HB2 | LYS | 9 | -13.233 | -9.286 -13.932 | 1.00 0.48 |
| ATOM | 41 | CG | LYS | 9 | -14.948 | -10.193 -13.007 | 1.00 0.60 |
| ATOM | 42 | HG1 | LYS | 9 | -15.632 | -9.455 -13.398 | 1.00 0.66 |
| ATOM | 43 | HG2 | LYS | 9 | -15.260 | -10.482 -12.014 | 1.00 0.78 |
| ATOM | 44 | CD | LYS | 9 | -14.951 | -11.421 -13.921 | 1.00 0.94 |
| ATOM | 45 | HD1 | LYS | 9 | -13.944 | -11.794 -14.033 | 1.00 1.57 |
| ATOM | 46 | HD2 | LYS | 9 | -15.344 | -11.147 -14.889 | 1.00 1.62 |
| ATOM | 47 | CE | LYS | 9 | -15.829 | -12.511 -13.303 | 1.00 0.57 |
| ATOM | 48 | HE1 | LYS | 9 | -16.776 | -12.086 -13.007 | 1.00 1.15 |
| ATOM | 49 | HE2 | LYS | 9 | -15.333 | -12.924 -12.437 | 1.00 1.10 |
| ATOM | 50 | NZ | LYS | 9 | -16.060 | -13.591 -14.304 | 1.00 1.61 |
| ATOM | 51 | HZ1 | LYS | 9 | -15.181 | -14.127 -14.445 | 1.00 2.14 |
| ATOM | 52 | HZ2 | LYS | 9 | -16.358 | -13.168 -15.207 | 1.00 2.13 |
| ATOM | 53 | HZ3 | LYS | 9 | -16.802 | -14.231 -13.959 | 1.00 2.14 |
| ATOM | 54 | C | LYS | 9 | -14.377 | -7.265 -12.605 | 1.00 0.32 |
| ATOM | 55 | O | LYS | 9 | -15.493 | -7.021 -12.191 | 1.00 0.34 |
| ATOM | 56 | N | TRP | 10 | -13.850 | -6.571 -13.577 | 1.00 0.31 |
| ATOM | 57 | HN | TRP | 10 | -12.947 | -6.781 -13.895 | 1.00 0.33 |
| ATOM | 58 | CA | TRP | 10 | -14.618 | -5.456 -14.201 | 1.00 0.30 |
| ATOM | 59 | HA | TRP | 10 | -15.030 | -4.826 -13.427 | 1.00 0.29 |
| ATOM | 60 | CB | TRP | 10 | -13.684 | -4.630 -15.088 | 1.00 0.29 |
| ATOM | 61 | HB1 | TRP | 10 | -14.264 | -3.917 -15.655 | 1.00 0.32 |
| ATOM | 62 | HB2 | TRP | 10 | -13.157 | -5.286 -15.765 | 1.00 0.33 |
| ATOM | 63 | CG | TRP | 10 | -12.699 | -3.901 -14.230 | 1.00 0.25 |
| ATOM | 64 | CD1 | TRP | 10 | -11.516 | -4.405 -13.812 | 1.00 0.30 |
| ATOM | 65 | HD1 | TRP | 10 | -11.137 | -5.390 -14.040 | 1.00 0.37 |
| ATOM | 66 | CD2 | TRP | 10 | -12.786 | -2.553 -13.683 | 1.00 0.21 |
| ATOM | 67 | NE1 | TRP | 10 | -10.872 | -3.454 -13.042 | 1.00 0.30 |
| ATOM | 68 | HE1 | TRP | 10 | -9.996 | -3.569 -12.617 | 1.00 0.36 |
| ATOM | 69 | CE2 | TRP | 10 | -11.614 | -2.295 -12.934 | 1.00 0.23 |
| ATOM | 70 | CE3 | TRP | 10 | -13.758 | -1.538 -13.763 | 1.00 0.24 |
| ATOM | 71 | HE3 | TRP | 10 | -14.663 | -1.706 -14.328 | 1.00 0.29 |
| ATOM | 72 | CZ2 | TRP | 10 | -11.412 | -1.075 -12.287 | 1.00 0.22 |
| ATOM | 73 | HZ2 | TRP | 10 | -10.509 | -0.903 -11.720 | 1.00 0.27 |
| ATOM | 74 | CZ3 | TRP | 10 | -13.558 | -0.309 -13.113 | 1.00 0.25 |
| ATOM | 75 | HZ3 | TRP | 10 | -14.310 | 0.463 -13.181 | 1.00 0.32 |
| ATOM | 76 | CH2 | TRP | 10 | -12.387 | -0.078 -12.376 | 1.00 0.23 |
| ATOM | 77 | HH2 | TRP | 10 | -12.238 | 0.870 -11.879 | 1.00 0.26 |
| ATOM | 78 | C | TRP | 10 | -15.755 | -6.031 -15.050 | 1.00 0.39 |
| ATOM | 79 | O | TRP | 10 | -15.641 | -7.098 -15.620 | 1.00 0.48 |
| ATOM | 80 | N | SER | 11 | -16.855 | -5.332 -15.132 | 1.00 0.43 |
| ATOM | 81 | HN | SER | 11 | -16.927 | -4.476 -14.660 | 1.00 0.44 |
| ATOM | 82 | CA | SER | 11 | -18.006 | -5.835 -15.936 | 1.00 0.52 |
| ATOM | 83 | HA | SER | 11 | -18.003 | -6.915 -15.930 | 1.00 0.59 |
| ATOM | 84 | CB | SER | 11 | -19.313 | -5.330 -15.325 | 1.00 0.64 |
| ATOM | 85 | HB1 | SER | 11 | -19.120 | -4.425 -14.763 | 1.00 1.16 |
| ATOM | 86 | HB2 | SER | 11 | -19.718 | -6.079 -14.666 | 1.00 1.20 |
| ATOM | 87 | OG | SER | 11 | -20.246 | -5.067 -16.365 | 1.00 1.39 |
| ATOM | 88 | HG | SER | 11 | -19.821 | -4.495 -17.008 | 1.00 1.92 |
| ATOM | 89 | C | SER | 11 | -17.893 | -5.335 -17.379 | 1.00 0.47 |
| ATOM | 90 | O | SER | 11 | -18.785 | -5.528 -18.181 | 1.00 0.60 |
| ATOM | 91 | N | LYS | 12 | -16.808 | -4.692 -17.715 | 1.00 0.42 |
| ATOM | 92 | HN | LYS | 12 | -16.101 | -4.543 -17.053 | 1.00 0.51 |
| ATOM | 93 | CA | LYS | 12 | -16.646 | -4.178 -19.107 | 1.00 0.41 |
| ATOM | 94 | HA | LYS | 12 | -17.243 | -4.775 -19.781 | 1.00 0.47 |
| ATOM | 95 | CB | LYS | 12 | -17.116 | -2.722 -19.167 | 1.00 0.43 |
| ATOM | 96 | HB1 | LYS | 12 | -18.168 | -2.674 -18.926 | 1.00 0.50 |
| ATOM | 97 | HB2 | LYS | 12 | -16.957 | -2.334 -20.163 | 1.00 0.46 |
| ATOM | 98 | CG | LYS | 12 | -16.327 | -1.882 -18.160 | 1.00 0.41 |
| ATOM | 99 | HG1 | LYS | 12 | -15.275 | -1.922 -18.401 | 1.00 0.37 |
| ATOM | 100 | HG2 | LYS | 12 | -16.484 | -2.272 -17.164 | 1.00 0.42 |
| ATOM | 101 | CD | LYS | 12 | -16.805 | -0.430 -18.223 | 1.00 0.50 |
| ATOM | 102 | HD1 | LYS | 12 | -17.856 | -0.386 -17.981 | 1.00 0.56 |
| ATOM | 103 | HD2 | LYS | 12 | -16.648 | -0.044 -19.220 | 1.00 0.65 |
| ATOM | 104 | CE | LYS | 12 | -16.018 | 0.412 -17.218 | 1.00 0.61 |
| ATOM | 105 | HE1 | LYS | 12 | -15.054 | 0.665 -17.636 | 1.00 1.15 |
| ATOM | 106 | HE2 | LYS | 12 | -15.879 | -0.151 -16.307 | 1.00 1.16 |
| ATOM | 107 | NZ | LYS | 12 | -16.773 | 1.661 -16.920 | 1.00 1.39 |
| ATOM | 108 | HZ1 | LYS | 12 | -16.498 | 2.018 -15.983 | 1.00 1.90 |
| ATOM | 109 | HZ2 | LYS | 12 | -17.794 | 1.458 -16.927 | 1.00 1.87 |
| ATOM | 110 | HZ3 | LYS | 12 | -16.556 | 2.379 -17.640 | 1.00 1.97 |
| ATOM | 111 | C | LYS | 12 | -15.175 | -4.269 -19.521 | 1.00 0.36 |
| ATOM | 112 | O | LYS | 12 | -14.284 | -4.250 -18.695 | 1.00 0.34 |
| ATOM | 113 | N | MET | 13 | -14.917 | -4.380 -20.796 | 1.00 0.37 |
| ATOM | 114 | HN | MET | 13 | -15.652 | -4.402 -21.443 | 1.00 0.40 |
| ATOM | 115 | CA | MET | 13 | -13.506 | -4.487 -21.269 | 1.00 0.38 |
| ATOM | 116 | HA | MET | 13 | -12.910 | -4.964 -20.506 | 1.00 0.39 |

FIG. 4A-2

```
ATOM    117  CB   MET   13    -13.469   -5.332  -22.543  1.00  0.46
ATOM    118  HB1  MET   13    -12.523   -5.189  -23.043  1.00  0.53
ATOM    119  HB2  MET   13    -14.273   -5.031  -23.199  1.00  0.42
ATOM    120  CG   MET   13    -13.632   -6.809  -22.178  1.00  0.64
ATOM    121  HG1  MET   13    -12.857   -7.097  -21.483  1.00  1.26
ATOM    122  HG2  MET   13    -13.556   -7.411  -23.071  1.00  1.37
ATOM    123  SD   MET   13    -15.252   -7.067  -21.414  1.00  1.22
ATOM    124  CE   MET   13    -14.663   -7.870  -19.903  1.00  0.57
ATOM    125  HE1  MET   13    -14.020   -7.189  -19.362  1.00  1.16
ATOM    126  HE2  MET   13    -14.107   -8.758  -20.158  1.00  1.09
ATOM    127  HE3  MET   13    -15.508   -8.141  -19.286  1.00  1.20
ATOM    128  C    MET   13    -12.936   -3.095  -21.560  1.00  0.32
ATOM    129  O    MET   13    -11.793   -2.957  -21.948  1.00  0.35
ATOM    130  N    ASN   14    -13.718   -2.064  -21.371  1.00  0.28
ATOM    131  HN   ASN   14    -14.635   -2.199  -21.052  1.00  0.29
ATOM    132  CA   ASN   14    -13.217   -0.681  -21.631  1.00  0.26
ATOM    133  HA   ASN   14    -12.359   -0.725  -22.286  1.00  0.29
ATOM    134  CB   ASN   14    -14.319    0.148  -22.297  1.00  0.30
ATOM    135  HB1  ASN   14    -14.025    1.186  -22.318  1.00  0.31
ATOM    136  HB2  ASN   14    -15.235    0.043  -21.735  1.00  0.31
ATOM    137  CG   ASN   14    -14.539   -0.346  -23.729  1.00  0.37
ATOM    138  OD1  ASN   14    -13.677   -0.981  -24.304  1.00  1.16
ATOM    139  ND2  ASN   14    -15.664   -0.077  -24.334  1.00  1.05
ATOM    140  HD21 ASN   14    -16.359    0.435  -23.871  1.00  1.81
ATOM    141  HD22 ASN   14    -15.812   -0.386  -25.252  1.00  1.06
ATOM    142  C    ASN   14    -12.813   -0.024  -20.309  1.00  0.22
ATOM    143  O    ASN   14    -13.566   -0.019  -19.357  1.00  0.23
ATOM    144  N    LEU   15    -11.630    0.533  -20.247  1.00  0.21
ATOM    145  HN   LEU   15    -11.042    0.517  -21.031  1.00  0.24
ATOM    146  CA   LEU   15    -11.171    1.194  -18.987  1.00  0.18
ATOM    147  HA   LEU   15    -12.025    1.447  -18.379  1.00  0.19
ATOM    148  CB   LEU   15    -10.250    0.243  -18.210  1.00  0.18
ATOM    149  HB1  LEU   15     -9.812    0.769  -17.375  1.00  0.19
ATOM    150  HB2  LEU   15     -9.463   -0.102  -18.865  1.00  0.21
ATOM    151  CG   LEU   15    -11.046   -0.964  -17.696  1.00  0.19
ATOM    152  HG   LEU   15    -11.547   -1.442  -18.525  1.00  0.20
ATOM    153  CD1  LEU   15    -10.086   -1.961  -17.044  1.00  0.20
ATOM    154  HD11 LEU   15     -9.726   -1.556  -16.110  1.00  0.98
ATOM    155  HD12 LEU   15     -9.251   -2.141  -17.704  1.00  1.04
ATOM    156  HD13 LEU   15    -10.604   -2.890  -16.857  1.00  1.07
ATOM    157  CD2  LEU   15    -12.083   -0.513  -16.658  1.00  0.21
ATOM    158  HD21 LEU   15    -12.114   -1.228  -15.850  1.00  1.07
ATOM    159  HD22 LEU   15    -13.055   -0.456  -17.122  1.00  1.00
ATOM    160  HD23 LEU   15    -11.814    0.457  -16.268  1.00  1.04
ATOM    161  C    LEU   15    -10.397    2.471  -19.334  1.00  0.18
ATOM    162  O    LEU   15     -9.785    2.570  -20.380  1.00  0.20
ATOM    163  N    THR   16    -10.425    3.447  -18.460  1.00  0.18
ATOM    164  HN   THR   16    -10.929    3.338  -17.627  1.00  0.18
ATOM    165  CA   THR   16     -9.699    4.729  -18.722  1.00  0.19
ATOM    166  HA   THR   16     -9.051    4.617  -19.574  1.00  0.20
ATOM    167  CB   THR   16    -10.716    5.839  -18.996  1.00  0.22
ATOM    168  HB   THR   16    -10.198    6.729  -19.315  1.00  0.24
ATOM    169  OG1  THR   16    -11.445    6.112  -17.808  1.00  0.23
ATOM    170  HG1  THR   16    -11.821    5.286  -17.495  1.00  0.98
ATOM    171  CG2  THR   16    -11.680    5.393  -20.096  1.00  0.26
ATOM    172  HG21 THR   16    -12.200    6.254  -20.489  1.00  1.05
ATOM    173  HG22 THR   16    -12.396    4.696  -19.686  1.00  1.02
ATOM    174  HG23 THR   16    -11.125    4.914  -20.889  1.00  1.05
ATOM    175  C    THR   16     -8.864    5.100  -17.495  1.00  0.17
ATOM    176  O    THR   16     -9.157    4.687  -16.391  1.00  0.16
ATOM    177  N    TYR   17     -7.826    5.878  -17.675  1.00  0.18
ATOM    178  HN   TYR   17     -7.603    6.202  -18.574  1.00  0.19
ATOM    179  CA   TYR   17     -6.981    6.268  -16.507  1.00  0.17
ATOM    180  HA   TYR   17     -7.585    6.233  -15.615  1.00  0.17
ATOM    181  CB   TYR   17     -5.814    5.288  -16.362  1.00  0.19
ATOM    182  HB1  TYR   17     -6.194    4.278  -16.347  1.00  0.19
ATOM    183  HB2  TYR   17     -5.292    5.488  -15.438  1.00  0.20
ATOM    184  CG   TYR   17     -4.857    5.445  -17.520  1.00  0.22
ATOM    185  CD1  TYR   17     -5.037    4.685  -18.682  1.00  0.26
ATOM    186  HD1  TYR   17     -5.867    3.998  -18.755  1.00  0.27
ATOM    187  CD2  TYR   17     -3.782    6.336  -17.426  1.00  0.25
ATOM    188  HD2  TYR   17     -3.643    6.923  -16.530  1.00  0.26
ATOM    189  CE1  TYR   17     -4.143    4.817  -19.751  1.00  0.31
ATOM    190  HE1  TYR   17     -4.282    4.231  -20.647  1.00  0.36
ATOM    191  CE2  TYR   17     -2.888    6.470  -18.496  1.00  0.30
ATOM    192  HE2  TYR   17     -2.059    7.158  -18.424  1.00  0.35
ATOM    193  CZ   TYR   17     -3.068    5.710  -19.658  1.00  0.32
```

FIG. 4A-3

| | | | | | | | | |
|---|---|---|---|---|---|---|---|---|
| ATOM | 194 | OH | TYR | 17 | -2.186 | 5.839 | -20.711 | 1.00 | 0.39 |
| ATOM | 195 | HH | TYR | 17 | -1.696 | 5.016 | -20.790 | 1.00 | 0.85 |
| ATOM | 196 | C | TYR | 17 | -6.448 | 7.692 | -16.690 | 1.00 | 0.19 |
| ATOM | 197 | O | TYR | 17 | -6.414 | 8.220 | -17.784 | 1.00 | 0.21 |
| ATOM | 198 | N | ARG | 18 | -6.044 | 8.320 | -15.616 | 1.00 | 0.19 |
| ATOM | 199 | HN | ARG | 18 | -6.089 | 7.874 | -14.747 | 1.00 | 0.19 |
| ATOM | 200 | CA | ARG | 18 | -5.523 | 9.714 | -15.712 | 1.00 | 0.22 |
| ATOM | 201 | HA | ARG | 18 | -5.131 | 9.877 | -16.704 | 1.00 | 0.24 |
| ATOM | 202 | CB | ARG | 18 | -6.674 | 10.691 | -15.447 | 1.00 | 0.27 |
| ATOM | 203 | HB1 | ARG | 18 | -6.978 | 10.613 | -14.412 | 1.00 | 0.31 |
| ATOM | 204 | HB2 | ARG | 18 | -7.507 | 10.442 | -16.083 | 1.00 | 0.30 |
| ATOM | 205 | CG | ARG | 18 | -6.229 | 12.127 | -15.733 | 1.00 | 0.35 |
| ATOM | 206 | HG1 | ARG | 18 | -5.504 | 12.137 | -16.531 | 1.00 | 0.93 |
| ATOM | 207 | HG2 | ARG | 18 | -5.790 | 12.549 | -14.843 | 1.00 | 0.85 |
| ATOM | 208 | CD | ARG | 18 | -7.447 | 12.946 | -16.149 | 1.00 | 0.81 |
| ATOM | 209 | HD1 | ARG | 18 | -8.216 | 12.867 | -15.378 | 1.00 | 1.29 |
| ATOM | 210 | HD2 | ARG | 18 | -7.838 | 12.561 | -17.068 | 1.00 | 1.63 |
| ATOM | 211 | NE | ARG | 18 | -7.030 | 14.362 | -16.406 | 1.00 | 1.52 |
| ATOM | 212 | HE | ARG | 18 | -7.071 | 14.711 | -17.318 | 1.00 | 2.11 |
| ATOM | 213 | CZ | ARG | 18 | -6.561 | 15.119 | -15.456 | 1.00 | 2.24 |
| ATOM | 214 | NH1 | ARG | 18 | -6.119 | 16.314 | -15.736 | 1.00 | 3.18 |
| ATOM | 215 | HH11 | ARG | 18 | -6.142 | 16.647 | -16.679 | 1.00 | 3.48 |
| ATOM | 216 | HH12 | ARG | 18 | -5.760 | 16.898 | -15.009 | 1.00 | 3.84 |
| ATOM | 217 | NH2 | ARG | 18 | -6.564 | 14.700 | -14.220 | 1.00 | 2.63 |
| ATOM | 218 | HH21 | ARG | 18 | -6.928 | 13.795 | -14.000 | 1.00 | 2.44 |
| ATOM | 219 | HH22 | ARG | 18 | -6.205 | 15.285 | -13.493 | 1.00 | 3.49 |
| ATOM | 220 | C | ARG | 18 | -4.413 | 9.931 | -14.676 | 1.00 | 0.21 |
| ATOM | 221 | O | ARG | 18 | -4.550 | 9.576 | -13.522 | 1.00 | 0.23 |
| ATOM | 222 | N | ILE | 19 | -3.314 | 10.514 | -15.079 | 1.00 | 0.21 |
| ATOM | 223 | HN | ILE | 19 | -3.223 | 10.794 | -16.014 | 1.00 | 0.22 |
| ATOM | 224 | CA | ILE | 19 | -2.196 | 10.755 | -14.118 | 1.00 | 0.23 |
| ATOM | 225 | HA | ILE | 19 | -2.200 | 9.985 | -13.360 | 1.00 | 0.25 |
| ATOM | 226 | CB | ILE | 19 | -0.864 | 10.721 | -14.875 | 1.00 | 0.25 |
| ATOM | 227 | HB | ILE | 19 | -0.862 | 11.491 | -15.633 | 1.00 | 0.25 |
| ATOM | 228 | CG1 | ILE | 19 | -0.702 | 9.341 | -15.531 | 1.00 | 0.29 |
| ATOM | 229 | HG11 | ILE | 19 | -1.607 | 9.092 | -16.065 | 1.00 | 0.82 |
| ATOM | 230 | HG12 | ILE | 19 | -0.525 | 8.601 | -14.765 | 1.00 | 0.97 |
| ATOM | 231 | CG2 | ILE | 19 | 0.291 | 10.962 | -13.893 | 1.00 | 0.29 |
| ATOM | 232 | HG21 | ILE | 19 | 1.231 | 10.914 | -14.420 | 1.00 | 1.08 |
| ATOM | 233 | HG22 | ILE | 19 | 0.272 | 10.206 | -13.123 | 1.00 | 1.09 |
| ATOM | 234 | HG23 | ILE | 19 | 0.187 | 11.937 | -13.440 | 1.00 | 1.00 |
| ATOM | 235 | CD1 | ILE | 19 | 0.477 | 9.345 | -16.512 | 1.00 | 0.93 |
| ATOM | 236 | HD11 | ILE | 19 | 1.402 | 9.216 | -15.970 | 1.00 | 1.59 |
| ATOM | 237 | HD12 | ILE | 19 | 0.501 | 10.280 | -17.050 | 1.00 | 1.50 |
| ATOM | 238 | HD13 | ILE | 19 | 0.360 | 8.533 | -17.214 | 1.00 | 1.55 |
| ATOM | 239 | C | ILE | 19 | -2.381 | 12.126 | -13.454 | 1.00 | 0.23 |
| ATOM | 240 | O | ILE | 19 | -2.355 | 13.150 | -14.108 | 1.00 | 0.23 |
| ATOM | 241 | N | VAL | 20 | -2.563 | 12.152 | -12.161 | 1.00 | 0.25 |
| ATOM | 242 | HN | VAL | 20 | -2.578 | 11.314 | -11.653 | 1.00 | 0.27 |
| ATOM | 243 | CA | VAL | 20 | -2.746 | 13.454 | -11.454 | 1.00 | 0.27 |
| ATOM | 244 | HA | VAL | 20 | -3.496 | 14.035 | -11.970 | 1.00 | 0.27 |
| ATOM | 245 | CB | VAL | 20 | -3.202 | 13.205 | -10.015 | 1.00 | 0.31 |
| ATOM | 246 | HB | VAL | 20 | -2.522 | 12.517 | -9.534 | 1.00 | 0.32 |
| ATOM | 247 | CG1 | VAL | 20 | -3.216 | 14.529 | -9.247 | 1.00 | 0.33 |
| ATOM | 248 | HG11 | VAL | 20 | -3.607 | 15.310 | -9.883 | 1.00 | 0.97 |
| ATOM | 249 | HG12 | VAL | 20 | -2.211 | 14.782 | -8.944 | 1.00 | 1.08 |
| ATOM | 250 | HG13 | VAL | 20 | -3.842 | 14.432 | -8.372 | 1.00 | 1.10 |
| ATOM | 251 | CG2 | VAL | 20 | -4.612 | 12.611 | -10.028 | 1.00 | 0.33 |
| ATOM | 252 | HG21 | VAL | 20 | -5.296 | 13.317 | -10.476 | 1.00 | 1.05 |
| ATOM | 253 | HG22 | VAL | 20 | -4.924 | 12.401 | -9.016 | 1.00 | 1.03 |
| ATOM | 254 | HG23 | VAL | 20 | -4.612 | 11.697 | -10.602 | 1.00 | 1.11 |
| ATOM | 255 | C | VAL | 20 | -1.424 | 14.231 | -11.451 | 1.00 | 0.27 |
| ATOM | 256 | O | VAL | 20 | -1.403 | 15.435 | -11.611 | 1.00 | 0.26 |
| ATOM | 257 | N | ASN | 21 | -0.321 | 13.555 | -11.259 | 1.00 | 0.28 |
| ATOM | 258 | HN | ASN | 21 | -0.357 | 12.585 | -11.124 | 1.00 | 0.30 |
| ATOM | 259 | CA | ASN | 21 | 0.992 | 14.265 | -11.235 | 1.00 | 0.29 |
| ATOM | 260 | HA | ASN | 21 | 0.973 | 15.076 | -11.949 | 1.00 | 0.26 |
| ATOM | 261 | CB | ASN | 21 | 1.235 | 14.829 | -9.834 | 1.00 | 0.33 |
| ATOM | 262 | HB1 | ASN | 21 | 0.544 | 15.637 | -9.646 | 1.00 | 0.33 |
| ATOM | 263 | HB2 | ASN | 21 | 2.249 | 15.199 | -9.766 | 1.00 | 0.35 |
| ATOM | 264 | CG | ASN | 21 | 1.022 | 13.727 | -8.795 | 1.00 | 0.40 |
| ATOM | 265 | OD1 | ASN | 21 | 0.459 | 12.694 | -9.097 | 1.00 | 1.01 |
| ATOM | 266 | ND2 | ASN | 21 | 1.445 | 13.908 | -7.574 | 1.00 | 0.88 |
| ATOM | 267 | HD21 | ASN | 21 | 1.895 | 14.743 | -7.330 | 1.00 | 1.50 |
| ATOM | 268 | HD22 | ASN | 21 | 1.312 | 13.208 | -6.901 | 1.00 | 0.88 |
| ATOM | 269 | C | ASN | 21 | 2.116 | 13.291 | -11.606 | 1.00 | 0.34 |
| ATOM | 270 | O | ASN | 21 | 1.929 | 12.090 | -11.619 | 1.00 | 0.37 |

FIG. 4A-4

| | | | | | | | | |
|---|---|---|---|---|---|---|---|---|
| ATOM | 271 | N | TYR | 22 | 3.274 | 13.810 | -11.933 | 1.00 0.38 |
| ATOM | 272 | HN | TYR | 22 | 3.387 | 14.783 | -11.932 | 1.00 0.38 |
| ATOM | 273 | CA | TYR | 22 | 4.417 | 12.935 | -12.340 | 1.00 0.46 |
| ATOM | 274 | HA | TYR | 22 | 4.067 | 11.929 | -12.509 | 1.00 0.45 |
| ATOM | 275 | CB | TYR | 22 | 5.028 | 13.481 | -13.630 | 1.00 0.49 |
| ATOM | 276 | HB1 | TYR | 22 | 5.845 | 12.846 | -13.938 | 1.00 0.56 |
| ATOM | 277 | HB2 | TYR | 22 | 5.397 | 14.482 | -13.457 | 1.00 0.53 |
| ATOM | 278 | CG | TYR | 22 | 3.981 | 13.513 | -14.714 | 1.00 0.43 |
| ATOM | 279 | CD1 | TYR | 22 | 3.684 | 12.352 | -15.436 | 1.00 0.38 |
| ATOM | 280 | HD1 | TYR | 22 | 4.199 | 11.430 | -15.212 | 1.00 0.39 |
| ATOM | 281 | CD2 | TYR | 22 | 3.313 | 14.708 | -15.003 | 1.00 0.46 |
| ATOM | 282 | HD2 | TYR | 22 | 3.543 | 15.603 | -14.445 | 1.00 0.51 |
| ATOM | 283 | CE1 | TYR | 22 | 2.718 | 12.386 | -16.447 | 1.00 0.36 |
| ATOM | 284 | HE1 | TYR | 22 | 2.490 | 11.491 | -17.004 | 1.00 0.36 |
| ATOM | 285 | CE2 | TYR | 22 | 2.345 | 14.742 | -16.013 | 1.00 0.44 |
| ATOM | 286 | HE2 | TYR | 22 | 1.828 | 15.663 | -16.235 | 1.00 0.49 |
| ATOM | 287 | CZ | TYR | 22 | 2.048 | 13.581 | -16.735 | 1.00 0.39 |
| ATOM | 288 | OH | TYR | 22 | 1.095 | 13.615 | -17.733 | 1.00 0.43 |
| ATOM | 289 | HH | TYR | 22 | 1.173 | 14.457 | -18.187 | 1.00 0.92 |
| ATOM | 290 | C | TYR | 22 | 5.499 | 12.923 | -11.258 | 1.00 0.56 |
| ATOM | 291 | O | TYR | 22 | 6.554 | 12.378 | -11.470 | 1.00 1.38 |
| ATOM | 292 | N | THR | 23 | 5.240 | 13.544 | -10.130 | 1.00 0.47 |
| ATOM | 293 | HN | THR | 23 | 4.372 | 13.987 | -10.023 | 1.00 1.08 |
| ATOM | 294 | CA | THR | 23 | 6.237 | 13.623 | -9.004 | 1.00 0.46 |
| ATOM | 295 | HA | THR | 23 | 5.848 | 14.338 | -8.304 | 1.00 0.48 |
| ATOM | 296 | CB | THR | 23 | 6.361 | 12.265 | -8.273 | 1.00 0.62 |
| ATOM | 297 | HB | THR | 23 | 5.383 | 11.969 | -7.921 | 1.00 0.68 |
| ATOM | 298 | OG1 | THR | 23 | 7.223 | 12.420 | -7.156 | 1.00 0.86 |
| ATOM | 299 | HG1 | THR | 23 | 7.941 | 11.788 | -7.244 | 1.00 1.28 |
| ATOM | 300 | CG2 | THR | 23 | 6.916 | 11.159 | -9.181 | 1.00 0.59 |
| ATOM | 301 | HG21 | THR | 23 | 7.753 | 11.533 | -9.748 | 1.00 1.08 |
| ATOM | 302 | HG22 | THR | 23 | 6.141 | 10.816 | -9.850 | 1.00 1.16 |
| ATOM | 303 | HG23 | THR | 23 | 7.245 | 10.332 | -8.570 | 1.00 1.22 |
| ATOM | 304 | C | THR | 23 | 7.623 | 14.115 | -9.523 | 1.00 0.40 |
| ATOM | 305 | O | THR | 23 | 8.077 | 13.699 | -10.565 | 1.00 0.45 |
| ATOM | 306 | N | PRO | 24 | 8.302 | 15.016 | -8.823 | 1.00 0.42 |
| ATOM | 307 | CA | PRO | 24 | 9.625 | 15.520 | -9.311 | 1.00 0.42 |
| ATOM | 308 | HA | PRO | 24 | 9.534 | 15.918 | -10.307 | 1.00 0.46 |
| ATOM | 309 | CB | PRO | 24 | 9.924 | 16.655 | -8.335 | 1.00 0.50 |
| ATOM | 310 | HB1 | PRO | 24 | 9.743 | 17.605 | -8.815 | 1.00 0.57 |
| ATOM | 311 | HB2 | PRO | 24 | 10.955 | 16.598 | -8.014 | 1.00 0.49 |
| ATOM | 312 | CG | PRO | 24 | 8.995 | 16.507 | -7.129 | 1.00 0.66 |
| ATOM | 313 | HG1 | PRO | 24 | 8.613 | 17.475 | -6.842 | 1.00 0.84 |
| ATOM | 314 | HG2 | PRO | 24 | 9.537 | 16.069 | -6.303 | 1.00 0.76 |
| ATOM | 315 | CD | PRO | 24 | 7.832 | 15.598 | -7.529 | 1.00 0.56 |
| ATOM | 316 | HD2 | PRO | 24 | 7.675 | 14.826 | -6.786 | 1.00 0.62 |
| ATOM | 317 | HD1 | PRO | 24 | 6.940 | 16.183 | -7.680 | 1.00 0.61 |
| ATOM | 318 | C | PRO | 24 | 10.743 | 14.470 | -9.253 | 1.00 0.40 |
| ATOM | 319 | O | PRO | 24 | 11.835 | 14.692 | -9.737 | 1.00 0.40 |
| ATOM | 320 | N | ASP | 25 | 10.490 | 13.337 | -8.662 | 1.00 0.44 |
| ATOM | 321 | HN | ASP | 25 | 9.608 | 13.172 | -8.270 | 1.00 0.48 |
| ATOM | 322 | CA | ASP | 25 | 11.554 | 12.295 | -8.577 | 1.00 0.48 |
| ATOM | 323 | HA | ASP | 25 | 12.393 | 12.695 | -8.025 | 1.00 0.51 |
| ATOM | 324 | CB | ASP | 25 | 11.016 | 11.062 | -7.847 | 1.00 0.57 |
| ATOM | 325 | HB1 | ASP | 25 | 11.719 | 10.249 | -7.945 | 1.00 0.61 |
| ATOM | 326 | HB2 | ASP | 25 | 10.068 | 10.773 | -8.276 | 1.00 0.56 |
| ATOM | 327 | CG | ASP | 25 | 10.827 | 11.394 | -6.364 | 1.00 0.67 |
| ATOM | 328 | OD1 | ASP | 25 | 10.079 | 10.689 | -5.709 | 1.00 1.23 |
| ATOM | 329 | OD2 | ASP | 25 | 11.437 | 12.348 | -5.908 | 1.00 1.34 |
| ATOM | 330 | C | ASP | 25 | 12.025 | 11.916 | -9.985 | 1.00 0.45 |
| ATOM | 331 | O | ASP | 25 | 13.179 | 11.597 | -10.191 | 1.00 0.55 |
| ATOM | 332 | N | MET | 26 | 11.146 | 11.948 | -10.955 | 1.00 0.40 |
| ATOM | 333 | HN | MET | 26 | 10.220 | 12.209 | -10.767 | 1.00 0.41 |
| ATOM | 334 | CA | MET | 26 | 11.553 | 11.590 | -12.348 | 1.00 0.42 |
| ATOM | 335 | HA | MET | 26 | 12.624 | 11.686 | -12.447 | 1.00 0.49 |
| ATOM | 336 | CB | MET | 26 | 11.144 | 10.149 | -12.656 | 1.00 0.53 |
| ATOM | 337 | HB1 | MET | 26 | 11.282 | 9.954 | -13.709 | 1.00 0.55 |
| ATOM | 338 | HB2 | MET | 26 | 10.105 | 10.006 | -12.397 | 1.00 0.51 |
| ATOM | 339 | CG | MET | 26 | 12.011 | 9.186 | -11.846 | 1.00 0.71 |
| ATOM | 340 | HG1 | MET | 26 | 11.783 | 9.288 | -10.796 | 1.00 0.73 |
| ATOM | 341 | HG2 | MET | 26 | 13.053 | 9.419 | -12.009 | 1.00 0.77 |
| ATOM | 342 | SD | MET | 26 | 11.683 | 7.485 | -12.380 | 1.00 0.89 |
| ATOM | 343 | CE | MET | 26 | 10.000 | 7.330 | -11.728 | 1.00 0.59 |
| ATOM | 344 | HE1 | MET | 26 | 9.292 | 7.456 | -12.534 | 1.00 1.25 |
| ATOM | 345 | HE2 | MET | 26 | 9.825 | 8.084 | -10.979 | 1.00 1.23 |
| ATOM | 346 | HE3 | MET | 26 | 9.877 | 6.352 | -11.285 | 1.00 1.23 |
| ATOM | 347 | C | MET | 26 | 10.872 | 12.530 | -13.344 | 1.00 0.34 |

FIG. 4A-5

| ATOM | 348 | O | MET | 26 | 9.897 | 13.184 | -13.031 | 1.00 | 0.32 |
|---|---|---|---|---|---|---|---|---|---|
| ATOM | 349 | N | THR | 27 | 11.385 | 12.604 | -14.544 | 1.00 | 0.33 |
| ATOM | 350 | HN | THR | 27 | 12.174 | 12.070 | -14.773 | 1.00 | 0.38 |
| ATOM | 351 | CA | THR | 27 | 10.775 | 13.504 | -15.562 | 1.00 | 0.32 |
| ATOM | 352 | HA | THR | 27 | 10.618 | 14.483 | -15.133 | 1.00 | 0.35 |
| ATOM | 353 | CB | THR | 27 | 11.711 | 13.616 | -16.768 | 1.00 | 0.39 |
| ATOM | 354 | HB | THR | 27 | 11.295 | 14.308 | -17.484 | 1.00 | 0.42 |
| ATOM | 355 | OG1 | THR | 27 | 11.852 | 12.338 | -17.371 | 1.00 | 0.37 |
| ATOM | 356 | HG1 | THR | 27 | 12.765 | 12.242 | -17.653 | 1.00 | 0.94 |
| ATOM | 357 | CG2 | THR | 27 | 13.080 | 14.121 | -16.313 | 1.00 | 0.51 |
| ATOM | 358 | HG21 | THR | 27 | 13.602 | 14.553 | -17.154 | 1.00 | 1.14 |
| ATOM | 359 | HG22 | THR | 27 | 13.655 | 13.297 | -15.918 | 1.00 | 1.11 |
| ATOM | 360 | HG23 | THR | 27 | 12.951 | 14.871 | -15.546 | 1.00 | 1.12 |
| ATOM | 361 | C | THR | 27 | 9.436 | 12.921 | -16.013 | 1.00 | 0.27 |
| ATOM | 362 | O | THR | 27 | 9.177 | 11.743 | -15.864 | 1.00 | 0.24 |
| ATOM | 363 | N | HIS | 28 | 8.580 | 13.740 | -16.554 | 1.00 | 0.32 |
| ATOM | 364 | HN | HIS | 28 | 8.807 | 14.688 | -16.657 | 1.00 | 0.37 |
| ATOM | 365 | CA | HIS | 28 | 7.253 | 13.241 | -17.004 | 1.00 | 0.34 |
| ATOM | 366 | HA | HIS | 28 | 6.715 | 12.833 | -16.161 | 1.00 | 0.36 |
| ATOM | 367 | CB | HIS | 28 | 6.457 | 14.403 | -17.601 | 1.00 | 0.46 |
| ATOM | 368 | HB1 | HIS | 28 | 5.428 | 14.104 | -17.736 | 1.00 | 0.71 |
| ATOM | 369 | HB2 | HIS | 28 | 6.880 | 14.676 | -18.557 | 1.00 | 0.88 |
| ATOM | 370 | CG | HIS | 28 | 6.516 | 15.583 | -16.669 | 1.00 | 0.73 |
| ATOM | 371 | ND1 | HIS | 28 | 6.056 | 16.838 | -17.036 | 1.00 | 1.66 |
| ATOM | 372 | HD1 | HIS | 28 | 5.659 | 17.080 | -17.898 | 1.00 | 2.30 |
| ATOM | 373 | CD2 | HIS | 28 | 6.987 | 15.716 | -15.387 | 1.00 | 1.33 |
| ATOM | 374 | HD2 | HIS | 28 | 7.423 | 14.922 | -14.798 | 1.00 | 2.01 |
| ATOM | 375 | CE1 | HIS | 28 | 6.258 | 17.664 | -15.993 | 1.00 | 1.95 |
| ATOM | 376 | HE1 | HIS | 28 | 5.993 | 18.711 | -15.990 | 1.00 | 2.70 |
| ATOM | 377 | NE2 | HIS | 28 | 6.823 | 17.031 | -14.962 | 1.00 | 1.71 |
| ATOM | 378 | C | HIS | 28 | 7.436 | 12.156 | -18.069 | 1.00 | 0.30 |
| ATOM | 379 | O | HIS | 28 | 6.737 | 11.164 | -18.082 | 1.00 | 0.30 |
| ATOM | 380 | N | SER | 29 | 8.362 | 12.338 | -18.970 | 1.00 | 0.31 |
| ATOM | 381 | HN | SER | 29 | 8.912 | 13.149 | -18.952 | 1.00 | 0.34 |
| ATOM | 382 | CA | SER | 29 | 8.567 | 11.319 | -20.039 | 1.00 | 0.32 |
| ATOM | 383 | HA | SER | 29 | 7.660 | 11.217 | -20.615 | 1.00 | 0.35 |
| ATOM | 384 | CB | SER | 29 | 9.699 | 11.775 | -20.959 | 1.00 | 0.38 |
| ATOM | 385 | HB1 | SER | 29 | 9.973 | 10.963 | -21.621 | 1.00 | 0.39 |
| ATOM | 386 | HB2 | SER | 29 | 10.555 | 12.056 | -20.368 | 1.00 | 0.37 |
| ATOM | 387 | OG | SER | 29 | 9.265 | 12.896 | -21.717 | 1.00 | 0.45 |
| ATOM | 388 | HG | SER | 29 | 9.157 | 12.614 | -22.628 | 1.00 | 0.96 |
| ATOM | 389 | C | SER | 29 | 8.931 | 9.964 | -19.424 | 1.00 | 0.26 |
| ATOM | 390 | O | SER | 29 | 8.479 | 8.930 | -19.876 | 1.00 | 0.26 |
| ATOM | 391 | N | GLU | 30 | 9.747 | 9.954 | -18.405 | 1.00 | 0.24 |
| ATOM | 392 | HN | GLU | 30 | 10.107 | 10.796 | -18.056 | 1.00 | 0.25 |
| ATOM | 393 | CA | GLU | 30 | 10.137 | 8.657 | -17.779 | 1.00 | 0.22 |
| ATOM | 394 | HA | GLU | 30 | 10.484 | 7.978 | -18.542 | 1.00 | 0.25 |
| ATOM | 395 | CB | GLU | 30 | 11.260 | 8.899 | -16.769 | 1.00 | 0.23 |
| ATOM | 396 | HB1 | GLU | 30 | 11.424 | 8.002 | -16.191 | 1.00 | 0.24 |
| ATOM | 397 | HB2 | GLU | 30 | 10.980 | 9.707 | -16.108 | 1.00 | 0.22 |
| ATOM | 398 | CG | GLU | 30 | 12.547 | 9.268 | -17.510 | 1.00 | 0.29 |
| ATOM | 399 | HG1 | GLU | 30 | 12.386 | 10.165 | -18.086 | 1.00 | 0.67 |
| ATOM | 400 | HG2 | GLU | 30 | 12.826 | 8.460 | -18.171 | 1.00 | 0.68 |
| ATOM | 401 | CD | GLU | 30 | 13.666 | 9.509 | -16.495 | 1.00 | 0.84 |
| ATOM | 402 | OE1 | GLU | 30 | 13.436 | 9.266 | -15.321 | 1.00 | 1.49 |
| ATOM | 403 | OE2 | GLU | 30 | 14.731 | 9.936 | -16.908 | 1.00 | 1.59 |
| ATOM | 404 | C | GLU | 30 | 8.935 | 8.046 | -17.051 | 1.00 | 0.17 |
| ATOM | 405 | O | GLU | 30 | 8.715 | 6.849 | -17.082 | 1.00 | 0.19 |
| ATOM | 406 | N | VAL | 31 | 8.163 | 8.861 | -16.387 | 1.00 | 0.16 |
| ATOM | 407 | HN | VAL | 31 | 8.366 | 9.819 | -16.371 | 1.00 | 0.17 |
| ATOM | 408 | CA | VAL | 31 | 6.983 | 8.341 | -15.640 | 1.00 | 0.16 |
| ATOM | 409 | HA | VAL | 31 | 7.292 | 7.527 | -14.999 | 1.00 | 0.17 |
| ATOM | 410 | CB | VAL | 31 | 6.402 | 9.464 | -14.782 | 1.00 | 0.20 |
| ATOM | 411 | HB | VAL | 31 | 6.261 | 10.344 | -15.392 | 1.00 | 0.22 |
| ATOM | 412 | CG1 | VAL | 31 | 5.058 | 9.021 | -14.208 | 1.00 | 0.23 |
| ATOM | 413 | HG11 | VAL | 31 | 5.135 | 8.000 | -13.867 | 1.00 | 0.97 |
| ATOM | 414 | HG12 | VAL | 31 | 4.298 | 9.090 | -14.973 | 1.00 | 1.07 |
| ATOM | 415 | HG13 | VAL | 31 | 4.793 | 9.659 | -13.378 | 1.00 | 1.07 |
| ATOM | 416 | CG2 | VAL | 31 | 7.364 | 9.785 | -13.636 | 1.00 | 0.24 |
| ATOM | 417 | HG21 | VAL | 31 | 7.528 | 8.897 | -13.045 | 1.00 | 1.05 |
| ATOM | 418 | HG22 | VAL | 31 | 6.936 | 10.557 | -13.013 | 1.00 | 1.03 |
| ATOM | 419 | HG23 | VAL | 31 | 8.304 | 10.129 | -14.040 | 1.00 | 0.99 |
| ATOM | 420 | C | VAL | 31 | 5.911 | 7.844 | -16.617 | 1.00 | 0.16 |
| ATOM | 421 | O | VAL | 31 | 5.293 | 6.817 | -16.406 | 1.00 | 0.17 |
| ATOM | 422 | N | GLU | 32 | 5.672 | 8.571 | -17.677 | 1.00 | 0.18 |
| ATOM | 423 | HN | GLU | 32 | 6.172 | 9.401 | -17.824 | 1.00 | 0.19 |
| ATOM | 424 | CA | GLU | 32 | 4.626 | 8.146 | -18.652 | 1.00 | 0.21 |

FIG. 4A-6

| | | | | | | | | |
|---|---|---|---|---|---|---|---|---|
| ATOM | 425 | HA  | GLU | 32 | 3.673  | 8.092  | -18.147 | 1.00 | 0.24 |
| ATOM | 426 | CB  | GLU | 32 | 4.533  | 9.170  | -19.787 | 1.00 | 0.27 |
| ATOM | 427 | HB1 | GLU | 32 | 3.922  | 8.772  | -20.582 | 1.00 | 0.31 |
| ATOM | 428 | HB2 | GLU | 32 | 5.524  | 9.379  | -20.164 | 1.00 | 0.28 |
| ATOM | 429 | CG  | GLU | 32 | 3.904  | 10.463 | -19.262 | 1.00 | 0.29 |
| ATOM | 430 | HG1 | GLU | 32 | 4.456  | 10.812 | -18.405 | 1.00 | 0.48 |
| ATOM | 431 | HG2 | GLU | 32 | 2.879  | 10.272 | -18.977 | 1.00 | 0.52 |
| ATOM | 432 | CD  | GLU | 32 | 3.937  | 11.529 | -20.359 | 1.00 | 0.70 |
| ATOM | 433 | OE1 | GLU | 32 | 4.969  | 12.161 | -20.513 | 1.00 | 1.37 |
| ATOM | 434 | OE2 | GLU | 32 | 2.929  | 11.696 | -21.026 | 1.00 | 1.45 |
| ATOM | 435 | C   | GLU | 32 | 4.962  | 6.773  | -19.235 | 1.00 | 0.20 |
| ATOM | 436 | O   | GLU | 32 | 4.126  | 5.893  | -19.280 | 1.00 | 0.20 |
| ATOM | 437 | N   | LYS | 33 | 6.168  | 6.575  | -19.689 | 1.00 | 0.20 |
| ATOM | 438 | HN  | LYS | 33 | 6.835  | 7.293  | -19.654 | 1.00 | 0.21 |
| ATOM | 439 | CA  | LYS | 33 | 6.518  | 5.249  | -20.269 | 1.00 | 0.21 |
| ATOM | 440 | HA  | LYS | 33 | 5.825  | 5.029  | -21.068 | 1.00 | 0.24 |
| ATOM | 441 | CB  | LYS | 33 | 7.940  | 5.281  | -20.843 | 1.00 | 0.26 |
| ATOM | 442 | HB1 | LYS | 33 | 7.987  | 6.024  | -21.624 | 1.00 | 0.31 |
| ATOM | 443 | HB2 | LYS | 33 | 8.179  | 4.312  | -21.257 | 1.00 | 0.31 |
| ATOM | 444 | CG  | LYS | 33 | 8.954  | 5.631  | -19.748 | 1.00 | 0.26 |
| ATOM | 445 | HG1 | LYS | 33 | 8.823  | 4.970  | -18.906 | 1.00 | 0.40 |
| ATOM | 446 | HG2 | LYS | 33 | 8.799  | 6.648  | -19.430 | 1.00 | 0.42 |
| ATOM | 447 | CD  | LYS | 33 | 10.380 | 5.469  | -20.291 | 1.00 | 0.48 |
| ATOM | 448 | HD1 | LYS | 33 | 10.466 | 4.517  | -20.793 | 1.00 | 0.74 |
| ATOM | 449 | HD2 | LYS | 33 | 11.080 | 5.505  | -19.469 | 1.00 | 1.11 |
| ATOM | 450 | CE  | LYS | 33 | 10.705 | 6.593  | -21.282 | 1.00 | 0.92 |
| ATOM | 451 | HE1 | LYS | 33 | 10.398 | 7.543  | -20.868 | 1.00 | 1.52 |
| ATOM | 452 | HE2 | LYS | 33 | 10.184 | 6.419  | -22.211 | 1.00 | 1.19 |
| ATOM | 453 | NZ  | LYS | 33 | 12.172 | 6.614  | -21.538 | 1.00 | 1.60 |
| ATOM | 454 | HZ1 | LYS | 33 | 12.668 | 6.957  | -20.692 | 1.00 | 1.99 |
| ATOM | 455 | HZ2 | LYS | 33 | 12.374 | 7.247  | -22.340 | 1.00 | 2.14 |
| ATOM | 456 | HZ3 | LYS | 33 | 12.498 | 5.653  | -21.763 | 1.00 | 2.03 |
| ATOM | 457 | C   | LYS | 33 | 6.399  | 4.158  | -19.202 | 1.00 | 0.19 |
| ATOM | 458 | O   | LYS | 33 | 6.054  | 3.035  | -19.495 | 1.00 | 0.20 |
| ATOM | 459 | N   | ALA | 34 | 6.682  | 4.471  | -17.966 | 1.00 | 0.17 |
| ATOM | 460 | HN  | ALA | 34 | 6.965  | 5.383  | -17.740 | 1.00 | 0.18 |
| ATOM | 461 | CA  | ALA | 34 | 6.589  | 3.428  | -16.904 | 1.00 | 0.16 |
| ATOM | 462 | HA  | ALA | 34 | 7.276  | 2.625  | -17.128 | 1.00 | 0.18 |
| ATOM | 463 | CB  | ALA | 34 | 6.952  | 4.043  | -15.551 | 1.00 | 0.16 |
| ATOM | 464 | HB1 | ALA | 34 | 6.483  | 3.476  | -14.761 | 1.00 | 1.02 |
| ATOM | 465 | HB2 | ALA | 34 | 6.604  | 5.065  | -15.516 | 1.00 | 0.98 |
| ATOM | 466 | HB3 | ALA | 34 | 8.024  | 4.022  | -15.423 | 1.00 | 1.02 |
| ATOM | 467 | C   | ALA | 34 | 5.164  | 2.875  | -16.844 | 1.00 | 0.16 |
| ATOM | 468 | O   | ALA | 34 | 4.954  | 1.677  | -16.847 | 1.00 | 0.17 |
| ATOM | 469 | N   | PHE | 35 | 4.182  | 3.729  | -16.792 | 1.00 | 0.16 |
| ATOM | 470 | HN  | PHE | 35 | 4.364  | 4.694  | -16.792 | 1.00 | 0.16 |
| ATOM | 471 | CA  | PHE | 35 | 2.781  | 3.230  | -16.736 | 1.00 | 0.17 |
| ATOM | 472 | HA  | PHE | 35 | 2.690  | 2.525  | -15.924 | 1.00 | 0.17 |
| ATOM | 473 | CB  | PHE | 35 | 1.815  | 4.396  | -16.508 | 1.00 | 0.18 |
| ATOM | 474 | HB1 | PHE | 35 | 0.802  | 4.060  | -16.672 | 1.00 | 0.19 |
| ATOM | 475 | HB2 | PHE | 35 | 2.045  | 5.192  | -17.200 | 1.00 | 0.19 |
| ATOM | 476 | CG  | PHE | 35 | 1.953  | 4.902  | -15.089 | 1.00 | 0.18 |
| ATOM | 477 | CD1 | PHE | 35 | 1.616  | 4.071  | -14.011 | 1.00 | 0.19 |
| ATOM | 478 | HD1 | PHE | 35 | 1.258  | 3.069  | -14.191 | 1.00 | 0.19 |
| ATOM | 479 | CD2 | PHE | 35 | 2.415  | 6.203  | -14.849 | 1.00 | 0.20 |
| ATOM | 480 | HD2 | PHE | 35 | 2.674  | 6.847  | -15.677 | 1.00 | 0.21 |
| ATOM | 481 | CE1 | PHE | 35 | 1.743  | 4.539  | -12.699 | 1.00 | 0.21 |
| ATOM | 482 | HE1 | PHE | 35 | 1.484  | 3.897  | -11.870 | 1.00 | 0.23 |
| ATOM | 483 | CE2 | PHE | 35 | 2.540  | 6.670  | -13.535 | 1.00 | 0.22 |
| ATOM | 484 | HE2 | PHE | 35 | 2.893  | 7.672  | -13.349 | 1.00 | 0.24 |
| ATOM | 485 | CZ  | PHE | 35 | 2.205  | 5.838  | -12.460 | 1.00 | 0.22 |
| ATOM | 486 | HZ  | PHE | 35 | 2.303  | 6.198  | -11.447 | 1.00 | 0.24 |
| ATOM | 487 | C   | PHE | 35 | 2.432  | 2.524  | -18.048 | 1.00 | 0.18 |
| ATOM | 488 | O   | PHE | 35 | 1.770  | 1.507  | -18.055 | 1.00 | 0.19 |
| ATOM | 489 | N   | LYS | 36 | 2.864  | 3.053  | -19.162 | 1.00 | 0.19 |
| ATOM | 490 | HN  | LYS | 36 | 3.394  | 3.878  | -19.144 | 1.00 | 0.19 |
| ATOM | 491 | CA  | LYS | 36 | 2.535  | 2.399  | -20.460 | 1.00 | 0.22 |
| ATOM | 492 | HA  | LYS | 36 | 1.462  | 2.358  | -20.574 | 1.00 | 0.23 |
| ATOM | 493 | CB  | LYS | 36 | 3.135  | 3.205  | -21.614 | 1.00 | 0.24 |
| ATOM | 494 | HB1 | LYS | 36 | 3.045  | 2.641  | -22.530 | 1.00 | 0.27 |
| ATOM | 495 | HB2 | LYS | 36 | 4.178  | 3.400  | -21.412 | 1.00 | 0.24 |
| ATOM | 496 | CG  | LYS | 36 | 2.384  | 4.530  | -21.758 | 1.00 | 0.27 |
| ATOM | 497 | HG1 | LYS | 36 | 2.471  | 5.097  | -20.844 | 1.00 | 0.69 |
| ATOM | 498 | HG2 | LYS | 36 | 1.341  | 4.332  | -21.963 | 1.00 | 0.68 |
| ATOM | 499 | CD  | LYS | 36 | 2.988  | 5.332  | -22.913 | 1.00 | 0.75 |
| ATOM | 500 | HD1 | LYS | 36 | 2.898  | 4.766  | -23.828 | 1.00 | 1.39 |
| ATOM | 501 | HD2 | LYS | 36 | 4.032  | 5.525  | -22.710 | 1.00 | 1.34 |

FIG. 4A-7

| ATOM | 502 | CE  | LYS | 36 |  2.243 |  6.659 | -23.065 | 1.00 | 1.15 |
|------|-----|-----|-----|----|--------|--------|---------|------|------|
| ATOM | 503 | HE1 | LYS | 36 |  2.728 |  7.415 | -22.464 | 1.00 | 1.64 |
| ATOM | 504 | HE2 | LYS | 36 |  1.221 |  6.540 | -22.736 | 1.00 | 1.61 |
| ATOM | 505 | NZ  | LYS | 36 |  2.260 |  7.076 | -24.496 | 1.00 | 1.99 |
| ATOM | 506 | HZ1 | LYS | 36 |  2.628 |  6.298 | -25.079 | 1.00 | 2.51 |
| ATOM | 507 | HZ2 | LYS | 36 |  2.871 |  7.911 | -24.605 | 1.00 | 2.40 |
| ATOM | 508 | HZ3 | LYS | 36 |  1.295 |  7.309 | -24.801 | 1.00 | 2.38 |
| ATOM | 509 | C   | LYS | 36 |  3.098 |  0.976 | -20.481 | 1.00 | 0.21 |
| ATOM | 510 | O   | LYS | 36 |  2.446 |  0.053 | -20.927 | 1.00 | 0.23 |
| ATOM | 511 | N   | LYS | 37 |  4.295 |  0.778 | -19.995 | 1.00 | 0.21 |
| ATOM | 512 | HN  | LYS | 37 |  4.810 |  1.527 | -19.629 | 1.00 | 0.20 |
| ATOM | 513 | CA  | LYS | 37 |  4.864 | -0.600 | -19.988 | 1.00 | 0.22 |
| ATOM | 514 | HA  | LYS | 37 |  4.926 | -0.974 | -21.000 | 1.00 | 0.24 |
| ATOM | 515 | CB  | LYS | 37 |  6.257 | -0.581 | -19.358 | 1.00 | 0.22 |
| ATOM | 516 | HB1 | LYS | 37 |  6.589 | -1.596 | -19.195 | 1.00 | 0.24 |
| ATOM | 517 | HB2 | LYS | 37 |  6.216 | -0.061 | -18.412 | 1.00 | 0.21 |
| ATOM | 518 | CG  | LYS | 37 |  7.244 |  0.130 | -20.285 | 1.00 | 0.26 |
| ATOM | 519 | HG1 | LYS | 37 |  6.921 |  1.140 | -20.459 | 1.00 | 0.25 |
| ATOM | 520 | HG2 | LYS | 37 |  7.296 | -0.398 | -21.227 | 1.00 | 0.28 |
| ATOM | 521 | CD  | LYS | 37 |  8.625 |  0.139 | -19.628 | 1.00 | 0.30 |
| ATOM | 522 | HD1 | LYS | 37 |  8.994 | -0.873 | -19.551 | 1.00 | 0.77 |
| ATOM | 523 | HD2 | LYS | 37 |  8.549 |  0.570 | -18.640 | 1.00 | 0.84 |
| ATOM | 524 | CE  | LYS | 37 |  9.594 |  0.968 | -20.473 | 1.00 | 0.90 |
| ATOM | 525 | HE1 | LYS | 37 | 10.530 |  1.076 | -19.943 | 1.00 | 1.47 |
| ATOM | 526 | HE2 | LYS | 37 |  9.169 |  1.945 | -20.652 | 1.00 | 1.59 |
| ATOM | 527 | NZ  | LYS | 37 |  9.836 |  0.286 | -21.774 | 1.00 | 1.77 |
| ATOM | 528 | HZ1 | LYS | 37 |  9.798 |  0.984 | -22.543 | 1.00 | 2.22 |
| ATOM | 529 | HZ2 | LYS | 37 |  9.106 | -0.439 | -21.926 | 1.00 | 2.28 |
| ATOM | 530 | HZ3 | LYS | 37 | 10.774 | -0.161 | -21.762 | 1.00 | 2.33 |
| ATOM | 531 | C   | LYS | 37 |  3.955 | -1.506 | -19.158 | 1.00 | 0.20 |
| ATOM | 532 | O   | LYS | 37 |  3.689 | -2.636 | -19.516 | 1.00 | 0.21 |
| ATOM | 533 | N   | ALA | 38 |  3.479 | -1.013 | -18.046 | 1.00 | 0.19 |
| ATOM | 534 | HN  | ALA | 38 |  3.711 | -0.098 | -17.777 | 1.00 | 0.19 |
| ATOM | 535 | CA  | ALA | 38 |  2.589 | -1.838 | -17.182 | 1.00 | 0.18 |
| ATOM | 536 | HA  | ALA | 38 |  3.116 | -2.727 | -16.870 | 1.00 | 0.19 |
| ATOM | 537 | CB  | ALA | 38 |  2.183 | -1.030 | -15.949 | 1.00 | 0.19 |
| ATOM | 538 | HB1 | ALA | 38 |  2.831 | -0.172 | -15.851 | 1.00 | 1.05 |
| ATOM | 539 | HB2 | ALA | 38 |  2.270 | -1.649 | -15.068 | 1.00 | 1.00 |
| ATOM | 540 | HB3 | ALA | 38 |  1.161 | -0.698 | -16.057 | 1.00 | 1.06 |
| ATOM | 541 | C   | ALA | 38 |  1.338 | -2.238 | -17.965 | 1.00 | 0.18 |
| ATOM | 542 | O   | ALA | 38 |  0.967 | -3.392 | -18.012 | 1.00 | 0.19 |
| ATOM | 543 | N   | PHE | 39 |  0.688 | -1.295 | -18.589 | 1.00 | 0.18 |
| ATOM | 544 | HN  | PHE | 39 |  1.005 | -0.368 | -18.547 | 1.00 | 0.18 |
| ATOM | 545 | CA  | PHE | 39 | -0.535 | -1.632 | -19.367 | 1.00 | 0.19 |
| ATOM | 546 | HA  | PHE | 39 | -1.248 | -2.122 | -18.720 | 1.00 | 0.19 |
| ATOM | 547 | CB  | PHE | 39 | -1.156 | -0.354 | -19.937 | 1.00 | 0.21 |
| ATOM | 548 | HB1 | PHE | 39 | -1.883 | -0.614 | -20.692 | 1.00 | 0.24 |
| ATOM | 549 | HB2 | PHE | 39 | -0.381 |  0.256 | -20.378 | 1.00 | 0.21 |
| ATOM | 550 | CG  | PHE | 39 | -1.836 |  0.416 | -18.829 | 1.00 | 0.20 |
| ATOM | 551 | CD1 | PHE | 39 | -3.010 | -0.080 | -18.250 | 1.00 | 0.25 |
| ATOM | 552 | HD1 | PHE | 39 | -3.429 | -1.014 | -18.595 | 1.00 | 0.30 |
| ATOM | 553 | CD2 | PHE | 39 | -1.294 |  1.627 | -18.380 | 1.00 | 0.17 |
| ATOM | 554 | HD2 | PHE | 39 | -0.389 |  2.012 | -18.827 | 1.00 | 0.18 |
| ATOM | 555 | CE1 | PHE | 39 | -3.642 |  0.633 | -17.224 | 1.00 | 0.28 |
| ATOM | 556 | HE1 | PHE | 39 | -4.548 |  0.250 | -16.779 | 1.00 | 0.34 |
| ATOM | 557 | CE2 | PHE | 39 | -1.926 |  2.341 | -17.354 | 1.00 | 0.18 |
| ATOM | 558 | HE2 | PHE | 39 | -1.507 |  3.275 | -17.007 | 1.00 | 0.17 |
| ATOM | 559 | CZ  | PHE | 39 | -3.099 |  1.843 | -16.776 | 1.00 | 0.23 |
| ATOM | 560 | HZ  | PHE | 39 | -3.587 |  2.394 | -15.985 | 1.00 | 0.26 |
| ATOM | 561 | C   | PHE | 39 | -0.154 | -2.571 | -20.508 | 1.00 | 0.18 |
| ATOM | 562 | O   | PHE | 39 | -0.862 | -3.509 | -20.817 | 1.00 | 0.18 |
| ATOM | 563 | N   | LYS | 40 |  0.963 | -2.330 | -21.136 | 1.00 | 0.19 |
| ATOM | 564 | HN  | LYS | 40 |  1.522 | -1.570 | -20.870 | 1.00 | 0.19 |
| ATOM | 565 | CA  | LYS | 40 |  1.388 | -3.214 | -22.254 | 1.00 | 0.19 |
| ATOM | 566 | HA  | LYS | 40 |  0.642 | -3.186 | -23.031 | 1.00 | 0.20 |
| ATOM | 567 | CB  | LYS | 40 |  2.730 | -2.707 | -22.804 | 1.00 | 0.21 |
| ATOM | 568 | HB1 | LYS | 40 |  3.466 | -2.723 | -22.014 | 1.00 | 0.21 |
| ATOM | 569 | HB2 | LYS | 40 |  2.610 | -1.692 | -23.155 | 1.00 | 0.25 |
| ATOM | 570 | CG  | LYS | 40 |  3.218 | -3.588 | -23.966 | 1.00 | 0.25 |
| ATOM | 571 | HG1 | LYS | 40 |  3.337 | -4.604 | -23.621 | 1.00 | 0.46 |
| ATOM | 572 | HG2 | LYS | 40 |  4.171 | -3.218 | -24.314 | 1.00 | 0.46 |
| ATOM | 573 | CD  | LYS | 40 |  2.213 | -3.560 | -25.121 | 1.00 | 0.38 |
| ATOM | 574 | HD1 | LYS | 40 |  1.840 | -2.555 | -25.253 | 1.00 | 0.54 |
| ATOM | 575 | HD2 | LYS | 40 |  1.392 | -4.227 | -24.905 | 1.00 | 0.56 |
| ATOM | 576 | CE  | LYS | 40 |  2.903 | -4.019 | -26.407 | 1.00 | 0.40 |
| ATOM | 577 | HE1 | LYS | 40 |  3.776 | -4.604 | -26.158 | 1.00 | 1.07 |
| ATOM | 578 | HE2 | LYS | 40 |  3.199 | -3.157 | -26.985 | 1.00 | 1.03 |

FIG. 4A-8

| | | | | | | | | |
|---|---|---|---|---|---|---|---|---|
| ATOM | 579 | NZ | LYS | 40 | 1.958 | -4.852 | -27.203 | 1.00 1.40 |
| ATOM | 580 | HZ1 | LYS | 40 | 1.571 | -5.607 | -26.602 | 1.00 1.95 |
| ATOM | 581 | HZ2 | LYS | 40 | 2.464 | -5.274 | -28.009 | 1.00 1.92 |
| ATOM | 582 | HZ3 | LYS | 40 | 1.181 | -4.258 | -27.552 | 1.00 2.02 |
| ATOM | 583 | C | LYS | 40 | 1.553 | -4.648 | -21.740 | 1.00 0.17 |
| ATOM | 584 | O | LYS | 40 | 1.034 | -5.583 | -22.314 | 1.00 0.17 |
| ATOM | 585 | N | VAL | 41 | 2.271 | -4.828 | -20.663 | 1.00 0.17 |
| ATOM | 586 | HN | VAL | 41 | 2.681 | -4.060 | -20.214 | 1.00 0.18 |
| ATOM | 587 | CA | VAL | 41 | 2.468 | -6.204 | -20.116 | 1.00 0.16 |
| ATOM | 588 | HA | VAL | 41 | 2.953 | -6.816 | -20.862 | 1.00 0.17 |
| ATOM | 589 | CB | VAL | 41 | 3.350 | -6.143 | -18.868 | 1.00 0.18 |
| ATOM | 590 | HB | VAL | 41 | 2.966 | -5.393 | -18.192 | 1.00 0.41 |
| ATOM | 591 | CG1 | VAL | 41 | 3.343 | -7.508 | -18.175 | 1.00 0.44 |
| ATOM | 592 | HG11 | VAL | 41 | 2.420 | -7.631 | -17.629 | 1.00 1.16 |
| ATOM | 593 | HG12 | VAL | 41 | 4.176 | -7.571 | -17.490 | 1.00 1.18 |
| ATOM | 594 | HG13 | VAL | 41 | 3.429 | -8.289 | -18.916 | 1.00 1.11 |
| ATOM | 595 | CG2 | VAL | 41 | 4.781 | -5.785 | -19.277 | 1.00 0.43 |
| ATOM | 596 | HG21 | VAL | 41 | 5.132 | -6.492 | -20.013 | 1.00 1.12 |
| ATOM | 597 | HG22 | VAL | 41 | 5.423 | -5.820 | -18.411 | 1.00 1.11 |
| ATOM | 598 | HG23 | VAL | 41 | 4.797 | -4.790 | -19.697 | 1.00 1.19 |
| ATOM | 599 | C | VAL | 41 | 1.122 | -6.833 | -19.751 | 1.00 0.16 |
| ATOM | 600 | O | VAL | 41 | 0.887 | -7.999 | -19.996 | 1.00 0.17 |
| ATOM | 601 | N | TRP | 42 | 0.240 | -6.080 | -19.152 | 1.00 0.16 |
| ATOM | 602 | HN | TRP | 42 | 0.448 | -5.143 | -18.950 | 1.00 0.17 |
| ATOM | 603 | CA | TRP | 42 | -1.079 | -6.655 | -18.761 | 1.00 0.17 |
| ATOM | 604 | HA | TRP | 42 | -0.927 | -7.642 | -18.352 | 1.00 0.17 |
| ATOM | 605 | CB | TRP | 42 | -1.739 | -5.767 | -17.699 | 1.00 0.18 |
| ATOM | 606 | HB1 | TRP | 42 | -2.787 | -6.018 | -17.621 | 1.00 0.19 |
| ATOM | 607 | HB2 | TRP | 42 | -1.638 | -4.730 | -17.983 | 1.00 0.20 |
| ATOM | 608 | CG | TRP | 42 | -1.073 | -5.990 | -16.377 | 1.00 0.18 |
| ATOM | 609 | CD1 | TRP | 42 | -0.311 | -5.082 | -15.724 | 1.00 0.22 |
| ATOM | 610 | HD1 | TRP | 42 | -0.092 | -4.084 | -16.066 | 1.00 0.28 |
| ATOM | 611 | CD2 | TRP | 42 | -1.095 | -7.182 | -15.539 | 1.00 0.19 |
| ATOM | 612 | NE1 | TRP | 42 | 0.140 | -5.643 | -14.543 | 1.00 0.22 |
| ATOM | 613 | HE1 | TRP | 42 | 0.714 | -5.194 | -13.887 | 1.00 0.25 |
| ATOM | 614 | CE2 | TRP | 42 | -0.315 | -6.935 | -14.384 | 1.00 0.20 |
| ATOM | 615 | CE3 | TRP | 42 | -1.707 | -8.441 | -15.669 | 1.00 0.25 |
| ATOM | 616 | HE3 | TRP | 42 | -2.309 | -8.658 | -16.539 | 1.00 0.27 |
| ATOM | 617 | CZ2 | TRP | 42 | -0.149 | -7.903 | -13.393 | 1.00 0.24 |
| ATOM | 618 | HZ2 | TRP | 42 | 0.454 | -7.691 | -12.521 | 1.00 0.25 |
| ATOM | 619 | CZ3 | TRP | 42 | -1.543 | -9.418 | -14.673 | 1.00 0.31 |
| ATOM | 620 | HZ3 | TRP | 42 | -2.018 | -10.381 | -14.782 | 1.00 0.39 |
| ATOM | 621 | CH2 | TRP | 42 | -0.764 | -9.149 | -13.538 | 1.00 0.30 |
| ATOM | 622 | HH2 | TRP | 42 | -0.642 | -9.904 | -12.775 | 1.00 0.35 |
| ATOM | 623 | C | TRP | 42 | -1.991 | -6.754 | -19.985 | 1.00 0.17 |
| ATOM | 624 | O | TRP | 42 | -2.726 | -7.706 | -20.138 | 1.00 0.18 |
| ATOM | 625 | N | SER | 43 | -1.952 | -5.782 | -20.855 | 1.00 0.17 |
| ATOM | 626 | HN | SER | 43 | -1.352 | -5.021 | -20.713 | 1.00 0.17 |
| ATOM | 627 | CA | SER | 43 | -2.831 | -5.825 | -22.062 | 1.00 0.18 |
| ATOM | 628 | HA | SER | 43 | -3.846 | -6.028 | -21.759 | 1.00 0.19 |
| ATOM | 629 | CB | SER | 43 | -2.779 | -4.474 | -22.775 | 1.00 0.20 |
| ATOM | 630 | HB1 | SER | 43 | -2.965 | -3.683 | -22.059 | 1.00 0.21 |
| ATOM | 631 | HB2 | SER | 43 | -3.533 | -4.442 | -23.543 | 1.00 0.23 |
| ATOM | 632 | OG | SER | 43 | -1.499 | -4.304 | -23.368 | 1.00 0.21 |
| ATOM | 633 | HG | SER | 43 | -1.031 | -5.140 | -23.309 | 1.00 0.97 |
| ATOM | 634 | C | SER | 43 | -2.358 | -6.922 | -23.019 | 1.00 0.18 |
| ATOM | 635 | O | SER | 43 | -3.085 | -7.350 | -23.893 | 1.00 0.21 |
| ATOM | 636 | N | ASP | 44 | -1.148 | -7.379 | -22.866 | 1.00 0.17 |
| ATOM | 637 | HN | ASP | 44 | -0.575 | -7.019 | -22.156 | 1.00 0.18 |
| ATOM | 638 | CA | ASP | 44 | -0.632 | -8.445 | -23.770 | 1.00 0.18 |
| ATOM | 639 | HA | ASP | 44 | -0.650 | -8.086 | -24.788 | 1.00 0.19 |
| ATOM | 640 | CB | ASP | 44 | 0.809 | -8.793 | -23.386 | 1.00 0.20 |
| ATOM | 641 | HB1 | ASP | 44 | 1.117 | -9.683 | -23.915 | 1.00 0.21 |
| ATOM | 642 | HB2 | ASP | 44 | 0.864 | -8.969 | -22.322 | 1.00 0.22 |
| ATOM | 643 | CG | ASP | 44 | 1.734 | -7.635 | -23.760 | 1.00 0.24 |
| ATOM | 644 | OD1 | ASP | 44 | 1.340 | -6.833 | -24.591 | 1.00 0.85 |
| ATOM | 645 | OD2 | ASP | 44 | 2.820 | -7.568 | -23.209 | 1.00 0.84 |
| ATOM | 646 | C | ASP | 44 | -1.499 | -9.705 | -23.665 | 1.00 0.19 |
| ATOM | 647 | O | ASP | 44 | -1.753 | -10.366 | -24.653 | 1.00 0.21 |
| ATOM | 648 | N | VAL | 45 | -1.927 | -10.058 | -22.475 | 1.00 0.21 |
| ATOM | 649 | HN | VAL | 45 | -1.689 | -9.519 | -21.693 | 1.00 0.21 |
| ATOM | 650 | CA | VAL | 45 | -2.749 | -11.299 | -22.302 | 1.00 0.26 |
| ATOM | 651 | HA | VAL | 45 | -2.833 | -11.811 | -23.247 | 1.00 0.28 |
| ATOM | 652 | CB | VAL | 45 | -2.045 | -12.222 | -21.303 | 1.00 0.30 |
| ATOM | 653 | HB | VAL | 45 | -2.645 | -13.107 | -21.146 | 1.00 0.37 |
| ATOM | 654 | CG1 | VAL | 45 | -0.678 | -12.626 | -21.866 | 1.00 0.36 |
| ATOM | 655 | HG11 | VAL | 45 | -0.210 | -11.766 | -22.323 | 1.00 1.07 |

FIG. 4A-9

| | | | | | | | | |
|---|---|---|---|---|---|---|---|---|
| ATOM | 656 | HG12 | VAL | 45 | -0.810 | -13.400 | -22.607 | 1.00 | 1.02 |
| ATOM | 657 | HG13 | VAL | 45 | -0.051 | -12.995 | -21.068 | 1.00 | 1.13 |
| ATOM | 658 | CG2 | VAL | 45 | -1.855 | -11.486 | -19.973 | 1.00 | 0.32 |
| ATOM | 659 | HG21 | VAL | 45 | -2.819 | -11.303 | -19.524 | 1.00 | 0.96 |
| ATOM | 660 | HG22 | VAL | 45 | -1.356 | -10.545 | -20.149 | 1.00 | 1.09 |
| ATOM | 661 | HG23 | VAL | 45 | -1.258 | -12.091 | -19.305 | 1.00 | 1.11 |
| ATOM | 662 | C | VAL | 45 | -4.160 | -10.966 | -21.790 | 1.00 | 0.29 |
| ATOM | 663 | O | VAL | 45 | -4.837 | -11.819 | -21.249 | 1.00 | 0.64 |
| ATOM | 664 | N | THR | 46 | -4.619 | -9.748 | -21.963 | 1.00 | 0.36 |
| ATOM | 665 | HN | THR | 46 | -4.062 | -9.076 | -22.409 | 1.00 | 0.65 |
| ATOM | 666 | CA | THR | 46 | -5.998 | -9.382 | -21.491 | 1.00 | 0.38 |
| ATOM | 667 | HA | THR | 46 | -6.567 | -10.277 | -21.320 | 1.00 | 0.44 |
| ATOM | 668 | CB | THR | 46 | -5.912 | -8.577 | -20.186 | 1.00 | 0.39 |
| ATOM | 669 | HB | THR | 46 | -6.889 | -8.193 | -19.943 | 1.00 | 0.46 |
| ATOM | 670 | OG1 | THR | 46 | -5.018 | -7.491 | -20.358 | 1.00 | 0.36 |
| ATOM | 671 | HG1 | THR | 46 | -5.532 | -6.719 | -20.608 | 1.00 | 0.94 |
| ATOM | 672 | CG2 | THR | 46 | -5.430 | -9.461 | -19.036 | 1.00 | 0.43 |
| ATOM | 673 | HG21 | THR | 46 | -4.929 | -10.327 | -19.429 | 1.00 | 1.08 |
| ATOM | 674 | HG22 | THR | 46 | -6.277 | -9.775 | -18.445 | 1.00 | 1.15 |
| ATOM | 675 | HG23 | THR | 46 | -4.746 | -8.901 | -18.415 | 1.00 | 1.05 |
| ATOM | 676 | C | THR | 46 | -6.668 | -8.482 | -22.553 | 1.00 | 0.32 |
| ATOM | 677 | O | THR | 46 | -6.124 | -7.450 | -22.892 | 1.00 | 0.32 |
| ATOM | 678 | N | PRO | 47 | -7.833 | -8.829 | -23.084 | 1.00 | 0.30 |
| ATOM | 679 | CA | PRO | 47 | -8.479 | -7.951 | -24.100 | 1.00 | 0.30 |
| ATOM | 680 | HA | PRO | 47 | -7.820 | -7.790 | -24.936 | 1.00 | 0.33 |
| ATOM | 681 | CB | PRO | 47 | -9.687 | -8.773 | -24.546 | 1.00 | 0.35 |
| ATOM | 682 | HB1 | PRO | 47 | -9.541 | -9.110 | -25.561 | 1.00 | 0.40 |
| ATOM | 683 | HB2 | PRO | 47 | -10.579 | -8.166 | -24.489 | 1.00 | 0.37 |
| ATOM | 684 | CG | PRO | 47 | -9.825 | -9.986 | -23.621 | 1.00 | 0.35 |
| ATOM | 685 | HG1 | PRO | 47 | -9.916 | -10.885 | -24.212 | 1.00 | 0.42 |
| ATOM | 686 | HG2 | PRO | 47 | -10.703 | -9.869 | -23.001 | 1.00 | 0.34 |
| ATOM | 687 | CD | PRO | 47 | -8.576 | -10.077 | -22.739 | 1.00 | 0.33 |
| ATOM | 688 | HD2 | PRO | 47 | -8.853 | -10.091 | -21.692 | 1.00 | 0.31 |
| ATOM | 689 | HD1 | PRO | 47 | -7.993 | -10.946 | -22.999 | 1.00 | 0.39 |
| ATOM | 690 | C | PRO | 47 | -8.933 | -6.614 | -23.506 | 1.00 | 0.25 |
| ATOM | 691 | O | PRO | 47 | -9.744 | -5.914 | -24.080 | 1.00 | 0.26 |
| ATOM | 692 | N | LEU | 48 | -8.418 | -6.252 | -22.362 | 1.00 | 0.26 |
| ATOM | 693 | HN | LEU | 48 | -7.766 | -6.828 | -21.912 | 1.00 | 0.29 |
| ATOM | 694 | CA | LEU | 48 | -8.827 | -4.960 | -21.742 | 1.00 | 0.26 |
| ATOM | 695 | HA | LEU | 48 | -9.904 | -4.905 | -21.696 | 1.00 | 0.27 |
| ATOM | 696 | CB | LEU | 48 | -8.241 | -4.858 | -20.329 | 1.00 | 0.31 |
| ATOM | 697 | HB1 | LEU | 48 | -8.476 | -3.892 | -19.909 | 1.00 | 0.34 |
| ATOM | 698 | HB2 | LEU | 48 | -7.167 | -4.968 | -20.385 | 1.00 | 0.33 |
| ATOM | 699 | CG | LEU | 48 | -8.816 | -5.964 | -19.434 | 1.00 | 0.34 |
| ATOM | 700 | HG | LEU | 48 | -8.808 | -6.900 | -19.972 | 1.00 | 0.32 |
| ATOM | 701 | CD1 | LEU | 48 | -7.952 | -6.091 | -18.177 | 1.00 | 0.41 |
| ATOM | 702 | HD11 | LEU | 48 | -8.002 | -5.171 | -17.613 | 1.00 | 1.11 |
| ATOM | 703 | HD12 | LEU | 48 | -6.928 | -6.283 | -18.462 | 1.00 | 1.05 |
| ATOM | 704 | HD13 | LEU | 48 | -8.315 | -6.906 | -17.570 | 1.00 | 1.15 |
| ATOM | 705 | CD2 | LEU | 48 | -10.255 | -5.628 | -19.016 | 1.00 | 0.36 |
| ATOM | 706 | HD21 | LEU | 48 | -10.569 | -4.707 | -19.478 | 1.00 | 1.10 |
| ATOM | 707 | HD22 | LEU | 48 | -10.299 | -5.524 | -17.942 | 1.00 | 1.09 |
| ATOM | 708 | HD23 | LEU | 48 | -10.912 | -6.428 | -19.325 | 1.00 | 1.04 |
| ATOM | 709 | C | LEU | 48 | -8.289 | -3.806 | -22.589 | 1.00 | 0.25 |
| ATOM | 710 | O | LEU | 48 | -7.174 | -3.849 | -23.071 | 1.00 | 0.26 |
| ATOM | 711 | N | ASN | 49 | -9.073 | -2.775 | -22.762 | 1.00 | 0.25 |
| ATOM | 712 | HN | ASN | 49 | -9.964 | -2.770 | -22.355 | 1.00 | 0.26 |
| ATOM | 713 | CA | ASN | 49 | -8.622 | -1.604 | -23.568 | 1.00 | 0.25 |
| ATOM | 714 | HA | ASN | 49 | -7.703 | -1.842 | -24.082 | 1.00 | 0.27 |
| ATOM | 715 | CB | ASN | 49 | -9.700 | -1.245 | -24.593 | 1.00 | 0.28 |
| ATOM | 716 | HB1 | ASN | 49 | -9.390 | -0.375 | -25.153 | 1.00 | 0.30 |
| ATOM | 717 | HB2 | ASN | 49 | -10.628 | -1.033 | -24.081 | 1.00 | 0.28 |
| ATOM | 718 | CG | ASN | 49 | -9.902 | -2.419 | -25.553 | 1.00 | 0.32 |
| ATOM | 719 | OD1 | ASN | 49 | -9.798 | -3.564 | -25.161 | 1.00 | 1.10 |
| ATOM | 720 | ND2 | ASN | 49 | -10.186 | -2.182 | -26.804 | 1.00 | 1.14 |
| ATOM | 721 | HD21 | ASN | 49 | -10.268 | -1.258 | -27.121 | 1.00 | 1.94 |
| ATOM | 722 | HD22 | ASN | 49 | -10.317 | -2.927 | -27.427 | 1.00 | 1.14 |
| ATOM | 723 | C | ASN | 49 | -8.391 | -0.417 | -22.633 | 1.00 | 0.24 |
| ATOM | 724 | O | ASN | 49 | -9.290 | 0.016 | -21.939 | 1.00 | 0.23 |
| ATOM | 725 | N | PHE | 50 | -7.192 | 0.107 | -22.606 | 1.00 | 0.24 |
| ATOM | 726 | HN | PHE | 50 | -6.485 | -0.264 | -23.173 | 1.00 | 0.26 |
| ATOM | 727 | CA | PHE | 50 | -6.896 | 1.263 | -21.710 | 1.00 | 0.23 |
| ATOM | 728 | HA | PHE | 50 | -7.688 | 1.380 | -20.985 | 1.00 | 0.21 |
| ATOM | 729 | CB | PHE | 50 | -5.574 | 1.016 | -20.981 | 1.00 | 0.24 |
| ATOM | 730 | HB1 | PHE | 50 | -5.357 | 1.853 | -20.334 | 1.00 | 0.25 |
| ATOM | 731 | HB2 | PHE | 50 | -4.780 | 0.907 | -21.705 | 1.00 | 0.27 |
| ATOM | 732 | CG | PHE | 50 | -5.676 | -0.243 | -20.154 | 1.00 | 0.23 |

FIG. 4A-10

| | | | | | | | | |
|---|---|---|---|---|---|---|---|---|
| ATOM | 733 | CD1 | PHE | 50 | -6.266 | -0.201 | -18.886 | 1.00 0.25 |
| ATOM | 734 | HD1 | PHE | 50 | -6.652 | 0.731 | -18.500 | 1.00 0.28 |
| ATOM | 735 | CD2 | PHE | 50 | -5.176 | -1.451 | -20.654 | 1.00 0.22 |
| ATOM | 736 | HD2 | PHE | 50 | -4.720 | -1.483 | -21.633 | 1.00 0.23 |
| ATOM | 737 | CE1 | PHE | 50 | -6.358 | -1.368 | -18.117 | 1.00 0.25 |
| ATOM | 738 | HE1 | PHE | 50 | -6.813 | -1.336 | -17.139 | 1.00 0.28 |
| ATOM | 739 | CE2 | PHE | 50 | -5.267 | -2.618 | -19.886 | 1.00 0.23 |
| ATOM | 740 | HE2 | PHE | 50 | -4.881 | -3.550 | -20.272 | 1.00 0.25 |
| ATOM | 741 | CZ | PHE | 50 | -5.858 | -2.576 | -18.618 | 1.00 0.24 |
| ATOM | 742 | HZ | PHE | 50 | -5.928 | -3.476 | -18.025 | 1.00 0.25 |
| ATOM | 743 | C | PHE | 50 | -6.777 | 2.538 | -22.545 | 1.00 0.26 |
| ATOM | 744 | O | PHE | 50 | -6.028 | 2.596 | -23.501 | 1.00 0.31 |
| ATOM | 745 | N | THR | 51 | -7.517 | 3.555 | -22.184 | 1.00 0.24 |
| ATOM | 746 | HN | THR | 51 | -8.109 | 3.468 | -21.413 | 1.00 0.22 |
| ATOM | 747 | CA | THR | 51 | -7.470 | 4.842 | -22.940 | 1.00 0.27 |
| ATOM | 748 | HA | THR | 51 | -6.775 | 4.762 | -23.762 | 1.00 0.31 |
| ATOM | 749 | CB | THR | 51 | -8.868 | 5.153 | -23.483 | 1.00 0.30 |
| ATOM | 750 | HB | THR | 51 | -9.562 | 5.248 | -22.663 | 1.00 0.29 |
| ATOM | 751 | OG1 | THR | 51 | -9.283 | 4.100 | -24.341 | 1.00 0.35 |
| ATOM | 752 | HG1 | THR | 51 | -9.638 | 4.491 | -25.142 | 1.00 0.84 |
| ATOM | 753 | CG2 | THR | 51 | -8.835 | 6.464 | -24.273 | 1.00 0.34 |
| ATOM | 754 | HG21 | THR | 51 | -9.805 | 6.640 | -24.716 | 1.00 1.02 |
| ATOM | 755 | HG22 | THR | 51 | -8.092 | 6.394 | -25.053 | 1.00 1.07 |
| ATOM | 756 | HG23 | THR | 51 | -8.588 | 7.280 | -23.611 | 1.00 1.13 |
| ATOM | 757 | C | THR | 51 | -7.024 | 5.969 | -22.001 | 1.00 0.25 |
| ATOM | 758 | O | THR | 51 | -7.553 | 6.139 | -20.920 | 1.00 0.22 |
| ATOM | 759 | N | ARG | 52 | -6.054 | 6.740 | -22.411 | 1.00 0.29 |
| ATOM | 760 | HN | ARG | 52 | -5.645 | 6.583 | -23.287 | 1.00 0.32 |
| ATOM | 761 | CA | ARG | 52 | -5.566 | 7.861 | -21.556 | 1.00 0.29 |
| ATOM | 762 | HA | ARG | 52 | -5.591 | 7.563 | -20.518 | 1.00 0.27 |
| ATOM | 763 | CB | ARG | 52 | -4.128 | 8.201 | -21.955 | 1.00 0.35 |
| ATOM | 764 | HB1 | ARG | 52 | -4.125 | 8.654 | -22.935 | 1.00 0.39 |
| ATOM | 765 | HB2 | ARG | 52 | -3.539 | 7.295 | -21.977 | 1.00 0.38 |
| ATOM | 766 | CG | ARG | 52 | -3.521 | 9.177 | -20.945 | 1.00 0.39 |
| ATOM | 767 | HG1 | ARG | 52 | -3.645 | 8.787 | -19.946 | 1.00 0.71 |
| ATOM | 768 | HG2 | ARG | 52 | -4.017 | 10.134 | -21.025 | 1.00 0.57 |
| ATOM | 769 | CD | ARG | 52 | -2.030 | 9.345 | -21.244 | 1.00 0.79 |
| ATOM | 770 | HD1 | ARG | 52 | -1.825 | 9.001 | -22.248 | 1.00 1.45 |
| ATOM | 771 | HD2 | ARG | 52 | -1.453 | 8.763 | -20.543 | 1.00 1.39 |
| ATOM | 772 | NE | ARG | 52 | -1.656 | 10.782 | -21.120 | 1.00 1.47 |
| ATOM | 773 | HE | ARG | 52 | -2.354 | 11.468 | -21.073 | 1.00 2.06 |
| ATOM | 774 | CZ | ARG | 52 | -0.398 | 11.127 | -21.071 | 1.00 2.09 |
| ATOM | 775 | NH1 | ARG | 52 | -0.070 | 12.385 | -20.960 | 1.00 3.05 |
| ATOM | 776 | HH11 | ARG | 52 | -0.782 | 13.084 | -20.911 | 1.00 3.45 |
| ATOM | 777 | HH12 | ARG | 52 | 0.894 | 12.649 | -20.923 | 1.00 3.60 |
| ATOM | 778 | NH2 | ARG | 52 | 0.532 | 10.213 | -21.138 | 1.00 2.31 |
| ATOM | 779 | HH21 | ARG | 52 | 0.281 | 9.249 | -21.226 | 1.00 2.16 |
| ATOM | 780 | HH22 | ARG | 52 | 1.496 | 10.477 | -21.102 | 1.00 3.05 |
| ATOM | 781 | C | ARG | 52 | -6.460 | 9.090 | -21.758 | 1.00 0.29 |
| ATOM | 782 | O | ARG | 52 | -6.719 | 9.495 | -22.875 | 1.00 0.33 |
| ATOM | 783 | N | LEU | 53 | -6.928 | 9.689 | -20.689 | 1.00 0.26 |
| ATOM | 784 | HN | LEU | 53 | -6.702 | 9.345 | -19.798 | 1.00 0.25 |
| ATOM | 785 | CA | LEU | 53 | -7.803 | 10.896 | -20.822 | 1.00 0.29 |
| ATOM | 786 | HA | LEU | 53 | -8.167 | 10.972 | -21.835 | 1.00 0.32 |
| ATOM | 787 | CB | LEU | 53 | -8.992 | 10.784 | -19.862 | 1.00 0.28 |
| ATOM | 788 | HB1 | LEU | 53 | -9.579 | 11.688 | -19.908 | 1.00 0.31 |
| ATOM | 789 | HB2 | LEU | 53 | -8.624 | 10.648 | -18.855 | 1.00 0.28 |
| ATOM | 790 | CG | LEU | 53 | -9.866 | 9.587 | -20.249 | 1.00 0.28 |
| ATOM | 791 | HG | LEU | 53 | -9.264 | 8.690 | -20.246 | 1.00 0.29 |
| ATOM | 792 | CD1 | LEU | 53 | -10.999 | 9.440 | -19.232 | 1.00 0.29 |
| ATOM | 793 | HD11 | LEU | 53 | -11.606 | 8.585 | -19.487 | 1.00 0.95 |
| ATOM | 794 | HD12 | LEU | 53 | -11.610 | 10.331 | -19.243 | 1.00 1.05 |
| ATOM | 795 | HD13 | LEU | 53 | -10.581 | 9.303 | -18.247 | 1.00 1.07 |
| ATOM | 796 | CD2 | LEU | 53 | -10.463 | 9.799 | -21.646 | 1.00 0.36 |
| ATOM | 797 | HD21 | LEU | 53 | -10.523 | 10.856 | -21.860 | 1.00 1.01 |
| ATOM | 798 | HD22 | LEU | 53 | -11.453 | 9.370 | -21.685 | 1.00 1.09 |
| ATOM | 799 | HD23 | LEU | 53 | -9.835 | 9.319 | -22.382 | 1.00 1.14 |
| ATOM | 800 | C | LEU | 53 | -7.000 | 12.154 | -20.483 | 1.00 0.33 |
| ATOM | 801 | O | LEU | 53 | -6.315 | 12.218 | -19.482 | 1.00 0.34 |
| ATOM | 802 | N | HIS | 54 | -7.080 | 13.154 | -21.319 | 1.00 0.41 |
| ATOM | 803 | HN | HIS | 54 | -7.637 | 13.075 | -22.121 | 1.00 0.45 |
| ATOM | 804 | CA | HIS | 54 | -6.324 | 14.413 | -21.062 | 1.00 0.47 |
| ATOM | 805 | HA | HIS | 54 | -5.292 | 14.183 | -20.851 | 1.00 0.54 |
| ATOM | 806 | CB | HIS | 54 | -6.407 | 15.314 | -22.297 | 1.00 0.60 |
| ATOM | 807 | HB1 | HIS | 54 | -6.018 | 16.291 | -22.052 | 1.00 0.64 |
| ATOM | 808 | HB2 | HIS | 54 | -7.438 | 15.407 | -22.603 | 1.00 0.61 |
| ATOM | 809 | CG | HIS | 54 | -5.602 | 14.726 | -23.426 | 1.00 0.74 |

FIG. 4A-11

```
ATOM    810  ND1  HIS   54     -5.645   15.254  -24.707   1.00   1.35
ATOM    811  HD1  HIS   54     -6.172   16.028  -24.996   1.00   1.86
ATOM    812  CD2  HIS   54     -4.740   13.656  -23.493   1.00   0.86
ATOM    813  HD2  HIS   54     -4.480   13.010  -22.668   1.00   1.34
ATOM    814  CE1  HIS   54     -4.834   14.512  -25.481   1.00   1.33
ATOM    815  HE1  HIS   54     -4.670   14.692  -26.533   1.00   1.83
ATOM    816  NE2  HIS   54     -4.257   13.525  -24.792   1.00   0.92
ATOM    817  C    HIS   54     -6.933   15.154  -19.867   1.00   0.43
ATOM    818  O    HIS   54     -6.230   15.714  -19.051   1.00   0.49
ATOM    819  N    ASP   55     -8.236   15.172  -19.767   1.00   0.42
ATOM    820  HN   ASP   55     -8.784   14.719  -20.442   1.00   0.45
ATOM    821  CA   ASP   55     -8.892   15.892  -18.635   1.00   0.49
ATOM    822  HA   ASP   55     -8.217   15.938  -17.796   1.00   0.54
ATOM    823  CB   ASP   55     -9.251   17.314  -19.073   1.00   0.65
ATOM    824  HB1  ASP   55     -9.876   17.774  -18.323   1.00   0.75
ATOM    825  HB2  ASP   55     -9.783   17.277  -20.013   1.00   0.68
ATOM    826  CG   ASP   55     -7.974   18.140  -19.244   1.00   0.71
ATOM    827  OD1  ASP   55     -7.978   19.037  -20.071   1.00   1.19
ATOM    828  OD2  ASP   55     -7.018   17.870  -18.536   1.00   1.28
ATOM    829  C    ASP   55    -10.167   15.156  -18.223   1.00   0.45
ATOM    830  O    ASP   55    -10.638   14.273  -18.912   1.00   0.44
ATOM    831  N    GLY   56    -10.728   15.518  -17.100   1.00   0.46
ATOM    832  HN   GLY   56    -10.328   16.233  -16.563   1.00   0.50
ATOM    833  CA   GLY   56    -11.975   14.848  -16.632   1.00   0.44
ATOM    834  HA1  GLY   56    -12.482   14.399  -17.472   1.00   0.44
ATOM    835  HA2  GLY   56    -12.622   15.579  -16.169   1.00   0.48
ATOM    836  C    GLY   56    -11.624   13.760  -15.614   1.00   0.40
ATOM    837  O    GLY   56    -10.473   13.543  -15.294   1.00   0.42
ATOM    838  N    ILE   57    -12.613   13.078  -15.105   1.00   0.37
ATOM    839  HN   ILE   57    -13.533   13.275  -15.380   1.00   0.39
ATOM    840  CA   ILE   57    -12.352   12.002  -14.106   1.00   0.35
ATOM    841  HA   ILE   57    -11.406   12.184  -13.616   1.00   0.38
ATOM    842  CB   ILE   57    -13.473   12.000  -13.064   1.00   0.41
ATOM    843  HB   ILE   57    -14.415   11.820  -13.561   1.00   0.42
ATOM    844  CG1  ILE   57    -13.508   13.363  -12.360   1.00   0.48
ATOM    845  HG11 ILE   57    -13.512   14.148  -13.101   1.00   0.48
ATOM    846  HG12 ILE   57    -12.631   13.465  -11.737   1.00   0.51
ATOM    847  CG2  ILE   57    -13.216   10.896  -12.037   1.00   0.44
ATOM    848  HG21 ILE   57    -13.315    9.932  -12.513   1.00   1.19
ATOM    849  HG22 ILE   57    -13.934   10.977  -11.235   1.00   1.09
ATOM    850  HG23 ILE   57    -12.218   11.000  -11.639   1.00   1.04
ATOM    851  CD1  ILE   57    -14.765   13.484  -11.488   1.00   0.56
ATOM    852  HD11 ILE   57    -15.459   12.693  -11.728   1.00   1.08
ATOM    853  HD12 ILE   57    -15.235   14.439  -11.668   1.00   1.24
ATOM    854  HD13 ILE   57    -14.487   13.413  -10.447   1.00   1.14
ATOM    855  C    ILE   57    -12.307   10.647  -14.817   1.00   0.30
ATOM    856  O    ILE   57    -13.139   10.353  -15.653   1.00   0.31
ATOM    857  N    ALA   58    -11.337    9.828  -14.493   1.00   0.26
ATOM    858  HN   ALA   58    -10.679   10.096  -13.817   1.00   0.27
ATOM    859  CA   ALA   58    -11.221    8.489  -15.148   1.00   0.23
ATOM    860  HA   ALA   58    -11.957    8.398  -15.932   1.00   0.25
ATOM    861  CB   ALA   58     -9.824    8.339  -15.749   1.00   0.23
ATOM    862  HB1  ALA   58     -9.843    7.585  -16.522   1.00   0.97
ATOM    863  HB2  ALA   58     -9.129    8.044  -14.976   1.00   1.11
ATOM    864  HB3  ALA   58     -9.513    9.280  -16.172   1.00   1.03
ATOM    865  C    ALA   58    -11.443    7.387  -14.114   1.00   0.23
ATOM    866  O    ALA   58    -11.389    7.617  -12.922   1.00   0.27
ATOM    867  N    ASP   59    -11.701    6.189  -14.564   1.00   0.25
ATOM    868  HN   ASP   59    -11.744    6.028  -15.530   1.00   0.28
ATOM    869  CA   ASP   59    -11.934    5.069  -13.613   1.00   0.27
ATOM    870  HA   ASP   59    -12.788    5.296  -12.991   1.00   0.34
ATOM    871  CB   ASP   59    -12.207    3.785  -14.400   1.00   0.33
ATOM    872  HB1  ASP   59    -12.203    2.942  -13.725   1.00   0.34
ATOM    873  HB2  ASP   59    -11.438    3.651  -15.147   1.00   0.32
ATOM    874  CG   ASP   59    -13.572    3.880  -15.084   1.00   0.44
ATOM    875  OD1  ASP   59    -13.791    3.139  -16.028   1.00   1.20
ATOM    876  OD2  ASP   59    -14.374    4.691  -14.653   1.00   1.14
ATOM    877  C    ASP   59    -10.700    4.863  -12.731   1.00   0.22
ATOM    878  O    ASP   59    -10.806    4.767  -11.524   1.00   0.27
ATOM    879  N    ILE   60     -9.534    4.780  -13.326   1.00   0.18
ATOM    880  HN   ILE   60     -9.478    4.850  -14.302   1.00   0.20
ATOM    881  CA   ILE   60     -8.291    4.561  -12.523   1.00   0.22
ATOM    882  HA   ILE   60     -8.554    4.303  -11.512   1.00   0.28
ATOM    883  CB   ILE   60     -7.502    3.404  -13.155   1.00   0.27
ATOM    884  HB   ILE   60     -7.255    3.655  -14.175   1.00   0.28
ATOM    885  CG1  ILE   60     -8.377    2.146  -13.136   1.00   0.30
ATOM    886  HG11 ILE   60     -9.327    2.365  -13.600   1.00   0.24
```

FIG. 4A-12

| | | | | | | | | |
|---|---|---|---|---|---|---|---|---|
| ATOM | 887 | HG12 | ILE | 60 | -8.541 | 1.839 | -12.113 | 1.00 | 0.36 |
| ATOM | 888 | CG2 | ILE | 60 | -6.210 | 3.127 | -12.369 | 1.00 | 0.39 |
| ATOM | 889 | HG21 | ILE | 60 | -6.456 | 2.704 | -11.409 | 1.00 | 1.05 |
| ATOM | 890 | HG22 | ILE | 60 | -5.658 | 4.043 | -12.228 | 1.00 | 1.10 |
| ATOM | 891 | HG23 | ILE | 60 | -5.600 | 2.428 | -12.921 | 1.00 | 1.12 |
| ATOM | 892 | CD1 | ILE | 60 | -7.688 | 1.015 | -13.904 | 1.00 | 0.38 |
| ATOM | 893 | HD11 | ILE | 60 | -7.209 | 1.413 | -14.786 | 1.00 | 1.07 |
| ATOM | 894 | HD12 | ILE | 60 | -8.424 | 0.280 | -14.196 | 1.00 | 1.14 |
| ATOM | 895 | HD13 | ILE | 60 | -6.948 | 0.549 | -13.270 | 1.00 | 1.04 |
| ATOM | 896 | C | ILE | 60 | -7.438 | 5.834 | -12.518 | 1.00 | 0.20 |
| ATOM | 897 | O | ILE | 60 | -6.731 | 6.115 | -13.464 | 1.00 | 0.25 |
| ATOM | 898 | N | MET | 61 | -7.473 | 6.585 | -11.448 | 1.00 | 0.20 |
| ATOM | 899 | HN | MET | 61 | -8.033 | 6.326 | -10.687 | 1.00 | 0.25 |
| ATOM | 900 | CA | MET | 61 | -6.641 | 7.822 | -11.373 | 1.00 | 0.20 |
| ATOM | 901 | HA | MET | 61 | -6.327 | 8.102 | -12.366 | 1.00 | 0.19 |
| ATOM | 902 | CB | MET | 61 | -7.464 | 8.963 | -10.773 | 1.00 | 0.24 |
| ATOM | 903 | HB1 | MET | 61 | -8.331 | 9.137 | -11.392 | 1.00 | 0.35 |
| ATOM | 904 | HB2 | MET | 61 | -6.860 | 9.856 | -10.743 | 1.00 | 0.33 |
| ATOM | 905 | CG | MET | 61 | -7.918 | 8.604 | -9.358 | 1.00 | 0.31 |
| ATOM | 906 | HG1 | MET | 61 | -7.146 | 8.870 | -8.653 | 1.00 | 0.66 |
| ATOM | 907 | HG2 | MET | 61 | -8.112 | 7.544 | -9.300 | 1.00 | 0.67 |
| ATOM | 908 | SD | MET | 61 | -9.433 | 9.519 | -8.967 | 1.00 | 0.54 |
| ATOM | 909 | CE | MET | 61 | -8.878 | 11.154 | -9.516 | 1.00 | 0.40 |
| ATOM | 910 | HE1 | MET | 61 | -9.492 | 11.914 | -9.056 | 1.00 | 1.06 |
| ATOM | 911 | HE2 | MET | 61 | -8.968 | 11.227 | -10.589 | 1.00 | 1.16 |
| ATOM | 912 | HE3 | MET | 61 | -7.846 | 11.298 | -9.232 | 1.00 | 1.12 |
| ATOM | 913 | C | MET | 61 | -5.396 | 7.540 | -10.524 | 1.00 | 0.20 |
| ATOM | 914 | O | MET | 61 | -5.478 | 6.951 | -9.463 | 1.00 | 0.22 |
| ATOM | 915 | N | ILE | 62 | -4.241 | 7.937 | -11.001 | 1.00 | 0.20 |
| ATOM | 916 | HN | ILE | 62 | -4.207 | 8.393 | -11.868 | 1.00 | 0.21 |
| ATOM | 917 | CA | ILE | 62 | -2.971 | 7.678 | -10.252 | 1.00 | 0.21 |
| ATOM | 918 | HA | ILE | 62 | -3.156 | 6.982 | -9.448 | 1.00 | 0.20 |
| ATOM | 919 | CB | ILE | 62 | -1.938 | 7.080 | -11.211 | 1.00 | 0.24 |
| ATOM | 920 | HB | ILE | 62 | -1.753 | 7.781 | -12.012 | 1.00 | 0.26 |
| ATOM | 921 | CG1 | ILE | 62 | -2.480 | 5.762 | -11.785 | 1.00 | 0.23 |
| ATOM | 922 | HG11 | ILE | 62 | -3.479 | 5.922 | -12.162 | 1.00 | 0.20 |
| ATOM | 923 | HG12 | ILE | 62 | -2.508 | 5.018 | -11.003 | 1.00 | 0.24 |
| ATOM | 924 | CG2 | ILE | 62 | -0.635 | 6.812 | -10.455 | 1.00 | 0.30 |
| ATOM | 925 | HG21 | ILE | 62 | -0.863 | 6.443 | -9.466 | 1.00 | 1.08 |
| ATOM | 926 | HG22 | ILE | 62 | -0.070 | 7.729 | -10.375 | 1.00 | 1.12 |
| ATOM | 927 | HG23 | ILE | 62 | -0.052 | 6.076 | -10.988 | 1.00 | 0.99 |
| ATOM | 928 | CD1 | ILE | 62 | -1.584 | 5.262 | -12.927 | 1.00 | 0.29 |
| ATOM | 929 | HD11 | ILE | 62 | -0.979 | 6.073 | -13.305 | 1.00 | 1.02 |
| ATOM | 930 | HD12 | ILE | 62 | -2.201 | 4.876 | -13.724 | 1.00 | 1.09 |
| ATOM | 931 | HD13 | ILE | 62 | -0.941 | 4.476 | -12.559 | 1.00 | 1.07 |
| ATOM | 932 | C | ILE | 62 | -2.423 | 8.988 | -9.677 | 1.00 | 0.22 |
| ATOM | 933 | O | ILE | 62 | -2.393 | 10.004 | -10.343 | 1.00 | 0.27 |
| ATOM | 934 | N | SER | 63 | -1.993 | 8.976 | -8.441 | 1.00 | 0.20 |
| ATOM | 935 | HN | SER | 63 | -2.028 | 8.147 | -7.916 | 1.00 | 0.18 |
| ATOM | 936 | CA | SER | 63 | -1.452 | 10.226 | -7.829 | 1.00 | 0.22 |
| ATOM | 937 | HA | SER | 63 | -0.998 | 10.836 | -8.597 | 1.00 | 0.26 |
| ATOM | 938 | CB | SER | 63 | -2.597 | 11.000 | -7.176 | 1.00 | 0.24 |
| ATOM | 939 | HB1 | SER | 63 | -3.448 | 11.012 | -7.845 | 1.00 | 0.25 |
| ATOM | 940 | HB2 | SER | 63 | -2.286 | 12.012 | -6.978 | 1.00 | 0.29 |
| ATOM | 941 | OG | SER | 63 | -2.951 | 10.369 | -5.952 | 1.00 | 0.25 |
| ATOM | 942 | HG | SER | 63 | -3.682 | 9.772 | -6.127 | 1.00 | 0.85 |
| ATOM | 943 | C | SER | 63 | -0.404 | 9.879 | -6.764 | 1.00 | 0.21 |
| ATOM | 944 | O | SER | 63 | -0.364 | 8.775 | -6.259 | 1.00 | 0.20 |
| ATOM | 945 | N | PHE | 64 | 0.440 | 10.823 | -6.419 | 1.00 | 0.24 |
| ATOM | 946 | HN | PHE | 64 | 0.380 | 11.705 | -6.841 | 1.00 | 0.27 |
| ATOM | 947 | CA | PHE | 64 | 1.490 | 10.569 | -5.382 | 1.00 | 0.24 |
| ATOM | 948 | HA | PHE | 64 | 1.560 | 9.511 | -5.179 | 1.00 | 0.22 |
| ATOM | 949 | CB | PHE | 64 | 2.840 | 11.084 | -5.895 | 1.00 | 0.28 |
| ATOM | 950 | HB1 | PHE | 64 | 3.564 | 11.047 | -5.097 | 1.00 | 0.32 |
| ATOM | 951 | HB2 | PHE | 64 | 2.730 | 12.103 | -6.235 | 1.00 | 0.32 |
| ATOM | 952 | CG | PHE | 64 | 3.316 | 10.220 | -7.040 | 1.00 | 0.28 |
| ATOM | 953 | CD1 | PHE | 64 | 4.112 | 9.096 | -6.788 | 1.00 | 0.30 |
| ATOM | 954 | HD1 | PHE | 64 | 4.385 | 8.844 | -5.774 | 1.00 | 0.32 |
| ATOM | 955 | CD2 | PHE | 64 | 2.963 | 10.545 | -8.355 | 1.00 | 0.33 |
| ATOM | 956 | HD2 | PHE | 64 | 2.350 | 11.412 | -8.550 | 1.00 | 0.37 |
| ATOM | 957 | CE1 | PHE | 64 | 4.553 | 8.297 | -7.850 | 1.00 | 0.36 |
| ATOM | 958 | HE1 | PHE | 64 | 5.166 | 7.430 | -7.656 | 1.00 | 0.40 |
| ATOM | 959 | CE2 | PHE | 64 | 3.403 | 9.747 | -9.417 | 1.00 | 0.40 |
| ATOM | 960 | HE2 | PHE | 64 | 3.130 | 9.998 | -10.431 | 1.00 | 0.47 |
| ATOM | 961 | CZ | PHE | 64 | 4.198 | 8.623 | -9.165 | 1.00 | 0.40 |
| ATOM | 962 | HZ | PHE | 64 | 4.538 | 8.007 | -9.984 | 1.00 | 0.47 |
| ATOM | 963 | C | PHE | 64 | 1.115 | 11.318 | -4.097 | 1.00 | 0.27 |

FIG. 4A-13

| | | | | | | | | |
|---|---|---|---|---|---|---|---|---|
| ATOM | 964 | O | PHE | 64 | 0.924 | 12.518 | -4.108 | 1.00 | 0.36 |
| ATOM | 965 | N | GLY | 65 | 0.996 | 10.617 | -2.996 | 1.00 | 0.30 |
| ATOM | 966 | HN | GLY | 65 | 1.146 | 9.649 | -3.017 | 1.00 | 0.33 |
| ATOM | 967 | CA | GLY | 65 | 0.615 | 11.282 | -1.709 | 1.00 | 0.38 |
| ATOM | 968 | HA1 | GLY | 65 | -0.152 | 10.697 | -1.224 | 1.00 | 0.46 |
| ATOM | 969 | HA2 | GLY | 65 | 0.230 | 12.270 | -1.913 | 1.00 | 0.45 |
| ATOM | 970 | C | GLY | 65 | 1.823 | 11.397 | -0.770 | 1.00 | 0.32 |
| ATOM | 971 | O | GLY | 65 | 2.926 | 11.007 | -1.098 | 1.00 | 0.40 |
| ATOM | 972 | N | ILE | 66 | 1.598 | 11.926 | 0.408 | 1.00 | 0.30 |
| ATOM | 973 | HN | ILE | 66 | 0.691 | 12.220 | 0.635 | 1.00 | 0.36 |
| ATOM | 974 | CA | ILE | 66 | 2.691 | 12.081 | 1.417 | 1.00 | 0.36 |
| ATOM | 975 | HA | ILE | 66 | 3.564 | 11.534 | 1.093 | 1.00 | 0.40 |
| ATOM | 976 | CB | ILE | 66 | 3.040 | 13.564 | 1.571 | 1.00 | 0.41 |
| ATOM | 977 | HB | ILE | 66 | 2.127 | 14.134 | 1.656 | 1.00 | 0.64 |
| ATOM | 978 | CG1 | ILE | 66 | 3.829 | 14.026 | 0.337 | 1.00 | 0.68 |
| ATOM | 979 | HG11 | ILE | 66 | 3.301 | 13.729 | -0.557 | 1.00 | 0.95 |
| ATOM | 980 | HG12 | ILE | 66 | 4.804 | 13.561 | 0.346 | 1.00 | 1.01 |
| ATOM | 981 | CG2 | ILE | 66 | 3.886 | 13.764 | 2.831 | 1.00 | 0.93 |
| ATOM | 982 | HG21 | ILE | 66 | 4.372 | 14.727 | 2.790 | 1.00 | 1.50 |
| ATOM | 983 | HG22 | ILE | 66 | 4.632 | 12.986 | 2.891 | 1.00 | 1.41 |
| ATOM | 984 | HG23 | ILE | 66 | 3.249 | 13.720 | 3.702 | 1.00 | 1.54 |
| ATOM | 985 | CD1 | ILE | 66 | 3.997 | 15.551 | 0.343 | 1.00 | 0.70 |
| ATOM | 986 | HD11 | ILE | 66 | 4.944 | 15.806 | 0.797 | 1.00 | 1.22 |
| ATOM | 987 | HD12 | ILE | 66 | 3.196 | 16.009 | 0.902 | 1.00 | 1.28 |
| ATOM | 988 | HD13 | ILE | 66 | 3.979 | 15.917 | -0.673 | 1.00 | 1.23 |
| ATOM | 989 | C | ILE | 66 | 2.207 | 11.519 | 2.760 | 1.00 | 0.46 |
| ATOM | 990 | O | ILE | 66 | 1.021 | 11.363 | 2.958 | 1.00 | 0.54 |
| ATOM | 991 | N | LYS | 67 | 3.129 | 11.205 | 3.659 | 1.00 | 0.59 |
| ATOM | 992 | HN | LYS | 67 | 4.073 | 11.343 | 3.434 | 1.00 | 0.64 |
| ATOM | 993 | CA | LYS | 67 | 2.780 | 10.630 | 5.014 | 1.00 | 0.74 |
| ATOM | 994 | HA | LYS | 67 | 3.072 | 9.594 | 5.038 | 1.00 | 0.83 |
| ATOM | 995 | CB | LYS | 67 | 3.550 | 11.404 | 6.102 | 1.00 | 0.90 |
| ATOM | 996 | HB1 | LYS | 67 | 3.237 | 12.438 | 6.089 | 1.00 | 0.89 |
| ATOM | 997 | HB2 | LYS | 67 | 4.608 | 11.352 | 5.891 | 1.00 | 0.96 |
| ATOM | 998 | CG | LYS | 67 | 3.287 | 10.815 | 7.504 | 1.00 | 1.08 |
| ATOM | 999 | HG1 | LYS | 67 | 2.254 | 10.524 | 7.598 | 1.00 | 1.31 |
| ATOM | 1000 | HG2 | LYS | 67 | 3.510 | 11.565 | 8.249 | 1.00 | 1.33 |
| ATOM | 1001 | CD | LYS | 67 | 4.179 | 9.590 | 7.746 | 1.00 | 0.98 |
| ATOM | 1002 | HD1 | LYS | 67 | 5.216 | 9.885 | 7.694 | 1.00 | 1.07 |
| ATOM | 1003 | HD2 | LYS | 67 | 3.979 | 8.839 | 6.999 | 1.00 | 1.07 |
| ATOM | 1004 | CE | LYS | 67 | 3.885 | 9.016 | 9.135 | 1.00 | 1.17 |
| ATOM | 1005 | HE1 | LYS | 67 | 4.331 | 8.036 | 9.220 | 1.00 | 1.64 |
| ATOM | 1006 | HE2 | LYS | 67 | 2.817 | 8.938 | 9.272 | 1.00 | 1.50 |
| ATOM | 1007 | NZ | LYS | 67 | 4.453 | 9.913 | 10.180 | 1.00 | 1.93 |
| ATOM | 1008 | HZ1 | LYS | 67 | 4.569 | 10.870 | 9.792 | 1.00 | 2.38 |
| ATOM | 1009 | HZ2 | LYS | 67 | 5.378 | 9.547 | 10.485 | 1.00 | 2.43 |
| ATOM | 1010 | HZ3 | LYS | 67 | 3.808 | 9.948 | 10.995 | 1.00 | 2.40 |
| ATOM | 1011 | C | LYS | 67 | 1.274 | 10.732 | 5.280 | 1.00 | 0.72 |
| ATOM | 1012 | O | LYS | 67 | 0.530 | 9.804 | 5.035 | 1.00 | 0.79 |
| ATOM | 1013 | N | GLU | 68 | 0.815 | 11.855 | 5.760 | 1.00 | 0.77 |
| ATOM | 1014 | HN | GLU | 68 | 1.425 | 12.601 | 5.939 | 1.00 | 0.84 |
| ATOM | 1015 | CA | GLU | 68 | -0.645 | 12.004 | 6.011 | 1.00 | 0.84 |
| ATOM | 1016 | HA | GLU | 68 | -1.014 | 11.130 | 6.530 | 1.00 | 0.99 |
| ATOM | 1017 | CB | GLU | 68 | -0.895 | 13.254 | 6.860 | 1.00 | 1.05 |
| ATOM | 1018 | HB1 | GLU | 68 | -0.393 | 13.149 | 7.810 | 1.00 | 1.23 |
| ATOM | 1019 | HB2 | GLU | 68 | -1.956 | 13.370 | 7.024 | 1.00 | 1.10 |
| ATOM | 1020 | CG | GLU | 68 | -0.353 | 14.487 | 6.134 | 1.00 | 1.15 |
| ATOM | 1021 | HG1 | GLU | 68 | -1.000 | 14.730 | 5.304 | 1.00 | 1.32 |
| ATOM | 1022 | HG2 | GLU | 68 | 0.642 | 14.281 | 5.768 | 1.00 | 1.28 |
| ATOM | 1023 | CD | GLU | 68 | -0.308 | 15.669 | 7.104 | 1.00 | 1.75 |
| ATOM | 1024 | OE1 | GLU | 68 | 0.246 | 16.692 | 6.736 | 1.00 | 2.45 |
| ATOM | 1025 | OE2 | GLU | 68 | -0.823 | 15.530 | 8.202 | 1.00 | 2.16 |
| ATOM | 1026 | C | GLU | 68 | -1.346 | 12.132 | 4.660 | 1.00 | 0.76 |
| ATOM | 1027 | O | GLU | 68 | -0.899 | 12.859 | 3.795 | 1.00 | 1.11 |
| ATOM | 1028 | N | HIS | 69 | -2.420 | 11.414 | 4.454 | 1.00 | 0.94 |
| ATOM | 1029 | HN | HIS | 69 | -2.755 | 10.815 | 5.155 | 1.00 | 1.32 |
| ATOM | 1030 | CA | HIS | 69 | -3.114 | 11.487 | 3.136 | 1.00 | 1.04 |
| ATOM | 1031 | HA | HIS | 69 | -2.877 | 12.437 | 2.679 | 1.00 | 1.25 |
| ATOM | 1032 | CB | HIS | 69 | -2.545 | 10.358 | 2.243 | 1.00 | 1.49 |
| ATOM | 1033 | HB1 | HIS | 69 | -1.750 | 9.862 | 2.783 | 1.00 | 2.12 |
| ATOM | 1034 | HB2 | HIS | 69 | -2.131 | 10.798 | 1.351 | 1.00 | 2.27 |
| ATOM | 1035 | CG | HIS | 69 | -3.570 | 9.333 | 1.837 | 1.00 | 0.95 |
| ATOM | 1036 | ND1 | HIS | 69 | -3.818 | 8.195 | 2.588 | 1.00 | 1.43 |
| ATOM | 1037 | HD1 | HIS | 69 | -3.415 | 7.972 | 3.453 | 1.00 | 1.83 |
| ATOM | 1038 | CD2 | HIS | 69 | -4.355 | 9.223 | 0.717 | 1.00 | 1.04 |
| ATOM | 1039 | HD2 | HIS | 69 | -4.403 | 9.946 | -0.082 | 1.00 | 1.41 |
| ATOM | 1040 | CE1 | HIS | 69 | -4.715 | 7.452 | 1.912 | 1.00 | 1.81 |

FIG. 4A-14

| | | | | | | | | |
|---|---|---|---|---|---|---|---|---|
| ATOM | 1041 | HE1 | HIS | 69 | -5.097 | 6.502 | 2.257 | 1.00 | 2.54 |
| ATOM | 1042 | NE2 | HIS | 69 | -5.075 | 8.032 | 0.765 | 1.00 | 1.53 |
| ATOM | 1043 | C | HIS | 69 | -4.643 | 11.435 | 3.341 | 1.00 | 1.14 |
| ATOM | 1044 | O | HIS | 69 | -5.392 | 10.889 | 2.556 | 1.00 | 1.76 |
| ATOM | 1045 | N | GLY | 70 | -5.108 | 12.065 | 4.393 | 1.00 | 1.49 |
| ATOM | 1046 | HN | GLY | 70 | -4.487 | 12.532 | 4.990 | 1.00 | 1.98 |
| ATOM | 1047 | CA | GLY | 70 | -6.576 | 12.123 | 4.665 | 1.00 | 1.86 |
| ATOM | 1048 | HA1 | GLY | 70 | -7.071 | 12.633 | 3.852 | 1.00 | 2.28 |
| ATOM | 1049 | HA2 | GLY | 70 | -6.746 | 12.667 | 5.583 | 1.00 | 2.09 |
| ATOM | 1050 | C | GLY | 70 | -7.155 | 10.716 | 4.801 | 1.00 | 1.81 |
| ATOM | 1051 | O | GLY | 70 | -8.182 | 10.404 | 4.232 | 1.00 | 2.53 |
| ATOM | 1052 | N | ASP | 71 | -6.513 | 9.863 | 5.545 | 1.00 | 1.55 |
| ATOM | 1053 | HN | ASP | 71 | -5.686 | 10.127 | 5.999 | 1.00 | 1.66 |
| ATOM | 1054 | CA | ASP | 71 | -7.047 | 8.484 | 5.701 | 1.00 | 1.91 |
| ATOM | 1055 | HA | ASP | 71 | -8.126 | 8.513 | 5.684 | 1.00 | 2.42 |
| ATOM | 1056 | CB | ASP | 71 | -6.546 | 7.620 | 4.546 | 1.00 | 2.67 |
| ATOM | 1057 | HB1 | ASP | 71 | -6.623 | 6.578 | 4.813 | 1.00 | 3.03 |
| ATOM | 1058 | HB2 | ASP | 71 | -5.514 | 7.865 | 4.341 | 1.00 | 2.88 |
| ATOM | 1059 | CG | ASP | 71 | -7.397 | 7.892 | 3.303 | 1.00 | 3.56 |
| ATOM | 1060 | OD1 | ASP | 71 | -8.476 | 7.330 | 3.215 | 1.00 | 4.08 |
| ATOM | 1061 | OD2 | ASP | 71 | -6.960 | 8.664 | 2.465 | 1.00 | 4.16 |
| ATOM | 1062 | C | ASP | 71 | -6.577 | 7.889 | 7.028 | 1.00 | 1.46 |
| ATOM | 1063 | O | ASP | 71 | -5.600 | 8.323 | 7.605 | 1.00 | 1.78 |
| ATOM | 1064 | N | PHE | 72 | -7.260 | 6.886 | 7.507 | 1.00 | 1.36 |
| ATOM | 1065 | HN | PHE | 72 | -8.038 | 6.546 | 7.018 | 1.00 | 1.67 |
| ATOM | 1066 | CA | PHE | 72 | -6.849 | 6.248 | 8.786 | 1.00 | 1.48 |
| ATOM | 1067 | HA | PHE | 72 | -6.504 | 7.007 | 9.473 | 1.00 | 1.75 |
| ATOM | 1068 | CB | PHE | 72 | -8.037 | 5.503 | 9.399 | 1.00 | 2.01 |
| ATOM | 1069 | HB1 | PHE | 72 | -8.374 | 6.028 | 10.281 | 1.00 | 2.58 |
| ATOM | 1070 | HB2 | PHE | 72 | -7.733 | 4.503 | 9.669 | 1.00 | 2.43 |
| ATOM | 1071 | CG | PHE | 72 | -9.161 | 5.434 | 8.395 | 1.00 | 2.30 |
| ATOM | 1072 | CD1 | PHE | 72 | -9.414 | 4.243 | 7.704 | 1.00 | 2.86 |
| ATOM | 1073 | HD1 | PHE | 72 | -8.802 | 3.372 | 7.887 | 1.00 | 3.09 |
| ATOM | 1074 | CD2 | PHE | 72 | -9.954 | 6.563 | 8.158 | 1.00 | 2.97 |
| ATOM | 1075 | HD2 | PHE | 72 | -9.758 | 7.482 | 8.691 | 1.00 | 3.28 |
| ATOM | 1076 | CE1 | PHE | 72 | -10.459 | 4.182 | 6.775 | 1.00 | 3.73 |
| ATOM | 1077 | HE1 | PHE | 72 | -10.655 | 3.264 | 6.242 | 1.00 | 4.46 |
| ATOM | 1078 | CE2 | PHE | 72 | -10.999 | 6.502 | 7.229 | 1.00 | 3.80 |
| ATOM | 1079 | HE2 | PHE | 72 | -11.610 | 7.374 | 7.045 | 1.00 | 4.54 |
| ATOM | 1080 | CZ | PHE | 72 | -11.252 | 5.312 | 6.537 | 1.00 | 4.08 |
| ATOM | 1081 | HZ | PHE | 72 | -12.058 | 5.264 | 5.821 | 1.00 | 4.92 |
| ATOM | 1082 | C | PHE | 72 | -5.716 | 5.266 | 8.500 | 1.00 | 1.41 |
| ATOM | 1083 | O | PHE | 72 | -5.384 | 4.430 | 9.318 | 1.00 | 2.20 |
| ATOM | 1084 | N | TYR | 73 | -5.120 | 5.371 | 7.338 | 1.00 | 1.12 |
| ATOM | 1085 | HN | TYR | 73 | -5.412 | 6.059 | 6.703 | 1.00 | 1.48 |
| ATOM | 1086 | CA | TYR | 73 | -3.999 | 4.457 | 6.972 | 1.00 | 1.25 |
| ATOM | 1087 | HA | TYR | 73 | -3.774 | 3.793 | 7.790 | 1.00 | 1.46 |
| ATOM | 1088 | CB | TYR | 73 | -4.391 | 3.635 | 5.742 | 1.00 | 1.86 |
| ATOM | 1089 | HB1 | TYR | 73 | -3.531 | 3.082 | 5.395 | 1.00 | 2.35 |
| ATOM | 1090 | HB2 | TYR | 73 | -4.726 | 4.300 | 4.961 | 1.00 | 2.46 |
| ATOM | 1091 | CG | TYR | 73 | -5.498 | 2.670 | 6.089 | 1.00 | 2.08 |
| ATOM | 1092 | CD1 | TYR | 73 | -5.241 | 1.585 | 6.934 | 1.00 | 2.58 |
| ATOM | 1093 | HD1 | TYR | 73 | -4.252 | 1.444 | 7.347 | 1.00 | 2.82 |
| ATOM | 1094 | CD2 | TYR | 73 | -6.779 | 2.853 | 5.553 | 1.00 | 2.85 |
| ATOM | 1095 | HD2 | TYR | 73 | -6.978 | 3.691 | 4.901 | 1.00 | 3.24 |
| ATOM | 1096 | CE1 | TYR | 73 | -6.264 | 0.683 | 7.244 | 1.00 | 3.48 |
| ATOM | 1097 | HE1 | TYR | 73 | -6.066 | -0.155 | 7.896 | 1.00 | 4.19 |
| ATOM | 1098 | CE2 | TYR | 73 | -7.802 | 1.952 | 5.865 | 1.00 | 3.68 |
| ATOM | 1099 | HE2 | TYR | 73 | -8.789 | 2.093 | 5.452 | 1.00 | 4.49 |
| ATOM | 1100 | CZ | TYR | 73 | -7.545 | 0.866 | 6.710 | 1.00 | 3.90 |
| ATOM | 1101 | OH | TYR | 73 | -8.554 | -0.024 | 7.013 | 1.00 | 5.00 |
| ATOM | 1102 | HH | TYR | 73 | -8.689 | -0.590 | 6.249 | 1.00 | 5.22 |
| ATOM | 1103 | C | TYR | 73 | -2.755 | 5.273 | 6.609 | 1.00 | 0.95 |
| ATOM | 1104 | O | TYR | 73 | -2.219 | 5.127 | 5.529 | 1.00 | 1.21 |
| ATOM | 1105 | N | PRO | 74 | -2.273 | 6.106 | 7.495 | 1.00 | 0.74 |
| ATOM | 1106 | CA | PRO | 74 | -1.054 | 6.895 | 7.197 | 1.00 | 0.82 |
| ATOM | 1107 | HA | PRO | 74 | -1.254 | 7.648 | 6.453 | 1.00 | 1.05 |
| ATOM | 1108 | CB | PRO | 74 | -0.746 | 7.558 | 8.543 | 1.00 | 1.18 |
| ATOM | 1109 | HB1 | PRO | 74 | -0.786 | 8.631 | 8.438 | 1.00 | 1.46 |
| ATOM | 1110 | HB2 | PRO | 74 | 0.239 | 7.261 | 8.876 | 1.00 | 1.28 |
| ATOM | 1111 | CG | PRO | 74 | -1.795 | 7.105 | 9.566 | 1.00 | 1.35 |
| ATOM | 1112 | HG1 | PRO | 74 | -2.229 | 7.967 | 10.049 | 1.00 | 1.70 |
| ATOM | 1113 | HG2 | PRO | 74 | -1.330 | 6.468 | 10.305 | 1.00 | 1.61 |
| ATOM | 1114 | CD | PRO | 74 | -2.889 | 6.328 | 8.828 | 1.00 | 1.04 |
| ATOM | 1115 | HD2 | PRO | 74 | -3.098 | 5.393 | 9.328 | 1.00 | 1.24 |
| ATOM | 1116 | HD1 | PRO | 74 | -3.778 | 6.929 | 8.733 | 1.00 | 1.14 |
| ATOM | 1117 | C | PRO | 74 | 0.097 | 5.988 | 6.765 | 1.00 | 0.65 |

FIG. 4A-15

| ATOM | 1118 | O | PRO | 74 | 0.136 | 4.822 | 7.106 | 1.00 | 0.66 |
|---|---|---|---|---|---|---|---|---|---|
| ATOM | 1119 | N | PHE | 75 | 1.038 | 6.503 | 6.032 | 1.00 | 0.56 |
| ATOM | 1120 | HN | PHE | 75 | 1.000 | 7.447 | 5.770 | 1.00 | 0.61 |
| ATOM | 1121 | CA | PHE | 75 | 2.179 | 5.651 | 5.605 | 1.00 | 0.45 |
| ATOM | 1122 | HA | PHE | 75 | 1.816 | 4.659 | 5.360 | 1.00 | 0.48 |
| ATOM | 1123 | CB | PHE | 75 | 2.859 | 6.266 | 4.379 | 1.00 | 0.42 |
| ATOM | 1124 | HB1 | PHE | 75 | 3.761 | 5.718 | 4.153 | 1.00 | 0.44 |
| ATOM | 1125 | HB2 | PHE | 75 | 3.104 | 7.298 | 4.582 | 1.00 | 0.45 |
| ATOM | 1126 | CG | PHE | 75 | 1.915 | 6.190 | 3.200 | 1.00 | 0.48 |
| ATOM | 1127 | CD1 | PHE | 75 | 1.764 | 4.986 | 2.501 | 1.00 | 0.41 |
| ATOM | 1128 | HD1 | PHE | 75 | 2.329 | 4.115 | 2.797 | 1.00 | 0.45 |
| ATOM | 1129 | CD2 | PHE | 75 | 1.184 | 7.320 | 2.812 | 1.00 | 0.74 |
| ATOM | 1130 | HD2 | PHE | 75 | 1.300 | 8.249 | 3.349 | 1.00 | 0.90 |
| ATOM | 1131 | CE1 | PHE | 75 | 0.882 | 4.911 | 1.415 | 1.00 | 0.50 |
| ATOM | 1132 | HE1 | PHE | 75 | 0.767 | 3.982 | 0.877 | 1.00 | 0.53 |
| ATOM | 1133 | CE2 | PHE | 75 | 0.304 | 7.245 | 1.724 | 1.00 | 0.85 |
| ATOM | 1134 | HE2 | PHE | 75 | -0.258 | 8.117 | 1.423 | 1.00 | 1.09 |
| ATOM | 1135 | CZ | PHE | 75 | 0.154 | 6.041 | 1.026 | 1.00 | 0.69 |
| ATOM | 1136 | HZ | PHE | 75 | -0.526 | 5.983 | 0.188 | 1.00 | 0.80 |
| ATOM | 1137 | C | PHE | 75 | 3.159 | 5.561 | 6.776 | 1.00 | 0.43 |
| ATOM | 1138 | O | PHE | 75 | 3.111 | 6.360 | 7.690 | 1.00 | 0.50 |
| ATOM | 1139 | N | ASP | 76 | 4.020 | 4.582 | 6.782 | 1.00 | 0.37 |
| ATOM | 1140 | HN | ASP | 76 | 4.028 | 3.929 | 6.050 | 1.00 | 0.32 |
| ATOM | 1141 | CA | ASP | 76 | 4.967 | 4.432 | 7.927 | 1.00 | 0.43 |
| ATOM | 1142 | HA | ASP | 76 | 4.551 | 4.906 | 8.804 | 1.00 | 0.50 |
| ATOM | 1143 | CB | ASP | 76 | 5.180 | 2.946 | 8.215 | 1.00 | 0.46 |
| ATOM | 1144 | HB1 | ASP | 76 | 4.224 | 2.467 | 8.365 | 1.00 | 0.49 |
| ATOM | 1145 | HB2 | ASP | 76 | 5.784 | 2.834 | 9.104 | 1.00 | 0.54 |
| ATOM | 1146 | CG | ASP | 76 | 5.892 | 2.295 | 7.028 | 1.00 | 0.38 |
| ATOM | 1147 | OD1 | ASP | 76 | 6.468 | 1.236 | 7.218 | 1.00 | 0.45 |
| ATOM | 1148 | OD2 | ASP | 76 | 5.846 | 2.864 | 5.950 | 1.00 | 0.30 |
| ATOM | 1149 | C | ASP | 76 | 6.314 | 5.074 | 7.596 | 1.00 | 0.42 |
| ATOM | 1150 | O | ASP | 76 | 7.314 | 4.770 | 8.216 | 1.00 | 0.54 |
| ATOM | 1151 | N | GLY | 77 | 6.347 | 5.958 | 6.632 | 1.00 | 0.35 |
| ATOM | 1152 | HN | GLY | 77 | 5.525 | 6.187 | 6.151 | 1.00 | 0.36 |
| ATOM | 1153 | CA | GLY | 77 | 7.634 | 6.625 | 6.267 | 1.00 | 0.38 |
| ATOM | 1154 | HA1 | GLY | 77 | 8.378 | 6.388 | 7.004 | 1.00 | 0.45 |
| ATOM | 1155 | HA2 | GLY | 77 | 7.484 | 7.696 | 6.238 | 1.00 | 0.44 |
| ATOM | 1156 | C | GLY | 77 | 8.084 | 6.131 | 4.884 | 1.00 | 0.31 |
| ATOM | 1157 | O | GLY | 77 | 7.262 | 5.767 | 4.068 | 1.00 | 0.37 |
| ATOM | 1158 | N | PRO | 78 | 9.370 | 6.117 | 4.603 | 1.00 | 0.33 |
| ATOM | 1159 | CA | PRO | 78 | 9.856 | 5.651 | 3.274 | 1.00 | 0.36 |
| ATOM | 1160 | HA | PRO | 78 | 9.435 | 6.254 | 2.488 | 1.00 | 0.42 |
| ATOM | 1161 | CB | PRO | 78 | 11.364 | 5.903 | 3.359 | 1.00 | 0.46 |
| ATOM | 1162 | HB1 | PRO | 78 | 11.671 | 6.542 | 2.545 | 1.00 | 0.56 |
| ATOM | 1163 | HB2 | PRO | 78 | 11.892 | 4.962 | 3.303 | 1.00 | 0.48 |
| ATOM | 1164 | CG | PRO | 78 | 11.675 | 6.592 | 4.694 | 1.00 | 0.64 |
| ATOM | 1165 | HG1 | PRO | 78 | 11.965 | 7.616 | 4.516 | 1.00 | 0.87 |
| ATOM | 1166 | HG2 | PRO | 78 | 12.478 | 6.068 | 5.194 | 1.00 | 0.83 |
| ATOM | 1167 | CD | PRO | 78 | 10.418 | 6.562 | 5.563 | 1.00 | 0.45 |
| ATOM | 1168 | HD2 | PRO | 78 | 10.535 | 5.848 | 6.369 | 1.00 | 0.48 |
| ATOM | 1169 | HD1 | PRO | 78 | 10.187 | 7.544 | 5.944 | 1.00 | 0.49 |
| ATOM | 1170 | C | PRO | 78 | 9.564 | 4.165 | 3.027 | 1.00 | 0.30 |
| ATOM | 1171 | O | PRO | 78 | 8.860 | 3.808 | 2.105 | 1.00 | 0.28 |
| ATOM | 1172 | N | SER | 79 | 10.102 | 3.297 | 3.840 | 1.00 | 0.31 |
| ATOM | 1173 | HN | SER | 79 | 10.670 | 3.604 | 4.577 | 1.00 | 0.35 |
| ATOM | 1174 | CA | SER | 79 | 9.855 | 1.837 | 3.647 | 1.00 | 0.30 |
| ATOM | 1175 | HA | SER | 79 | 9.916 | 1.599 | 2.595 | 1.00 | 0.30 |
| ATOM | 1176 | CB | SER | 79 | 10.911 | 1.037 | 4.410 | 1.00 | 0.37 |
| ATOM | 1177 | HB1 | SER | 79 | 11.888 | 1.465 | 4.225 | 1.00 | 0.42 |
| ATOM | 1178 | HB2 | SER | 79 | 10.901 | 0.013 | 4.076 | 1.00 | 0.39 |
| ATOM | 1179 | OG | SER | 79 | 10.617 | 1.080 | 5.800 | 1.00 | 0.38 |
| ATOM | 1180 | HG | SER | 79 | 11.173 | 1.752 | 6.201 | 1.00 | 0.98 |
| ATOM | 1181 | C | SER | 79 | 8.463 | 1.470 | 4.173 | 1.00 | 0.27 |
| ATOM | 1182 | O | SER | 79 | 7.888 | 2.183 | 4.971 | 1.00 | 0.25 |
| ATOM | 1183 | N | GLY | 80 | 7.927 | 0.356 | 3.734 | 1.00 | 0.31 |
| ATOM | 1184 | HN | GLY | 80 | 8.420 | -0.200 | 3.095 | 1.00 | 0.37 |
| ATOM | 1185 | CA | GLY | 80 | 6.576 | -0.081 | 4.207 | 1.00 | 0.30 |
| ATOM | 1186 | HA1 | GLY | 80 | 6.224 | 0.586 | 4.977 | 1.00 | 0.31 |
| ATOM | 1187 | HA2 | GLY | 80 | 6.646 | -1.083 | 4.607 | 1.00 | 0.36 |
| ATOM | 1188 | C | GLY | 80 | 5.584 | -0.070 | 3.042 | 1.00 | 0.25 |
| ATOM | 1189 | O | GLY | 80 | 5.850 | -0.601 | 1.981 | 1.00 | 0.25 |
| ATOM | 1190 | N | LEU | 81 | 4.440 | 0.531 | 3.232 | 1.00 | 0.23 |
| ATOM | 1191 | HN | LEU | 81 | 4.246 | 0.951 | 4.096 | 1.00 | 0.25 |
| ATOM | 1192 | CA | LEU | 81 | 3.428 | 0.577 | 2.138 | 1.00 | 0.21 |
| ATOM | 1193 | HA | LEU | 81 | 3.259 | -0.417 | 1.761 | 1.00 | 0.22 |
| ATOM | 1194 | CB | LEU | 81 | 2.123 | 1.164 | 2.692 | 1.00 | 0.24 |

FIG. 4A-16

| | | | | | | | | |
|---|---|---|---|---|---|---|---|---|
| ATOM | 1195 | HB1 | LEU | 81 | 1.587 | 1.658 | 1.896 | 1.00 0.25 |
| ATOM | 1196 | HB2 | LEU | 81 | 2.356 | 1.881 | 3.465 | 1.00 0.29 |
| ATOM | 1197 | CG | LEU | 81 | 1.240 | 0.058 | 3.283 | 1.00 0.28 |
| ATOM | 1198 | HG | LEU | 81 | 1.856 | -0.678 | 3.779 | 1.00 0.31 |
| ATOM | 1199 | CD1 | LEU | 81 | 0.265 | 0.680 | 4.285 | 1.00 0.33 |
| ATOM | 1200 | HD11 | LEU | 81 | 0.071 | 1.706 | 4.009 | 1.00 1.05 |
| ATOM | 1201 | HD12 | LEU | 81 | 0.696 | 0.649 | 5.274 | 1.00 1.10 |
| ATOM | 1202 | HD13 | LEU | 81 | -0.662 | 0.125 | 4.278 | 1.00 1.06 |
| ATOM | 1203 | CD2 | LEU | 81 | 0.426 | -0.606 | 2.168 | 1.00 0.31 |
| ATOM | 1204 | HD21 | LEU | 81 | 1.087 | -0.997 | 1.412 | 1.00 1.02 |
| ATOM | 1205 | HD22 | LEU | 81 | -0.233 | 0.126 | 1.724 | 1.00 1.09 |
| ATOM | 1206 | HD23 | LEU | 81 | -0.161 | -1.411 | 2.584 | 1.00 1.06 |
| ATOM | 1207 | C | LEU | 81 | 3.953 | 1.475 | 1.017 | 1.00 0.20 |
| ATOM | 1208 | O | LEU | 81 | 3.988 | 2.679 | 1.141 | 1.00 0.22 |
| ATOM | 1209 | N | LEU | 82 | 4.366 | 0.899 | -0.078 | 1.00 0.18 |
| ATOM | 1210 | HN | LEU | 82 | 4.334 | -0.077 | -0.162 | 1.00 0.18 |
| ATOM | 1211 | CA | LEU | 82 | 4.901 | 1.728 | -1.195 | 1.00 0.18 |
| ATOM | 1212 | HA | LEU | 82 | 5.519 | 2.520 | -0.799 | 1.00 0.19 |
| ATOM | 1213 | CB | LEU | 82 | 5.728 | 0.840 | -2.128 | 1.00 0.18 |
| ATOM | 1214 | HB1 | LEU | 82 | 6.235 | 1.457 | -2.854 | 1.00 0.20 |
| ATOM | 1215 | HB2 | LEU | 82 | 5.071 | 0.151 | -2.640 | 1.00 0.20 |
| ATOM | 1216 | CG | LEU | 82 | 6.763 | 0.050 | -1.323 | 1.00 0.18 |
| ATOM | 1217 | HG | LEU | 82 | 6.262 | -0.523 | -0.556 | 1.00 0.22 |
| ATOM | 1218 | CD1 | LEU | 82 | 7.513 | -0.898 | -2.259 | 1.00 0.17 |
| ATOM | 1219 | HD11 | LEU | 82 | 8.102 | -0.321 | -2.957 | 1.00 0.97 |
| ATOM | 1220 | HD12 | LEU | 82 | 6.802 | -1.503 | -2.802 | 1.00 0.95 |
| ATOM | 1221 | HD13 | LEU | 82 | 8.163 | -1.537 | -1.681 | 1.00 0.98 |
| ATOM | 1222 | CD2 | LEU | 82 | 7.764 | 1.010 | -0.675 | 1.00 0.23 |
| ATOM | 1223 | HD21 | LEU | 82 | 8.019 | 1.790 | -1.375 | 1.00 1.03 |
| ATOM | 1224 | HD22 | LEU | 82 | 8.657 | 0.466 | -0.403 | 1.00 1.07 |
| ATOM | 1225 | HD23 | LEU | 82 | 7.326 | 1.447 | 0.209 | 1.00 1.02 |
| ATOM | 1226 | C | LEU | 82 | 3.740 | 2.329 | -1.986 | 1.00 0.19 |
| ATOM | 1227 | O | LEU | 82 | 3.882 | 3.341 | -2.646 | 1.00 0.21 |
| ATOM | 1228 | N | ALA | 83 | 2.594 | 1.711 | -1.919 | 1.00 0.21 |
| ATOM | 1229 | HN | ALA | 83 | 2.512 | 0.899 | -1.376 | 1.00 0.24 |
| ATOM | 1230 | CA | ALA | 83 | 1.410 | 2.225 | -2.662 | 1.00 0.22 |
| ATOM | 1231 | HA | ALA | 83 | 1.217 | 3.251 | -2.381 | 1.00 0.22 |
| ATOM | 1232 | CB | ALA | 83 | 1.668 | 2.140 | -4.171 | 1.00 0.23 |
| ATOM | 1233 | HB1 | ALA | 83 | 2.522 | 2.746 | -4.429 | 1.00 0.98 |
| ATOM | 1234 | HB2 | ALA | 83 | 0.801 | 2.497 | -4.705 | 1.00 1.00 |
| ATOM | 1235 | HB3 | ALA | 83 | 1.860 | 1.113 | -4.445 | 1.00 1.05 |
| ATOM | 1236 | C | ALA | 83 | 0.204 | 1.350 | -2.317 | 1.00 0.27 |
| ATOM | 1237 | O | ALA | 83 | 0.342 | 0.301 | -1.720 | 1.00 0.36 |
| ATOM | 1238 | N | HIS | 84 | -0.976 | 1.762 | -2.686 | 1.00 0.24 |
| ATOM | 1239 | HN | HIS | 84 | -1.075 | 2.609 | -3.170 | 1.00 0.20 |
| ATOM | 1240 | CA | HIS | 84 | -2.173 | 0.933 | -2.370 | 1.00 0.30 |
| ATOM | 1241 | HA | HIS | 84 | -1.940 | -0.108 | -2.542 | 1.00 0.36 |
| ATOM | 1242 | CB | HIS | 84 | -2.562 | 1.127 | -0.903 | 1.00 0.40 |
| ATOM | 1243 | HB1 | HIS | 84 | -1.695 | 0.965 | -0.278 | 1.00 0.48 |
| ATOM | 1244 | HB2 | HIS | 84 | -3.332 | 0.419 | -0.638 | 1.00 0.45 |
| ATOM | 1245 | CG | HIS | 84 | -3.074 | 2.525 | -0.692 | 1.00 0.44 |
| ATOM | 1246 | ND1 | HIS | 84 | -4.384 | 2.781 | -0.321 | 1.00 1.32 |
| ATOM | 1247 | HD1 | HIS | 84 | -5.084 | 2.112 | -0.169 | 1.00 2.02 |
| ATOM | 1248 | CD2 | HIS | 84 | -2.465 | 3.752 | -0.788 | 1.00 0.74 |
| ATOM | 1249 | HD2 | HIS | 84 | -1.432 | 3.915 | -1.060 | 1.00 1.58 |
| ATOM | 1250 | CE1 | HIS | 84 | -4.521 | 4.114 | -0.208 | 1.00 1.21 |
| ATOM | 1251 | HE1 | HIS | 84 | -5.441 | 4.606 | 0.071 | 1.00 1.87 |
| ATOM | 1252 | NE2 | HIS | 84 | -3.381 | 4.754 | -0.482 | 1.00 0.53 |
| ATOM | 1253 | C | HIS | 84 | -3.337 | 1.343 | -3.274 | 1.00 0.25 |
| ATOM | 1254 | O | HIS | 84 | -3.347 | 2.417 | -3.843 | 1.00 0.23 |
| ATOM | 1255 | N | ALA | 85 | -4.313 | 0.489 | -3.417 | 1.00 0.27 |
| ATOM | 1256 | HN | ALA | 85 | -4.279 | -0.374 | -2.954 | 1.00 0.34 |
| ATOM | 1257 | CA | ALA | 85 | -5.474 | 0.817 | -4.291 | 1.00 0.24 |
| ATOM | 1258 | HA | ALA | 85 | -5.582 | 1.890 | -4.364 | 1.00 0.22 |
| ATOM | 1259 | CB | ALA | 85 | -5.236 | 0.231 | -5.685 | 1.00 0.25 |
| ATOM | 1260 | HB1 | ALA | 85 | -5.079 | -0.835 | -5.605 | 1.00 1.05 |
| ATOM | 1261 | HB2 | ALA | 85 | -4.364 | 0.690 | -6.126 | 1.00 1.05 |
| ATOM | 1262 | HB3 | ALA | 85 | -6.097 | 0.420 | -6.308 | 1.00 1.06 |
| ATOM | 1263 | C | ALA | 85 | -6.748 | 0.210 | -3.698 | 1.00 0.26 |
| ATOM | 1264 | O | ALA | 85 | -6.694 | -0.611 | -2.804 | 1.00 0.33 |
| ATOM | 1265 | N | PHE | 86 | -7.892 | 0.605 | -4.198 | 1.00 0.28 |
| ATOM | 1266 | HN | PHE | 86 | -7.905 | 1.264 | -4.922 | 1.00 0.31 |
| ATOM | 1267 | CA | PHE | 86 | -9.179 | 0.053 | -3.677 | 1.00 0.34 |
| ATOM | 1268 | HA | PHE | 86 | -9.000 | -0.443 | -2.737 | 1.00 0.39 |
| ATOM | 1269 | CB | PHE | 86 | -10.170 | 1.205 | -3.471 | 1.00 0.36 |
| ATOM | 1270 | HB1 | PHE | 86 | -11.177 | 0.821 | -3.459 | 1.00 0.42 |
| ATOM | 1271 | HB2 | PHE | 86 | -10.068 | 1.913 | -4.279 | 1.00 0.33 |

FIG. 4A-17

| ATOM | 1272 | CG | PHE | 86 | -9.877 | 1.896 | -2.159 | 1.00 | 0.39 |
|------|------|------|-----|----|--------|-------|--------|------|------|
| ATOM | 1273 | CD1 | PHE | 86 | -8.784 | 2.764 | -2.050 | 1.00 | 0.46 |
| ATOM | 1274 | HD1 | PHE | 86 | -8.146 | 2.939 | -2.903 | 1.00 | 0.67 |
| ATOM | 1275 | CD2 | PHE | 86 | -10.703 | 1.670 | -1.051 | 1.00 | 0.67 |
| ATOM | 1276 | HD2 | PHE | 86 | -11.546 | 1.001 | -1.133 | 1.00 | 0.91 |
| ATOM | 1277 | CE1 | PHE | 86 | -8.516 | 3.406 | -0.835 | 1.00 | 0.50 |
| ATOM | 1278 | HE1 | PHE | 86 | -7.673 | 4.075 | -0.751 | 1.00 | 0.69 |
| ATOM | 1279 | CE2 | PHE | 86 | -10.435 | 2.311 | 0.165 | 1.00 | 0.74 |
| ATOM | 1280 | HE2 | PHE | 86 | -11.071 | 2.136 | 1.020 | 1.00 | 1.02 |
| ATOM | 1281 | CZ | PHE | 86 | -9.342 | 3.179 | 0.273 | 1.00 | 0.54 |
| ATOM | 1282 | HZ | PHE | 86 | -9.135 | 3.674 | 1.211 | 1.00 | 0.62 |
| ATOM | 1283 | C | PHE | 86 | -9.746 | -0.940 | -4.710 | 1.00 | 0.36 |
| ATOM | 1284 | O | PHE | 86 | -9.480 | -0.812 | -5.889 | 1.00 | 0.34 |
| ATOM | 1285 | N | PRO | 87 | -10.516 | -1.926 | -4.293 | 1.00 | 0.43 |
| ATOM | 1286 | CA | PRO | 87 | -11.082 | -2.914 | -5.257 | 1.00 | 0.46 |
| ATOM | 1287 | HA | PRO | 87 | -10.296 | -3.524 | -5.665 | 1.00 | 0.53 |
| ATOM | 1288 | CB | PRO | 87 | -11.990 | -3.770 | -4.370 | 1.00 | 0.60 |
| ATOM | 1289 | HB1 | PRO | 87 | -11.644 | -4.792 | -4.377 | 1.00 | 0.69 |
| ATOM | 1290 | HB2 | PRO | 87 | -13.004 | -3.727 | -4.742 | 1.00 | 0.73 |
| ATOM | 1291 | CG | PRO | 87 | -11.943 | -3.225 | -2.937 | 1.00 | 0.58 |
| ATOM | 1292 | HG1 | PRO | 87 | -11.694 | -4.022 | -2.253 | 1.00 | 0.61 |
| ATOM | 1293 | HG2 | PRO | 87 | -12.905 | -2.808 | -2.676 | 1.00 | 0.66 |
| ATOM | 1294 | CD | PRO | 87 | -10.872 | -2.135 | -2.861 | 1.00 | 0.50 |
| ATOM | 1295 | HD2 | PRO | 87 | -11.277 | -1.235 | -2.421 | 1.00 | 0.50 |
| ATOM | 1296 | HD1 | PRO | 87 | -10.014 | -2.484 | -2.309 | 1.00 | 0.52 |
| ATOM | 1297 | C | PRO | 87 | -11.895 | -2.246 | -6.379 | 1.00 | 0.40 |
| ATOM | 1298 | O | PRO | 87 | -12.221 | -1.078 | -6.299 | 1.00 | 0.42 |
| ATOM | 1299 | N | PRO | 88 | -12.221 | -2.981 | -7.419 | 1.00 | 0.44 |
| ATOM | 1300 | CA | PRO | 88 | -13.007 | -2.416 | -8.554 | 1.00 | 0.48 |
| ATOM | 1301 | HA | PRO | 88 | -12.443 | -1.645 | -9.053 | 1.00 | 0.52 |
| ATOM | 1302 | CB | PRO | 88 | -13.163 | -3.622 | -9.488 | 1.00 | 0.61 |
| ATOM | 1303 | HB1 | PRO | 88 | -12.604 | -3.449 | -10.395 | 1.00 | 0.83 |
| ATOM | 1304 | HB2 | PRO | 88 | -14.204 | -3.772 | -9.728 | 1.00 | 0.74 |
| ATOM | 1305 | CG | PRO | 88 | -12.609 | -4.863 | -8.781 | 1.00 | 0.57 |
| ATOM | 1306 | HG1 | PRO | 88 | -11.945 | -5.395 | -9.446 | 1.00 | 0.71 |
| ATOM | 1307 | HG2 | PRO | 88 | -13.425 | -5.508 | -8.488 | 1.00 | 0.64 |
| ATOM | 1308 | CD | PRO | 88 | -11.835 | -4.413 | -7.540 | 1.00 | 0.56 |
| ATOM | 1309 | HD2 | PRO | 88 | -12.146 | -4.977 | -6.671 | 1.00 | 0.62 |
| ATOM | 1310 | HD1 | PRO | 88 | -10.773 | -4.503 | -7.702 | 1.00 | 0.65 |
| ATOM | 1311 | C | PRO | 88 | -14.372 | -1.873 | -8.109 | 1.00 | 0.47 |
| ATOM | 1312 | O | PRO | 88 | -15.380 | -2.551 | -8.172 | 1.00 | 0.88 |
| ATOM | 1313 | N | GLY | 89 | -14.400 | -0.647 | -7.661 | 1.00 | 0.63 |
| ATOM | 1314 | HN | GLY | 89 | -13.571 | -0.129 | -7.626 | 1.00 | 1.01 |
| ATOM | 1315 | CA | GLY | 89 | -15.681 | -0.026 | -7.209 | 1.00 | 0.65 |
| ATOM | 1316 | HA1 | GLY | 89 | -15.536 | 0.422 | -6.239 | 1.00 | 0.62 |
| ATOM | 1317 | HA2 | GLY | 89 | -16.455 | -0.778 | -7.148 | 1.00 | 0.78 |
| ATOM | 1318 | C | GLY | 89 | -16.092 | 1.057 | -8.210 | 1.00 | 0.74 |
| ATOM | 1319 | O | GLY | 89 | -15.541 | 1.151 | -9.289 | 1.00 | 0.84 |
| ATOM | 1320 | N | PRO | 90 | -17.044 | 1.878 | -7.852 | 1.00 | 0.95 |
| ATOM | 1321 | CA | PRO | 90 | -17.499 | 2.973 | -8.750 | 1.00 | 1.19 |
| ATOM | 1322 | HA | PRO | 90 | -17.819 | 2.565 | -9.697 | 1.00 | 1.37 |
| ATOM | 1323 | CB | PRO | 90 | -18.720 | 3.532 | -7.990 | 1.00 | 1.55 |
| ATOM | 1324 | HB1 | PRO | 90 | -19.602 | 3.432 | -8.605 | 1.00 | 1.85 |
| ATOM | 1325 | HB2 | PRO | 90 | -18.572 | 4.567 | -7.740 | 1.00 | 1.74 |
| ATOM | 1326 | CG | PRO | 90 | -18.913 | 2.724 | -6.702 | 1.00 | 1.46 |
| ATOM | 1327 | HG1 | PRO | 90 | -19.828 | 2.155 | -6.763 | 1.00 | 1.60 |
| ATOM | 1328 | HG2 | PRO | 90 | -18.959 | 3.396 | -5.857 | 1.00 | 1.57 |
| ATOM | 1329 | CD | PRO | 90 | -17.729 | 1.769 | -6.539 | 1.00 | 1.17 |
| ATOM | 1330 | HD2 | PRO | 90 | -17.083 | 2.099 | -5.736 | 1.00 | 1.17 |
| ATOM | 1331 | HD1 | PRO | 90 | -18.067 | 0.759 | -6.375 | 1.00 | 1.28 |
| ATOM | 1332 | C | PRO | 90 | -16.375 | 4.011 | -8.972 | 1.00 | 1.14 |
| ATOM | 1333 | O | PRO | 90 | -15.269 | 3.649 | -9.320 | 1.00 | 1.53 |
| ATOM | 1334 | N | ASN | 91 | -16.624 | 5.282 | -8.790 | 1.00 | 1.17 |
| ATOM | 1335 | HN | ASN | 91 | -17.514 | 5.578 | -8.517 | 1.00 | 1.40 |
| ATOM | 1336 | CA | ASN | 91 | -15.541 | 6.286 | -9.008 | 1.00 | 1.38 |
| ATOM | 1337 | HA | ASN | 91 | -15.147 | 6.169 | -10.005 | 1.00 | 1.58 |
| ATOM | 1338 | CB | ASN | 91 | -16.116 | 7.700 | -8.857 | 1.00 | 1.87 |
| ATOM | 1339 | HB1 | ASN | 91 | -15.336 | 8.372 | -8.532 | 1.00 | 2.33 |
| ATOM | 1340 | HB2 | ASN | 91 | -16.908 | 7.686 | -8.122 | 1.00 | 1.96 |
| ATOM | 1341 | CG | ASN | 91 | -16.678 | 8.184 | -10.197 | 1.00 | 2.69 |
| ATOM | 1342 | OD1 | ASN | 91 | -16.132 | 7.890 | -11.242 | 1.00 | 3.20 |
| ATOM | 1343 | ND2 | ASN | 91 | -17.748 | 8.931 | -10.212 | 1.00 | 3.47 |
| ATOM | 1344 | HD21 | ASN | 91 | -18.186 | 9.176 | -9.370 | 1.00 | 3.59 |
| ATOM | 1345 | HD22 | ASN | 91 | -18.112 | 9.249 | -11.064 | 1.00 | 4.20 |
| ATOM | 1346 | C | ASN | 91 | -14.404 | 6.098 | -7.992 | 1.00 | 1.15 |
| ATOM | 1347 | O | ASN | 91 | -13.242 | 6.135 | -8.344 | 1.00 | 1.26 |
| ATOM | 1348 | N | TYR | 92 | -14.719 | 5.924 | -6.735 | 1.00 | 1.01 |

FIG. 4A-18

| | | | | | | | | |
|---|---|---|---|---|---|---|---|---|
| ATOM | 1349 | HN | TYR | 92 | -15.660 | 5.916 | -6.462 | 1.00 | 1.08 |
| ATOM | 1350 | CA | TYR | 92 | -13.639 | 5.768 | -5.711 | 1.00 | 0.97 |
| ATOM | 1351 | HA | TYR | 92 | -12.994 | 6.632 | -5.739 | 1.00 | 1.14 |
| ATOM | 1352 | CB | TYR | 92 | -14.262 | 5.652 | -4.319 | 1.00 | 1.09 |
| ATOM | 1353 | HB1 | TYR | 92 | -13.543 | 5.214 | -3.643 | 1.00 | 1.62 |
| ATOM | 1354 | HB2 | TYR | 92 | -15.135 | 5.020 | -4.369 | 1.00 | 1.45 |
| ATOM | 1355 | CG | TYR | 92 | -14.656 | 7.018 | -3.810 | 1.00 | 1.52 |
| ATOM | 1356 | CD1 | TYR | 92 | -13.672 | 7.979 | -3.549 | 1.00 | 2.14 |
| ATOM | 1357 | HD1 | TYR | 92 | -12.631 | 7.747 | -3.719 | 1.00 | 2.46 |
| ATOM | 1358 | CD2 | TYR | 92 | -16.006 | 7.320 | -3.588 | 1.00 | 2.44 |
| ATOM | 1359 | HD2 | TYR | 92 | -16.766 | 6.580 | -3.789 | 1.00 | 2.86 |
| ATOM | 1360 | CE1 | TYR | 92 | -14.037 | 9.241 | -3.066 | 1.00 | 3.06 |
| ATOM | 1361 | HE1 | TYR | 92 | -13.278 | 9.982 | -2.865 | 1.00 | 3.78 |
| ATOM | 1362 | CE2 | TYR | 92 | -16.370 | 8.582 | -3.107 | 1.00 | 3.33 |
| ATOM | 1363 | HE2 | TYR | 92 | -17.411 | 8.815 | -2.936 | 1.00 | 4.19 |
| ATOM | 1364 | CZ | TYR | 92 | -15.386 | 9.542 | -2.846 | 1.00 | 3.50 |
| ATOM | 1365 | OH | TYR | 92 | -15.746 | 10.786 | -2.368 | 1.00 | 4.57 |
| ATOM | 1366 | HH | TYR | 92 | -15.602 | 10.791 | -1.419 | 1.00 | 4.91 |
| ATOM | 1367 | C | TYR | 92 | -12.808 | 4.508 | -5.966 | 1.00 | 0.78 |
| ATOM | 1368 | O | TYR | 92 | -11.605 | 4.506 | -5.798 | 1.00 | 0.81 |
| ATOM | 1369 | N | GLY | 93 | -13.436 | 3.430 | -6.337 | 1.00 | 0.64 |
| ATOM | 1370 | HN | GLY | 93 | -14.410 | 3.441 | -6.445 | 1.00 | 0.70 |
| ATOM | 1371 | CA | GLY | 93 | -12.674 | 2.170 | -6.560 | 1.00 | 0.51 |
| ATOM | 1372 | HA1 | GLY | 93 | -13.366 | 1.366 | -6.740 | 1.00 | 0.51 |
| ATOM | 1373 | HA2 | GLY | 93 | -12.090 | 1.947 | -5.678 | 1.00 | 0.51 |
| ATOM | 1374 | C | GLY | 93 | -11.739 | 2.310 | -7.761 | 1.00 | 0.49 |
| ATOM | 1375 | O | GLY | 93 | -11.832 | 3.242 | -8.534 | 1.00 | 0.61 |
| ATOM | 1376 | N | GLY | 94 | -10.844 | 1.373 | -7.923 | 1.00 | 0.45 |
| ATOM | 1377 | HN | GLY | 94 | -10.799 | 0.627 | -7.288 | 1.00 | 0.44 |
| ATOM | 1378 | CA | GLY | 94 | -9.902 | 1.420 | -9.075 | 1.00 | 0.55 |
| ATOM | 1379 | HA1 | GLY | 94 | -10.459 | 1.569 | -9.988 | 1.00 | 0.63 |
| ATOM | 1380 | HA2 | GLY | 94 | -9.363 | 0.485 | -9.133 | 1.00 | 0.58 |
| ATOM | 1381 | C | GLY | 94 | -8.905 | 2.569 | -8.901 | 1.00 | 0.60 |
| ATOM | 1382 | O | GLY | 94 | -8.109 | 2.838 | -9.772 | 1.00 | 1.14 |
| ATOM | 1383 | N | ASP | 95 | -8.933 | 3.252 | -7.790 | 1.00 | 0.24 |
| ATOM | 1384 | HN | ASP | 95 | -9.581 | 3.028 | -7.089 | 1.00 | 0.52 |
| ATOM | 1385 | CA | ASP | 95 | -7.976 | 4.382 | -7.597 | 1.00 | 0.24 |
| ATOM | 1386 | HA | ASP | 95 | -7.888 | 4.939 | -8.518 | 1.00 | 0.28 |
| ATOM | 1387 | CB | ASP | 95 | -8.493 | 5.303 | -6.491 | 1.00 | 0.26 |
| ATOM | 1388 | HB1 | ASP | 95 | -9.500 | 5.617 | -6.724 | 1.00 | 0.28 |
| ATOM | 1389 | HB2 | ASP | 95 | -7.853 | 6.170 | -6.415 | 1.00 | 0.30 |
| ATOM | 1390 | CG | ASP | 95 | -8.494 | 4.549 | -5.162 | 1.00 | 0.28 |
| ATOM | 1391 | OD1 | ASP | 95 | -8.543 | 5.200 | -4.132 | 1.00 | 1.08 |
| ATOM | 1392 | OD2 | ASP | 95 | -8.440 | 3.331 | -5.198 | 1.00 | 1.14 |
| ATOM | 1393 | C | ASP | 95 | -6.605 | 3.827 | -7.202 | 1.00 | 0.23 |
| ATOM | 1394 | O | ASP | 95 | -6.479 | 2.683 | -6.815 | 1.00 | 0.24 |
| ATOM | 1395 | N | ALA | 96 | -5.573 | 4.626 | -7.297 | 1.00 | 0.23 |
| ATOM | 1396 | HN | ALA | 96 | -5.692 | 5.546 | -7.614 | 1.00 | 0.23 |
| ATOM | 1397 | CA | ALA | 96 | -4.215 | 4.131 | -6.926 | 1.00 | 0.25 |
| ATOM | 1398 | HA | ALA | 96 | -4.307 | 3.360 | -6.175 | 1.00 | 0.25 |
| ATOM | 1399 | CB | ALA | 96 | -3.527 | 3.553 | -8.164 | 1.00 | 0.30 |
| ATOM | 1400 | HB1 | ALA | 96 | -2.528 | 3.236 | -7.905 | 1.00 | 1.08 |
| ATOM | 1401 | HB2 | ALA | 96 | -3.476 | 4.309 | -8.934 | 1.00 | 1.08 |
| ATOM | 1402 | HB3 | ALA | 96 | -4.090 | 2.706 | -8.528 | 1.00 | 1.03 |
| ATOM | 1403 | C | ALA | 96 | -3.375 | 5.284 | -6.372 | 1.00 | 0.25 |
| ATOM | 1404 | O | ALA | 96 | -3.222 | 6.313 | -7.005 | 1.00 | 0.29 |
| ATOM | 1405 | N | HXS | 97 | -2.831 | 5.113 | -5.192 | 1.00 | 0.25 |
| ATOM | 1406 | HN | HXS | 97 | -2.976 | 4.271 | -4.710 | 1.00 | 0.28 |
| ATOM | 1407 | CA | HXS | 97 | -1.996 | 6.187 | -4.574 | 1.00 | 0.27 |
| ATOM | 1408 | HA | HXS | 97 | -2.010 | 7.068 | -5.198 | 1.00 | 0.28 |
| ATOM | 1409 | CB | HXS | 97 | -2.564 | 6.537 | -3.197 | 1.00 | 0.33 |
| ATOM | 1410 | HB1 | HXS | 97 | -1.969 | 7.319 | -2.750 | 1.00 | 0.44 |
| ATOM | 1411 | HB2 | HXS | 97 | -2.540 | 5.661 | -2.566 | 1.00 | 0.39 |
| ATOM | 1412 | CG | HXS | 97 | -3.983 | 7.009 | -3.349 | 1.00 | 0.37 |
| ATOM | 1413 | ND1 | HXS | 97 | -4.697 | 7.052 | -2.163 | 1.00 | 0.80 |
| ATOM | 1414 | CD2 | HXS | 97 | -4.783 | 7.420 | -4.384 | 1.00 | 0.55 |
| ATOM | 1415 | HD2 | HXS | 97 | -4.517 | 7.497 | -5.428 | 1.00 | 0.94 |
| ATOM | 1416 | CE1 | HXS | 97 | -5.918 | 7.487 | -2.498 | 1.00 | 0.86 |
| ATOM | 1417 | HE1 | HXS | 97 | -6.724 | 7.632 | -1.795 | 1.00 | 1.24 |
| ATOM | 1418 | NE2 | HXS | 97 | -6.018 | 7.722 | -3.819 | 1.00 | 0.59 |
| ATOM | 1419 | HE2 | HXS | 97 | -6.812 | 8.044 | -4.294 | 1.00 | 0.72 |
| ATOM | 1420 | C | HXS | 97 | -0.552 | 5.700 | -4.420 | 1.00 | 0.26 |
| ATOM | 1421 | O | HXS | 97 | -0.299 | 4.525 | -4.237 | 1.00 | 0.39 |
| ATOM | 1422 | N | PHE | 98 | 0.391 | 6.604 | -4.496 | 1.00 | 0.18 |
| ATOM | 1423 | HN | PHE | 98 | 0.147 | 7.540 | -4.648 | 1.00 | 0.23 |
| ATOM | 1424 | CA | PHE | 98 | 1.832 | 6.230 | -4.360 | 1.00 | 0.17 |
| ATOM | 1425 | HA | PHE | 98 | 1.921 | 5.190 | -4.085 | 1.00 | 0.18 |

FIG. 4A-19

| ATOM | 1426 | CB | PHE | 98 | 2.543 | 6.472 | -5.691 | 1.00 | 0.18 |
| ATOM | 1427 | HB1 | PHE | 98 | 3.611 | 6.464 | -5.536 | 1.00 | 0.21 |
| ATOM | 1428 | HB2 | PHE | 98 | 2.243 | 7.431 | -6.085 | 1.00 | 0.20 |
| ATOM | 1429 | CG | PHE | 98 | 2.169 | 5.391 | -6.674 | 1.00 | 0.19 |
| ATOM | 1430 | CD1 | PHE | 98 | 3.114 | 4.428 | -7.048 | 1.00 | 0.22 |
| ATOM | 1431 | HD1 | PHE | 98 | 4.110 | 4.456 | -6.631 | 1.00 | 0.25 |
| ATOM | 1432 | CD2 | PHE | 98 | 0.880 | 5.355 | -7.214 | 1.00 | 0.22 |
| ATOM | 1433 | HD2 | PHE | 98 | 0.151 | 6.098 | -6.924 | 1.00 | 0.24 |
| ATOM | 1434 | CE1 | PHE | 98 | 2.768 | 3.429 | -7.963 | 1.00 | 0.25 |
| ATOM | 1435 | HE1 | PHE | 98 | 3.496 | 2.685 | -8.252 | 1.00 | 0.29 |
| ATOM | 1436 | CE2 | PHE | 98 | 0.533 | 4.355 | -8.127 | 1.00 | 0.26 |
| ATOM | 1437 | HE2 | PHE | 98 | -0.462 | 4.327 | -8.542 | 1.00 | 0.31 |
| ATOM | 1438 | CZ | PHE | 98 | 1.478 | 3.392 | -8.503 | 1.00 | 0.26 |
| ATOM | 1439 | HZ | PHE | 98 | 1.214 | 2.622 | -9.211 | 1.00 | 0.30 |
| ATOM | 1440 | C | PHE | 98 | 2.487 | 7.104 | -3.286 | 1.00 | 0.17 |
| ATOM | 1441 | O | PHE | 98 | 2.081 | 8.226 | -3.058 | 1.00 | 0.19 |
| ATOM | 1442 | N | ASP | 99 | 3.498 | 6.604 | -2.625 | 1.00 | 0.19 |
| ATOM | 1443 | HN | ASP | 99 | 3.813 | 5.693 | -2.820 | 1.00 | 0.22 |
| ATOM | 1444 | CA | ASP | 99 | 4.167 | 7.424 | -1.570 | 1.00 | 0.20 |
| ATOM | 1445 | HA | ASP | 99 | 3.421 | 7.956 | -0.998 | 1.00 | 0.20 |
| ATOM | 1446 | CB | ASP | 99 | 4.973 | 6.516 | -0.638 | 1.00 | 0.25 |
| ATOM | 1447 | HB1 | ASP | 99 | 5.567 | 7.122 | 0.029 | 1.00 | 0.28 |
| ATOM | 1448 | HB2 | ASP | 99 | 5.624 | 5.884 | -1.226 | 1.00 | 0.30 |
| ATOM | 1449 | CG | ASP | 99 | 4.023 | 5.646 | 0.180 | 1.00 | 0.41 |
| ATOM | 1450 | OD1 | ASP | 99 | 2.838 | 5.680 | -0.100 | 1.00 | 0.89 |
| ATOM | 1451 | OD2 | ASP | 99 | 4.497 | 4.968 | 1.079 | 1.00 | 0.27 |
| ATOM | 1452 | C | ASP | 99 | 5.123 | 8.426 | -2.224 | 1.00 | 0.21 |
| ATOM | 1453 | O | ASP | 99 | 6.020 | 8.054 | -2.954 | 1.00 | 0.25 |
| ATOM | 1454 | N | ASP | 100 | 4.946 | 9.694 | -1.962 | 1.00 | 0.23 |
| ATOM | 1455 | HN | ASP | 100 | 4.222 | 9.976 | -1.365 | 1.00 | 0.23 |
| ATOM | 1456 | CA | ASP | 100 | 5.857 | 10.710 | -2.565 | 1.00 | 0.29 |
| ATOM | 1457 | HA | ASP | 100 | 6.169 | 10.379 | -3.545 | 1.00 | 0.31 |
| ATOM | 1458 | CB | ASP | 100 | 5.127 | 12.049 | -2.684 | 1.00 | 0.34 |
| ATOM | 1459 | HB1 | ASP | 100 | 5.130 | 12.544 | -1.727 | 1.00 | 0.34 |
| ATOM | 1460 | HB2 | ASP | 100 | 4.109 | 11.879 | -2.999 | 1.00 | 0.34 |
| ATOM | 1461 | CG | ASP | 100 | 5.844 | 12.929 | -3.710 | 1.00 | 0.43 |
| ATOM | 1462 | OD1 | ASP | 100 | 5.240 | 13.887 | -4.164 | 1.00 | 1.21 |
| ATOM | 1463 | OD2 | ASP | 100 | 6.984 | 12.630 | -4.025 | 1.00 | 1.12 |
| ATOM | 1464 | C | ASP | 100 | 7.085 | 10.885 | -1.667 | 1.00 | 0.30 |
| ATOM | 1465 | O | ASP | 100 | 8.032 | 11.559 | -2.018 | 1.00 | 0.32 |
| ATOM | 1466 | N | ASP | 101 | 7.074 | 10.280 | -0.510 | 1.00 | 0.31 |
| ATOM | 1467 | HN | ASP | 101 | 6.298 | 9.741 | -0.249 | 1.00 | 0.32 |
| ATOM | 1468 | CA | ASP | 101 | 8.236 | 10.407 | 0.415 | 1.00 | 0.33 |
| ATOM | 1469 | HA | ASP | 101 | 8.647 | 11.403 | 0.345 | 1.00 | 0.36 |
| ATOM | 1470 | CB | ASP | 101 | 7.778 | 10.142 | 1.851 | 1.00 | 0.39 |
| ATOM | 1471 | HB1 | ASP | 101 | 8.641 | 10.060 | 2.495 | 1.00 | 0.41 |
| ATOM | 1472 | HB2 | ASP | 101 | 7.216 | 9.220 | 1.884 | 1.00 | 0.39 |
| ATOM | 1473 | CG | ASP | 101 | 6.896 | 11.296 | 2.330 | 1.00 | 0.45 |
| ATOM | 1474 | OD1 | ASP | 101 | 7.027 | 12.380 | 1.786 | 1.00 | 1.25 |
| ATOM | 1475 | OD2 | ASP | 101 | 6.104 | 11.076 | 3.231 | 1.00 | 1.09 |
| ATOM | 1476 | C | ASP | 101 | 9.304 | 9.385 | 0.028 | 1.00 | 0.30 |
| ATOM | 1477 | O | ASP | 101 | 10.411 | 9.405 | 0.529 | 1.00 | 0.29 |
| ATOM | 1478 | N | GLU | 102 | 8.971 | 8.484 | -0.849 | 1.00 | 0.30 |
| ATOM | 1479 | HN | GLU | 102 | 8.068 | 8.484 | -1.230 | 1.00 | 0.31 |
| ATOM | 1480 | CA | GLU | 102 | 9.950 | 7.444 | -1.266 | 1.00 | 0.29 |
| ATOM | 1481 | HA | GLU | 102 | 10.649 | 7.263 | -0.463 | 1.00 | 0.30 |
| ATOM | 1482 | CB | GLU | 102 | 9.195 | 6.155 | -1.585 | 1.00 | 0.35 |
| ATOM | 1483 | HB1 | GLU | 102 | 9.873 | 5.437 | -2.020 | 1.00 | 0.36 |
| ATOM | 1484 | HB2 | GLU | 102 | 8.397 | 6.368 | -2.282 | 1.00 | 0.40 |
| ATOM | 1485 | CG | GLU | 102 | 8.611 | 5.584 | -0.293 | 1.00 | 0.46 |
| ATOM | 1486 | HG1 | GLU | 102 | 8.020 | 6.342 | 0.200 | 1.00 | 1.18 |
| ATOM | 1487 | HG2 | GLU | 102 | 9.415 | 5.276 | 0.356 | 1.00 | 1.03 |
| ATOM | 1488 | CD | GLU | 102 | 7.724 | 4.381 | -0.616 | 1.00 | 0.83 |
| ATOM | 1489 | OE1 | GLU | 102 | 7.601 | 4.060 | -1.786 | 1.00 | 1.63 |
| ATOM | 1490 | OE2 | GLU | 102 | 7.184 | 3.801 | 0.314 | 1.00 | 0.87 |
| ATOM | 1491 | C | GLU | 102 | 10.707 | 7.917 | -2.508 | 1.00 | 0.25 |
| ATOM | 1492 | O | GLU | 102 | 10.359 | 8.910 | -3.115 | 1.00 | 0.25 |
| ATOM | 1493 | N | THR | 103 | 11.741 | 7.213 | -2.886 | 1.00 | 0.25 |
| ATOM | 1494 | HN | THR | 103 | 12.003 | 6.416 | -2.379 | 1.00 | 0.28 |
| ATOM | 1495 | CA | THR | 103 | 12.525 | 7.620 | -4.088 | 1.00 | 0.23 |
| ATOM | 1496 | HA | THR | 103 | 12.356 | 8.665 | -4.301 | 1.00 | 0.23 |
| ATOM | 1497 | CB | THR | 103 | 14.016 | 7.383 | -3.824 | 1.00· | 0.27 |
| ATOM | 1498 | HB | THR | 103 | 14.169 | 6.359 | -3.521 | 1.00 | 0.30 |
| ATOM | 1499 | OG1 | THR | 103 | 14.455 | 8.252 | -2.789 | 1.00 | 0.29 |
| ATOM | 1500 | HG1 | THR | 103 | 15.334 | 8.564 | -3.016 | 1.00 | 0.86 |
| ATOM | 1501 | CG2 | THR | 103 | 14.820 | 7.656 | -5.098 | 1.00 | 0.29 |
| ATOM | 1502 | HG21 | THR | 103 | 15.864 | 7.777 | -4.846 | 1.00 | 1.08 |

FIG. 4A-20

| ATOM | 1503 | HG22 | THR | 103 | 14.457 | 8.557 | -5.569 | 1.00 | 1.08 |
|---|---|---|---|---|---|---|---|---|---|
| ATOM | 1504 | HG23 | THR | 103 | 14.710 | 6.824 | -5.779 | 1.00 | 1.01 |
| ATOM | 1505 | C | THR | 103 | 12.083 | 6.777 | -5.281 | 1.00 | 0.22 |
| ATOM | 1506 | O | THR | 103 | 12.417 | 5.614 | -5.394 | 1.00 | 0.23 |
| ATOM | 1507 | N | TRP | 104 | 11.332 | 7.358 | -6.175 | 1.00 | 0.21 |
| ATOM | 1508 | HN | TRP | 104 | 11.076 | 8.297 | -6.063 | 1.00 | 0.23 |
| ATOM | 1509 | CA | TRP | 104 | 10.867 | 6.598 | -7.364 | 1.00 | 0.21 |
| ATOM | 1510 | HA | TRP | 104 | 10.750 | 5.556 | -7.104 | 1.00 | 0.20 |
| ATOM | 1511 | CB | TRP | 104 | 9.525 | 7.165 | -7.831 | 1.00 | 0.23 |
| ATOM | 1512 | HB1 | TRP | 104 | 9.188 | 6.623 | -8.702 | 1.00 | 0.24 |
| ATOM | 1513 | HB2 | TRP | 104 | 9.641 | 8.210 | -8.078 | 1.00 | 0.25 |
| ATOM | 1514 | CG | TRP | 104 | 8.520 | 7.018 | -6.731 | 1.00 | 0.24 |
| ATOM | 1515 | CD1 | TRP | 104 | 8.098 | 8.019 | -5.924 | 1.00 | 0.31 |
| ATOM | 1516 | HD1 | TRP | 104 | 8.427 | 9.045 | -5.972 | 1.00 | 0.36 |
| ATOM | 1517 | CD2 | TRP | 104 | 7.811 | 5.821 | -6.300 | 1.00 | 0.21 |
| ATOM | 1518 | NE1 | TRP | 104 | 7.176 | 7.512 | -5.026 | 1.00 | 0.31 |
| ATOM | 1519 | HE1 | TRP | 104 | 6.718 | 8.030 | -4.331 | 1.00 | 0.36 |
| ATOM | 1520 | CE2 | TRP | 104 | 6.963 | 6.162 | -5.220 | 1.00 | 0.24 |
| ATOM | 1521 | CE3 | TRP | 104 | 7.819 | 4.486 | -6.739 | 1.00 | 0.18 |
| ATOM | 1522 | HE3 | TRP | 104 | 8.458 | 4.198 | -7.559 | 1.00 | 0.19 |
| ATOM | 1523 | CZ2 | TRP | 104 | 6.153 | 5.213 | -4.596 | 1.00 | 0.23 |
| ATOM | 1524 | HZ2 | TRP | 104 | 5.515 | 5.499 | -3.774 | 1.00 | 0.27 |
| ATOM | 1525 | CZ3 | TRP | 104 | 7.005 | 3.527 | -6.114 | 1.00 | 0.20 |
| ATOM | 1526 | HZ3 | TRP | 104 | 7.019 | 2.504 | -6.460 | 1.00 | 0.23 |
| ATOM | 1527 | CH2 | TRP | 104 | 6.173 | 3.891 | -5.045 | 1.00 | 0.21 |
| ATOM | 1528 | HH2 | TRP | 104 | 5.548 | 3.150 | -4.568 | 1.00 | 0.23 |
| ATOM | 1529 | C | TRP | 104 | 11.911 | 6.732 | -8.474 | 1.00 | 0.21 |
| ATOM | 1530 | O | TRP | 104 | 12.276 | 7.824 | -8.864 | 1.00 | 0.24 |
| ATOM | 1531 | N | THR | 105 | 12.403 | 5.630 | -8.973 | 1.00 | 0.20 |
| ATOM | 1532 | HN | THR | 105 | 12.098 | 4.763 | -8.633 | 1.00 | 0.19 |
| ATOM | 1533 | CA | THR | 105 | 13.437 | 5.685 | -10.048 | 1.00 | 0.21 |
| ATOM | 1534 | HA | THR | 105 | 13.415 | 6.652 | -10.525 | 1.00 | 0.24 |
| ATOM | 1535 | CB | THR | 105 | 14.817 | 5.459 | -9.428 | 1.00 | 0.21 |
| ATOM | 1536 | HB | THR | 105 | 15.018 | 6.233 | -8.704 | 1.00 | 0.21 |
| ATOM | 1537 | OG1 | THR | 105 | 15.806 | 5.497 | -10.447 | 1.00 | 0.24 |
| ATOM | 1538 | HG1 | THR | 105 | 15.882 | 6.404 | -10.752 | 1.00 | 0.86 |
| ATOM | 1539 | CG2 | THR | 105 | 14.846 | 4.101 | -8.729 | 1.00 | 0.21 |
| ATOM | 1540 | HG21 | THR | 105 | 15.178 | 4.233 | -7.711 | 1.00 | 1.04 |
| ATOM | 1541 | HG22 | THR | 105 | 15.524 | 3.442 | -9.249 | 1.00 | 1.07 |
| ATOM | 1542 | HG23 | THR | 105 | 13.854 | 3.674 | -8.731 | 1.00 | 0.99 |
| ATOM | 1543 | C | THR | 105 | 13.166 | 4.597 | -11.087 | 1.00 | 0.23 |
| ATOM | 1544 | O | THR | 105 | 12.521 | 3.606 | -10.808 | 1.00 | 0.23 |
| ATOM | 1545 | N | SER | 106 | 13.668 | 4.769 | -12.282 | 1.00 | 0.26 |
| ATOM | 1546 | HN | SER | 106 | 14.194 | 5.572 | -12.480 | 1.00 | 0.29 |
| ATOM | 1547 | CA | SER | 106 | 13.454 | 3.739 | -13.337 | 1.00 | 0.29 |
| ATOM | 1548 | HA | SER | 106 | 12.570 | 3.163 | -13.111 | 1.00 | 0.30 |
| ATOM | 1549 | CB | SER | 106 | 13.290 | 4.423 | -14.695 | 1.00 | 0.35 |
| ATOM | 1550 | HB1 | SER | 106 | 14.249 | 4.467 | -15.193 | 1.00 | 1.09 |
| ATOM | 1551 | HB2 | SER | 106 | 12.916 | 5.424 | -14.554 | 1.00 | 0.96 |
| ATOM | 1552 | OG | SER | 106 | 12.365 | 3.685 | -15.483 | 1.00 | 1.44 |
| ATOM | 1553 | HG | SER | 106 | 11.671 | 4.285 | -15.766 | 1.00 | 1.97 |
| ATOM | 1554 | C | SER | 106 | 14.674 | 2.817 | -13.372 | 1.00 | 0.28 |
| ATOM | 1555 | O | SER | 106 | 14.669 | 1.781 | -14.006 | 1.00 | 0.31 |
| ATOM | 1556 | N | SER | 107 | 15.715 | 3.187 | -12.677 | 1.00 | 0.26 |
| ATOM | 1557 | HN | SER | 107 | 15.687 | 4.023 | -12.166 | 1.00 | 0.25 |
| ATOM | 1558 | CA | SER | 107 | 16.940 | 2.340 | -12.641 | 1.00 | 0.27 |
| ATOM | 1559 | HA | SER | 107 | 17.018 | 1.778 | -13.560 | 1.00 | 0.29 |
| ATOM | 1560 | CB | SER | 107 | 18.175 | 3.226 | -12.474 | 1.00 | 0.28 |
| ATOM | 1561 | HB1 | SER | 107 | 18.292 | 3.847 | -13.353 | 1.00 | 1.12 |
| ATOM | 1562 | HB2 | SER | 107 | 19.049 | 2.609 | -12.355 | 1.00 | 1.04 |
| ATOM | 1563 | OG | SER | 107 | 18.017 | 4.040 | -11.320 | 1.00 | 1.29 |
| ATOM | 1564 | HG | SER | 107 | 18.556 | 4.827 | -11.436 | 1.00 | 1.82 |
| ATOM | 1565 | C | SER | 107 | 16.836 | 1.376 | -11.460 | 1.00 | 0.26 |
| ATOM | 1566 | O | SER | 107 | 15.829 | 1.324 | -10.781 | 1.00 | 0.26 |
| ATOM | 1567 | N | SER | 108 | 17.859 | 0.609 | -11.203 | 1.00 | 0.28 |
| ATOM | 1568 | HN | SER | 108 | 18.666 | 0.658 | -11.757 | 1.00 | 0.31 |
| ATOM | 1569 | CA | SER | 108 | 17.788 | -0.342 | -10.061 | 1.00 | 0.30 |
| ATOM | 1570 | HA | SER | 108 | 16.775 | -0.706 | -9.967 | 1.00 | 0.30 |
| ATOM | 1571 | CB | SER | 108 | 18.728 | -1.527 | -10.330 | 1.00 | 0.36 |
| ATOM | 1572 | HB1 | SER | 108 | 19.561 | -1.505 | -9.642 | 1.00 | 1.09 |
| ATOM | 1573 | HB2 | SER | 108 | 19.103 | -1.468 | -11.338 | 1.00 | 0.95 |
| ATOM | 1574 | OG | SER | 108 | 18.005 | -2.741 | -10.176 | 1.00 | 1.47 |
| ATOM | 1575 | HG | SER | 108 | 18.550 | -3.456 | -10.513 | 1.00 | 2.00 |
| ATOM | 1576 | C | SER | 108 | 18.181 | 0.390 | -8.767 | 1.00 | 0.28 |
| ATOM | 1577 | O | SER | 108 | 19.279 | 0.265 | -8.261 | 1.00 | 0.33 |
| ATOM | 1578 | N | LYS | 109 | 17.272 | 1.157 | -8.224 | 1.00 | 0.24 |
| ATOM | 1579 | HN | LYS | 109 | 16.392 | 1.241 | -8.646 | 1.00 | 0.23 |

FIG. 4A-21

```
ATOM   1580  CA   LYS   109      17.561    1.897   -6.960  1.00  0.23
ATOM   1581  HA   LYS   109      18.275    1.341   -6.370  1.00  0.25
ATOM   1582  CB   LYS   109      18.123    3.293   -7.268  1.00  0.24
ATOM   1583  HB1  LYS   109      18.172    3.868   -6.355  1.00  0.27
ATOM   1584  HB2  LYS   109      17.472    3.793   -7.970  1.00  0.25
ATOM   1585  CG   LYS   109      19.525    3.177   -7.868  1.00  0.30
ATOM   1586  HG1  LYS   109      19.476    2.615   -8.785  1.00  0.54
ATOM   1587  HG2  LYS   109      20.177    2.675   -7.170  1.00  0.70
ATOM   1588  CD   LYS   109      20.072    4.574   -8.169  1.00  0.75
ATOM   1589  HD1  LYS   109      20.124    5.144   -7.254  1.00  1.27
ATOM   1590  HD2  LYS   109      19.420    5.074   -8.870  1.00  1.27
ATOM   1591  CE   LYS   109      21.475    4.453   -8.770  1.00  1.13
ATOM   1592  HE1  LYS   109      21.396    4.264   -9.830  1.00  1.68
ATOM   1593  HE2  LYS   109      22.000    3.636   -8.297  1.00  1.68
ATOM   1594  NZ   LYS   109      22.224    5.721   -8.545  1.00  1.79
ATOM   1595  HZ1  LYS   109      21.689    6.516   -8.948  1.00  2.22
ATOM   1596  HZ2  LYS   109      23.155    5.660   -9.006  1.00  2.17
ATOM   1597  HZ3  LYS   109      22.351    5.873   -7.525  1.00  2.34
ATOM   1598  C    LYS   109      16.259    2.052   -6.175  1.00  0.21
ATOM   1599  O    LYS   109      15.190    2.110   -6.747  1.00  0.20
ATOM   1600  N    GLY   110      16.338    2.124   -4.873  1.00  0.23
ATOM   1601  HN   GLY   110      17.212    2.079   -4.432  1.00  0.26
ATOM   1602  CA   GLY   110      15.099    2.283   -4.056  1.00  0.22
ATOM   1603  HA1  GLY   110      14.751    3.302   -4.124  1.00  0.23
ATOM   1604  HA2  GLY   110      15.316    2.044   -3.024  1.00  0.25
ATOM   1605  C    GLY   110      14.013    1.342   -4.581  1.00  0.19
ATOM   1606  O    GLY   110      14.281    0.216   -4.949  1.00  0.20
ATOM   1607  N    TYR   111      12.789    1.801   -4.626  1.00  0.17
ATOM   1608  HN   TYR   111      12.599    2.716   -4.330  1.00  0.18
ATOM   1609  CA   TYR   111      11.683    0.941   -5.136  1.00  0.15
ATOM   1610  HA   TYR   111      11.975   -0.098   -5.088  1.00  0.16
ATOM   1611  CB   TYR   111      10.437    1.162   -4.277  1.00  0.15
ATOM   1612  HB1  TYR   111       9.633    0.540   -4.641  1.00  0.15
ATOM   1613  HB2  TYR   111      10.143    2.200   -4.330  1.00  0.16
ATOM   1614  CG   TYR   111      10.745    0.798   -2.844  1.00  0.17
ATOM   1615  CD1  TYR   111      10.648   -0.533   -2.422  1.00  0.17
ATOM   1616  HD1  TYR   111      10.354   -1.301   -3.121  1.00  0.17
ATOM   1617  CD2  TYR   111      11.127    1.794   -1.936  1.00  0.20
ATOM   1618  HD2  TYR   111      11.201    2.821   -2.261  1.00  0.23
ATOM   1619  CE1  TYR   111      10.933   -0.868   -1.093  1.00  0.19
ATOM   1620  HE1  TYR   111      10.858   -1.895   -0.767  1.00  0.20
ATOM   1621  CE2  TYR   111      11.412    1.459   -0.607  1.00  0.22
ATOM   1622  HE2  TYR   111      11.706    2.227    0.093  1.00  0.26
ATOM   1623  CZ   TYR   111      11.315    0.127   -0.185  1.00  0.21
ATOM   1624  OH   TYR   111      11.595   -0.204    1.125  1.00  0.23
ATOM   1625  HH   TYR   111      12.543   -0.121    1.255  1.00  0.95
ATOM   1626  C    TYR   111      11.374    1.321   -6.588  1.00  0.14
ATOM   1627  O    TYR   111      10.949    2.424   -6.871  1.00  0.15
ATOM   1628  N    ASN   112      11.581    0.421   -7.511  1.00  0.15
ATOM   1629  HN   ASN   112      11.924   -0.464   -7.264  1.00  0.17
ATOM   1630  CA   ASN   112      11.295    0.739   -8.939  1.00  0.16
ATOM   1631  HA   ASN   112      11.870    1.605   -9.235  1.00  0.16
ATOM   1632  CB   ASN   112      11.677   -0.450   -9.822  1.00  0.19
ATOM   1633  HB1  ASN   112      11.025   -1.276   -9.607  1.00  0.22
ATOM   1634  HB2  ASN   112      12.698   -0.739   -9.622  1.00  0.19
ATOM   1635  CG   ASN   112      11.531   -0.060  -11.295  1.00  0.24
ATOM   1636  OD1  ASN   112      10.446    0.248  -11.748  1.00  0.96
ATOM   1637  ND2  ASN   112      12.583   -0.059  -12.067  1.00  1.06
ATOM   1638  HD21 ASN   112      13.458   -0.308  -11.704  1.00  1.80
ATOM   1639  HD22 ASN   112      12.497    0.189  -13.012  1.00  1.08
ATOM   1640  C    ASN   112       9.803    1.040   -9.108  1.00  0.15
ATOM   1641  O    ASN   112       8.953    0.310   -8.637  1.00  0.14
ATOM   1642  N    LEU   113       9.482    2.112   -9.777  1.00  0.15
ATOM   1643  HN   LEU   113      10.187    2.684  -10.145  1.00  0.16
ATOM   1644  CA   LEU   113       8.049    2.475   -9.984  1.00  0.15
ATOM   1645  HA   LEU   113       7.582    2.620   -9.025  1.00  0.14
ATOM   1646  CB   LEU   113       7.981    3.781  -10.791  1.00  0.16
ATOM   1647  HB1  LEU   113       8.513    3.646  -11.721  1.00  0.17
ATOM   1648  HB2  LEU   113       8.452    4.571  -10.226  1.00  0.16
ATOM   1649  CG   LEU   113       6.523    4.177  -11.095  1.00  0.17
ATOM   1650  HG   LEU   113       6.041    3.387  -11.652  1.00  0.18
ATOM   1651  CD1  LEU   113       5.748    4.421   -9.793  1.00  0.18
ATOM   1652  HD11 LEU   113       4.841    4.969  -10.007  1.00  0.99
ATOM   1653  HD12 LEU   113       6.359    4.991   -9.110  1.00  1.00
ATOM   1654  HD13 LEU   113       5.490    3.474   -9.343  1.00  0.97
ATOM   1655  CD2  LEU   113       6.526    5.457  -11.943  1.00  0.20
ATOM   1656  HD21 LEU   113       6.115    6.277  -11.374  1.00  1.05
```

FIG. 4A-22

| | | | | | | | | |
|---|---|---|---|---|---|---|---|---|
| ATOM | 1657 | HD22 | LEU | 113 | 5.930 | 5.302 | -12.830 | 1.00 | 1.03 |
| ATOM | 1658 | HD23 | LEU | 113 | 7.539 | 5.696 | -12.231 | 1.00 | 1.00 |
| ATOM | 1659 | C | LEU | 113 | 7.320 | 1.361 | -10.743 | 1.00 | 0.15 |
| ATOM | 1660 | O | LEU | 113 | 6.203 | 1.014 | -10.419 | 1.00 | 0.15 |
| ATOM | 1661 | N | PHE | 114 | 7.928 | 0.817 | -11.762 | 1.00 | 0.16 |
| ATOM | 1662 | HN | PHE | 114 | 8.822 | 1.123 | -12.020 | 1.00 | 0.17 |
| ATOM | 1663 | CA | PHE | 114 | 7.245 | -0.250 | -12.555 | 1.00 | 0.17 |
| ATOM | 1664 | HA | PHE | 114 | 6.338 | 0.151 | -12.980 | 1.00 | 0.18 |
| ATOM | 1665 | CB | PHE | 114 | 8.159 | -0.720 | -13.685 | 1.00 | 0.21 |
| ATOM | 1666 | HB1 | PHE | 114 | 9.077 | -1.108 | -13.271 | 1.00 | 0.22 |
| ATOM | 1667 | HB2 | PHE | 114 | 8.380 | 0.111 | -14.340 | 1.00 | 0.22 |
| ATOM | 1668 | CG | PHE | 114 | 7.457 | -1.807 | -14.464 | 1.00 | 0.24 |
| ATOM | 1669 | CD1 | PHE | 114 | 7.545 | -3.135 | -14.031 | 1.00 | 0.35 |
| ATOM | 1670 | HD1 | PHE | 114 | 8.105 | -3.376 | -13.147 | 1.00 | 0.43 |
| ATOM | 1671 | CD2 | PHE | 114 | 6.724 | -1.494 | -15.613 | 1.00 | 0.24 |
| ATOM | 1672 | HD2 | PHE | 114 | 6.655 | -0.470 | -15.950 | 1.00 | 0.28 |
| ATOM | 1673 | CE1 | PHE | 114 | 6.902 | -4.149 | -14.741 | 1.00 | 0.39 |
| ATOM | 1674 | HE1 | PHE | 114 | 6.975 | -5.171 | -14.402 | 1.00 | 0.50 |
| ATOM | 1675 | CE2 | PHE | 114 | 6.078 | -2.512 | -16.327 | 1.00 | 0.26 |
| ATOM | 1676 | HE2 | PHE | 114 | 5.511 | -2.273 | -17.214 | 1.00 | 0.30 |
| ATOM | 1677 | CZ | PHE | 114 | 6.168 | -3.839 | -15.890 | 1.00 | 0.32 |
| ATOM | 1678 | HZ | PHE | 114 | 5.670 | -4.623 | -16.438 | 1.00 | 0.35 |
| ATOM | 1679 | C | PHE | 114 | 6.900 | -1.452 | -11.676 | 1.00 | 0.17 |
| ATOM | 1680 | O | PHE | 114 | 5.842 | -2.034 | -11.806 | 1.00 | 0.17 |
| ATOM | 1681 | N | LEU | 115 | 7.774 | -1.846 | -10.797 | 1.00 | 0.18 |
| ATOM | 1682 | HN | LEU | 115 | 8.631 | -1.380 | -10.706 | 1.00 | 0.18 |
| ATOM | 1683 | CA | LEU | 115 | 7.463 | -3.028 | -9.946 | 1.00 | 0.20 |
| ATOM | 1684 | HA | LEU | 115 | 7.297 | -3.882 | -10.579 | 1.00 | 0.21 |
| ATOM | 1685 | CB | LEU | 115 | 8.634 | -3.304 | -8.984 | 1.00 | 0.23 |
| ATOM | 1686 | HB1 | LEU | 115 | 8.237 | -3.650 | -8.041 | 1.00 | 0.26 |
| ATOM | 1687 | HB2 | LEU | 115 | 9.172 | -2.387 | -8.821 | 1.00 | 0.22 |
| ATOM | 1688 | CG | LEU | 115 | 9.612 | -4.369 | -9.539 | 1.00 | 0.28 |
| ATOM | 1689 | HG | LEU | 115 | 10.397 | -4.525 | -8.812 | 1.00 | 0.33 |
| ATOM | 1690 | CD1 | LEU | 115 | 8.886 | -5.702 | -9.749 | 1.00 | 0.36 |
| ATOM | 1691 | HD11 | LEU | 115 | 9.551 | -6.514 | -9.498 | 1.00 | 0.99 |
| ATOM | 1692 | HD12 | LEU | 115 | 8.578 | -5.795 | -10.779 | 1.00 | 1.11 |
| ATOM | 1693 | HD13 | LEU | 115 | 8.017 | -5.740 | -9.109 | 1.00 | 1.13 |
| ATOM | 1694 | CD2 | LEU | 115 | 10.249 | -3.903 | -10.859 | 1.00 | 0.30 |
| ATOM | 1695 | HD21 | LEU | 115 | 10.497 | -4.761 | -11.466 | 1.00 | 1.10 |
| ATOM | 1696 | HD22 | LEU | 115 | 11.149 | -3.351 | -10.645 | 1.00 | 1.06 |
| ATOM | 1697 | HD23 | LEU | 115 | 9.567 | -3.272 | -11.395 | 1.00 | 1.01 |
| ATOM | 1698 | C | LEU | 115 | 6.194 | -2.748 | -9.136 | 1.00 | 0.19 |
| ATOM | 1699 | O | LEU | 115 | 5.280 | -3.548 | -9.106 | 1.00 | 0.20 |
| ATOM | 1700 | N | VAL | 116 | 6.130 | -1.624 | -8.475 | 1.00 | 0.18 |
| ATOM | 1701 | HN | VAL | 116 | 6.879 | -0.993 | -8.508 | 1.00 | 0.18 |
| ATOM | 1702 | CA | VAL | 116 | 4.919 | -1.305 | -7.664 | 1.00 | 0.19 |
| ATOM | 1703 | HA | VAL | 116 | 4.686 | -2.146 | -7.028 | 1.00 | 0.21 |
| ATOM | 1704 | CB | VAL | 116 | 5.203 | -0.078 | -6.794 | 1.00 | 0.20 |
| ATOM | 1705 | HB | VAL | 116 | 5.581 | 0.722 | -7.414 | 1.00 | 0.19 |
| ATOM | 1706 | CG1 | VAL | 116 | 3.914 | 0.381 | -6.103 | 1.00 | 0.22 |
| ATOM | 1707 | HG11 | VAL | 116 | 3.253 | 0.832 | -6.828 | 1.00 | 1.05 |
| ATOM | 1708 | HG12 | VAL | 116 | 4.155 | 1.105 | -5.339 | 1.00 | 1.05 |
| ATOM | 1709 | HG13 | VAL | 116 | 3.426 | -0.470 | -5.650 | 1.00 | 1.03 |
| ATOM | 1710 | CG2 | VAL | 116 | 6.246 | -0.443 | -5.737 | 1.00 | 0.21 |
| ATOM | 1711 | HG21 | VAL | 116 | 7.188 | -0.654 | -6.221 | 1.00 | 1.02 |
| ATOM | 1712 | HG22 | VAL | 116 | 5.917 | -1.317 | -5.194 | 1.00 | 0.98 |
| ATOM | 1713 | HG23 | VAL | 116 | 6.370 | 0.382 | -5.052 | 1.00 | 1.03 |
| ATOM | 1714 | C | VAL | 116 | 3.724 | -1.020 | -8.582 | 1.00 | 0.18 |
| ATOM | 1715 | O | VAL | 116 | 2.615 | -1.433 | -8.312 | 1.00 | 0.19 |
| ATOM | 1716 | N | ALA | 117 | 3.934 | -0.307 | -9.659 | 1.00 | 0.17 |
| ATOM | 1717 | HN | ALA | 117 | 4.833 | 0.028 | -9.859 | 1.00 | 0.16 |
| ATOM | 1718 | CA | ALA | 117 | 2.796 | 0.007 | -10.572 | 1.00 | 0.17 |
| ATOM | 1719 | HA | ALA | 117 | 2.064 | 0.598 | -10.044 | 1.00 | 0.19 |
| ATOM | 1720 | CB | ALA | 117 | 3.306 | 0.795 | -11.780 | 1.00 | 0.18 |
| ATOM | 1721 | HB1 | ALA | 117 | 4.378 | 0.709 | -11.840 | 1.00 | 1.05 |
| ATOM | 1722 | HB2 | ALA | 117 | 3.033 | 1.834 | -11.674 | 1.00 | 1.01 |
| ATOM | 1723 | HB3 | ALA | 117 | 2.863 | 0.397 | -12.682 | 1.00 | 0.98 |
| ATOM | 1724 | C | ALA | 117 | 2.150 | -1.291 | -11.058 | 1.00 | 0.17 |
| ATOM | 1725 | O | ALA | 117 | 0.956 | -1.480 | -10.951 | 1.00 | 0.19 |
| ATOM | 1726 | N | ALA | 118 | 2.931 | -2.187 | -11.588 | 1.00 | 0.16 |
| ATOM | 1727 | HN | ALA | 118 | 3.893 | -2.015 | -11.663 | 1.00 | 0.16 |
| ATOM | 1728 | CA | ALA | 118 | 2.366 | -3.472 | -12.083 | 1.00 | 0.17 |
| ATOM | 1729 | HA | ALA | 118 | 1.643 | -3.273 | -12.859 | 1.00 | 0.19 |
| ATOM | 1730 | CB | ALA | 118 | 3.491 | -4.335 | -12.653 | 1.00 | 0.17 |
| ATOM | 1731 | HB1 | ALA | 118 | 3.125 | -5.338 | -12.812 | 1.00 | 1.05 |
| ATOM | 1732 | HB2 | ALA | 118 | 4.316 | -4.358 | -11.956 | 1.00 | 1.02 |
| ATOM | 1733 | HB3 | ALA | 118 | 3.824 | -3.920 | -13.593 | 1.00 | 1.03 |

FIG. 4A-23

```
ATOM   1734  C    ALA   118    1.687   -4.220  -10.935  1.00  0.17
ATOM   1735  O    ALA   118    0.699   -4.901  -11.124  1.00  0.18
ATOM   1736  N    HIS   119    2.225   -4.123   -9.751  1.00  0.16
ATOM   1737  HN   HIS   119    3.035   -3.585   -9.623  1.00  0.16
ATOM   1738  CA   HIS   119    1.627   -4.855   -8.599  1.00  0.17
ATOM   1739  HA   HIS   119    1.576   -5.907   -8.833  1.00  0.18
ATOM   1740  CB   HIS   119    2.513   -4.655   -7.368  1.00  0.19
ATOM   1741  HB1  HIS   119    2.547   -3.605   -7.116  1.00  0.19
ATOM   1742  HB2  HIS   119    3.512   -5.005   -7.584  1.00  0.20
ATOM   1743  CG   HIS   119    1.950   -5.431   -6.210  1.00  0.21
ATOM   1744  ND1  HIS   119    2.228   -6.775   -6.020  1.00  0.26
ATOM   1745  HD1  HIS   119    2.791   -7.336   -6.593  1.00  0.30
ATOM   1746  CD2  HIS   119    1.128   -5.067   -5.172  1.00  0.20
ATOM   1747  HD2  HIS   119    0.719   -4.079   -5.019  1.00  0.21
ATOM   1748  CE1  HIS   119    1.585   -7.168   -4.906  1.00  0.27
ATOM   1749  HE1  HIS   119    1.622   -8.171   -4.509  1.00  0.33
ATOM   1750  NE2  HIS   119    0.899   -6.166   -4.350  1.00  0.23
ATOM   1751  C    HIS   119    0.215   -4.333   -8.299  1.00  0.17
ATOM   1752  O    HIS   119   -0.721   -5.101   -8.185  1.00  0.18
ATOM   1753  N    GLU   120    0.043   -3.044   -8.160  1.00  0.18
ATOM   1754  HN   GLU   120    0.801   -2.430   -8.248  1.00  0.18
ATOM   1755  CA   GLU   120   -1.322   -2.520   -7.860  1.00  0.20
ATOM   1756  HA   GLU   120   -1.666   -2.977   -6.943  1.00  0.21
ATOM   1757  CB   GLU   120   -1.294   -0.999   -7.668  1.00  0.22
ATOM   1758  HB1  GLU   120   -0.719   -0.763   -6.785  1.00  0.37
ATOM   1759  HB2  GLU   120   -2.302   -0.635   -7.542  1.00  0.33
ATOM   1760  CG   GLU   120   -0.663   -0.314   -8.875  1.00  0.41
ATOM   1761  HG1  GLU   120   -1.125   -0.668   -9.781  1.00  0.63
ATOM   1762  HG2  GLU   120    0.393   -0.531   -8.895  1.00  0.87
ATOM   1763  CD   GLU   120   -0.875    1.194   -8.757  1.00  0.94
ATOM   1764  OE1  GLU   120   -0.757    1.703   -7.654  1.00  1.67
ATOM   1765  OE2  GLU   120   -1.151    1.816   -9.769  1.00  1.56
ATOM   1766  C    GLU   120   -2.291   -2.903   -8.984  1.00  0.20
ATOM   1767  O    GLU   120   -3.432   -3.238   -8.737  1.00  0.21
ATOM   1768  N    PHE   121   -1.853   -2.872  -10.217  1.00  0.19
ATOM   1769  HN   PHE   121   -0.928   -2.608  -10.405  1.00  0.19
ATOM   1770  CA   PHE   121   -2.767   -3.251  -11.331  1.00  0.21
ATOM   1771  HA   PHE   121   -3.628   -2.600  -11.317  1.00  0.23
ATOM   1772  CB   PHE   121   -2.053   -3.130  -12.685  1.00  0.22
ATOM   1773  HB1  PHE   121   -2.576   -3.726  -13.419  1.00  0.24
ATOM   1774  HB2  PHE   121   -1.041   -3.493  -12.587  1.00  0.21
ATOM   1775  CG   PHE   121   -2.026   -1.684  -13.141  1.00  0.25
ATOM   1776  CD1  PHE   121   -0.804   -1.019  -13.308  1.00  0.27
ATOM   1777  HD1  PHE   121    0.121   -1.535  -13.113  1.00  0.40
ATOM   1778  CD2  PHE   121   -3.227   -1.007  -13.403  1.00  0.45
ATOM   1779  HD2  PHE   121   -4.173   -1.513  -13.281  1.00  0.60
ATOM   1780  CE1  PHE   121   -0.781    0.314  -13.733  1.00  0.29
ATOM   1781  HE1  PHE   121    0.163    0.824  -13.862  1.00  0.39
ATOM   1782  CE2  PHE   121   -3.202    0.327  -13.828  1.00  0.49
ATOM   1783  HE2  PHE   121   -4.127    0.847  -14.029  1.00  0.68
ATOM   1784  CZ   PHE   121   -1.979    0.988  -13.993  1.00  0.34
ATOM   1785  HZ   PHE   121   -1.961    2.017  -14.321  1.00  0.38
ATOM   1786  C    PHE   121   -3.228   -4.693  -11.120  1.00  0.20
ATOM   1787  O    PHE   121   -4.374   -5.027  -11.344  1.00  0.21
ATOM   1788  N    GLY   122   -2.344   -5.551  -10.690  1.00  0.18
ATOM   1789  HN   GLY   122   -1.424   -5.262  -10.514  1.00  0.17
ATOM   1790  CA   GLY   122   -2.737   -6.970  -10.464  1.00  0.20
ATOM   1791  HA1  GLY   122   -1.890   -7.523  -10.092  1.00  0.21
ATOM   1792  HA2  GLY   122   -3.072   -7.404  -11.394  1.00  0.21
ATOM   1793  C    GLY   122   -3.867   -7.022   -9.435  1.00  0.20
ATOM   1794  O    GLY   122   -4.823   -7.756   -9.589  1.00  0.22
ATOM   1795  N    HIS   123   -3.778   -6.240   -8.392  1.00  0.20
ATOM   1796  HN   HIS   123   -3.005   -5.644   -8.287  1.00  0.20
ATOM   1797  CA   HIS   123   -4.864   -6.243   -7.371  1.00  0.22
ATOM   1798  HA   HIS   123   -5.047   -7.255   -7.042  1.00  0.23
ATOM   1799  CB   HIS   123   -4.456   -5.382   -6.174  1.00  0.25
ATOM   1800  HB1  HIS   123   -5.324   -5.180   -5.564  1.00  0.30
ATOM   1801  HB2  HIS   123   -4.041   -4.449   -6.527  1.00  0.25
ATOM   1802  CG   HIS   123   -3.427   -6.108   -5.354  1.00  0.27
ATOM   1803  ND1  HIS   123   -3.736   -7.247   -4.628  1.00  0.37
ATOM   1804  HD1  HIS   123   -4.611   -7.685   -4.581  1.00  0.45
ATOM   1805  CD2  HIS   123   -2.096   -5.866   -5.125  1.00  0.25
ATOM   1806  HD2  HIS   123   -1.532   -5.046   -5.545  1.00  0.27
ATOM   1807  CE1  HIS   123   -2.614   -7.644   -4.001  1.00  0.38
ATOM   1808  HE1  HIS   123   -2.553   -8.514   -3.367  1.00  0.47
ATOM   1809  NE2  HIS   123   -1.584   -6.837   -4.269  1.00  0.29
ATOM   1810  C    HIS   123   -6.137   -5.671   -7.993  1.00  0.23
```

FIG. 4A-24

```
ATOM   1811   O    HIS  123    -7.229   -6.148   -7.755  1.00  0.25
ATOM   1812   N    SER  124    -6.002   -4.646   -8.788  1.00  0.23
ATOM   1813   HN   SER  124    -5.110   -4.278   -8.962  1.00  0.22
ATOM   1814   CA   SER  124    -7.196   -4.030   -9.429  1.00  0.25
ATOM   1815   HA   SER  124    -7.928   -3.790   -8.672  1.00  0.27
ATOM   1816   CB   SER  124    -6.778   -2.751  -10.156  1.00  0.27
ATOM   1817   HB1  SER  124    -6.219   -2.119   -9.478  1.00  0.29
ATOM   1818   HB2  SER  124    -7.654   -2.224  -10.494  1.00  0.29
ATOM   1819   OG   SER  124    -5.975   -3.091  -11.279  1.00  0.25
ATOM   1820   HG   SER  124    -6.545   -3.131  -12.050  1.00  0.88
ATOM   1821   C    SER  124    -7.805   -5.006  -10.437  1.00  0.24
ATOM   1822   O    SER  124    -8.975   -4.932  -10.755  1.00  0.26
ATOM   1823   N    LEU  125    -7.022   -5.913  -10.952  1.00  0.22
ATOM   1824   HN   LEU  125    -6.078   -5.953  -10.690  1.00  0.21
ATOM   1825   CA   LEU  125    -7.562   -6.879  -11.949  1.00  0.23
ATOM   1826   HA   LEU  125    -8.285   -6.374  -12.568  1.00  0.24
ATOM   1827   CB   LEU  125    -6.420   -7.398  -12.827  1.00  0.22
ATOM   1828   HB1  LEU  125    -6.759   -8.247  -13.398  1.00  0.24
ATOM   1829   HB2  LEU  125    -5.594   -7.698  -12.197  1.00  0.22
ATOM   1830   CG   LEU  125    -5.956   -6.280  -13.779  1.00  0.22
ATOM   1831   HG   LEU  125    -5.928   -5.343  -13.241  1.00  0.24
ATOM   1832   CD1  LEU  125    -4.556   -6.601  -14.302  1.00  0.25
ATOM   1833   HD11 LEU  125    -4.588   -7.515  -14.874  1.00  0.99
ATOM   1834   HD12 LEU  125    -3.879   -6.719  -13.471  1.00  1.00
ATOM   1835   HD13 LEU  125    -4.215   -5.794  -14.933  1.00  1.05
ATOM   1836   CD2  LEU  125    -6.913   -6.155  -14.976  1.00  0.24
ATOM   1837   HD21 LEU  125    -7.793   -5.604  -14.682  1.00  1.05
ATOM   1838   HD22 LEU  125    -7.201   -7.135  -15.324  1.00  1.00
ATOM   1839   HD23 LEU  125    -6.415   -5.627  -15.775  1.00  1.03
ATOM   1840   C    LEU  125    -8.256   -8.044  -11.234  1.00  0.24
ATOM   1841   O    LEU  125    -8.790   -8.935  -11.864  1.00  0.33
ATOM   1842   N    GLY  126    -8.277   -8.035   -9.927  1.00  0.24
ATOM   1843   HN   GLY  126    -7.858   -7.298   -9.435  1.00  0.29
ATOM   1844   CA   GLY  126    -8.968   -9.132   -9.185  1.00  0.27
ATOM   1845   HA1  GLY  126    -9.748   -9.545   -9.807  1.00  0.29
ATOM   1846   HA2  GLY  126    -9.408   -8.727   -8.285  1.00  0.29
ATOM   1847   C    GLY  126    -7.985  -10.245   -8.809  1.00  0.26
ATOM   1848   O    GLY  126    -8.377  -11.268   -8.283  1.00  0.30
ATOM   1849   N    LEU  127    -6.719  -10.068   -9.063  1.00  0.23
ATOM   1850   HN   LEU  127    -6.410   -9.239   -9.484  1.00  0.22
ATOM   1851   CA   LEU  127    -5.744  -11.138   -8.700  1.00  0.25
ATOM   1852   HA   LEU  127    -6.212  -12.099   -8.815  1.00  0.28
ATOM   1853   CB   LEU  127    -4.507  -11.052   -9.602  1.00  0.23
ATOM   1854   HB1  LEU  127    -3.733  -11.696   -9.211  1.00  0.25
ATOM   1855   HB2  LEU  127    -4.156  -10.033   -9.602  1.00  0.22
ATOM   1856   CG   LEU  127    -4.844  -11.471  -11.045  1.00  0.24
ATOM   1857   HG   LEU  127    -5.707  -10.915  -11.384  1.00  0.23
ATOM   1858   CD1  LEU  127    -3.646  -11.159  -11.962  1.00  0.24
ATOM   1859   HD11 LEU  127    -4.001  -10.692  -12.868  1.00  1.00
ATOM   1860   HD12 LEU  127    -3.126  -12.073  -12.208  1.00  1.02
ATOM   1861   HD13 LEU  127    -2.962  -10.491  -11.460  1.00  1.03
ATOM   1862   CD2  LEU  127    -5.150  -12.980  -11.109  1.00  0.30
ATOM   1863   HD21 LEU  127    -5.021  -13.334  -12.121  1.00  1.04
ATOM   1864   HD22 LEU  127    -6.169  -13.159  -10.805  1.00  1.11
ATOM   1865   HD23 LEU  127    -4.478  -13.515  -10.454  1.00  1.03
ATOM   1866   C    LEU  127    -5.315  -10.969   -7.241  1.00  0.28
ATOM   1867   O    LEU  127    -5.245   -9.872   -6.723  1.00  0.32
ATOM   1868   N    ASP  128    -5.027  -12.059   -6.581  1.00  0.32
ATOM   1869   HN   ASP  128    -5.093  -12.928   -7.029  1.00  0.34
ATOM   1870   CA   ASP  128    -4.598  -11.997   -5.154  1.00  0.39
ATOM   1871   HA   ASP  128    -4.882  -11.046   -4.728  1.00  0.40
ATOM   1872   CB   ASP  128    -5.271  -13.130   -4.375  1.00  0.48
ATOM   1873   HB1  ASP  128    -4.779  -14.064   -4.600  1.00  0.48
ATOM   1874   HB2  ASP  128    -6.311  -13.193   -4.661  1.00  0.50
ATOM   1875   CG   ASP  128    -5.171  -12.854   -2.873  1.00  0.55
ATOM   1876   OD1  ASP  128    -4.082  -12.980   -2.339  1.00  1.23
ATOM   1877   OD2  ASP  128    -6.185  -12.521   -2.283  1.00  1.22
ATOM   1878   C    ASP  128    -3.078  -12.159   -5.082  1.00  0.37
ATOM   1879   O    ASP  128    -2.424  -12.387   -6.080  1.00  0.59
ATOM   1880   N    HIS  129    -2.507  -12.042   -3.914  1.00  0.23
ATOM   1881   HN   HIS  129    -3.048  -11.856   -3.118  1.00  0.32
ATOM   1882   CA   HIS  129    -1.029  -12.189   -3.797  1.00  0.22
ATOM   1883   HA   HIS  129    -0.543  -11.439   -4.401  1.00  0.21
ATOM   1884   CB   HIS  129    -0.606  -12.019   -2.335  1.00  0.23
ATOM   1885   HB1  HIS  129     0.430  -12.302   -2.227  1.00  0.24
ATOM   1886   HB2  HIS  129    -1.217  -12.653   -1.710  1.00  0.25
ATOM   1887   CG   HIS  129    -0.779  -10.585   -1.912  1.00  0.22
```

FIG. 4A-25

```
ATOM   1888  ND1 HIS   129     -1.862 -10.161  -1.156  1.00  0.35
ATOM   1889  HD1 HIS   129     -2.602 -10.720  -0.841  1.00  0.53
ATOM   1890  CD2 HIS   129     -0.007  -9.468  -2.118  1.00  0.34
ATOM   1891  HD2 HIS   129      0.918  -9.447  -2.673  1.00  0.54
ATOM   1892  CE1 HIS   129     -1.711  -8.842  -0.936  1.00  0.31
ATOM   1893  HE1 HIS   129     -2.406  -8.239  -0.370  1.00  0.44
ATOM   1894  NE2 HIS   129     -0.597  -8.369  -1.501  1.00  0.28
ATOM   1895  C   HIS   129     -0.614 -13.584  -4.277  1.00  0.24
ATOM   1896  O   HIS   129     -1.267 -14.568  -3.991  1.00  0.28
ATOM   1897  N   SER   130      0.474 -13.671  -4.999  1.00  0.24
ATOM   1898  HN  SER   130      0.984 -12.862  -5.210  1.00  0.23
ATOM   1899  CA  SER   130      0.949 -14.996  -5.498  1.00  0.29
ATOM   1900  HA  SER   130      0.139 -15.710  -5.464  1.00  0.33
ATOM   1901  CB  SER   130      1.442 -14.852  -6.938  1.00  0.32
ATOM   1902  HB1 SER   130      2.201 -14.082  -6.982  1.00  0.31
ATOM   1903  HB2 SER   130      0.618 -14.577  -7.576  1.00  0.35
ATOM   1904  OG  SER   130      1.980 -16.092  -7.378  1.00  0.40
ATOM   1905  HG  SER   130      1.254 -16.714  -7.469  1.00  0.97
ATOM   1906  C   SER   130      2.096 -15.484  -4.609  1.00  0.28
ATOM   1907  O   SER   130      2.801 -14.696  -4.009  1.00  0.29
ATOM   1908  N   LYS   131      2.287 -16.775  -4.514  1.00  0.30
ATOM   1909  HN  LYS   131      1.705 -17.393  -5.003  1.00  0.32
ATOM   1910  CA  LYS   131      3.386 -17.310  -3.656  1.00  0.32
ATOM   1911  HA  LYS   131      3.665 -16.567  -2.923  1.00  0.34
ATOM   1912  CB  LYS   131      2.903 -18.572  -2.936  1.00  0.39
ATOM   1913  HB1 LYS   131      3.714 -18.988  -2.355  1.00  0.42
ATOM   1914  HB2 LYS   131      2.572 -19.298  -3.664  1.00  0.40
ATOM   1915  CG  LYS   131      1.743 -18.214  -2.003  1.00  0.45
ATOM   1916  HG1 LYS   131      0.932 -17.798  -2.581  1.00  0.79
ATOM   1917  HG2 LYS   131      2.077 -17.488  -1.276  1.00  1.01
ATOM   1918  CD  LYS   131      1.255 -19.472  -1.280  1.00  1.18
ATOM   1919  HD1 LYS   131      2.064 -19.890  -0.698  1.00  1.86
ATOM   1920  HD2 LYS   131      0.921 -20.199  -2.006  1.00  1.66
ATOM   1921  CE  LYS   131      0.096 -19.108  -0.349  1.00  1.52
ATOM   1922  HE1 LYS   131     -0.788 -18.908  -0.937  1.00  1.92
ATOM   1923  HE2 LYS   131      0.355 -18.229   0.222  1.00  1.93
ATOM   1924  NZ  LYS   131     -0.174 -20.242   0.581  1.00  2.23
ATOM   1925  HZ1 LYS   131     -1.103 -20.109   1.030  1.00  2.72
ATOM   1926  HZ2 LYS   131      0.565 -20.272   1.313  1.00  2.53
ATOM   1927  HZ3 LYS   131     -0.174 -21.135   0.050  1.00  2.72
ATOM   1928  C   LYS   131      4.604 -17.649  -4.521  1.00  0.31
ATOM   1929  O   LYS   131      5.612 -18.116  -4.027  1.00  0.34
ATOM   1930  N   ASP   132      4.532 -17.411  -5.804  1.00  0.29
ATOM   1931  HN  ASP   132      3.717 -17.028  -6.190  1.00  0.28
ATOM   1932  CA  ASP   132      5.703 -17.719  -6.674  1.00  0.30
ATOM   1933  HA  ASP   132      6.187 -18.601  -6.302  1.00  0.32
ATOM   1934  CB  ASP   132      5.225 -17.970  -8.108  1.00  0.32
ATOM   1935  HB1 ASP   132      4.727 -17.090  -8.483  1.00  0.31
ATOM   1936  HB2 ASP   132      4.539 -18.804  -8.118  1.00  0.34
ATOM   1937  CG  ASP   132      6.430 -18.289  -8.996  1.00  0.35
ATOM   1938  OD1 ASP   132      6.457 -19.371  -9.558  1.00  1.10
ATOM   1939  OD2 ASP   132      7.306 -17.446  -9.097  1.00  1.15
ATOM   1940  C   ASP   132      6.656 -16.501  -6.659  1.00  0.28
ATOM   1941  O   ASP   132      6.226 -15.399  -6.939  1.00  0.28
ATOM   1942  N   PRO   133      7.930 -16.658  -6.328  1.00  0.30
ATOM   1943  CA  PRO   133      8.852 -15.484  -6.296  1.00  0.31
ATOM   1944  HA  PRO   133      8.517 -14.766  -5.566  1.00  0.32
ATOM   1945  CB  PRO   133     10.173 -16.097  -5.832  1.00  0.36
ATOM   1946  HB1 PRO   133     10.441 -15.694  -4.867  1.00  0.36
ATOM   1947  HB2 PRO   133     10.949 -15.869  -6.549  1.00  0.41
ATOM   1948  CG  PRO   133     10.007 -17.615  -5.721  1.00  0.42
ATOM   1949  HG1 PRO   133     10.293 -17.940  -4.732  1.00  0.51
ATOM   1950  HG2 PRO   133     10.630 -18.103  -6.457  1.00  0.51
ATOM   1951  CD  PRO   133      8.540 -17.972  -5.969  1.00  0.35
ATOM   1952  HD2 PRO   133      8.456 -18.679  -6.785  1.00  0.34
ATOM   1953  HD1 PRO   133      8.091 -18.362  -5.069  1.00  0.38
ATOM   1954  C   PRO   133      9.032 -14.810  -7.662  1.00  0.31
ATOM   1955  O   PRO   133      9.496 -13.691  -7.749  1.00  0.34
ATOM   1956  N   GLY   134      8.684 -15.477  -8.729  1.00  0.32
ATOM   1957  HN  GLY   134      8.320 -16.382  -8.647  1.00  0.35
ATOM   1958  CA  GLY   134      8.860 -14.856 -10.074  1.00  0.34
ATOM   1959  HA1 GLY   134      9.048 -15.630 -10.803  1.00  0.37
ATOM   1960  HA2 GLY   134      9.701 -14.177 -10.047  1.00  0.36
ATOM   1961  C   GLY   134      7.598 -14.087 -10.471  1.00  0.29
ATOM   1962  O   GLY   134      7.563 -13.420 -11.486  1.00  0.29
ATOM   1963  N   ALA   135      6.563 -14.168  -9.683  1.00  0.27
ATOM   1964  HN  ALA   135      6.607 -14.709  -8.867  1.00  0.28
```

FIG. 4A-26

| | | | | | | | | |
|---|---|---|---|---|---|---|---|---|
| ATOM | 1965 | CA | ALA | 135 | 5.312 | -13.434 | -10.026 | 1.00 | 0.24 |
| ATOM | 1966 | HA | ALA | 135 | 5.199 | -13.401 | -11.099 | 1.00 | 0.25 |
| ATOM | 1967 | CB | ALA | 135 | 4.109 | -14.151 | -9.410 | 1.00 | 0.25 |
| ATOM | 1968 | HB1 | ALA | 135 | 3.633 | -14.765 | -10.160 | 1.00 | 1.07 |
| ATOM | 1969 | HB2 | ALA | 135 | 3.405 | -13.421 | -9.041 | 1.00 | 1.01 |
| ATOM | 1970 | HB3 | ALA | 135 | 4.442 | -14.774 | -8.593 | 1.00 | 1.04 |
| ATOM | 1971 | C | ALA | 135 | 5.388 | -12.007 | -9.479 | 1.00 | 0.21 |
| ATOM | 1972 | O | ALA | 135 | 5.968 | -11.760 | -8.440 | 1.00 | 0.23 |
| ATOM | 1973 | N | LEU | 136 | 4.799 | -11.067 | -10.164 | 1.00 | 0.22 |
| ATOM | 1974 | HN | LEU | 136 | 4.330 | -11.286 | -10.996 | 1.00 | 0.24 |
| ATOM | 1975 | CA | LEU | 136 | 4.830 | -9.660 | -9.676 | 1.00 | 0.23 |
| ATOM | 1976 | HA | LEU | 136 | 5.842 | -9.382 | -9.427 | 1.00 | 0.25 |
| ATOM | 1977 | CB | LEU | 136 | 4.279 | -8.724 | -10.761 | 1.00 | 0.25 |
| ATOM | 1978 | HB1 | LEU | 136 | 4.193 | -7.724 | -10.365 | 1.00 | 0.27 |
| ATOM | 1979 | HB2 | LEU | 136 | 3.302 | -9.072 | -11.064 | 1.00 | 0.26 |
| ATOM | 1980 | CG | LEU | 136 | 5.213 | -8.709 | -11.980 | 1.00 | 0.26 |
| ATOM | 1981 | HG | LEU | 136 | 5.312 | -9.713 | -12.368 | 1.00 | 0.29 |
| ATOM | 1982 | CD1 | LEU | 136 | 4.624 | -7.801 | -13.063 | 1.00 | 0.29 |
| ATOM | 1983 | HD11 | LEU | 136 | 3.546 | -7.848 | -13.030 | 1.00 | 1.06 |
| ATOM | 1984 | HD12 | LEU | 136 | 4.967 | -8.126 | -14.033 | 1.00 | 1.05 |
| ATOM | 1985 | HD13 | LEU | 136 | 4.944 | -6.784 | -12.893 | 1.00 | 1.06 |
| ATOM | 1986 | CD2 | LEU | 136 | 6.592 | -8.176 | -11.578 | 1.00 | 0.32 |
| ATOM | 1987 | HD21 | LEU | 136 | 6.485 | -7.477 | -10.762 | 1.00 | 1.05 |
| ATOM | 1988 | HD22 | LEU | 136 | 7.046 | -7.677 | -12.422 | 1.00 | 1.09 |
| ATOM | 1989 | HD23 | LEU | 136 | 7.220 | -8.998 | -11.269 | 1.00 | 0.97 |
| ATOM | 1990 | C | LEU | 136 | 3.954 | -9.556 | -8.427 | 1.00 | 0.25 |
| ATOM | 1991 | O | LEU | 136 | 4.201 | -8.761 | -7.542 | 1.00 | 0.30 |
| ATOM | 1992 | N | MET | 137 | 2.924 | -10.353 | -8.357 | 1.00 | 0.28 |
| ATOM | 1993 | HN | MET | 137 | 2.744 | -10.981 | -9.087 | 1.00 | 0.31 |
| ATOM | 1994 | CA | MET | 137 | 2.016 | -10.309 | -7.177 | 1.00 | 0.33 |
| ATOM | 1995 | HA | MET | 137 | 1.768 | -9.283 | -6.959 | 1.00 | 0.38 |
| ATOM | 1996 | CB | MET | 137 | 0.734 | -11.087 | -7.494 | 1.00 | 0.42 |
| ATOM | 1997 | HB1 | MET | 137 | 0.118 | -11.136 | -6.615 | 1.00 | 0.57 |
| ATOM | 1998 | HB2 | MET | 137 | 0.995 | -12.089 | -7.803 | 1.00 | 0.50 |
| ATOM | 1999 | CG | MET | 137 | -0.035 | -10.391 | -8.625 | 1.00 | 0.58 |
| ATOM | 2000 | HG1 | MET | 137 | -0.909 | -10.975 | -8.875 | 1.00 | 1.13 |
| ATOM | 2001 | HG2 | MET | 137 | 0.601 | -10.311 | -9.494 | 1.00 | 1.22 |
| ATOM | 2002 | SD | MET | 137 | -0.551 | -8.729 | -8.108 | 1.00 | 0.83 |
| ATOM | 2003 | CE | MET | 137 | -2.048 | -9.184 | -7.194 | 1.00 | 0.39 |
| ATOM | 2004 | HE1 | MET | 137 | -2.231 | -8.450 | -6.426 | 1.00 | 1.14 |
| ATOM | 2005 | HE2 | MET | 137 | -1.927 | -10.151 | -6.741 | 1.00 | 1.07 |
| ATOM | 2006 | HE3 | MET | 137 | -2.885 | -9.212 | -7.872 | 1.00 | 1.06 |
| ATOM | 2007 | C | MET | 137 | 2.700 | -10.925 | -5.951 | 1.00 | 0.27 |
| ATOM | 2008 | O | MET | 137 | 2.050 | -11.287 | -4.990 | 1.00 | 0.28 |
| ATOM | 2009 | N | PHE | 138 | 4.000 | -11.042 | -5.964 | 1.00 | 0.25 |
| ATOM | 2010 | HN | PHE | 138 | 4.514 | -10.741 | -6.743 | 1.00 | 0.28 |
| ATOM | 2011 | CA | PHE | 138 | 4.699 | -11.628 | -4.785 | 1.00 | 0.23 |
| ATOM | 2012 | HA | PHE | 138 | 4.225 | -12.557 | -4.534 | 1.00 | 0.26 |
| ATOM | 2013 | CB | PHE | 138 | 6.167 | -11.877 | -5.152 | 1.00 | 0.25 |
| ATOM | 2014 | HB1 | PHE | 138 | 6.710 | -10.945 | -5.104 | 1.00 | 0.24 |
| ATOM | 2015 | HB2 | PHE | 138 | 6.221 | -12.270 | -6.156 | 1.00 | 0.27 |
| ATOM | 2016 | CG | PHE | 138 | 6.790 | -12.873 | -4.194 | 1.00 | 0.28 |
| ATOM | 2017 | CD1 | PHE | 138 | 6.295 | -14.184 | -4.113 | 1.00 | 0.32 |
| ATOM | 2018 | HD1 | PHE | 138 | 5.465 | -14.490 | -4.731 | 1.00 | 0.33 |
| ATOM | 2019 | CD2 | PHE | 138 | 7.871 | -12.486 | -3.392 | 1.00 | 0.30 |
| ATOM | 2020 | HD2 | PHE | 138 | 8.256 | -11.481 | -3.455 | 1.00 | 0.30 |
| ATOM | 2021 | CE1 | PHE | 138 | 6.881 | -15.100 | -3.230 | 1.00 | 0.38 |
| ATOM | 2022 | HE1 | PHE | 138 | 6.500 | -16.109 | -3.168 | 1.00 | 0.42 |
| ATOM | 2023 | CE2 | PHE | 138 | 8.455 | -13.404 | -2.511 | 1.00 | 0.36 |
| ATOM | 2024 | HE2 | PHE | 138 | 9.288 | -13.104 | -1.894 | 1.00 | 0.39 |
| ATOM | 2025 | CZ | PHE | 138 | 7.960 | -14.710 | -2.430 | 1.00 | 0.39 |
| ATOM | 2026 | HZ | PHE | 138 | 8.411 | -15.417 | -1.749 | 1.00 | 0.44 |
| ATOM | 2027 | C | PHE | 138 | 4.601 | -10.615 | -3.615 | 1.00 | 0.20 |
| ATOM | 2028 | O | PHE | 138 | 4.874 | -9.447 | -3.808 | 1.00 | 0.22 |
| ATOM | 2029 | N | PRO | 139 | 4.185 | -11.019 | -2.421 | 1.00 | 0.22 |
| ATOM | 2030 | CA | PRO | 139 | 4.044 | -10.048 | -1.291 | 1.00 | 0.25 |
| ATOM | 2031 | HA | PRO | 139 | 3.262 | -9.340 | -1.509 | 1.00 | 0.27 |
| ATOM | 2032 | CB | PRO | 139 | 3.600 | -10.936 | -0.127 | 1.00 | 0.31 |
| ATOM | 2033 | HB1 | PRO | 139 | 2.615 | -10.638 | 0.199 | 1.00 | 0.38 |
| ATOM | 2034 | HB2 | PRO | 139 | 4.299 | -10.835 | 0.691 | 1.00 | 0.42 |
| ATOM | 2035 | CG | PRO | 139 | 3.562 | -12.392 | -0.597 | 1.00 | 0.33 |
| ATOM | 2036 | HG1 | PRO | 139 | 2.588 | -12.812 | -0.396 | 1.00 | 0.41 |
| ATOM | 2037 | HG2 | PRO | 139 | 4.317 | -12.961 | -0.074 | 1.00 | 0.42 |
| ATOM | 2038 | CD | PRO | 139 | 3.834 | -12.435 | -2.102 | 1.00 | 0.27 |
| ATOM | 2039 | HD2 | PRO | 139 | 4.661 | -13.100 | -2.318 | 1.00 | 0.28 |
| ATOM | 2040 | HD1 | PRO | 139 | 2.946 | -12.732 | -2.637 | 1.00 | 0.30 |
| ATOM | 2041 | C | PRO | 139 | 5.337 | -9.305 | -0.926 | 1.00 | 0.26 |

FIG. 4A-27

| ATOM | 2042 | O | PRO | 139 | 5.302 | -8.351 | -0.173 | 1.00 | 0.44 |
| --- | --- | --- | --- | --- | --- | --- | --- | --- | --- |
| ATOM | 2043 | N | ILE | 140 | 6.467 | -9.726 | -1.437 | 1.00 | 0.24 |
| ATOM | 2044 | HN | ILE | 140 | 6.474 | -10.500 | -2.038 | 1.00 | 0.37 |
| ATOM | 2045 | CA | ILE | 140 | 7.749 | -9.031 | -1.094 | 1.00 | 0.23 |
| ATOM | 2046 | HA | ILE | 140 | 7.572 | -8.308 | -0.312 | 1.00 | 0.24 |
| ATOM | 2047 | CB | ILE | 140 | 8.775 | -10.054 | -0.600 | 1.00 | 0.25 |
| ATOM | 2048 | HB | ILE | 140 | 8.978 | -10.770 | -1.379 | 1.00 | 0.25 |
| ATOM | 2049 | CG1 | ILE | 140 | 8.207 | -10.768 | 0.632 | 1.00 | 0.29 |
| ATOM | 2050 | HG11 | ILE | 140 | 7.246 | -11.196 | 0.384 | 1.00 | 0.32 |
| ATOM | 2051 | HG12 | ILE | 140 | 8.084 | -10.055 | 1.434 | 1.00 | 0.33 |
| ATOM | 2052 | CG2 | ILE | 140 | 10.070 | -9.332 | -0.214 | 1.00 | 0.26 |
| ATOM | 2053 | HG21 | ILE | 140 | 9.850 | -8.567 | 0.517 | 1.00 | 1.04 |
| ATOM | 2054 | HG22 | ILE | 140 | 10.505 | -8.876 | -1.090 | 1.00 | 1.06 |
| ATOM | 2055 | HG23 | ILE | 140 | 10.768 | -10.040 | 0.207 | 1.00 | 1.04 |
| ATOM | 2056 | CD1 | ILE | 140 | 9.156 | -11.883 | 1.082 | 1.00 | 0.30 |
| ATOM | 2057 | HD11 | ILE | 140 | 9.716 | -12.250 | 0.236 | 1.00 | 1.08 |
| ATOM | 2058 | HD12 | ILE | 140 | 8.582 | -12.691 | 1.511 | 1.00 | 0.98 |
| ATOM | 2059 | HD13 | ILE | 140 | 9.838 | -11.495 | 1.824 | 1.00 | 1.08 |
| ATOM | 2060 | C | ILE | 140 | 8.284 | -8.301 | -2.329 | 1.00 | 0.22 |
| ATOM | 2061 | O | ILE | 140 | 8.265 | -8.817 | -3.429 | 1.00 | 0.22 |
| ATOM | 2062 | N | TYR | 141 | 8.745 | -7.092 | -2.150 | 1.00 | 0.21 |
| ATOM | 2063 | HN | TYR | 141 | 8.736 | -6.696 | -1.254 | 1.00 | 0.22 |
| ATOM | 2064 | CA | TYR | 141 | 9.265 | -6.303 | -3.304 | 1.00 | 0.21 |
| ATOM | 2065 | HA | TYR | 141 | 8.560 | -6.348 | -4.120 | 1.00 | 0.20 |
| ATOM | 2066 | CB | TYR | 141 | 9.444 | -4.847 | -2.865 | 1.00 | 0.21 |
| ATOM | 2067 | HB1 | TYR | 141 | 10.050 | -4.810 | -1.972 | 1.00 | 0.22 |
| ATOM | 2068 | HB2 | TYR | 141 | 8.476 | -4.413 | -2.661 | 1.00 | 0.22 |
| ATOM | 2069 | CG | TYR | 141 | 10.122 | -4.066 | -3.962 | 1.00 | 0.23 |
| ATOM | 2070 | CD1 | TYR | 141 | 11.515 | -4.104 | -4.089 | 1.00 | 0.25 |
| ATOM | 2071 | HD1 | TYR | 141 | 12.104 | -4.697 | -3.404 | 1.00 | 0.26 |
| ATOM | 2072 | CD2 | TYR | 141 | 9.359 | -3.298 | -4.848 | 1.00 | 0.24 |
| ATOM | 2073 | HD2 | TYR | 141 | 8.284 | -3.268 | -4.750 | 1.00 | 0.25 |
| ATOM | 2074 | CE1 | TYR | 141 | 12.146 | -3.376 | -5.103 | 1.00 | 0.28 |
| ATOM | 2075 | HE1 | TYR | 141 | 13.221 | -3.405 | -5.201 | 1.00 | 0.32 |
| ATOM | 2076 | CE2 | TYR | 141 | 9.989 | -2.569 | -5.862 | 1.00 | 0.27 |
| ATOM | 2077 | HE2 | TYR | 141 | 9.401 | -1.975 | -6.544 | 1.00 | 0.30 |
| ATOM | 2078 | CZ | TYR | 141 | 11.383 | -2.608 | -5.990 | 1.00 | 0.29 |
| ATOM | 2079 | OH | TYR | 141 | 12.005 | -1.892 | -6.991 | 1.00 | 0.33 |
| ATOM | 2080 | HH | TYR | 141 | 12.781 | -2.385 | -7.269 | 1.00 | 0.90 |
| ATOM | 2081 | C | TYR | 141 | 10.615 | -6.864 | -3.761 | 1.00 | 0.22 |
| ATOM | 2082 | O | TYR | 141 | 11.522 | -7.050 | -2.973 | 1.00 | 0.23 |
| ATOM | 2083 | N | THR | 142 | 10.750 | -7.130 | -5.035 | 1.00 | 0.22 |
| ATOM | 2084 | HN | THR | 142 | 10.002 | -6.968 | -5.648 | 1.00 | 0.22 |
| ATOM | 2085 | CA | THR | 142 | 12.035 | -7.675 | -5.563 | 1.00 | 0.24 |
| ATOM | 2086 | HA | THR | 142 | 12.835 | -7.447 | -4.874 | 1.00 | 0.25 |
| ATOM | 2087 | CB | THR | 142 | 11.917 | -9.193 | -5.723 | 1.00 | 0.25 |
| ATOM | 2088 | HB | THR | 142 | 11.645 | -9.635 | -4.777 | 1.00 | 0.26 |
| ATOM | 2089 | OG1 | THR | 142 | 13.165 | -9.720 | -6.152 | 1.00 | 0.29 |
| ATOM | 2090 | HG1 | THR | 142 | 13.274 | -9.505 | -7.081 | 1.00 | 0.97 |
| ATOM | 2091 | CG2 | THR | 142 | 10.840 | -9.517 | -6.760 | 1.00 | 0.25 |
| ATOM | 2092 | HG21 | THR | 142 | 10.577 | -10.562 | -6.691 | 1.00 | 1.04 |
| ATOM | 2093 | HG22 | THR | 142 | 11.217 | -9.304 | -7.749 | 1.00 | 1.05 |
| ATOM | 2094 | HG23 | THR | 142 | 9.965 | -8.913 | -6.570 | 1.00 | 1.06 |
| ATOM | 2095 | C | THR | 142 | 12.339 | -7.040 | -6.924 | 1.00 | 0.23 |
| ATOM | 2096 | O | THR | 142 | 11.454 | -6.810 | -7.724 | 1.00 | 0.23 |
| ATOM | 2097 | N | TYR | 143 | 13.586 | -6.758 | -7.195 | 1.00 | 0.25 |
| ATOM | 2098 | HN | TYR | 143 | 14.285 | -6.955 | -6.538 | 1.00 | 0.27 |
| ATOM | 2099 | CA | TYR | 143 | 13.948 | -6.144 | -8.506 | 1.00 | 0.26 |
| ATOM | 2100 | HA | TYR | 143 | 13.174 | -5.452 | -8.804 | 1.00 | 0.25 |
| ATOM | 2101 | CB | TYR | 143 | 15.277 | -5.395 | -8.370 | 1.00 | 0.29 |
| ATOM | 2102 | HB1 | TYR | 143 | 16.072 | -6.104 | -8.190 | 1.00 | 0.33 |
| ATOM | 2103 | HB2 | TYR | 143 | 15.217 | -4.704 | -7.542 | 1.00 | 0.30 |
| ATOM | 2104 | CG | TYR | 143 | 15.563 | -4.633 | -9.642 | 1.00 | 0.27 |
| ATOM | 2105 | CD1 | TYR | 143 | 14.931 | -3.406 | -9.880 | 1.00 | 0.25 |
| ATOM | 2106 | HD1 | TYR | 143 | 14.234 | -3.008 | -9.156 | 1.00 | 0.26 |
| ATOM | 2107 | CD2 | TYR | 143 | 16.466 | -5.148 | -10.581 | 1.00 | 0.31 |
| ATOM | 2108 | HD2 | TYR | 143 | 16.954 | -6.094 | -10.398 | 1.00 | 0.35 |
| ATOM | 2109 | CE1 | TYR | 143 | 15.201 | -2.695 | -11.055 | 1.00 | 0.26 |
| ATOM | 2110 | HE1 | TYR | 143 | 14.713 | -1.749 | -11.238 | 1.00 | 0.28 |
| ATOM | 2111 | CE2 | TYR | 143 | 16.735 | -4.436 | -11.756 | 1.00 | 0.31 |
| ATOM | 2112 | HE2 | TYR | 143 | 17.432 | -4.833 | -12.480 | 1.00 | 0.36 |
| ATOM | 2113 | CZ | TYR | 143 | 16.103 | -3.210 | -11.994 | 1.00 | 0.28 |
| ATOM | 2114 | OH | TYR | 143 | 16.369 | -2.509 | -13.152 | 1.00 | 0.30 |
| ATOM | 2115 | HH | TYR | 143 | 17.068 | -2.969 | -13.624 | 1.00 | 0.95 |
| ATOM | 2116 | C | TYR | 143 | 14.080 | -7.244 | -9.563 | 1.00 | 0.27 |
| ATOM | 2117 | O | TYR | 143 | 14.552 | -8.328 | -9.283 | 1.00 | 0.31 |
| ATOM | 2118 | N | THR | 144 | 13.660 | -6.976 | -10.772 | 1.00 | 0.29 |

FIG. 4A-28

| | | | | | | | | |
|---|---|---|---|---|---|---|---|---|
| ATOM | 2119 | HN | THR | 144 | 13.277 | -6.096 | -10.972 | 1.00 | 0.32 |
| ATOM | 2120 | CA | THR | 144 | 13.753 | -8.008 | -11.847 | 1.00 | 0.32 |
| ATOM | 2121 | HA | THR | 144 | 14.479 | -8.758 | -11.573 | 1.00 | 0.35 |
| ATOM | 2122 | CB | THR | 144 | 12.385 | -8.666 | -12.031 | 1.00 | 0.37 |
| ATOM | 2123 | HB | THR | 144 | 11.922 | -8.814 | -11.067 | 1.00 | 0.84 |
| ATOM | 2124 | OG1 | THR | 144 | 12.549 | -9.918 | -12.683 | 1.00 | 1.00 |
| ATOM | 2125 | HG1 | THR | 144 | 13.280 | -9.836 | -13.301 | 1.00 | 1.42 |
| ATOM | 2126 | CG2 | THR | 144 | 11.499 | -7.757 | -12.882 | 1.00 | 0.82 |
| ATOM | 2127 | HG21 | THR | 144 | 10.461 | -7.991 | -12.699 | 1.00 | 1.51 |
| ATOM | 2128 | HG22 | THR | 144 | 11.724 | -7.911 | -13.927 | 1.00 | 1.24 |
| ATOM | 2129 | HG23 | THR | 144 | 11.687 | -6.726 | -12.622 | 1.00 | 1.49 |
| ATOM | 2130 | C | THR | 144 | 14.169 | -7.351 | -13.165 | 1.00 | 0.34 |
| ATOM | 2131 | O | THR | 144 | 13.922 | -6.183 | -13.392 | 1.00 | 0.32 |
| ATOM | 2132 | N | GLY | 145 | 14.789 | -8.094 | -14.043 | 1.00 | 0.43 |
| ATOM | 2133 | HN | GLY | 145 | 14.971 | -9.037 | -13.846 | 1.00 | 0.49 |
| ATOM | 2134 | CA | GLY | 145 | 15.205 | -7.510 | -15.350 | 1.00 | 0.49 |
| ATOM | 2135 | HA1 | GLY | 145 | 15.842 | -8.207 | -15.872 | 1.00 | 0.57 |
| ATOM | 2136 | HA2 | GLY | 145 | 15.742 | -6.587 | -15.178 | 1.00 | 0.50 |
| ATOM | 2137 | C | GLY | 145 | 13.957 | -7.233 | -16.191 | 1.00 | 0.47 |
| ATOM | 2138 | O | GLY | 145 | 13.331 | -8.138 | -16.706 | 1.00 | 0.53 |
| ATOM | 2139 | N | LYS | 146 | 13.583 | -5.990 | -16.322 | 1.00 | 0.46 |
| ATOM | 2140 | HN | LYS | 146 | 14.097 | -5.277 | -15.889 | 1.00 | 0.48 |
| ATOM | 2141 | CA | LYS | 146 | 12.367 | -5.653 | -17.116 | 1.00 | 0.49 |
| ATOM | 2142 | HA | LYS | 146 | 11.578 | -6.350 | -16.876 | 1.00 | 0.51 |
| ATOM | 2143 | CB | LYS | 146 | 11.911 | -4.235 | -16.764 | 1.00 | 0.52 |
| ATOM | 2144 | HB1 | LYS | 146 | 10.973 | -4.032 | -17.254 | 1.00 | 0.58 |
| ATOM | 2145 | HB2 | LYS | 146 | 12.657 | -3.533 | -17.103 | 1.00 | 0.57 |
| ATOM | 2146 | CG | LYS | 146 | 11.744 | -4.128 | -15.238 | 1.00 | 0.55 |
| ATOM | 2147 | HG1 | LYS | 146 | 12.690 | -3.853 | -14.798 | 1.00 | 0.83 |
| ATOM | 2148 | HG2 | LYS | 146 | 11.442 | -5.089 | -14.849 | 1.00 | 1.14 |
| ATOM | 2149 | CD | LYS | 146 | 10.684 | -3.077 | -14.854 | 1.00 | 1.23 |
| ATOM | 2150 | HD1 | LYS | 146 | 10.308 | -3.309 | -13.871 | 1.00 | 1.78 |
| ATOM | 2151 | HD2 | LYS | 146 | 9.865 | -3.098 | -15.556 | 1.00 | 1.79 |
| ATOM | 2152 | CE | LYS | 146 | 11.298 | -1.671 | -14.828 | 1.00 | 2.01 |
| ATOM | 2153 | HE1 | LYS | 146 | 11.615 | -1.439 | -13.822 | 1.00 | 2.47 |
| ATOM | 2154 | HE2 | LYS | 146 | 10.556 | -0.952 | -15.143 | 1.00 | 2.39 |
| ATOM | 2155 | NZ | LYS | 146 | 12.468 | -1.601 | -15.745 | 1.00 | 2.91 |
| ATOM | 2156 | HZ1 | LYS | 146 | 12.847 | -0.633 | -15.750 | 1.00 | 3.39 |
| ATOM | 2157 | HZ2 | LYS | 146 | 12.170 | -1.861 | -16.707 | 1.00 | 3.28 |
| ATOM | 2158 | HZ3 | LYS | 146 | 13.205 | -2.257 | -15.420 | 1.00 | 3.27 |
| ATOM | 2159 | C | LYS | 146 | 12.677 | -5.732 | -18.613 | 1.00 | 0.59 |
| ATOM | 2160 | O | LYS | 146 | 11.845 | -5.426 | -19.444 | 1.00 | 1.16 |
| ATOM | 2161 | N | SER | 147 | 13.868 | -6.131 | -18.967 | 1.00 | 0.78 |
| ATOM | 2162 | HN | SER | 147 | 14.530 | -6.366 | -18.283 | 1.00 | 1.26 |
| ATOM | 2163 | CA | SER | 147 | 14.226 | -6.214 | -20.413 | 1.00 | 0.87 |
| ATOM | 2164 | HA | SER | 147 | 14.141 | -5.234 | -20.859 | 1.00 | 1.03 |
| ATOM | 2165 | CB | SER | 147 | 15.667 | -6.709 | -20.554 | 1.00 | 0.95 |
| ATOM | 2166 | HB1 | SER | 147 | 15.798 | -7.158 | -21.530 | 1.00 | 1.42 |
| ATOM | 2167 | HB2 | SER | 147 | 15.871 | -7.445 | -19.794 | 1.00 | 1.34 |
| ATOM | 2168 | OG | SER | 147 | 16.561 | -5.616 | -20.395 | 1.00 | 1.71 |
| ATOM | 2169 | HG | SER | 147 | 17.097 | -5.555 | -21.190 | 1.00 | 2.16 |
| ATOM | 2170 | C | SER | 147 | 13.288 | -7.185 | -21.138 | 1.00 | 0.79 |
| ATOM | 2171 | O | SER | 147 | 12.747 | -6.865 | -22.178 | 1.00 | 1.40 |
| ATOM | 2172 | N | HIS | 148 | 13.098 | -8.366 | -20.605 | 1.00 | 0.66 |
| ATOM | 2173 | HN | HIS | 148 | 13.551 | -8.602 | -19.768 | 1.00 | 1.10 |
| ATOM | 2174 | CA | HIS | 148 | 12.199 | -9.360 | -21.272 | 1.00 | 0.65 |
| ATOM | 2175 | HA | HIS | 148 | 11.629 | -8.874 | -22.048 | 1.00 | 0.74 |
| ATOM | 2176 | CB | HIS | 148 | 13.041 | -10.479 | -21.887 | 1.00 | 0.79 |
| ATOM | 2177 | HB1 | HIS | 148 | 12.401 | -11.312 | -22.138 | 1.00 | 1.14 |
| ATOM | 2178 | HB2 | HIS | 148 | 13.786 | -10.801 | -21.174 | 1.00 | 1.30 |
| ATOM | 2179 | CG | HIS | 148 | 13.723 | -9.980 | -23.130 | 1.00 | 1.66 |
| ATOM | 2180 | ND1 | HIS | 148 | 13.104 | -9.116 | -24.019 | 1.00 | 2.52 |
| ATOM | 2181 | HD1 | HIS | 148 | 12.200 | -8.747 | -23.934 | 1.00 | 2.81 |
| ATOM | 2182 | CD2 | HIS | 148 | 14.969 | -10.226 | -23.652 | 1.00 | 2.62 |
| ATOM | 2183 | HD2 | HIS | 148 | 15.715 | -10.867 | -23.206 | 1.00 | 3.00 |
| ATOM | 2184 | CE1 | HIS | 148 | 13.970 | -8.875 | -25.020 | 1.00 | 3.46 |
| ATOM | 2185 | HE1 | HIS | 148 | 13.759 | -8.233 | -25.863 | 1.00 | 4.33 |
| ATOM | 2186 | NE2 | HIS | 148 | 15.123 | -9.528 | -24.846 | 1.00 | 3.55 |
| ATOM | 2187 | C | HIS | 148 | 11.238 | -9.971 | -20.249 | 1.00 | 0.55 |
| ATOM | 2188 | O | HIS | 148 | 10.743 | -11.064 | -20.435 | 1.00 | 0.60 |
| ATOM | 2189 | N | PHE | 149 | 10.978 | -9.293 | -19.167 | 1.00 | 0.57 |
| ATOM | 2190 | HN | PHE | 149 | 11.392 | -8.417 | -19.021 | 1.00 | 0.73 |
| ATOM | 2191 | CA | PHE | 149 | 10.060 | -9.871 | -18.145 | 1.00 | 0.48 |
| ATOM | 2192 | HA | PHE | 149 | 10.416 | -10.849 | -17.857 | 1.00 | 0.51 |
| ATOM | 2193 | CB | PHE | 149 | 10.022 | -8.967 | -16.911 | 1.00 | 0.44 |
| ATOM | 2194 | HB1 | PHE | 149 | 9.603 | -8.008 | -17.177 | 1.00 | 0.44 |
| ATOM | 2195 | HB2 | PHE | 149 | 11.023 | -8.831 | -16.530 | 1.00 | 0.48 |

FIG. 4A-29

| | | | | | | | | |
|---|---|---|---|---|---|---|---|---|
| ATOM | 2196 | CG | PHE | 149 | 9.161 | -9.615 | -15.851 | 1.00 | 0.40 |
| ATOM | 2197 | CD1 | PHE | 149 | 7.766 | -9.507 | -15.919 | 1.00 | 0.36 |
| ATOM | 2198 | HD1 | PHE | 149 | 7.305 | -8.956 | -16.726 | 1.00 | 0.38 |
| ATOM | 2199 | CD2 | PHE | 149 | 9.757 | -10.328 | -14.804 | 1.00 | 0.42 |
| ATOM | 2200 | HD2 | PHE | 149 | 10.832 | -10.412 | -14.750 | 1.00 | 0.48 |
| ATOM | 2201 | CE1 | PHE | 149 | 6.969 | -10.112 | -14.941 | 1.00 | 0.35 |
| ATOM | 2202 | HE1 | PHE | 149 | 5.894 | -10.031 | -14.996 | 1.00 | 0.37 |
| ATOM | 2203 | CE2 | PHE | 149 | 8.958 | -10.932 | -13.825 | 1.00 | 0.40 |
| ATOM | 2204 | HE2 | PHE | 149 | 9.417 | -11.482 | -13.016 | 1.00 | 0.45 |
| ATOM | 2205 | CZ | PHE | 149 | 7.564 | -10.825 | -13.894 | 1.00 | 0.37 |
| ATOM | 2206 | HZ | PHE | 149 | 6.948 | -11.291 | -13.140 | 1.00 | 0.38 |
| ATOM | 2207 | C | PHE | 149 | 8.641 | -9.993 | -18.706 | 1.00 | 0.43 |
| ATOM | 2208 | O | PHE | 149 | 8.080 | -9.044 | -19.217 | 1.00 | 0.45 |
| ATOM | 2209 | N | MET | 150 | 8.050 | -11.153 | -18.575 | 1.00 | 0.43 |
| ATOM | 2210 | HN | MET | 150 | 8.523 | -11.888 | -18.133 | 1.00 | 0.50 |
| ATOM | 2211 | CA | MET | 150 | 6.651 | -11.357 | -19.051 | 1.00 | 0.39 |
| ATOM | 2212 | HA | MET | 150 | 6.189 | -10.400 | -19.245 | 1.00 | 0.38 |
| ATOM | 2213 | CB | MET | 150 | 6.632 | -12.207 | -20.328 | 1.00 | 0.44 |
| ATOM | 2214 | HB1 | MET | 150 | 5.610 | -12.374 | -20.632 | 1.00 | 0.45 |
| ATOM | 2215 | HB2 | MET | 150 | 7.109 | -13.157 | -20.134 | 1.00 | 0.47 |
| ATOM | 2216 | CG | MET | 150 | 7.381 | -11.477 | -21.446 | 1.00 | 0.50 |
| ATOM | 2217 | HG1 | MET | 150 | 8.401 | -11.831 | -21.485 | 1.00 | 0.98 |
| ATOM | 2218 | HG2 | MET | 150 | 7.376 | -10.415 | -21.253 | 1.00 | 0.86 |
| ATOM | 2219 | SD | MET | 150 | 6.571 | -11.806 | -23.033 | 1.00 | 1.32 |
| ATOM | 2220 | CE | MET | 150 | 7.378 | -13.384 | -23.393 | 1.00 | 2.23 |
| ATOM | 2221 | HE1 | MET | 150 | 7.326 | -14.022 | -22.521 | 1.00 | 2.66 |
| ATOM | 2222 | HE2 | MET | 150 | 8.411 | -13.211 | -23.647 | 1.00 | 2.74 |
| ATOM | 2223 | HE3 | MET | 150 | 6.879 | -13.861 | -24.225 | 1.00 | 2.74 |
| ATOM | 2224 | C | MET | 150 | 5.877 | -12.071 | -17.943 | 1.00 | 0.32 |
| ATOM | 2225 | O | MET | 150 | 6.435 | -12.837 | -17.183 | 1.00 | 0.32 |
| ATOM | 2226 | N | LEU | 151 | 4.605 | -11.819 | -17.827 | 1.00 | 0.28 |
| ATOM | 2227 | HN | LEU | 151 | 4.169 | -11.188 | -18.437 | 1.00 | 0.30 |
| ATOM | 2228 | CA | LEU | 151 | 3.821 | -12.478 | -16.746 | 1.00 | 0.24 |
| ATOM | 2229 | HA | LEU | 151 | 4.120 | -12.064 | -15.803 | 1.00 | 0.24 |
| ATOM | 2230 | CB | LEU | 151 | 2.327 | -12.212 | -16.966 | 1.00 | 0.24 |
| ATOM | 2231 | HB1 | LEU | 151 | 1.765 | -12.626 | -16.145 | 1.00 | 0.25 |
| ATOM | 2232 | HB2 | LEU | 151 | 2.012 | -12.680 | -17.887 | 1.00 | 0.28 |
| ATOM | 2233 | CG | LEU | 151 | 2.061 | -10.703 | -17.047 | 1.00 | 0.28 |
| ATOM | 2234 | HG | LEU | 151 | 2.900 | -10.208 | -17.512 | 1.00 | 0.52 |
| ATOM | 2235 | CD1 | LEU | 151 | 0.804 | -10.457 | -17.881 | 1.00 | 0.35 |
| ATOM | 2236 | HD11 | LEU | 151 | 0.506 | -9.424 | -17.788 | 1.00 | 1.07 |
| ATOM | 2237 | HD12 | LEU | 151 | 0.007 | -11.095 | -17.526 | 1.00 | 1.02 |
| ATOM | 2238 | HD13 | LEU | 151 | 1.009 | -10.682 | -18.917 | 1.00 | 1.17 |
| ATOM | 2239 | CD2 | LEU | 151 | 1.848 | -10.140 | -15.638 | 1.00 | 0.46 |
| ATOM | 2240 | HD21 | LEU | 151 | 2.078 | -9.084 | -15.635 | 1.00 | 1.14 |
| ATOM | 2241 | HD22 | LEU | 151 | 2.495 | -10.650 | -14.941 | 1.00 | 1.16 |
| ATOM | 2242 | HD23 | LEU | 151 | 0.820 | -10.284 | -15.345 | 1.00 | 1.11 |
| ATOM | 2243 | C | LEU | 151 | 4.076 | -14.004 | -16.794 | 1.00 | 0.24 |
| ATOM | 2244 | O | LEU | 151 | 3.879 | -14.613 | -17.826 | 1.00 | 0.28 |
| ATOM | 2245 | N | PRO | 152 | 4.504 | -14.641 | -15.711 | 1.00 | 0.22 |
| ATOM | 2246 | CA | PRO | 152 | 4.748 | -16.112 | -15.751 | 1.00 | 0.23 |
| ATOM | 2247 | HA | PRO | 152 | 5.480 | -16.354 | -16.503 | 1.00 | 0.24 |
| ATOM | 2248 | CB | PRO | 152 | 5.323 | -16.404 | -14.364 | 1.00 | 0.24 |
| ATOM | 2249 | HB1 | PRO | 152 | 6.361 | -16.686 | -14.453 | 1.00 | 0.29 |
| ATOM | 2250 | HB2 | PRO | 152 | 4.766 | -17.208 | -13.903 | 1.00 | 0.26 |
| ATOM | 2251 | CG | PRO | 152 | 5.209 | -15.141 | -13.507 | 1.00 | 0.32 |
| ATOM | 2252 | HG1 | PRO | 152 | 6.166 | -14.917 | -13.061 | 1.00 | 0.44 |
| ATOM | 2253 | HG2 | PRO | 152 | 4.473 | -15.295 | -12.730 | 1.00 | 0.41 |
| ATOM | 2254 | CD | PRO | 152 | 4.778 | -13.976 | -14.402 | 1.00 | 0.25 |
| ATOM | 2255 | HD2 | PRO | 152 | 3.886 | -13.507 | -14.008 | 1.00 | 0.25 |
| ATOM | 2256 | HD1 | PRO | 152 | 5.581 | -13.263 | -14.503 | 1.00 | 0.27 |
| ATOM | 2257 | C | PRO | 152 | 3.462 | -16.915 | -15.974 | 1.00 | 0.21 |
| ATOM | 2258 | O | PRO | 152 | 2.378 | -16.371 | -16.038 | 1.00 | 0.20 |
| ATOM | 2259 | N | ASP | 153 | 3.582 | -18.209 | -16.090 | 1.00 | 0.23 |
| ATOM | 2260 | HN | ASP | 153 | 4.468 | -18.622 | -16.031 | 1.00 | 0.25 |
| ATOM | 2261 | CA | ASP | 153 | 2.380 | -19.063 | -16.304 | 1.00 | 0.23 |
| ATOM | 2262 | HA | ASP | 153 | 1.890 | -18.772 | -17.221 | 1.00 | 0.23 |
| ATOM | 2263 | CB | ASP | 153 | 2.813 | -20.526 | -16.401 | 1.00 | 0.25 |
| ATOM | 2264 | HB1 | ASP | 153 | 1.943 | -21.163 | -16.363 | 1.00 | 0.26 |
| ATOM | 2265 | HB2 | ASP | 153 | 3.470 | -20.762 | -15.576 | 1.00 | 0.26 |
| ATOM | 2266 | CG | ASP | 153 | 3.550 | -20.752 | -17.722 | 1.00 | 0.27 |
| ATOM | 2267 | OD1 | ASP | 153 | 4.768 | -20.687 | -17.717 | 1.00 | 1.08 |
| ATOM | 2268 | OD2 | ASP | 153 | 2.884 | -20.994 | -18.715 | 1.00 | 1.14 |
| ATOM | 2269 | C | ASP | 153 | 1.409 | -18.899 | -15.133 | 1.00 | 0.21 |
| ATOM | 2270 | O | ASP | 153 | 0.208 | -18.858 | -15.310 | 1.00 | 0.21 |
| ATOM | 2271 | N | ASP | 154 | 1.919 | -18.820 | -13.935 | 1.00 | 0.21 |
| ATOM | 2272 | HN | ASP | 154 | 2.891 | -18.866 | -13.813 | 1.00 | 0.22 |

FIG. 4A-30

```
ATOM   2273  CA   ASP   154     1.025  -18.678  -12.752  1.00  0.21
ATOM   2274  HA   ASP   154     0.431  -19.572  -12.641  1.00  0.22
ATOM   2275  CB   ASP   154     1.880  -18.474  -11.496  1.00  0.23
ATOM   2276  HB1  ASP   154     2.466  -17.572  -11.602  1.00  0.22
ATOM   2277  HB2  ASP   154     2.541  -19.319  -11.370  1.00  0.25
ATOM   2278  CG   ASP   154     0.975  -18.347  -10.267  1.00  0.25
ATOM   2279  OD1  ASP   154     1.276  -18.982   -9.269  1.00  1.13
ATOM   2280  OD2  ASP   154     0.004  -17.613  -10.340  1.00  1.07
ATOM   2281  C    ASP   154     0.102  -17.473  -12.943  1.00  0.19
ATOM   2282  O    ASP   154    -1.095  -17.564  -12.759  1.00  0.19
ATOM   2283  N    ASP   155     0.645  -16.345  -13.303  1.00  0.19
ATOM   2284  HN   ASP   155     1.613  -16.288  -13.443  1.00  0.21
ATOM   2285  CA   ASP   155    -0.210  -15.140  -13.496  1.00  0.19
ATOM   2286  HA   ASP   155    -0.843  -15.011  -12.631  1.00  0.20
ATOM   2287  CB   ASP   155     0.683  -13.909  -13.653  1.00  0.21
ATOM   2288  HB1  ASP   155     0.087  -13.067  -13.969  1.00  0.22
ATOM   2289  HB2  ASP   155     1.443  -14.113  -14.393  1.00  0.22
ATOM   2290  CG   ASP   155     1.351  -13.588  -12.315  1.00  0.24
ATOM   2291  OD1  ASP   155     2.355  -12.896  -12.327  1.00  1.07
ATOM   2292  OD2  ASP   155     0.845  -14.038  -11.300  1.00  1.14
ATOM   2293  C    ASP   155    -1.087  -15.300  -14.744  1.00  0.19
ATOM   2294  O    ASP   155    -2.240  -14.918  -14.750  1.00  0.19
ATOM   2295  N    VAL   156    -0.555  -15.850  -15.802  1.00  0.19
ATOM   2296  HN   VAL   156     0.379  -16.147  -15.787  1.00  0.19
ATOM   2297  CA   VAL   156    -1.372  -16.013  -17.041  1.00  0.21
ATOM   2298  HA   VAL   156    -1.726  -15.044  -17.362  1.00  0.22
ATOM   2299  CB   VAL   156    -0.519  -16.630  -18.148  1.00  0.23
ATOM   2300  HB   VAL   156    -0.034  -17.521  -17.776  1.00  0.23
ATOM   2301  CG1  VAL   156    -1.416  -16.995  -19.333  1.00  0.27
ATOM   2302  HG11 VAL   156    -2.273  -16.338  -19.348  1.00  1.00
ATOM   2303  HG12 VAL   156    -1.747  -18.018  -19.235  1.00  1.05
ATOM   2304  HG13 VAL   156    -0.861  -16.882  -20.253  1.00  1.05
ATOM   2305  CG2  VAL   156     0.535  -15.618  -18.600  1.00  0.26
ATOM   2306  HG21 VAL   156     0.990  -15.162  -17.733  1.00  1.07
ATOM   2307  HG22 VAL   156     0.067  -14.856  -19.204  1.00  1.05
ATOM   2308  HG23 VAL   156     1.293  -16.123  -19.180  1.00  1.00
ATOM   2309  C    VAL   156    -2.574  -16.919  -16.754  1.00  0.20
ATOM   2310  O    VAL   156    -3.694  -16.615  -17.107  1.00  0.21
ATOM   2311  N    GLN   157    -2.356  -18.035  -16.124  1.00  0.20
ATOM   2312  HN   GLN   157    -1.447  -18.277  -15.847  1.00  0.20
ATOM   2313  CA   GLN   157    -3.498  -18.941  -15.824  1.00  0.22
ATOM   2314  HA   GLN   157    -3.987  -19.214  -16.747  1.00  0.24
ATOM   2315  CB   GLN   157    -2.995  -20.204  -15.117  1.00  0.24
ATOM   2316  HB1  GLN   157    -3.838  -20.774  -14.756  1.00  0.26
ATOM   2317  HB2  GLN   157    -2.368  -19.922  -14.282  1.00  0.23
ATOM   2318  CG   GLN   157    -2.184  -21.064  -16.095  1.00  0.25
ATOM   2319  HG1  GLN   157    -1.174  -20.686  -16.152  1.00  0.94
ATOM   2320  HG2  GLN   157    -2.636  -21.032  -17.074  1.00  0.87
ATOM   2321  CD   GLN   157    -2.152  -22.510  -15.598  1.00  1.19
ATOM   2322  OE1  GLN   157    -2.594  -22.799  -14.504  1.00  1.89
ATOM   2323  NE2  GLN   157    -1.646  -23.437  -16.364  1.00  1.96
ATOM   2324  HE21 GLN   157    -1.291  -23.203  -17.247  1.00  2.18
ATOM   2325  HE22 GLN   157    -1.624  -24.368  -16.058  1.00  2.65
ATOM   2326  C    GLN   157    -4.505  -18.214  -14.925  1.00  0.22
ATOM   2327  O    GLN   157    -5.702  -18.356  -15.077  1.00  0.24
ATOM   2328  N    GLY   158    -4.027  -17.456  -13.974  1.00  0.21
ATOM   2329  HN   GLY   158    -3.057  -17.370  -13.859  1.00  0.20
ATOM   2330  CA   GLY   158    -4.952  -16.741  -13.045  1.00  0.22
ATOM   2331  HA1  GLY   158    -4.380  -16.319  -12.232  1.00  0.22
ATOM   2332  HA2  GLY   158    -5.667  -17.446  -12.646  1.00  0.25
ATOM   2333  C    GLY   158    -5.704  -15.615  -13.766  1.00  0.20
ATOM   2334  O    GLY   158    -6.918  -15.552  -13.730  1.00  0.21
ATOM   2335  N    ILE   159    -5.007  -14.713  -14.405  1.00  0.18
ATOM   2336  HN   ILE   159    -4.028  -14.763  -14.418  1.00  0.18
ATOM   2337  CA   ILE   159    -5.713  -13.593  -15.097  1.00  0.19
ATOM   2338  HA   ILE   159    -6.301  -13.054  -14.375  1.00  0.20
ATOM   2339  CB   ILE   159    -4.679  -12.648  -15.735  1.00  0.19
ATOM   2340  HB   ILE   159    -3.950  -12.367  -14.988  1.00  0.20
ATOM   2341  CG1  ILE   159    -5.355  -11.384  -16.284  1.00  0.24
ATOM   2342  HG11 ILE   159    -6.308  -11.645  -16.717  1.00  0.26
ATOM   2343  HG12 ILE   159    -4.725  -10.952  -17.045  1.00  0.28
ATOM   2344  CG2  ILE   159    -3.968  -13.361  -16.880  1.00  0.21
ATOM   2345  HG21 ILE   159    -2.998  -12.914  -17.036  1.00  1.01
ATOM   2346  HG22 ILE   159    -4.556  -13.274  -17.781  1.00  1.01
ATOM   2347  HG23 ILE   159    -3.848  -14.398  -16.628  1.00  1.04
ATOM   2348  CD1  ILE   159    -5.571  -10.356  -15.166  1.00  0.27
ATOM   2349  HD11 ILE   159    -6.322   -9.644  -15.476  1.00  1.05
```

FIG. 4A-31

```
ATOM   2350  HD12 ILE   159      -4.644   -9.838  -14.978  1.00  1.06
ATOM   2351  HD13 ILE   159      -5.893  -10.848  -14.265  1.00  1.02
ATOM   2352  C    ILE   159      -6.644  -14.162  -16.173  1.00  0.21
ATOM   2353  O    ILE   159      -7.754  -13.700  -16.347  1.00  0.23
ATOM   2354  N    GLN   160      -6.215  -15.168  -16.885  1.00  0.22
ATOM   2355  HN   GLN   160      -5.322  -15.538  -16.726  1.00  0.21
ATOM   2356  CA   GLN   160      -7.097  -15.763  -17.930  1.00  0.27
ATOM   2357  HA   GLN   160      -7.457  -14.979  -18.580  1.00  0.29
ATOM   2358  CB   GLN   160      -6.317  -16.786  -18.756  1.00  0.31
ATOM   2359  HB1  GLN   160      -6.999  -17.334  -19.389  1.00  0.35
ATOM   2360  HB2  GLN   160      -5.809  -17.472  -18.093  1.00  0.30
ATOM   2361  CG   GLN   160      -5.289  -16.062  -19.626  1.00  0.34
ATOM   2362  HG1  GLN   160      -4.606  -15.512  -18.997  1.00  0.92
ATOM   2363  HG2  GLN   160      -5.799  -15.378  -20.290  1.00  0.91
ATOM   2364  CD   GLN   160      -4.508  -17.087  -20.451  1.00  1.11
ATOM   2365  OE1  GLN   160      -4.451  -18.248  -20.100  1.00  1.88
ATOM   2366  NE2  GLN   160      -3.901  -16.704  -21.540  1.00  1.83
ATOM   2367  HE21 GLN   160      -3.947  -15.767  -21.824  1.00  2.13
ATOM   2368  HE22 GLN   160      -3.398  -17.353  -22.075  1.00  2.46
ATOM   2369  C    GLN   160      -8.290  -16.447  -17.261  1.00  0.28
ATOM   2370  O    GLN   160      -9.386  -16.449  -17.779  1.00  0.31
ATOM   2371  N    SER   161      -8.086  -17.035  -16.117  1.00  0.27
ATOM   2372  HN   SER   161      -7.193  -17.030  -15.714  1.00  0.25
ATOM   2373  CA   SER   161      -9.213  -17.718  -15.424  1.00  0.30
ATOM   2374  HA   SER   161      -9.658  -18.444  -16.089  1.00  0.34
ATOM   2375  CB   SER   161      -8.690  -18.427  -14.174  1.00  0.33
ATOM   2376  HB1  SER   161      -7.861  -19.067  -14.444  1.00  0.35
ATOM   2377  HB2  SER   161      -9.476  -19.024  -13.741  1.00  0.36
ATOM   2378  OG   SER   161      -8.267  -17.455  -13.227  1.00  0.33
ATOM   2379  HG   SER   161      -9.045  -16.986  -12.915  1.00  0.94
ATOM   2380  C    SER   161     -10.267  -16.684  -15.019  1.00  0.30
ATOM   2381  O    SER   161     -11.433  -16.997  -14.882  1.00  0.35
ATOM   2382  N    LEU   162      -9.867  -15.457  -14.815  1.00  0.27
ATOM   2383  HN   LEU   162      -8.920  -15.225  -14.921  1.00  0.26
ATOM   2384  CA   LEU   162     -10.852  -14.413  -14.405  1.00  0.29
ATOM   2385  HA   LEU   162     -11.637  -14.869  -13.821  1.00  0.33
ATOM   2386  CB   LEU   162     -10.141  -13.350  -13.563  1.00  0.28
ATOM   2387  HB1  LEU   162     -10.802  -12.509  -13.411  1.00  0.29
ATOM   2388  HB2  LEU   162      -9.256  -13.017  -14.086  1.00  0.27
ATOM   2389  CG   LEU   162      -9.736  -13.937  -12.206  1.00  0.30
ATOM   2390  HG   LEU   162      -9.157  -14.836  -12.367  1.00  0.30
ATOM   2391  CD1  LEU   162      -8.883  -12.918  -11.450  1.00  0.33
ATOM   2392  HD11 LEU   162      -8.496  -13.370  -10.549  1.00  1.03
ATOM   2393  HD12 LEU   162      -9.490  -12.063  -11.191  1.00  1.01
ATOM   2394  HD13 LEU   162      -8.062  -12.601  -12.075  1.00  1.12
ATOM   2395  CD2  LEU   162     -10.980  -14.272  -11.374  1.00  0.33
ATOM   2396  HD21 LEU   162     -11.227  -15.315  -11.502  1.00  1.05
ATOM   2397  HD22 LEU   162     -11.812  -13.664  -11.697  1.00  1.09
ATOM   2398  HD23 LEU   162     -10.776  -14.078  -10.332  1.00  1.01
ATOM   2399  C    LEU   162     -11.461  -13.742  -15.643  1.00  0.30
ATOM   2400  O    LEU   162     -12.664  -13.615  -15.757  1.00  0.36
ATOM   2401  N    TYR   163     -10.645  -13.300  -16.564  1.00  0.27
ATOM   2402  HN   TYR   163      -9.677  -13.404  -16.452  1.00  0.26
ATOM   2403  CA   TYR   163     -11.188  -12.626  -17.783  1.00  0.31
ATOM   2404  HA   TYR   163     -12.144  -12.182  -17.549  1.00  0.33
ATOM   2405  CB   TYR   163     -10.219  -11.531  -18.236  1.00  0.29
ATOM   2406  HB1  TYR   163     -10.562  -11.112  -19.170  1.00  0.32
ATOM   2407  HB2  TYR   163      -9.234  -11.952  -18.371  1.00  0.29
ATOM   2408  CG   TYR   163     -10.162  -10.444  -17.190  1.00  0.25
ATOM   2409  CD1  TYR   163      -9.223  -10.520  -16.155  1.00  0.23
ATOM   2410  HD1  TYR   163      -8.545  -11.359  -16.103  1.00  0.23
ATOM   2411  CD2  TYR   163     -11.042   -9.357  -17.258  1.00  0.27
ATOM   2412  HD2  TYR   163     -11.767   -9.298  -18.056  1.00  0.30
ATOM   2413  CE1  TYR   163      -9.164   -9.511  -15.187  1.00  0.24
ATOM   2414  HE1  TYR   163      -8.439   -9.571  -14.388  1.00  0.25
ATOM   2415  CE2  TYR   163     -10.984   -8.348  -16.289  1.00  0.27
ATOM   2416  HE2  TYR   163     -11.663   -7.510  -16.340  1.00  0.30
ATOM   2417  CZ   TYR   163     -10.044   -8.425  -15.253  1.00  0.27
ATOM   2418  OH   TYR   163      -9.985   -7.430  -14.299  1.00  0.31
ATOM   2419  HH   TYR   163     -10.344   -7.782  -13.481  1.00  0.99
ATOM   2420  C    TYR   163     -11.367  -13.647  -18.909  1.00  0.37
ATOM   2421  O    TYR   163     -11.953  -13.357  -19.933  1.00  0.43
ATOM   2422  N    GLY   164     -10.865  -14.836  -18.729  1.00  0.38
ATOM   2423  HN   GLY   164     -10.394  -15.046  -17.896  1.00  0.35
ATOM   2424  CA   GLY   164     -11.001  -15.877  -19.789  1.00  0.47
ATOM   2425  HA1  GLY   164     -11.851  -15.651  -20.413  1.00  0.53
ATOM   2426  HA2  GLY   164     -11.142  -16.844  -19.326  1.00  0.54
```

FIG. 4A-32

```
ATOM   2427   C    GLY  164     -9.735  -15.902  -20.648  1.00  0.55
ATOM   2428   O    GLY  164     -9.761  -15.580  -21.819  1.00  1.01
TER    2429        GLY  164
HETATM 2430   ZN   ZN   166     -0.218   -6.515   -2.613  1.00  0.24
HETATM 2431   ZN   ZN   167     -3.506    6.833   -0.714  1.00  0.97
HETATM 2432   CA   CA   168      6.060    3.350    3.030  1.00  0.23
HETATM 2433   C1   WAY  169      2.180   -4.315    1.627  0.00  0.30
HETATM 2434   C2   WAY  169      0.865   -4.629    1.215  0.00  0.33
HETATM 2435   1CE1 WAY  169     -0.170   -4.517    2.143  0.00  0.38
HETATM 2436   1CZ  WAY  169      0.074   -4.157    3.457  0.00  0.40
HETATM 2437   1CE2 WAY  169      1.355   -3.807    3.841  0.00  0.38
HETATM 2438   C6   WAY  169      2.395   -3.805    2.922  0.00  0.33
HETATM 2439   1HE1 WAY  169     -1.190   -4.713    1.839  0.00  0.42
HETATM 2440   1HZ  WAY  169     -0.734   -4.151    4.173  0.00  0.45
HETATM 2441   1HE2 WAY  169      1.535   -3.534    4.872  0.00  0.42
HETATM 2442   C10  WAY  169      0.444   -5.080   -0.136  0.00  0.36
HETATM 2443   O11  WAY  169      0.467   -6.264   -0.463  0.00  0.58
HETATM 2444   N12  WAY  169     -0.019   -4.195   -1.032  0.00  0.61
HETATM 2445   O13  WAY  169     -0.045   -4.608   -2.371  0.00  0.68
HETATM 2446   H14  WAY  169     -0.357   -3.297   -0.743  0.00  0.88
HETATM 2447   H15  WAY  169     -0.953   -4.727   -2.645  0.00  1.13
HETATM 2448   1CH1 WAY  169      3.728   -3.247    3.360  0.00  0.37
HETATM 2449   1HH1 WAY  169      3.702   -2.162    3.422  0.00  1.07
HETATM 2450   1HH2 WAY  169      4.519   -3.516    2.664  0.00  1.06
HETATM 2451   1HH3 WAY  169      4.013   -3.623    4.339  0.00  1.11
HETATM 2452   N20  WAY  169      3.274   -4.485    0.819  0.00  0.29
HETATM 2453   S21  WAY  169      3.865   -3.175    0.021  0.00  0.25
HETATM 2454   2CB  WAY  169      3.882   -5.812    0.684  0.00  0.32
HETATM 2455   2CE1 WAY  169      7.334   -6.241    2.178  0.00  1.09
HETATM 2456   2CZ  WAY  169      6.971   -6.520    3.488  0.00  0.53
HETATM 2457   N25  WAY  169      5.697   -6.659    3.876  0.00  1.47
HETATM 2458   2CD2 WAY  169      4.747   -6.451    2.954  0.00  1.37
HETATM 2459   C27  WAY  169      5.010   -6.084    1.640  0.00  0.36
HETATM 2460   2CD1 WAY  169      6.338   -5.982    1.250  0.00  1.14
HETATM 2461   2HE1 WAY  169      8.374   -6.224    1.881  0.00  1.94
HETATM 2462   2HZ  WAY  169      7.752   -6.630    4.227  0.00  0.61
HETATM 2463   2HD2 WAY  169      3.708   -6.570    3.227  0.00  2.23
HETATM 2464   2HD1 WAY  169      6.599   -5.706    0.239  0.00  2.05
HETATM 2465   2HB1 WAY  169      4.245   -5.905   -0.339  0.00  0.31
HETATM 2466   2HB2 WAY  169      3.095   -6.552    0.832  0.00  0.34
HETATM 2467   C35  WAY  169      4.187   -3.617   -1.665  0.00  0.23
HETATM 2468   3CD1 WAY  169      3.310   -3.216   -2.661  0.00  0.25
HETATM 2469   3CE1 WAY  169      3.622   -3.465   -3.992  0.00  0.27
HETATM 2470   C38  WAY  169      4.769   -4.183   -4.326  0.00  0.24
HETATM 2471   3CE2 WAY  169      5.602   -4.644   -3.308  0.00  0.23
HETATM 2472   3CD2 WAY  169      5.315   -4.359   -1.979  0.00  0.23
HETATM 2473   3HD1 WAY  169      2.392   -2.714   -2.389  0.00  0.29
HETATM 2474   3HE1 WAY  169      2.961   -3.091   -4.758  0.00  0.31
HETATM 2475   3HE2 WAY  169      6.481   -5.228   -3.535  0.00  0.26
HETATM 2476   3HD2 WAY  169      5.959   -4.707   -1.184  0.00  0.27
HETATM 2477   O45  WAY  169      5.078   -4.439   -5.664  0.00  0.27
HETATM 2478   3CH  WAY  169      6.245   -5.202   -5.904  0.00  0.28
HETATM 2479   3HH1 WAY  169      6.379   -5.372   -6.973  0.00  0.31
HETATM 2480   3HH2 WAY  169      6.178   -6.172   -5.407  0.00  0.28
HETATM 2481   3HH3 WAY  169      7.127   -4.683   -5.526  0.00  0.29
HETATM 2482   O50  WAY  169      5.123   -2.847    0.614  0.00  0.27
HETATM 2483   O51  WAY  169      2.834   -2.186    0.004  0.00  0.25
END
```

FIG. 5

| | | Atom Type | Res. | | X | Y | Z | Occ. | B | MOL. |
|---|---|---|---|---|---|---|---|---|---|---|
| ATOM | 1 | CB | THR | 7 | 73.468 | 27.410 | 6.079 | 1.00 | 42.70 | A_13 |
| ATOM | 2 | OG1 | THR | 7 | 72.149 | 27.911 | 6.358 | 1.00 | 37.82 | A_13 |
| ATOM | 4 | CG2 | THR | 7 | 73.843 | 26.297 | 7.068 | 1.00 | 25.79 | A_13 |
| ATOM | 5 | C | THR | 7 | 75.936 | 28.076 | 6.227 | 1.00 | 28.29 | A_13 |
| ATOM | 6 | O | THR | 7 | 76.497 | 28.090 | 7.332 | 1.00 | 22.94 | A_13 |
| ATOM | 9 | N | THR | 7 | 74.360 | 29.396 | 4.862 | 1.00 | 20.25 | A_13 |
| ATOM | 11 | CA | THR | 7 | 74.501 | 28.593 | 6.099 | 1.00 | 21.49 | A_13 |
| ATOM | 12 | N | LEU | 8 | 76.547 | 27.691 | 5.099 | 1.00 | 32.90 | A_13 |
| ATOM | 14 | CA | LEU | 8 | 77.915 | 27.150 | 5.105 | 1.00 | 31.85 | A_13 |
| ATOM | 15 | CB | LEU | 8 | 77.952 | 25.759 | 4.438 | 1.00 | 21.38 | A_13 |
| ATOM | 16 | CG | LEU | 8 | 78.016 | 25.576 | 2.910 | 1.00 | 29.31 | A_13 |
| ATOM | 17 | CD1 | LEU | 8 | 79.463 | 25.509 | 2.425 | 1.00 | 16.78 | A_13 |
| ATOM | 18 | CD2 | LEU | 8 | 77.334 | 24.292 | 2.527 | 1.00 | 23.37 | A_13 |
| ATOM | 19 | C | LEU | 8 | 78.956 | 28.070 | 4.465 | 1.00 | 24.01 | A_13 |
| ATOM | 20 | O | LEU | 8 | 78.835 | 28.415 | 3.293 | 1.00 | 26.18 | A_13 |
| ATOM | 21 | N | LYS | 9 | 79.980 | 28.424 | 5.251 | 1.00 | 36.26 | A_13 |
| ATOM | 23 | CA | LYS | 9 | 81.106 | 29.298 | 4.867 | 1.00 | 23.24 | A_13 |
| ATOM | 24 | CB | LYS | 9 | 82.438 | 28.521 | 4.977 | 1.00 | 25.52 | A_13 |
| ATOM | 25 | CG | LYS | 9 | 82.767 | 27.570 | 3.815 | 1.00 | 19.05 | A_13 |
| ATOM | 26 | CD | LYS | 9 | 83.661 | 28.243 | 2.753 | 1.00 | 31.69 | A_13 |
| ATOM | 27 | CE | LYS | 9 | 83.451 | 27.688 | 1.323 | 1.00 | 25.30 | A_13 |
| ATOM | 28 | NZ | LYS | 9 | 82.056 | 27.938 | 0.797 | 1.00 | 20.65 | A_13 |
| ATOM | 32 | C | LYS | 9 | 81.042 | 30.073 | 3.526 | 1.00 | 31.41 | A_13 |
| ATOM | 33 | O | LYS | 9 | 80.764 | 29.505 | 2.466 | 1.00 | 22.31 | A_13 |
| ATOM | 34 | N | TRP | 10 | 81.327 | 31.372 | 3.573 | 1.00 | 15.84 | A_13 |
| ATOM | 36 | CA | TRP | 10 | 81.312 | 32.172 | 2.361 | 1.00 | 10.58 | A_13 |
| ATOM | 37 | CB | TRP | 10 | 81.636 | 33.620 | 2.680 | 1.00 | 21.39 | A_13 |
| ATOM | 38 | CG | TRP | 10 | 80.529 | 34.337 | 3.343 | 1.00 | 22.84 | A_13 |
| ATOM | 39 | CD2 | TRP | 10 | 79.479 | 35.074 | 2.697 | 1.00 | 20.41 | A_13 |
| ATOM | 40 | CE2 | TRP | 10 | 78.676 | 35.631 | 3.718 | 1.00 | 24.50 | A_13 |
| ATOM | 41 | CE3 | TRP | 10 | 79.142 | 35.320 | 1.357 | 1.00 | 13.29 | A_13 |
| ATOM | 42 | CD1 | TRP | 10 | 80.327 | 34.469 | 4.682 | 1.00 | 13.40 | A_13 |
| ATOM | 43 | NE1 | TRP | 10 | 79.220 | 35.253 | 4.919 | 1.00 | 18.40 | A_13 |
| ATOM | 45 | CZ2 | TRP | 10 | 77.550 | 36.418 | 3.442 | 1.00 | 12.63 | A_13 |
| ATOM | 46 | CZ3 | TRP | 10 | 78.021 | 36.105 | 1.083 | 1.00 | 19.89 | A_13 |
| ATOM | 47 | CH2 | TRP | 10 | 77.242 | 36.641 | 2.120 | 1.00 | 13.62 | A_13 |
| ATOM | 48 | C | TRP | 10 | 82.377 | 31.594 | 1.455 | 1.00 | 22.95 | A_13 |
| ATOM | 49 | O | TRP | 10 | 83.450 | 31.221 | 1.920 | 1.00 | 16.28 | A_13 |
| ATOM | 50 | N | SER | 11 | 82.087 | 31.533 | 0.167 | 1.00 | 14.81 | A_13 |
| ATOM | 52 | CA | SER | 11 | 83.017 | 30.975 | -0.801 | 1.00 | 19.50 | A_13 |
| ATOM | 53 | CB | SER | 11 | 82.282 | 30.596 | -2.086 | 1.00 | 24.36 | A_13 |
| ATOM | 54 | OG | SER | 11 | 81.605 | 29.353 | -1.958 | 1.00 | 40.49 | A_13 |
| ATOM | 56 | C | SER | 11 | 84.190 | 31.867 | -1.134 | 1.00 | 16.53 | A_13 |
| ATOM | 57 | O | SER | 11 | 85.132 | 31.423 | -1.779 | 1.00 | 23.48 | A_13 |
| ATOM | 58 | N | LYS | 12 | 84.153 | 33.113 | -0.686 | 1.00 | 12.50 | A_13 |
| ATOM | 60 | CA | LYS | 12 | 85.232 | 34.057 | -0.961 | 1.00 | 17.05 | A_13 |
| ATOM | 61 | CB | LYS | 12 | 84.741 | 35.168 | -1.891 | 1.00 | 17.32 | A_13 |
| ATOM | 62 | CG | LYS | 12 | 83.526 | 35.898 | -1.350 | 1.00 | 18.49 | A_13 |
| ATOM | 63 | CD | LYS | 12 | 82.788 | 36.644 | -2.446 | 1.00 | 18.29 | A_13 |
| ATOM | 64 | CE | LYS | 12 | 81.534 | 37.282 | -1.888 | 1.00 | 18.44 | A_13 |
| ATOM | 65 | NZ | LYS | 12 | 80.805 | 38.094 | -2.895 | 1.00 | 16.65 | A_13 |
| ATOM | 69 | C | LYS | 12 | 85.687 | 34.662 | 0.344 | 1.00 | 11.16 | A_13 |
| ATOM | 70 | O | LYS | 12 | 84.946 | 34.637 | 1.319 | 1.00 | 12.63 | A_13 |
| ATOM | 71 | N | MET | 13 | 86.915 | 35.185 | 0.355 | 1.00 | 15.52 | A_13 |
| ATOM | 73 | CA | MET | 13 | 87.516 | 35.801 | 1.537 | 1.00 | 11.04 | A_13 |
| ATOM | 74 | CB | MET | 13 | 89.028 | 35.547 | 1.565 | 1.00 | 16.57 | A_13 |
| ATOM | 75 | CG | MET | 13 | 89.431 | 34.082 | 1.707 | 1.00 | 20.92 | A_13 |
| ATOM | 76 | SD | MET | 13 | 88.905 | 33.235 | 3.227 | 1.00 | 20.10 | A_13 |
| ATOM | 77 | CE | MET | 13 | 87.486 | 32.313 | 2.604 | 1.00 | 16.29 | A_13 |
| ATOM | 78 | C | MET | 13 | 87.258 | 37.296 | 1.572 | 1.00 | 13.23 | A_13 |
| ATOM | 79 | O | MET | 13 | 87.247 | 37.916 | 2.634 | 1.00 | 22.80 | A_13 |
| ATOM | 80 | N | ASN | 14 | 87.111 | 37.875 | 0.389 | 1.00 | 15.02 | A_13 |
| ATOM | 82 | CA | ASN | 14 | 86.853 | 39.294 | 0.241 | 1.00 | 33.02 | A_13 |
| ATOM | 83 | CB | ASN | 14 | 87.445 | 39.801 | -1.082 | 1.00 | 19.42 | A_13 |
| ATOM | 84 | CG | ASN | 14 | 88.925 | 39.482 | -1.217 | 1.00 | 30.32 | A_13 |
| ATOM | 85 | OD1 | ASN | 14 | 89.343 | 38.341 | -1.031 | 1.00 | 30.12 | A_13 |
| ATOM | 86 | ND2 | ASN | 14 | 89.723 | 40.489 | -1.549 | 1.00 | 28.22 | A_13 |
| ATOM | 89 | C | ASN | 14 | 85.337 | 39.482 | 0.277 | 1.00 | 27.58 | A_13 |
| ATOM | 90 | O | ASN | 14 | 84.606 | 38.935 | -0.568 | 1.00 | 28.01 | A_13 |
| ATOM | 91 | N | LEU | 15 | 84.868 | 40.212 | 1.287 | 1.00 | 19.06 | A_13 |
| ATOM | 93 | CA | LEU | 15 | 83.444 | 40.450 | 1.459 | 1.00 | 20.03 | A_13 |
| ATOM | 94 | CB | LEU | 15 | 82.930 | 39.690 | 2.691 | 1.00 | 19.55 | A_13 |
| ATOM | 95 | CG | LEU | 15 | 83.027 | 38.166 | 2.593 | 1.00 | 19.02 | A_13 |
| ATOM | 96 | CD1 | LEU | 15 | 83.216 | 37.555 | 3.962 | 1.00 | 17.48 | A_13 |
| ATOM | 97 | CD2 | LEU | 15 | 81.799 | 37.604 | 1.903 | 1.00 | 23.43 | A_13 |
| ATOM | 98 | C | LEU | 15 | 83.161 | 41.928 | 1.609 | 1.00 | 19.52 | A_13 |
| ATOM | 99 | O | LEU | 15 | 83.980 | 42.676 | 2.130 | 1.00 | 15.98 | A_13 |

FIG. 5A-1

```
ATOM    100  N    THR   16      81.983  42.343   1.162  1.00 21.22      A_13
ATOM    102  CA   THR   16      81.578  43.736   1.252  1.00 10.00      A_13
ATOM    103  CB   THR   16      81.194  44.257  -0.109  1.00 10.00      A_13
ATOM    104  OG1  THR   16      80.225  43.370  -0.681  1.00 22.43      A_13
ATOM    106  CG2  THR   16      82.427  44.383  -1.009  1.00 15.42      A_13
ATOM    107  C    THR   16      80.368  43.869   2.184  1.00 14.48      A_13
ATOM    108  O    THR   16      79.647  42.897   2.445  1.00 15.74      A_13
ATOM    109  N    TYR   17      80.176  45.065   2.716  1.00 15.89      A_13
ATOM    111  CA   TYR   17      79.064  45.340   3.604  1.00 13.19      A_13
ATOM    112  CB   TYR   17      79.480  45.195   5.067  1.00 21.42      A_13
ATOM    113  CG   TYR   17      80.448  46.236   5.580  1.00 26.23      A_13
ATOM    114  CD1  TYR   17      81.824  46.081   5.412  1.00 16.37      A_13
ATOM    115  CE1  TYR   17      82.724  46.981   5.988  1.00 12.90      A_13
ATOM    116  CD2  TYR   17      79.990  47.329   6.331  1.00 17.15      A_13
ATOM    117  CE2  TYR   17      80.880  48.235   6.912  1.00 24.15      A_13
ATOM    118  CZ   TYR   17      82.244  48.057   6.743  1.00 23.38      A_13
ATOM    119  OH   TYR   17      83.121  48.942   7.343  1.00 19.47      A_13
ATOM    121  C    TYR   17      78.573  46.740   3.343  1.00 10.00      A_13
ATOM    122  O    TYR   17      79.298  47.559   2.782  1.00 19.27      A_13
ATOM    123  N    ARG   18      77.349  47.019   3.762  1.00 18.52      A_13
ATOM    125  CA   ARG   18      76.762  48.332   3.577  1.00 10.00      A_13
ATOM    126  CB   ARG   18      75.970  48.363   2.274  1.00 10.00      A_13
ATOM    127  CG   ARG   18      75.134  49.619   2.094  1.00 14.01      A_13
ATOM    128  CD   ARG   18      74.266  49.524   0.846  1.00 13.91      A_13
ATOM    129  NE   ARG   18      73.298  50.615   0.782  1.00 13.55      A_13
ATOM    131  CZ   ARG   18      72.165  50.571   0.092  1.00 10.00      A_13
ATOM    132  NH1  ARG   18      71.855  49.488  -0.602  1.00 14.30      A_13
ATOM    135  NH2  ARG   18      71.331  51.604   0.125  1.00 28.79      A_13
ATOM    138  C    ARG   18      75.842  48.640   4.741  1.00 10.65      A_13
ATOM    139  O    ARG   18      75.037  47.796   5.141  1.00 12.86      A_13
ATOM    140  N    ILE   19      76.014  49.814   5.332  1.00 25.54      A_13
ATOM    142  CA   ILE   19      75.169  50.265   6.436  1.00 24.52      A_13
ATOM    143  CB   ILE   19      75.944  51.236   7.350  1.00 18.37      A_13
ATOM    144  CG2  ILE   19      75.034  51.765   8.485  1.00 13.87      A_13
ATOM    145  CG1  ILE   19      77.204  50.545   7.888  1.00 27.67      A_13
ATOM    146  CD1  ILE   19      78.203  51.501   8.557  1.00 22.81      A_13
ATOM    147  C    ILE   19      74.062  51.027   5.698  1.00 21.11      A_13
ATOM    148  O    ILE   19      74.261  52.179   5.300  1.00 10.00      A_13
ATOM    149  N    VAL   20      72.916  50.378   5.487  1.00 19.76      A_13
ATOM    151  CA   VAL   20      71.829  51.014   4.735  1.00 18.20      A_13
ATOM    152  CB   VAL   20      70.774  49.983   4.193  1.00 15.42      A_13
ATOM    153  CG1  VAL   20      71.384  48.570   4.088  1.00 10.00      A_13
ATOM    154  CG2  VAL   20      69.496  50.030   4.992  1.00 18.62      A_13
ATOM    155  C    VAL   20      71.175  52.206   5.443  1.00 11.67      A_13
ATOM    156  O    VAL   20      70.652  53.110   4.798  1.00 18.36      A_13
ATOM    157  N    ASN   21      71.153  52.187   6.773  1.00 10.94      A_13
ATOM    159  CA   ASN   21      70.609  53.316   7.544  1.00 11.99      A_13
ATOM    160  CB   ASN   21      69.078  53.307   7.675  1.00 10.00      A_13
ATOM    161  CG   ASN   21      68.533  51.978   8.107  1.00 14.93      A_13
ATOM    162  OD1  ASN   21      67.627  51.449   7.486  1.00 21.54      A_13
ATOM    163  ND2  ASN   21      69.105  51.408   9.148  1.00 10.00      A_13
ATOM    166  C    ASN   21      71.291  53.382   8.897  1.00 18.90      A_13
ATOM    167  O    ASN   21      72.006  52.447   9.283  1.00 12.49      A_13
ATOM    168  N    TYR   22      71.053  54.471   9.618  1.00 17.47      A_13
ATOM    170  CA   TYR   22      71.681  54.708  10.910  1.00 24.85      A_13
ATOM    171  CB   TYR   22      72.556  55.954  10.818  1.00 13.52      A_13
ATOM    172  CG   TYR   22      73.791  55.748   9.991  1.00 10.00      A_13
ATOM    173  CD1  TYR   22      75.033  55.600  10.598  1.00 14.05      A_13
ATOM    174  CE1  TYR   22      76.180  55.370   9.841  1.00 13.69      A_13
ATOM    175  CD2  TYR   22      73.717  55.663   8.608  1.00 10.00      A_13
ATOM    176  CE2  TYR   22      74.848  55.432   7.847  1.00 17.10      A_13
ATOM    177  CZ   TYR   22      76.077  55.288   8.476  1.00 14.43      A_13
ATOM    178  OH   TYR   22      77.204  55.072   7.737  1.00 10.00      A_13
ATOM    180  C    TYR   22      70.726  54.862  12.076  1.00 25.95      A_13
ATOM    181  O    TYR   22      69.593  55.311  11.916  1.00 10.00      A_13
ATOM    182  N    THR   23      71.187  54.483  13.259  1.00 20.30      A_13
ATOM    184  CA   THR   23      70.367  54.606  14.450  1.00 29.11      A_13
ATOM    185  CB   THR   23      70.821  53.635  15.584  1.00 10.90      A_13
ATOM    186  OG1  THR   23      70.136  53.968  16.792  1.00 10.00      A_13
ATOM    188  CG2  THR   23      72.328  53.752  15.852  1.00 16.51      A_13
ATOM    189  C    THR   23      70.459  56.038  14.959  1.00 18.14      A_13
ATOM    190  O    THR   23      71.360  56.785  14.575  1.00 10.00      A_13
ATOM    191  N    PRO   24      69.433  56.487  15.691  1.00 12.76      A_13
ATOM    192  CD   PRO   24      68.061  55.950  15.716  1.00 15.26      A_13
ATOM    193  CA   PRO   24      69.453  57.844  16.232  1.00 22.70      A_13
ATOM    194  CB   PRO   24      67.985  58.086  16.585  1.00 28.52      A_13
ATOM    195  CG   PRO   24      67.448  56.706  16.841  1.00 15.78      A_13
```

FIG. 5A-2

| | | | | | | | | | |
|---|---|---|---|---|---|---|---|---|---|
| ATOM | 196 | C | PRO | 24 | 70.346 | 57.945 | 17.475 | 1.00 24.52 | A_13 |
| ATOM | 197 | O | PRO | 24 | 70.790 | 59.040 | 17.831 | 1.00 10.00 | A_13 |
| ATOM | 198 | N | ASP | 25 | 70.614 | 56.797 | 18.105 | 1.00 11.82 | A_13 |
| ATOM | 200 | CA | ASP | 25 | 71.416 | 56.721 | 19.336 | 1.00 12.31 | A_13 |
| ATOM | 201 | CB | ASP | 25 | 71.339 | 55.317 | 19.917 | 1.00 25.26 | A_13 |
| ATOM | 202 | CG | ASP | 25 | 69.927 | 54.782 | 19.977 | 1.00 10.00 | A_13 |
| ATOM | 203 | OD1 | ASP | 25 | 69.783 | 53.567 | 20.159 | 1.00 20.90 | A_13 |
| ATOM | 204 | OD2 | ASP | 25 | 68.960 | 55.558 | 19.841 | 1.00 18.45 | A_13 |
| ATOM | 205 | C | ASP | 25 | 72.891 | 57.113 | 19.286 | 1.00 14.34 | A_13 |
| ATOM | 206 | O | ASP | 25 | 73.449 | 57.511 | 20.301 | 1.00 11.77 | A_13 |
| ATOM | 207 | N | MET | 26 | 73.546 | 56.873 | 18.157 | 1.00 20.78 | A_13 |
| ATOM | 209 | CA | MET | 26 | 74.960 | 57.208 | 18.010 | 1.00 20.03 | A_13 |
| ATOM | 210 | CB | MET | 26 | 75.791 | 55.928 | 17.916 | 1.00 13.86 | A_13 |
| ATOM | 211 | CG | MET | 26 | 75.966 | 55.181 | 19.231 | 1.00 19.00 | A_13 |
| ATOM | 212 | SD | MET | 26 | 76.043 | 53.404 | 18.941 | 1.00 14.67 | A_13 |
| ATOM | 213 | CE | MET | 26 | 77.737 | 53.223 | 18.385 | 1.00 19.74 | A_13 |
| ATOM | 214 | C | MET | 26 | 75.157 | 58.047 | 16.754 | 1.00 13.32 | A_13 |
| ATOM | 215 | O | MET | 26 | 74.274 | 58.086 | 15.900 | 1.00 16.81 | A_13 |
| ATOM | 216 | N | THR | 27 | 76.285 | 58.749 | 16.656 | 1.00 10.29 | A_13 |
| ATOM | 218 | CA | THR | 27 | 76.568 | 59.564 | 15.470 | 1.00 17.00 | A_13 |
| ATOM | 219 | CB | THR | 27 | 77.710 | 60.596 | 15.700 | 1.00 11.79 | A_13 |
| ATOM | 220 | OG1 | THR | 27 | 78.969 | 59.921 | 15.729 | 1.00 23.77 | A_13 |
| ATOM | 222 | CG2 | THR | 27 | 77.519 | 61.342 | 17.020 | 1.00 21.98 | A_13 |
| ATOM | 223 | C | THR | 27 | 76.996 | 58.634 | 14.347 | 1.00 13.37 | A_13 |
| ATOM | 224 | O | THR | 27 | 77.411 | 57.500 | 14.608 | 1.00 11.05 | A_13 |
| ATOM | 225 | N | HIS | 28 | 76.972 | 59.124 | 13.113 | 1.00 10.00 | A_13 |
| ATOM | 227 | CA | HIS | 28 | 77.362 | 58.300 | 11.980 | 1.00 10.96 | A_13 |
| ATOM | 228 | CB | HIS | 28 | 77.240 | 59.071 | 10.657 | 1.00 16.07 | A_13 |
| ATOM | 229 | CG | HIS | 28 | 75.829 | 59.382 | 10.264 | 1.00 15.53 | A_13 |
| ATOM | 230 | CD2 | HIS | 28 | 74.707 | 59.531 | 11.016 | 1.00 21.47 | A_13 |
| ATOM | 231 | ND1 | HIS | 28 | 75.440 | 59.597 | 8.959 | 1.00 30.32 | A_13 |
| ATOM | 233 | CE1 | HIS | 28 | 74.149 | 59.868 | 8.920 | 1.00 19.38 | A_13 |
| ATOM | 234 | NE2 | HIS | 28 | 73.680 | 59.833 | 10.160 | 1.00 29.43 | A_13 |
| ATOM | 236 | C | HIS | 28 | 78.769 | 57.735 | 12.151 | 1.00 14.80 | A_13 |
| ATOM | 237 | O | HIS | 28 | 79.005 | 56.568 | 11.851 | 1.00 28.24 | A_13 |
| ATOM | 238 | N | SER | 29 | 79.703 | 58.548 | 12.634 | 1.00 14.00 | A_13 |
| ATOM | 240 | CA | SER | 29 | 81.068 | 58.070 | 12.854 | 1.00 19.57 | A_13 |
| ATOM | 241 | CB | SER | 29 | 82.001 | 59.219 | 13.242 | 1.00 17.84 | A_13 |
| ATOM | 242 | OG | SER | 29 | 82.383 | 59.936 | 12.084 | 1.00 28.25 | A_13 |
| ATOM | 244 | C | SER | 29 | 81.134 | 56.983 | 13.917 | 1.00 15.23 | A_13 |
| ATOM | 245 | O | SER | 29 | 81.818 | 55.973 | 13.733 | 1.00 13.73 | A_13 |
| ATOM | 246 | N | GLU | 30 | 80.428 | 57.182 | 15.027 | 1.00 27.71 | A_13 |
| ATOM | 248 | CA | GLU | 30 | 80.430 | 56.186 | 16.100 | 1.00 23.60 | A_13 |
| ATOM | 249 | CB | GLU | 30 | 79.571 | 56.635 | 17.289 | 1.00 21.72 | A_13 |
| ATOM | 250 | CG | GLU | 30 | 80.048 | 57.913 | 17.973 | 1.00 24.07 | A_13 |
| ATOM | 251 | CD | GLU | 30 | 79.205 | 58.279 | 19.185 | 1.00 21.06 | A_13 |
| ATOM | 252 | OE1 | GLU | 30 | 79.784 | 58.660 | 20.218 | 1.00 46.95 | A_13 |
| ATOM | 253 | OE2 | GLU | 30 | 77.963 | 58.185 | 19.119 | 1.00 18.27 | A_13 |
| ATOM | 254 | C | GLU | 30 | 79.895 | 54.877 | 15.553 | 1.00 18.75 | A_13 |
| ATOM | 255 | O | GLU | 30 | 80.456 | 53.809 | 15.815 | 1.00 13.06 | A_13 |
| ATOM | 256 | N | VAL | 31 | 78.839 | 54.970 | 14.746 | 1.00 16.23 | A_13 |
| ATOM | 258 | CA | VAL | 31 | 78.225 | 53.781 | 14.146 | 1.00 22.33 | A_13 |
| ATOM | 259 | CB | VAL | 31 | 76.899 | 54.135 | 13.390 | 1.00 23.53 | A_13 |
| ATOM | 260 | CG1 | VAL | 31 | 76.384 | 52.920 | 12.628 | 1.00 14.39 | A_13 |
| ATOM | 261 | CG2 | VAL | 31 | 75.829 | 54.587 | 14.377 | 1.00 10.00 | A_13 |
| ATOM | 262 | C | VAL | 31 | 79.208 | 53.040 | 13.216 | 1.00 20.29 | A_13 |
| ATOM | 263 | O | VAL | 31 | 79.330 | 51.814 | 13.282 | 1.00 14.02 | A_13 |
| ATOM | 264 | N | GLU | 32 | 79.913 | 53.790 | 12.370 | 1.00 23.94 | A_13 |
| ATOM | 266 | CA | GLU | 32 | 80.887 | 53.219 | 11.446 | 1.00 10.18 | A_13 |
| ATOM | 267 | CB | GLU | 32 | 81.406 | 54.285 | 10.502 | 1.00 16.50 | A_13 |
| ATOM | 268 | CG | GLU | 32 | 80.424 | 54.605 | 9.427 | 1.00 20.84 | A_13 |
| ATOM | 269 | CD | GLU | 32 | 80.330 | 56.080 | 9.155 | 1.00 22.31 | A_13 |
| ATOM | 270 | OE1 | GLU | 32 | 79.285 | 56.509 | 8.639 | 1.00 29.39 | A_13 |
| ATOM | 271 | OE2 | GLU | 32 | 81.294 | 56.812 | 9.458 | 1.00 22.01 | A_13 |
| ATOM | 272 | C | GLU | 32 | 82.056 | 52.565 | 12.137 | 1.00 18.93 | A_13 |
| ATOM | 273 | O | GLU | 32 | 82.474 | 51.470 | 11.753 | 1.00 24.42 | A_13 |
| ATOM | 274 | N | LYS | 33 | 82.610 | 53.241 | 13.139 | 1.00 19.78 | A_13 |
| ATOM | 276 | CA | LYS | 33 | 83.726 | 52.661 | 13.873 | 1.00 28.68 | A_13 |
| ATOM | 277 | CB | LYS | 33 | 84.340 | 53.681 | 14.837 | 1.00 18.54 | A_13 |
| ATOM | 278 | CG | LYS | 33 | 85.016 | 54.855 | 14.135 | 1.00 31.19 | A_13 |
| ATOM | 279 | CD | LYS | 33 | 86.135 | 54.425 | 13.148 | 1.00 40.31 | A_13 |
| ATOM | 280 | CE | LYS | 33 | 85.600 | 53.972 | 11.785 | 1.00 21.99 | A_13 |
| ATOM | 281 | NZ | LYS | 33 | 86.646 | 53.779 | 10.773 | 1.00 33.20 | A_13 |
| ATOM | 285 | C | LYS | 33 | 83.242 | 51.407 | 14.594 | 1.00 12.66 | A_13 |
| ATOM | 286 | O | LYS | 33 | 83.892 | 50.361 | 14.552 | 1.00 15.54 | A_13 |
| ATOM | 287 | N | ALA | 34 | 82.036 | 51.481 | 15.148 | 1.00 20.70 | A_13 |
| ATOM | 289 | CA | ALA | 34 | 81.453 | 50.344 | 15.843 | 1.00 10.00 | A_13 |

FIG. 5A-3

```
ATOM  290  CB   ALA  34   80.040  50.651  16.279  1.00  18.59  A_13
ATOM  291  C    ALA  34   81.468  49.119  14.940  1.00  13.45  A_13
ATOM  292  O    ALA  34   82.067  48.095  15.284  1.00  15.90  A_13
ATOM  293  N    PHE  35   80.857  49.234  13.766  1.00  19.57  A_13
ATOM  295  CA   PHE  35   80.802  48.112  12.812  1.00  26.77  A_13
ATOM  296  CB   PHE  35   79.837  48.423  11.660  1.00  17.34  A_13
ATOM  297  CG   PHE  35   78.390  48.477  12.077  1.00  30.55  A_13
ATOM  298  CD1  PHE  35   77.838  47.464  12.863  1.00  26.58  A_13
ATOM  299  CD2  PHE  35   77.570  49.512  11.653  1.00  10.00  A_13
ATOM  300  CE1  PHE  35   76.494  47.485  13.212  1.00  12.45  A_13
ATOM  301  CE2  PHE  35   76.224  49.538  12.002  1.00  17.92  A_13
ATOM  302  CZ   PHE  35   75.684  48.525  12.777  1.00  13.29  A_13
ATOM  303  C    PHE  35   82.170  47.754  12.236  1.00  11.31  A_13
ATOM  304  O    PHE  35   82.493  46.573  12.034  1.00  11.37  A_13
ATOM  305  N    LYS  36   82.962  48.778  11.945  1.00  17.06  A_13
ATOM  307  CA   LYS  36   84.293  48.573  11.400  1.00  17.41  A_13
ATOM  308  CB   LYS  36   84.991  49.922  11.208  1.00  11.20  A_13
ATOM  309  CG   LYS  36   86.282  49.792  10.439  1.00  28.84  A_13
ATOM  310  CD   LYS  36   87.246  50.917  10.738  1.00  24.52  A_13
ATOM  311  CE   LYS  36   88.542  50.703   9.978  1.00  12.87  A_13
ATOM  312  NZ   LYS  36   88.264  50.536   8.514  1.00  23.69  A_13
ATOM  316  C    LYS  36   85.122  47.685  12.345  1.00  16.09  A_13
ATOM  317  O    LYS  36   85.701  46.686  11.938  1.00  21.50  A_13
ATOM  318  N    LYS  37   85.173  48.057  13.613  1.00  12.42  A_13
ATOM  320  CA   LYS  37   85.926  47.303  14.591  1.00  12.36  A_13
ATOM  321  CB   LYS  37   85.953  48.066  15.917  1.00  13.65  A_13
ATOM  322  CG   LYS  37   86.744  47.374  17.028  1.00  13.38  A_13
ATOM  323  CD   LYS  37   88.192  47.125  16.616  1.00  38.32  A_13
ATOM  324  CE   LYS  37   88.750  45.825  17.205  1.00  34.46  A_13
ATOM  325  NZ   LYS  37   88.234  44.576  16.557  1.00  12.49  A_13
ATOM  329  C    LYS  37   85.372  45.887  14.786  1.00  17.04  A_13
ATOM  330  O    LYS  37   86.131  44.958  15.053  1.00  18.14  A_13
ATOM  331  N    ALA  38   84.061  45.711  14.649  1.00  24.47  A_13
ATOM  333  CA   ALA  38   83.452  44.392  14.822  1.00  11.03  A_13
ATOM  334  CB   ALA  38   81.941  44.504  14.890  1.00  14.71  A_13
ATOM  335  C    ALA  38   83.900  43.451  13.697  1.00  20.27  A_13
ATOM  336  O    ALA  38   84.143  42.266  13.936  1.00  18.80  A_13
ATOM  337  N    PHE  39   84.021  43.971  12.477  1.00  22.58  A_13
ATOM  339  CA   PHE  39   84.492  43.158  11.355  1.00  18.87  A_13
ATOM  340  CB   PHE  39   84.350  43.899  10.027  1.00  19.91  A_13
ATOM  341  CG   PHE  39   82.993  43.783   9.414  1.00  10.00  A_13
ATOM  342  CD1  PHE  39   82.266  44.915   9.097  1.00  17.54  A_13
ATOM  343  CD2  PHE  39   82.438  42.533   9.143  1.00  15.92  A_13
ATOM  344  CE1  PHE  39   81.008  44.808   8.520  1.00  20.75  A_13
ATOM  345  CE2  PHE  39   81.186  42.418   8.569  1.00  10.00  A_13
ATOM  346  CZ   PHE  39   80.467  43.555   8.252  1.00  10.00  A_13
ATOM  347  C    PHE  39   85.955  42.827  11.589  1.00  16.52  A_13
ATOM  348  O    PHE  39   86.382  41.689  11.387  1.00  19.70  A_13
ATOM  349  N    LYS  40   86.699  43.822  12.072  1.00  21.31  A_13
ATOM  351  CA   LYS  40   88.117  43.673  12.369  1.00  20.07  A_13
ATOM  352  CB   LYS  40   88.703  44.967  12.927  1.00  13.77  A_13
ATOM  353  CG   LYS  40   90.192  44.885  13.171  1.00  11.54  A_13
ATOM  354  CD   LYS  40   90.757  46.242  13.507  1.00  10.34  A_13
ATOM  355  CE   LYS  40   92.236  46.142  13.838  1.00  11.24  A_13
ATOM  356  NZ   LYS  40   92.468  45.518  15.179  1.00  27.33  A_13
ATOM  360  C    LYS  40   88.352  42.534  13.337  1.00  12.06  A_13
ATOM  361  O    LYS  40   89.252  41.719  13.124  1.00  25.09  A_13
ATOM  362  N    VAL  41   87.495  42.418  14.349  1.00  12.26  A_13
ATOM  364  CA   VAL  41   87.630  41.331  15.325  1.00  17.89  A_13
ATOM  365  CB   VAL  41   86.351  41.205  16.216  1.00  10.00  A_13
ATOM  366  CG1  VAL  41   86.298  39.865  16.894  1.00  23.82  A_13
ATOM  367  CG2  VAL  41   86.329  42.274  17.259  1.00  17.65  A_13
ATOM  368  C    VAL  41   87.822  40.009  14.560  1.00  23.06  A_13
ATOM  369  O    VAL  41   88.664  39.168  14.912  1.00  11.82  A_13
ATOM  370  N    TRP  42   87.069  39.871  13.471  1.00  21.42  A_13
ATOM  372  CA   TRP  42   87.085  38.666  12.661  1.00  21.32  A_13
ATOM  373  CB   TRP  42   85.713  38.476  12.009  1.00  18.84  A_13
ATOM  374  CG   TRP  42   84.605  38.387  13.025  1.00  25.92  A_13
ATOM  375  CD2  TRP  42   84.437  37.369  14.024  1.00  16.65  A_13
ATOM  376  CE2  TRP  42   83.260  37.680  14.737  1.00  17.58  A_13
ATOM  377  CE3  TRP  42   85.165  36.223  14.380  1.00  11.14  A_13
ATOM  378  CD1  TRP  42   83.563  39.249  13.179  1.00  10.00  A_13
ATOM  379  NE1  TRP  42   82.755  38.832  14.200  1.00  10.91  A_13
ATOM  381  CZ2  TRP  42   82.785  36.879  15.793  1.00  14.81  A_13
ATOM  382  CZ3  TRP  42   84.691  35.425  15.436  1.00  23.68  A_13
ATOM  383  CH2  TRP  42   83.513  35.759  16.125  1.00  12.75  A_13
ATOM  384  C    TRP  42   88.190  38.600  11.623  1.00  27.45  A_13
```

FIG. 5A-4

| ATOM | 385 | O | TRP | 42 | 88.834 | 37.556 | 11.472 | 1.00 | 11.84 | A_13 |
|---|---|---|---|---|---|---|---|---|---|---|
| ATOM | 386 | N | SER | 43 | 88.413 | 39.702 | 10.909 | 1.00 | 25.46 | A_13 |
| ATOM | 388 | CA | SER | 43 | 89.449 | 39.740 | 9.881 | 1.00 | 19.61 | A_13 |
| ATOM | 389 | CB | SER | 43 | 89.342 | 40.993 | 8.991 | 1.00 | 16.16 | A_13 |
| ATOM | 390 | OG | SER | 43 | 89.495 | 42.199 | 9.709 | 1.00 | 26.34 | A_13 |
| ATOM | 392 | C | SER | 43 | 90.837 | 39.615 | 10.491 | 1.00 | 11.53 | A_13 |
| ATOM | 393 | O | SER | 43 | 91.758 | 39.119 | 9.834 | 1.00 | 17.99 | A_13 |
| ATOM | 394 | N | ASP | 44 | 90.949 | 39.973 | 11.771 | 1.00 | 10.00 | A_13 |
| ATOM | 396 | CA | ASP | 44 | 92.206 | 39.908 | 12.505 | 1.00 | 16.90 | A_13 |
| ATOM | 397 | CB | ASP | 44 | 92.057 | 40.588 | 13.857 | 1.00 | 17.79 | A_13 |
| ATOM | 398 | CG | ASP | 44 | 92.544 | 42.013 | 13.839 | 1.00 | 15.93 | A_13 |
| ATOM | 399 | OD1 | ASP | 44 | 92.605 | 42.618 | 14.920 | 1.00 | 17.21 | A_13 |
| ATOM | 400 | OD2 | ASP | 44 | 92.874 | 42.533 | 12.754 | 1.00 | 19.50 | A_13 |
| ATOM | 401 | C | ASP | 44 | 92.781 | 38.523 | 12.729 | 1.00 | 26.12 | A_13 |
| ATOM | 402 | O | ASP | 44 | 93.996 | 38.362 | 12.897 | 1.00 | 21.21 | A_13 |
| ATOM | 403 | N | VAL | 45 | 91.911 | 37.523 | 12.745 | 1.00 | 20.89 | A_13 |
| ATOM | 405 | CA | VAL | 45 | 92.353 | 36.161 | 12.996 | 1.00 | 27.53 | A_13 |
| ATOM | 406 | CB | VAL | 45 | 91.853 | 35.678 | 14.381 | 1.00 | 16.30 | A_13 |
| ATOM | 407 | CG1 | VAL | 45 | 92.557 | 36.472 | 15.504 | 1.00 | 10.00 | A_13 |
| ATOM | 408 | CG2 | VAL | 45 | 90.348 | 35.857 | 14.495 | 1.00 | 10.86 | A_13 |
| ATOM | 409 | C | VAL | 45 | 91.928 | 35.187 | 11.911 | 1.00 | 24.33 | A_13 |
| ATOM | 410 | O | VAL | 45 | 91.864 | 33.978 | 12.157 | 1.00 | 18.84 | A_13 |
| ATOM | 411 | N | THR | 46 | 91.750 | 35.705 | 10.694 | 1.00 | 16.30 | A_13 |
| ATOM | 413 | CA | THR | 46 | 91.293 | 34.893 | 9.574 | 1.00 | 14.48 | A_13 |
| ATOM | 414 | CB | THR | 46 | 89.750 | 34.796 | 9.662 | 1.00 | 22.05 | A_13 |
| ATOM | 415 | OG1 | THR | 46 | 89.279 | 33.609 | 9.028 | 1.00 | 31.53 | A_13 |
| ATOM | 417 | CG2 | THR | 46 | 89.112 | 36.014 | 9.040 | 1.00 | 10.99 | A_13 |
| ATOM | 418 | C | THR | 46 | 91.716 | 35.575 | 8.257 | 1.00 | 25.10 | A_13 |
| ATOM | 419 | O | THR | 46 | 92.022 | 36.764 | 8.256 | 1.00 | 17.64 | A_13 |
| ATOM | 420 | N | PRO | 47 | 91.688 | 34.845 | 7.114 | 1.00 | 15.31 | A_13 |
| ATOM | 421 | CD | PRO | 47 | 91.459 | 33.398 | 6.985 | 1.00 | 17.94 | A_13 |
| ATOM | 422 | CA | PRO | 47 | 92.069 | 35.416 | 5.815 | 1.00 | 21.50 | A_13 |
| ATOM | 423 | CB | PRO | 47 | 92.199 | 34.182 | 4.911 | 1.00 | 17.57 | A_13 |
| ATOM | 424 | CG | PRO | 47 | 92.369 | 33.041 | 5.848 | 1.00 | 27.45 | A_13 |
| ATOM | 425 | C | PRO | 47 | 90.991 | 36.348 | 5.256 | 1.00 | 21.44 | A_13 |
| ATOM | 426 | O | PRO | 47 | 91.095 | 36.788 | 4.116 | 1.00 | 11.08 | A_13 |
| ATOM | 427 | N | LEU | 48 | 89.918 | 36.567 | 6.018 | 1.00 | 10.00 | A_13 |
| ATOM | 429 | CA | LEU | 48 | 88.826 | 37.434 | 5.581 | 1.00 | 22.09 | A_13 |
| ATOM | 430 | CB | LEU | 48 | 87.575 | 37.212 | 6.432 | 1.00 | 15.92 | A_13 |
| ATOM | 431 | CG | LEU | 48 | 86.848 | 35.867 | 6.435 | 1.00 | 13.58 | A_13 |
| ATOM | 432 | CD1 | LEU | 48 | 85.931 | 35.811 | 7.654 | 1.00 | 25.90 | A_13 |
| ATOM | 433 | CD2 | LEU | 48 | 86.073 | 35.666 | 5.157 | 1.00 | 16.47 | A_13 |
| ATOM | 434 | C | LEU | 48 | 89.156 | 38.916 | 5.641 | 1.00 | 21.20 | A_13 |
| ATOM | 435 | O | LEU | 48 | 89.936 | 39.366 | 6.480 | 1.00 | 17.28 | A_13 |
| ATOM | 436 | N | ASN | 49 | 88.569 | 39.670 | 4.723 | 1.00 | 26.12 | A_13 |
| ATOM | 438 | CA | ASN | 49 | 88.738 | 41.112 | 4.717 | 1.00 | 26.84 | A_13 |
| ATOM | 439 | CB | ASN | 49 | 89.936 | 41.569 | 3.885 | 1.00 | 18.29 | A_13 |
| ATOM | 440 | CG | ASN | 49 | 90.010 | 40.912 | 2.568 | 1.00 | 22.55 | A_13 |
| ATOM | 441 | OD1 | ASN | 49 | 90.928 | 40.131 | 2.305 | 1.00 | 24.41 | A_13 |
| ATOM | 442 | ND2 | ASN | 49 | 89.068 | 41.235 | 1.693 | 1.00 | 46.51 | A_13 |
| ATOM | 445 | C | ASN | 49 | 87.416 | 41.705 | 4.259 | 1.00 | 12.18 | A_13 |
| ATOM | 446 | O | ASN | 49 | 86.732 | 41.128 | 3.400 | 1.00 | 20.77 | A_13 |
| ATOM | 447 | N | PHE | 50 | 87.025 | 42.802 | 4.900 | 1.00 | 21.39 | A_13 |
| ATOM | 449 | CA | PHE | 50 | 85.738 | 43.439 | 4.642 | 1.00 | 10.00 | A_13 |
| ATOM | 450 | CB | PHE | 50 | 84.914 | 43.440 | 5.932 | 1.00 | 11.45 | A_13 |
| ATOM | 451 | CG | PHE | 50 | 84.863 | 42.098 | 6.629 | 1.00 | 10.63 | A_13 |
| ATOM | 452 | CD1 | PHE | 50 | 85.886 | 41.705 | 7.490 | 1.00 | 10.00 | A_13 |
| ATOM | 453 | CD2 | PHE | 50 | 83.809 | 41.216 | 6.395 | 1.00 | 14.63 | A_13 |
| ATOM | 454 | CE1 | PHE | 50 | 85.858 | 40.457 | 8.097 | 1.00 | 26.88 | A_13 |
| ATOM | 455 | CE2 | PHE | 50 | 83.773 | 39.963 | 7.000 | 1.00 | 21.13 | A_13 |
| ATOM | 456 | CZ | PHE | 50 | 84.801 | 39.581 | 7.852 | 1.00 | 10.30 | A_13 |
| ATOM | 457 | C | PHE | 50 | 85.867 | 44.842 | 4.093 | 1.00 | 22.56 | A_13 |
| ATOM | 458 | O | PHE | 50 | 86.638 | 45.644 | 4.612 | 1.00 | 19.33 | A_13 |
| ATOM | 459 | N | THR | 51 | 85.099 | 45.129 | 3.044 | 1.00 | 21.47 | A_13 |
| ATOM | 461 | CA | THR | 51 | 85.125 | 46.433 | 2.371 | 1.00 | 24.21 | A_13 |
| ATOM | 462 | CB | THR | 51 | 85.602 | 46.306 | 0.895 | 1.00 | 15.39 | A_13 |
| ATOM | 463 | OG1 | THR | 51 | 86.950 | 45.811 | 0.853 | 1.00 | 24.33 | A_13 |
| ATOM | 465 | CG2 | THR | 51 | 85.551 | 47.654 | 0.192 | 1.00 | 25.47 | A_13 |
| ATOM | 466 | C | THR | 51 | 83.735 | 47.048 | 2.359 | 1.00 | 22.17 | A_13 |
| ATOM | 467 | O | THR | 51 | 82.766 | 46.421 | 1.912 | 1.00 | 20.53 | A_13 |
| ATOM | 468 | N | ARG | 52 | 83.653 | 48.294 | 2.797 | 1.00 | 16.53 | A_13 |
| ATOM | 470 | CA | ARG | 52 | 82.393 | 49.004 | 2.871 | 1.00 | 10.00 | A_13 |
| ATOM | 471 | CB | ARG | 52 | 82.490 | 50.085 | 3.939 | 1.00 | 10.00 | A_13 |
| ATOM | 472 | CG | ARG | 52 | 81.201 | 50.778 | 4.259 | 1.00 | 12.47 | A_13 |
| ATOM | 473 | CD | ARG | 52 | 81.462 | 51.879 | 5.278 | 1.00 | 19.61 | A_13 |
| ATOM | 474 | NE | ARG | 52 | 80.371 | 52.836 | 5.333 | 1.00 | 30.55 | A_13 |
| ATOM | 476 | CZ | ARG | 52 | 80.489 | 54.074 | 5.795 | 1.00 | 24.06 | A_13 |

FIG. 5A-5

```
ATOM    477  NH1 ARG    52      81.661  54.508   6.257  1.00 21.24      A_13
ATOM    480  NH2 ARG    52      79.421  54.862   5.829  1.00 27.78      A_13
ATOM    483  C   ARG    52      81.980  49.620   1.540  1.00 30.22      A_13
ATOM    484  O   ARG    52      82.782  50.269   0.859  1.00 16.27      A_13
ATOM    485  N   LEU    53      80.730  49.372   1.161  1.00 21.07      A_13
ATOM    487  CA  LEU    53      80.159  49.914  -0.062  1.00 15.73      A_13
ATOM    488  CB  LEU    53      79.435  48.831  -0.868  1.00 11.53      A_13
ATOM    489  CG  LEU    53      80.304  47.770  -1.530  1.00 10.00      A_13
ATOM    490  CD1 LEU    53      79.429  46.790  -2.296  1.00 13.21      A_13
ATOM    491  CD2 LEU    53      81.280  48.443  -2.448  1.00 12.78      A_13
ATOM    492  C   LEU    53      79.149  50.932   0.421  1.00 10.00      A_13
ATOM    493  O   LEU    53      78.463  50.713   1.411  1.00 13.62      A_13
ATOM    494  N   HIS    54      79.043  52.041  -0.283  1.00 15.73      A_13
ATOM    496  CA  HIS    54      78.102  53.065   0.126  1.00 12.47      A_13
ATOM    497  CB  HIS    54      78.765  54.435   0.011  1.00 15.18      A_13
ATOM    498  CG  HIS    54      79.967  54.589   0.884  1.00 21.27      A_13
ATOM    499  CD2 HIS    54      81.207  54.056   0.798  1.00 25.30      A_13
ATOM    500  ND1 HIS    54      79.951  55.338   2.043  1.00 16.48      A_13
ATOM    502  CE1 HIS    54      81.127  55.255   2.633  1.00 21.62      A_13
ATOM    503  NE2 HIS    54      81.910  54.482   1.899  1.00 29.91      A_13
ATOM    505  C   HIS    54      76.796  53.044  -0.664  1.00 15.50      A_13
ATOM    506  O   HIS    54      75.914  53.849  -0.403  1.00 21.80      A_13
ATOM    507  N   ASP    55      76.707  52.178  -1.671  1.00 18.31      A_13
ATOM    509  CA  ASP    55      75.509  52.077  -2.502  1.00 17.23      A_13
ATOM    510  CB  ASP    55      75.645  52.928  -3.773  1.00 19.94      A_13
ATOM    511  CG  ASP    55      75.864  54.393  -3.495  1.00 26.81      A_13
ATOM    512  OD1 ASP    55      75.059  54.991  -2.741  1.00 35.97      A_13
ATOM    513  OD2 ASP    55      76.839  54.948  -4.058  1.00 25.09      A_13
ATOM    514  C   ASP    55      75.343  50.645  -2.970  1.00 21.50      A_13
ATOM    515  O   ASP    55      76.286  49.862  -2.929  1.00 17.45      A_13
ATOM    516  N   GLY    56      74.160  50.337  -3.489  1.00 10.31      A_13
ATOM    518  CA  GLY    56      73.897  49.014  -4.014  1.00 13.67      A_13
ATOM    519  C   GLY    56      73.842  47.869  -3.030  1.00 17.61      A_13
ATOM    520  O   GLY    56      73.683  48.065  -1.825  1.00 12.57      A_13
ATOM    521  N   ILE    57      73.943  46.653  -3.560  1.00 22.27      A_13
ATOM    523  CA  ILE    57      73.895  45.460  -2.737  1.00 11.39      A_13
ATOM    524  CB  ILE    57      72.941  44.391  -3.347  1.00 22.87      A_13
ATOM    525  CG2 ILE    57      73.365  42.995  -2.955  1.00 22.98      A_13
ATOM    526  CG1 ILE    57      71.522  44.582  -2.787  1.00 30.87      A_13
ATOM    527  CD1 ILE    57      71.002  46.022  -2.796  1.00 28.15      A_13
ATOM    528  C   ILE    57      75.289  44.919  -2.446  1.00 22.32      A_13
ATOM    529  O   ILE    57      76.140  44.849  -3.332  1.00 25.00      A_13
ATOM    530  N   ALA    58      75.517  44.631  -1.168  1.00 25.02      A_13
ATOM    532  CA  ALA    58      76.773  44.105  -0.669  1.00 15.45      A_13
ATOM    533  CB  ALA    58      77.366  45.060   0.358  1.00 11.62      A_13
ATOM    534  C   ALA    58      76.438  42.780  -0.006  1.00 12.08      A_13
ATOM    535  O   ALA    58      75.289  42.521   0.307  1.00 13.30      A_13
ATOM    536  N   ASP    59      77.449  41.968   0.247  1.00 14.79      A_13
ATOM    538  CA  ASP    59      77.245  40.675   0.880  1.00 18.50      A_13
ATOM    539  CB  ASP    59      78.608  39.974   1.093  1.00 10.83      A_13
ATOM    540  CG  ASP    59      79.425  39.858  -0.210  1.00 23.35      A_13
ATOM    541  OD1 ASP    59      80.598  40.266  -0.236  1.00 17.98      A_13
ATOM    542  OD2 ASP    59      78.896  39.379  -1.230  1.00 16.89      A_13
ATOM    543  C   ASP    59      76.480  40.806   2.200  1.00 13.69      A_13
ATOM    544  O   ASP    59      75.402  40.227   2.380  1.00 15.93      A_13
ATOM    545  N   ILE    60      77.025  41.596   3.109  1.00 13.15      A_13
ATOM    547  CA  ILE    60      76.422  41.800   4.412  1.00 12.20      A_13
ATOM    548  CB  ILE    60      77.500  41.695   5.508  1.00 12.12      A_13
ATOM    549  CG2 ILE    60      76.921  42.060   6.864  1.00 19.27      A_13
ATOM    550  CG1 ILE    60      78.118  40.287   5.481  1.00 10.00      A_13
ATOM    551  CD1 ILE    60      79.330  40.120   6.360  1.00 10.00      A_13
ATOM    552  C   ILE    60      75.743  43.164   4.456  1.00 17.78      A_13
ATOM    553  O   ILE    60      76.410  44.193   4.478  1.00 18.65      A_13
ATOM    554  N   MET    61      74.416  43.168   4.431  1.00 12.54      A_13
ATOM    556  CA  MET    61      73.640  44.416   4.476  1.00 12.86      A_13
ATOM    557  CB  MET    61      72.385  44.314   3.604  1.00 18.16      A_13
ATOM    558  CG  MET    61      72.634  43.979   2.141  1.00 10.00      A_13
ATOM    559  SD  MET    61      73.374  45.314   1.251  1.00 10.69      A_13
ATOM    560  CE  MET    61      71.836  46.299   0.764  1.00 10.00      A_13
ATOM    561  C   MET    61      73.239  44.666   5.921  1.00 10.15      A_13
ATOM    562  O   MET    61      72.584  43.838   6.547  1.00 18.13      A_13
ATOM    563  N   ILE    62      73.706  45.784   6.456  1.00 15.60      A_13
ATOM    565  CA  ILE    62      73.452  46.170   7.837  1.00 18.55      A_13
ATOM    566  CB  ILE    62      74.723  46.828   8.437  1.00 10.00      A_13
ATOM    567  CG2 ILE    62      74.498  47.163   9.900  1.00 26.36      A_13
ATOM    568  CG1 ILE    62      75.936  45.897   8.302  1.00 11.04      A_13
ATOM    569  CD1 ILE    62      77.228  46.481   8.891  1.00 10.00      A_13
```

FIG. 5A-6

| | | | | | | | | | |
|---|---|---|---|---|---|---|---|---|---|
| ATOM | 570 | C | ILE | 62 | 72.289 | 47.172 | 7.920 | 1.00 17.99 | A_13 |
| ATOM | 571 | O | ILE | 62 | 72.335 | 48.208 | 7.264 | 1.00 12.72 | A_13 |
| ATOM | 572 | N | SER | 63 | 71.285 | 46.896 | 8.751 | 1.00 10.00 | A_13 |
| ATOM | 574 | CA | SER | 63 | 70.149 | 47.803 | 8.882 | 1.00 12.52 | A_13 |
| ATOM | 575 | CB | SER | 63 | 69.016 | 47.364 | 7.956 | 1.00 13.06 | A_13 |
| ATOM | 576 | OG | SER | 63 | 68.448 | 46.146 | 8.415 | 1.00 27.90 | A_13 |
| ATOM | 578 | C | SER | 63 | 69.625 | 47.854 | 10.314 | 1.00 13.14 | A_13 |
| ATOM | 579 | O | SER | 63 | 69.869 | 46.951 | 11.101 | 1.00 22.10 | A_13 |
| ATOM | 580 | N | PHE | 64 | 68.919 | 48.932 | 10.640 | 1.00 21.17 | A_13 |
| ATOM | 582 | CA | PHE | 64 | 68.317 | 49.139 | 11.954 | 1.00 22.01 | A_13 |
| ATOM | 583 | CB | PHE | 64 | 68.777 | 50.468 | 12.574 | 1.00 10.98 | A_13 |
| ATOM | 584 | CG | PHE | 64 | 70.189 | 50.448 | 13.092 | 1.00 10.00 | A_13 |
| ATOM | 585 | CD1 | PHE | 64 | 70.473 | 49.885 | 14.322 | 1.00 10.00 | A_13 |
| ATOM | 586 | CD2 | PHE | 64 | 71.229 | 51.016 | 12.357 | 1.00 16.56 | A_13 |
| ATOM | 587 | CE1 | PHE | 64 | 71.777 | 49.885 | 14.825 | 1.00 10.00 | A_13 |
| ATOM | 588 | CE2 | PHE | 64 | 72.540 | 51.025 | 12.846 | 1.00 10.00 | A_13 |
| ATOM | 589 | CZ | PHE | 64 | 72.812 | 50.459 | 14.081 | 1.00 18.83 | A_13 |
| ATOM | 590 | C | PHE | 64 | 66.825 | 49.207 | 11.675 | 1.00 22.55 | A_13 |
| ATOM | 591 | O | PHE | 64 | 66.405 | 49.940 | 10.779 | 1.00 19.49 | A_13 |
| ATOM | 592 | N | GLY | 65 | 66.031 | 48.485 | 12.453 | 1.00 13.69 | A_13 |
| ATOM | 594 | CA | GLY | 65 | 64.593 | 48.491 | 12.238 | 1.00 10.70 | A_13 |
| ATOM | 595 | C | GLY | 65 | 63.894 | 48.138 | 13.521 | 1.00 12.62 | A_13 |
| ATOM | 596 | O | GLY | 65 | 64.559 | 47.777 | 14.491 | 1.00 18.29 | A_13 |
| ATOM | 597 | N | ILE | 66 | 62.577 | 48.309 | 13.565 | 1.00 13.69 | A_13 |
| ATOM | 599 | CA | ILE | 66 | 61.803 | 47.968 | 14.760 | 1.00 21.58 | A_13 |
| ATOM | 600 | CB | ILE | 66 | 61.227 | 49.228 | 15.503 | 1.00 30.51 | A_13 |
| ATOM | 601 | CG2 | ILE | 66 | 62.351 | 50.110 | 16.025 | 1.00 10.43 | A_13 |
| ATOM | 602 | CG1 | ILE | 66 | 60.332 | 50.062 | 14.586 | 1.00 14.56 | A_13 |
| ATOM | 603 | CD1 | ILE | 66 | 59.587 | 51.149 | 15.333 | 1.00 16.94 | A_13 |
| ATOM | 604 | C | ILE | 66 | 60.662 | 47.030 | 14.361 | 1.00 10.81 | A_13 |
| ATOM | 605 | O | ILE | 66 | 60.311 | 46.962 | 13.188 | 1.00 10.00 | A_13 |
| ATOM | 606 | N | LYS | 67 | 60.143 | 46.271 | 15.330 | 1.00 10.00 | A_13 |
| ATOM | 608 | CA | LYS | 67 | 59.036 | 45.327 | 15.103 | 1.00 10.23 | A_13 |
| ATOM | 609 | CB | LYS | 67 | 57.689 | 46.042 | 15.268 | 1.00 10.29 | A_13 |
| ATOM | 610 | CG | LYS | 67 | 57.584 | 46.895 | 16.510 | 1.00 14.63 | A_13 |
| ATOM | 611 | CD | LYS | 67 | 57.646 | 46.056 | 17.774 | 1.00 14.94 | A_13 |
| ATOM | 612 | CE | LYS | 67 | 57.382 | 46.923 | 18.986 | 1.00 22.99 | A_13 |
| ATOM | 613 | NZ | LYS | 67 | 57.480 | 46.174 | 20.258 | 1.00 28.27 | A_13 |
| ATOM | 617 | C | LYS | 67 | 59.113 | 44.633 | 13.726 | 1.00 17.91 | A_13 |
| ATOM | 618 | O | LYS | 67 | 60.167 | 44.106 | 13.366 | 1.00 24.01 | A_13 |
| ATOM | 619 | N | GLU | 68 | 58.027 | 44.690 | 12.949 | 1.00 12.72 | A_13 |
| ATOM | 621 | CA | GLU | 68 | 57.960 | 44.067 | 11.624 | 1.00 16.06 | A_13 |
| ATOM | 622 | CB | GLU | 68 | 56.505 | 44.019 | 11.128 | 1.00 26.89 | A_13 |
| ATOM | 623 | CG | GLU | 68 | 55.566 | 43.258 | 12.087 | 1.00 36.97 | A_13 |
| ATOM | 624 | CD | GLU | 68 | 54.217 | 43.973 | 12.381 | 1.00 41.61 | A_13 |
| ATOM | 625 | OE1 | GLU | 68 | 53.289 | 43.921 | 11.537 | 1.00 17.31 | A_13 |
| ATOM | 626 | OE2 | GLU | 68 | 54.074 | 44.561 | 13.485 | 1.00 26.72 | A_13 |
| ATOM | 627 | C | GLU | 68 | 58.823 | 44.911 | 10.705 | 1.00 22.50 | A_13 |
| ATOM | 628 | O | GLU | 68 | 58.587 | 46.093 | 10.532 | 1.00 20.64 | A_13 |
| ATOM | 629 | N | HIS | 69 | 59.848 | 44.315 | 10.120 | 1.00 16.43 | A_13 |
| ATOM | 631 | CA | HIS | 69 | 60.732 | 45.102 | 9.283 | 1.00 13.69 | A_13 |
| ATOM | 632 | CB | HIS | 69 | 61.930 | 45.603 | 10.103 | 1.00 10.97 | A_13 |
| ATOM | 633 | CG | HIS | 69 | 62.786 | 44.502 | 10.643 | 1.00 24.02 | A_13 |
| ATOM | 634 | CD2 | HIS | 69 | 63.873 | 43.876 | 10.133 | 1.00 10.00 | A_13 |
| ATOM | 635 | ND1 | HIS | 69 | 62.512 | 43.876 | 11.839 | 1.00 17.68 | A_13 |
| ATOM | 637 | CE1 | HIS | 69 | 63.384 | 42.912 | 12.041 | 1.00 12.53 | A_13 |
| ATOM | 638 | NE2 | HIS | 69 | 64.228 | 42.888 | 11.020 | 1.00 10.00 | A_13 |
| ATOM | 639 | C | HIS | 69 | 61.214 | 44.469 | 7.983 | 1.00 21.28 | A_13 |
| ATOM | 640 | O | HIS | 69 | 62.314 | 44.780 | 7.529 | 1.00 18.74 | A_13 |
| ATOM | 641 | N | GLY | 70 | 60.451 | 43.537 | 7.411 | 1.00 13.11 | A_13 |
| ATOM | 643 | CA | GLY | 70 | 60.832 | 42.968 | 6.127 | 1.00 10.00 | A_13 |
| ATOM | 644 | C | GLY | 70 | 61.262 | 41.533 | 5.936 | 1.00 10.00 | A_13 |
| ATOM | 645 | O | GLY | 70 | 61.523 | 41.125 | 4.794 | 1.00 15.12 | A_13 |
| ATOM | 646 | N | ASP | 71 | 61.412 | 40.768 | 7.012 | 1.00 19.99 | A_13 |
| ATOM | 648 | CA | ASP | 71 | 61.842 | 39.381 | 6.862 | 1.00 19.99 | A_13 |
| ATOM | 649 | CB | ASP | 71 | 63.332 | 39.223 | 7.218 | 1.00 10.00 | A_13 |
| ATOM | 650 | CG | ASP | 71 | 63.672 | 39.752 | 8.592 | 1.00 23.52 | A_13 |
| ATOM | 651 | OD1 | ASP | 71 | 64.846 | 40.110 | 8.803 | 1.00 13.38 | A_13 |
| ATOM | 652 | OD2 | ASP | 71 | 62.774 | 39.812 | 9.464 | 1.00 12.94 | A_13 |
| ATOM | 653 | C | ASP | 71 | 60.998 | 38.377 | 7.632 | 1.00 22.07 | A_13 |
| ATOM | 654 | O | ASP | 71 | 61.319 | 37.190 | 7.649 | 1.00 24.45 | A_13 |
| ATOM | 655 | N | PHE | 72 | 59.946 | 38.865 | 8.292 | 1.00 14.15 | A_13 |
| ATOM | 657 | CA | PHE | 72 | 59.040 | 38.035 | 9.094 | 1.00 10.00 | A_13 |
| ATOM | 658 | CB | PHE | 72 | 58.410 | 36.905 | 8.272 | 1.00 10.00 | A_13 |
| ATOM | 659 | CG | PHE | 72 | 57.360 | 37.387 | 7.332 | 1.00 10.00 | A_13 |
| ATOM | 660 | CD1 | PHE | 72 | 56.115 | 37.773 | 7.815 | 1.00 23.01 | A_13 |
| ATOM | 661 | CD2 | PHE | 72 | 57.624 | 37.507 | 5.973 | 1.00 12.52 | A_13 |

FIG. 5A-7

```
ATOM    662  CE1  PHE  72    55.144  38.290   6.950  1.00 18.99    A_13
ATOM    663  CE2  PHE  72    56.662  38.023   5.091  1.00 13.37    A_13
ATOM    664  CZ   PHE  72    55.420  38.413   5.576  1.00 22.50    A_13
ATOM    665  C    PHE  72    59.634  37.523  10.392  1.00 16.31    A_13
ATOM    666  O    PHE  72    59.111  36.596  11.021  1.00 15.64    A_13
ATOM    667  N    TYR  73    60.737  38.141  10.793  1.00 18.10    A_13
ATOM    669  CA   TYR  73    61.407  37.827  12.046  1.00 14.01    A_13
ATOM    670  CB   TYR  73    62.845  37.331  11.803  1.00 21.08    A_13
ATOM    671  CG   TYR  73    62.915  35.965  11.138  1.00 22.48    A_13
ATOM    672  CD1  TYR  73    63.579  35.788   9.923  1.00 30.23    A_13
ATOM    673  CE1  TYR  73    63.615  34.538   9.291  1.00 24.04    A_13
ATOM    674  CD2  TYR  73    62.288  34.856  11.710  1.00 19.23    A_13
ATOM    675  CE2  TYR  73    62.320  33.606  11.083  1.00 29.35    A_13
ATOM    676  CZ   TYR  73    62.984  33.460   9.875  1.00 12.50    A_13
ATOM    677  OH   TYR  73    63.018  32.246   9.241  1.00 17.89    A_13
ATOM    679  C    TYR  73    61.360  39.203  12.721  1.00 22.00    A_13
ATOM    680  O    TYR  73    62.365  39.919  12.819  1.00 10.93    A_13
ATOM    681  N    PRO  74    60.175  39.570  13.221  1.00 19.94    A_13
ATOM    682  CD   PRO  74    58.969  38.723  13.278  1.00 15.69    A_13
ATOM    683  CA   PRO  74    59.934  40.843  13.886  1.00 16.75    A_13
ATOM    684  CB   PRO  74    58.417  40.836  14.067  1.00 17.27    A_13
ATOM    685  CG   PRO  74    58.131  39.407  14.335  1.00 16.24    A_13
ATOM    686  C    PRO  74    60.640  41.037  15.216  1.00 17.39    A_13
ATOM    687  O    PRO  74    60.779  40.105  16.023  1.00 10.00    A_13
ATOM    688  N    PHE  75    61.098  42.264  15.431  1.00 10.00    A_13
ATOM    690  CA   PHE  75    61.743  42.618  16.675  1.00 16.45    A_13
ATOM    691  CB   PHE  75    62.613  43.865  16.512  1.00 20.71    A_13
ATOM    692  CG   PHE  75    63.931  43.590  15.841  1.00 23.32    A_13
ATOM    693  CD1  PHE  75    64.694  42.482  16.200  1.00 12.03    A_13
ATOM    694  CD2  PHE  75    64.405  44.420  14.842  1.00 22.30    A_13
ATOM    695  CE1  PHE  75    65.905  42.214  15.572  1.00 17.64    A_13
ATOM    696  CE2  PHE  75    65.622  44.148  14.208  1.00 15.43    A_13
ATOM    697  CZ   PHE  75    66.367  43.044  14.576  1.00 10.00    A_13
ATOM    698  C    PHE  75    60.632  42.784  17.707  1.00 25.73    A_13
ATOM    699  O    PHE  75    59.443  42.778  17.370  1.00 18.57    A_13
ATOM    700  N    ASP  76    61.009  43.002  18.952  1.00 20.50    A_13
ATOM    702  CA   ASP  76    60.023  43.049  20.006  1.00 13.89    A_13
ATOM    703  CB   ASP  76    60.241  41.805  20.873  1.00 20.69    A_13
ATOM    704  CG   ASP  76    61.672  41.685  21.378  1.00 22.52    A_13
ATOM    705  OD1  ASP  76    61.947  40.771  22.174  1.00 20.06    A_13
ATOM    706  OD2  ASP  76    62.525  42.506  20.998  1.00 10.69    A_13
ATOM    707  C    ASP  76    59.971  44.277  20.900  1.00 25.20    A_13
ATOM    708  O    ASP  76    59.397  44.207  21.986  1.00 29.52    A_13
ATOM    709  N    GLY  77    60.585  45.379  20.488  1.00 10.00    A_13
ATOM    711  CA   GLY  77    60.575  46.553  21.334  1.00 10.00    A_13
ATOM    712  C    GLY  77    61.769  46.514  22.266  1.00 10.00    A_13
ATOM    713  O    GLY  77    62.735  45.797  21.987  1.00 18.49    A_13
ATOM    714  N    PRO  78    61.785  47.344  23.322  1.00 16.07    A_13
ATOM    715  CD   PRO  78    60.790  48.426  23.505  1.00 15.88    A_13
ATOM    716  CA   PRO  78    62.855  47.439  24.330  1.00 16.23    A_13
ATOM    717  CB   PRO  78    62.261  48.391  25.363  1.00 22.96    A_13
ATOM    718  CG   PRO  78    61.470  49.349  24.501  1.00 22.37    A_13
ATOM    719  C    PRO  78    63.150  46.090  24.969  1.00 25.32    A_13
ATOM    720  O    PRO  78    62.227  45.356  25.272  1.00 20.04    A_13
ATOM    721  N    SER  79    64.432  45.750  25.099  1.00 20.93    A_13
ATOM    723  CA   SER  79    64.878  44.478  25.689  1.00 20.51    A_13
ATOM    724  CB   SER  79    64.364  44.311  27.131  1.00 23.69    A_13
ATOM    725  OG   SER  79    65.028  45.211  28.006  1.00 33.37    A_13
ATOM    727  C    SER  79    64.557  43.248  24.863  1.00 20.39    A_13
ATOM    728  O    SER  79    64.124  43.362  23.708  1.00 17.27    A_13
ATOM    729  N    GLY  80    64.825  42.071  25.415  1.00 13.38    A_13
ATOM    731  CA   GLY  80    64.564  40.850  24.678  1.00 10.11    A_13
ATOM    732  C    GLY  80    65.471  40.808  23.458  1.00 13.15    A_13
ATOM    733  O    GLY  80    66.614  41.251  23.538  1.00 31.80    A_13
ATOM    734  N    LEU  81    64.939  40.393  22.310  1.00 29.05    A_13
ATOM    736  CA   LEU  81    65.720  40.317  21.078  1.00 29.63    A_13
ATOM    737  CB   LEU  81    64.789  40.033  19.905  1.00 19.67    A_13
ATOM    738  CG   LEU  81    65.121  38.872  18.971  1.00 21.79    A_13
ATOM    739  CD1  LEU  81    64.215  38.980  17.773  1.00 23.87    A_13
ATOM    740  CD2  LEU  81    66.590  38.918  18.518  1.00 22.09    A_13
ATOM    741  C    LEU  81    66.442  41.649  20.835  1.00 19.25    A_13
ATOM    742  O    LEU  81    65.808  42.700  20.872  1.00 14.95    A_13
ATOM    743  N    LEU  82    67.760  41.599  20.657  1.00 25.03    A_13
ATOM    745  CA   LEU  82    68.573  42.795  20.421  1.00 27.35    A_13
ATOM    746  CB   LEU  82    69.868  42.747  21.244  1.00 12.74    A_13
ATOM    747  CG   LEU  82    69.802  42.748  22.773  1.00 16.50    A_13
ATOM    748  CD1  LEU  82    68.590  43.520  23.263  1.00 17.99    A_13
```

FIG. 5A-8

```
ATOM   749  CD2  LEU  82   69.744  41.343  23.279  1.00  13.28  A_13
ATOM   750  C    LEU  82   68.938  42.945  18.949  1.00  24.79  A_13
ATOM   751  O    LEU  82   68.812  44.039  18.363  1.00  14.36  A_13
ATOM   752  N    ALA  83   69.387  41.839  18.359  1.00  21.15  A_13
ATOM   754  CA   ALA  83   69.790  41.819  16.961  1.00  15.64  A_13
ATOM   755  CB   ALA  83   71.180  42.410  16.820  1.00  15.74  A_13
ATOM   756  C    ALA  83   69.806  40.400  16.444  1.00  19.37  A_13
ATOM   757  O    ALA  83   69.864  39.458  17.227  1.00  20.42  A_13
ATOM   758  N    HIS  84   69.746  40.252  15.126  1.00  10.72  A_13
ATOM   760  CA   HIS  84   69.808  38.939  14.502  1.00  20.51  A_13
ATOM   761  CB   HIS  84   68.454  38.185  14.476  1.00  12.34  A_13
ATOM   762  CG   HIS  84   67.361  38.849  13.679  1.00  24.79  A_13
ATOM   763  CD2  HIS  84   67.381  39.489  12.488  1.00  10.00  A_13
ATOM   764  ND1  HIS  84   66.052  38.869  14.104  1.00  13.50  A_13
ATOM   766  CE1  HIS  84   65.307  39.497  13.210  1.00  14.37  A_13
ATOM   767  NE2  HIS  84   66.087  39.886  12.220  1.00  15.00  A_13
ATOM   768  C    HIS  84   70.418  39.088  13.130  1.00  22.78  A_13
ATOM   769  O    HIS  84   70.338  40.162  12.532  1.00  10.00  A_13
ATOM   770  N    ALA  85   71.086  38.027  12.685  1.00  13.43  A_13
ATOM   772  CA   ALA  85   71.746  37.983  11.402  1.00  10.00  A_13
ATOM   773  CB   ALA  85   73.234  38.132  11.596  1.00  10.05  A_13
ATOM   774  C    ALA  85   71.426  36.661  10.721  1.00  17.89  A_13
ATOM   775  O    ALA  85   70.900  35.746  11.346  1.00  19.43  A_13
ATOM   776  N    PHE  86   71.697  36.585   9.425  1.00  13.49  A_13
ATOM   778  CA   PHE  86   71.459  35.372   8.651  1.00  12.49  A_13
ATOM   779  CB   PHE  86   70.739  35.728   7.344  1.00  10.00  A_13
ATOM   780  CG   PHE  86   69.348  36.240   7.529  1.00  19.96  A_13
ATOM   781  CD1  PHE  86   68.252  35.434   7.212  1.00  21.89  A_13
ATOM   782  CD2  PHE  86   69.119  37.530   8.003  1.00  10.63  A_13
ATOM   783  CE1  PHE  86   66.946  35.900   7.364  1.00  16.59  A_13
ATOM   784  CE2  PHE  86   67.829  38.009   8.158  1.00  19.06  A_13
ATOM   785  CZ   PHE  86   66.732  37.194   7.838  1.00  24.79  A_13
ATOM   786  C    PHE  86   72.802  34.721   8.298  1.00  11.05  A_13
ATOM   787  O    PHE  86   73.774  35.435   8.041  1.00  25.56  A_13
ATOM   788  N    PRO  87   72.892  33.375   8.304  1.00  19.41  A_13
ATOM   789  CD   PRO  87   71.876  32.383   8.717  1.00  17.25  A_13
ATOM   790  CA   PRO  87   74.149  32.686   7.956  1.00  29.29  A_13
ATOM   791  CB   PRO  87   73.800  31.198   8.135  1.00  18.88  A_13
ATOM   792  CG   PRO  87   72.329  31.160   7.939  1.00  20.17  A_13
ATOM   793  C    PRO  87   74.562  32.999   6.503  1.00  10.00  A_13
ATOM   794  O    PRO  87   73.728  33.448   5.703  1.00  20.68  A_13
ATOM   795  N    PRO  88   75.814  32.701   6.120  1.00  10.00  A_13
ATOM   796  CD   PRO  88   76.796  31.854   6.831  1.00  19.58  A_13
ATOM   797  CA   PRO  88   76.280  32.977   4.756  1.00  12.43  A_13
ATOM   798  CB   PRO  88   77.600  32.201   4.676  1.00  18.69  A_13
ATOM   799  CG   PRO  88   78.073  32.163   6.098  1.00  18.48  A_13
ATOM   800  C    PRO  88   75.304  32.510   3.672  1.00  24.39  A_13
ATOM   801  O    PRO  88   74.596  31.522   3.854  1.00  16.92  A_13
ATOM   802  N    GLY  89   75.266  33.230   2.560  1.00  10.73  A_13
ATOM   804  CA   GLY  89   74.386  32.868   1.471  1.00  10.00  A_13
ATOM   805  C    GLY  89   73.960  34.127   0.772  1.00  10.94  A_13
ATOM   806  O    GLY  89   74.143  35.218   1.307  1.00  19.86  A_13
ATOM   807  N    PRO  90   73.390  34.019  -0.432  1.00  26.31  A_13
ATOM   808  CD   PRO  90   73.090  32.792  -1.192  1.00  18.46  A_13
ATOM   809  CA   PRO  90   72.960  35.212  -1.163  1.00  25.07  A_13
ATOM   810  CB   PRO  90   72.670  34.651  -2.556  1.00  15.47  A_13
ATOM   811  CG   PRO  90   72.108  33.289  -2.236  1.00  24.63  A_13
ATOM   812  C    PRO  90   71.726  35.879  -0.543  1.00  20.41  A_13
ATOM   813  O    PRO  90   71.176  35.390   0.442  1.00  17.00  A_13
ATOM   814  N    ASN  91   71.303  37.000  -1.125  1.00  18.43  A_13
ATOM   816  CA   ASN  91   70.127  37.721  -0.653  1.00  14.03  A_13
ATOM   817  CB   ASN  91   68.863  36.932  -0.999  1.00  15.26  A_13
ATOM   818  CG   ASN  91   68.860  36.430  -2.439  1.00  36.74  A_13
ATOM   819  OD1  ASN  91   68.497  35.282  -2.701  1.00  29.56  A_13
ATOM   820  ND2  ASN  91   69.265  37.286  -3.376  1.00  27.03  A_13
ATOM   823  C    ASN  91   70.226  37.986   0.849  1.00  24.66  A_13
ATOM   824  O    ASN  91   71.257  38.479   1.313  1.00  17.43  A_13
ATOM   825  N    TYR  92   69.198  37.632   1.622  1.00  17.69  A_13
ATOM   827  CA   TYR  92   69.233  37.876   3.061  1.00  10.17  A_13
ATOM   828  CB   TYR  92   67.942  37.428   3.744  1.00  16.78  A_13
ATOM   829  CG   TYR  92   66.786  38.364   3.523  1.00  26.17  A_13
ATOM   830  CD1  TYR  92   66.015  38.803   4.581  1.00  17.79  A_13
ATOM   831  CE1  TYR  92   64.947  39.678   4.380  1.00  29.60  A_13
ATOM   832  CD2  TYR  92   66.467  38.818   2.250  1.00  25.90  A_13
ATOM   833  CE2  TYR  92   65.406  39.691   2.040  1.00  30.60  A_13
ATOM   834  CZ   TYR  92   64.647  40.117   3.107  1.00  12.31  A_13
ATOM   835  OH   TYR  92   63.575  40.967   2.886  1.00  26.07  A_13
```

FIG. 5A-9

| ATOM | 837 | C   | TYR | 92  | 70.427 | 37.245 | 3.763  | 1.00 | 11.94 | A_13 |
|------|-----|-----|-----|-----|--------|--------|--------|------|-------|------|
| ATOM | 838 | O   | TYR | 92  | 70.752 | 37.617 | 4.882  | 1.00 | 17.58 | A_13 |
| ATOM | 839 | N   | GLY | 93  | 71.095 | 36.311 | 3.097  | 1.00 | 24.67 | A_13 |
| ATOM | 841 | CA  | GLY | 93  | 72.250 | 35.666 | 3.691  | 1.00 | 18.05 | A_13 |
| ATOM | 842 | C   | GLY | 93  | 73.295 | 36.681 | 4.116  | 1.00 | 10.00 | A_13 |
| ATOM | 843 | O   | GLY | 93  | 73.573 | 37.656 | 3.391  | 1.00 | 10.13 | A_13 |
| ATOM | 844 | N   | GLY | 94  | 73.812 | 36.495 | 5.328  | 1.00 | 12.44 | A_13 |
| ATOM | 846 | CA  | GLY | 94  | 74.827 | 37.372 | 5.872  | 1.00 | 10.00 | A_13 |
| ATOM | 847 | C   | GLY | 94  | 74.358 | 38.694 | 6.456  | 1.00 | 17.29 | A_13 |
| ATOM | 848 | O   | GLY | 94  | 75.052 | 39.271 | 7.284  | 1.00 | 14.53 | A_13 |
| ATOM | 849 | N   | ASP | 95  | 73.221 | 39.206 | 5.993  | 1.00 | 10.00 | A_13 |
| ATOM | 851 | CA  | ASP | 95  | 72.689 | 40.485 | 6.472  | 1.00 | 16.35 | A_13 |
| ATOM | 852 | CB  | ASP | 95  | 71.332 | 40.777 | 5.814  | 1.00 | 10.00 | A_13 |
| ATOM | 853 | CG  | ASP | 95  | 71.421 | 40.904 | 4.309  | 1.00 | 14.54 | A_13 |
| ATOM | 854 | OD1 | ASP | 95  | 70.406 | 41.256 | 3.673  | 1.00 | 11.86 | A_13 |
| ATOM | 855 | OD2 | ASP | 95  | 72.502 | 40.647 | 3.753  | 1.00 | 15.39 | A_13 |
| ATOM | 856 | C   | ASP | 95  | 72.548 | 40.523 | 7.994  | 1.00 | 22.31 | A_13 |
| ATOM | 857 | O   | ASP | 95  | 72.279 | 39.497 | 8.635  | 1.00 | 10.88 | A_13 |
| ATOM | 858 | N   | ALA | 96  | 72.703 | 41.711 | 8.566  | 1.00 | 18.45 | A_13 |
| ATOM | 860 | CA  | ALA | 96  | 72.609 | 41.877 | 10.011 | 1.00 | 15.08 | A_13 |
| ATOM | 861 | CB  | ALA | 96  | 73.982 | 42.244 | 10.587 | 1.00 | 19.20 | A_13 |
| ATOM | 862 | C   | ALA | 96  | 71.587 | 42.961 | 10.345 | 1.00 | 14.91 | A_13 |
| ATOM | 863 | O   | ALA | 96  | 71.702 | 44.092 | 9.876  | 1.00 | 10.00 | A_13 |
| ATOM | 864 | N   | HIS | 97  | 70.635 | 42.646 | 11.215 | 1.00 | 14.01 | A_13 |
| ATOM | 866 | CA  | HIS | 97  | 69.599 | 43.620 | 11.581 | 1.00 | 11.35 | A_13 |
| ATOM | 867 | CB  | HIS | 97  | 68.207 | 43.083 | 11.203 | 1.00 | 20.32 | A_13 |
| ATOM | 868 | CG  | HIS | 97  | 68.027 | 42.786 | 9.742  | 1.00 | 15.00 | A_13 |
| ATOM | 869 | CD2 | HIS | 97  | 68.734 | 43.186 | 8.654  | 1.00 | 10.00 | A_13 |
| ATOM | 870 | ND1 | HIS | 97  | 67.014 | 41.978 | 9.257  | 1.00 | 14.03 | A_13 |
| ATOM | 871 | CE1 | HIS | 97  | 67.108 | 41.895 | 7.936  | 1.00 | 10.00 | A_13 |
| ATOM | 872 | NE2 | HIS | 97  | 68.142 | 42.618 | 7.552  | 1.00 | 17.10 | A_13 |
| ATOM | 874 | C   | HIS | 97  | 69.650 | 43.952 | 13.078 | 1.00 | 13.37 | A_13 |
| ATOM | 875 | O   | HIS | 97  | 69.736 | 43.055 | 13.908 | 1.00 | 13.48 | A_13 |
| ATOM | 876 | N   | PHE | 98  | 69.596 | 45.237 | 13.423 | 1.00 | 21.01 | A_13 |
| ATOM | 878 | CA  | PHE | 98  | 69.634 | 45.668 | 14.823 | 1.00 | 11.27 | A_13 |
| ATOM | 879 | CB  | PHE | 98  | 70.817 | 46.615 | 15.055 | 1.00 | 10.00 | A_13 |
| ATOM | 880 | CG  | PHE | 98  | 72.138 | 46.011 | 14.703 | 1.00 | 20.49 | A_13 |
| ATOM | 881 | CD1 | PHE | 98  | 72.984 | 45.524 | 15.707 | 1.00 | 17.49 | A_13 |
| ATOM | 882 | CD2 | PHE | 98  | 72.506 | 45.853 | 13.365 | 1.00 | 13.51 | A_13 |
| ATOM | 883 | CE1 | PHE | 98  | 74.171 | 44.888 | 15.382 | 1.00 | 20.00 | A_13 |
| ATOM | 884 | CE2 | PHE | 98  | 73.693 | 45.215 | 13.024 | 1.00 | 10.00 | A_13 |
| ATOM | 885 | CZ  | PHE | 98  | 74.527 | 44.728 | 14.029 | 1.00 | 10.00 | A_13 |
| ATOM | 886 | C   | PHE | 98  | 68.336 | 46.336 | 15.245 | 1.00 | 25.38 | A_13 |
| ATOM | 887 | O   | PHE | 98  | 67.815 | 47.218 | 14.552 | 1.00 | 10.00 | A_13 |
| ATOM | 888 | N   | ASP | 99  | 67.817 | 45.924 | 16.394 | 1.00 | 21.68 | A_13 |
| ATOM | 890 | CA  | ASP | 99  | 66.567 | 46.476 | 16.886 | 1.00 | 10.00 | A_13 |
| ATOM | 891 | CB  | ASP | 99  | 66.039 | 45.604 | 18.010 | 1.00 | 10.00 | A_13 |
| ATOM | 892 | CG  | ASP | 99  | 64.648 | 45.998 | 18.473 | 1.00 | 14.00 | A_13 |
| ATOM | 893 | OD1 | ASP | 99  | 64.104 | 45.272 | 19.329 | 1.00 | 15.19 | A_13 |
| ATOM | 894 | OD2 | ASP | 99  | 64.089 | 47.011 | 18.001 | 1.00 | 17.01 | A_13 |
| ATOM | 895 | C   | ASP | 99  | 66.817 | 47.871 | 17.391 | 1.00 | 13.06 | A_13 |
| ATOM | 896 | O   | ASP | 99  | 67.528 | 48.056 | 18.374 | 1.00 | 10.00 | A_13 |
| ATOM | 897 | N   | ASP | 100 | 66.203 | 48.856 | 16.746 | 1.00 | 15.56 | A_13 |
| ATOM | 899 | CA  | ASP | 100 | 66.397 | 50.232 | 17.177 | 1.00 | 18.23 | A_13 |
| ATOM | 900 | CB  | ASP | 100 | 66.121 | 51.228 | 16.041 | 1.00 | 15.05 | A_13 |
| ATOM | 901 | CG  | ASP | 100 | 67.275 | 52.180 | 15.838 | 1.00 | 11.67 | A_13 |
| ATOM | 902 | OD1 | ASP | 100 | 67.602 | 52.516 | 14.683 | 1.00 | 21.07 | A_13 |
| ATOM | 903 | OD2 | ASP | 100 | 67.879 | 52.569 | 16.860 | 1.00 | 14.72 | A_13 |
| ATOM | 904 | C   | ASP | 100 | 65.610 | 50.572 | 18.445 | 1.00 | 10.00 | A_13 |
| ATOM | 905 | O   | ASP | 100 | 65.767 | 51.635 | 19.009 | 1.00 | 17.18 | A_13 |
| ATOM | 906 | N   | ASP | 101 | 64.755 | 49.669 | 18.895 | 1.00 | 14.57 | A_13 |
| ATOM | 908 | CA  | ASP | 101 | 64.031 | 49.924 | 20.123 | 1.00 | 17.59 | A_13 |
| ATOM | 909 | CB  | ASP | 101 | 62.769 | 49.051 | 20.236 | 1.00 | 12.50 | A_13 |
| ATOM | 910 | CG  | ASP | 101 | 61.532 | 49.721 | 19.606 | 1.00 | 17.12 | A_13 |
| ATOM | 911 | OD1 | ASP | 101 | 60.599 | 49.023 | 19.179 | 1.00 | 10.39 | A_13 |
| ATOM | 912 | OD2 | ASP | 101 | 61.480 | 50.962 | 19.536 | 1.00 | 18.09 | A_13 |
| ATOM | 913 | C   | ASP | 101 | 64.994 | 49.766 | 21.306 | 1.00 | 19.33 | A_13 |
| ATOM | 914 | O   | ASP | 101 | 64.610 | 49.972 | 22.456 | 1.00 | 10.00 | A_13 |
| ATOM | 915 | N   | GLU | 102 | 66.213 | 49.301 | 21.019 | 1.00 | 16.15 | A_13 |
| ATOM | 917 | CA  | GLU | 102 | 67.267 | 49.194 | 22.044 | 1.00 | 13.43 | A_13 |
| ATOM | 918 | CB  | GLU | 102 | 68.264 | 48.085 | 21.720 | 1.00 | 18.25 | A_13 |
| ATOM | 919 | CG  | GLU | 102 | 67.697 | 46.704 | 21.636 | 1.00 | 10.00 | A_13 |
| ATOM | 920 | CD  | GLU | 102 | 66.650 | 46.467 | 22.672 | 1.00 | 11.18 | A_13 |
| ATOM | 921 | OE1 | GLU | 102 | 66.872 | 46.746 | 23.870 | 1.00 | 16.09 | A_13 |
| ATOM | 922 | OE2 | GLU | 102 | 65.572 | 46.033 | 22.271 | 1.00 | 26.76 | A_13 |
| ATOM | 923 | C   | GLU | 102 | 68.070 | 50.495 | 22.007 | 1.00 | 11.07 | A_13 |
| ATOM | 924 | O   | GLU | 102 | 68.103 | 51.161 | 20.971 | 1.00 | 13.97 | A_13 |

FIG. 5A-10

| | | | | | | | | | | |
|---|---|---|---|---|---|---|---|---|---|---|
| ATOM | 925 | N | THR | 103 | 68.774 | 50.823 | 23.091 | 1.00 | 22.82 | A_13 |
| ATOM | 927 | CA | THR | 103 | 69.606 | 52.034 | 23.102 | 1.00 | 13.45 | A_13 |
| ATOM | 928 | CB | THR | 103 | 69.571 | 52.793 | 24.459 | 1.00 | 20.78 | A_13 |
| ATOM | 929 | OG1 | THR | 103 | 68.236 | 53.228 | 24.745 | 1.00 | 10.69 | A_13 |
| ATOM | 931 | CG2 | THR | 103 | 70.445 | 54.046 | 24.378 | 1.00 | 19.45 | A_13 |
| ATOM | 932 | C | THR | 103 | 71.030 | 51.571 | 22.822 | 1.00 | 12.42 | A_13 |
| ATOM | 933 | O | THR | 103 | 71.639 | 50.896 | 23.642 | 1.00 | 19.81 | A_13 |
| ATOM | 934 | N | TRP | 104 | 71.525 | 51.854 | 21.626 | 1.00 | 10.00 | A_13 |
| ATOM | 936 | CA | TRP | 104 | 72.873 | 51.448 | 21.248 | 1.00 | 13.61 | A_13 |
| ATOM | 937 | CB | TRP | 104 | 72.943 | 51.221 | 19.739 | 1.00 | 29.21 | A_13 |
| ATOM | 938 | CG | TRP | 104 | 71.970 | 50.174 | 19.313 | 1.00 | 21.39 | A_13 |
| ATOM | 939 | CD2 | TRP | 104 | 72.101 | 48.760 | 19.501 | 1.00 | 25.13 | A_13 |
| ATOM | 940 | CE2 | TRP | 104 | 70.937 | 48.156 | 18.964 | 1.00 | 28.84 | A_13 |
| ATOM | 941 | CE3 | TRP | 104 | 73.088 | 47.941 | 20.070 | 1.00 | 13.36 | A_13 |
| ATOM | 942 | CD1 | TRP | 104 | 70.765 | 50.372 | 18.694 | 1.00 | 21.59 | A_13 |
| ATOM | 943 | NE1 | TRP | 104 | 70.139 | 49.163 | 18.484 | 1.00 | 19.91 | A_13 |
| ATOM | 945 | CZ2 | TRP | 104 | 70.738 | 46.768 | 18.977 | 1.00 | 10.00 | A_13 |
| ATOM | 946 | CZ3 | TRP | 104 | 72.888 | 46.568 | 20.084 | 1.00 | 14.54 | A_13 |
| ATOM | 947 | CH2 | TRP | 104 | 71.720 | 45.995 | 19.539 | 1.00 | 11.93 | A_13 |
| ATOM | 948 | C | TRP | 104 | 73.912 | 52.453 | 21.725 | 1.00 | 16.59 | A_13 |
| ATOM | 949 | O | TRP | 104 | 73.707 | 53.671 | 21.642 | 1.00 | 12.90 | A_13 |
| ATOM | 950 | N | THR | 105 | 75.013 | 51.949 | 22.268 | 1.00 | 20.85 | A_13 |
| ATOM | 952 | CA | THR | 105 | 76.040 | 52.831 | 22.794 | 1.00 | 12.38 | A_13 |
| ATOM | 953 | CB | THR | 105 | 75.974 | 52.890 | 24.322 | 1.00 | 14.39 | A_13 |
| ATOM | 954 | OG1 | THR | 105 | 76.345 | 51.609 | 24.849 | 1.00 | 16.42 | A_13 |
| ATOM | 956 | CG2 | THR | 105 | 74.575 | 53.273 | 24.797 | 1.00 | 12.17 | A_13 |
| ATOM | 957 | C | THR | 105 | 77.437 | 52.378 | 22.457 | 1.00 | 10.00 | A_13 |
| ATOM | 958 | O | THR | 105 | 77.644 | 51.261 | 22.012 | 1.00 | 18.98 | A_13 |
| ATOM | 959 | N | SER | 106 | 78.385 | 53.277 | 22.704 | 1.00 | 26.01 | A_13 |
| ATOM | 961 | CA | SER | 106 | 79.809 | 53.043 | 22.502 | 1.00 | 17.80 | A_13 |
| ATOM | 962 | CB | SER | 106 | 80.466 | 54.284 | 21.888 | 1.00 | 20.63 | A_13 |
| ATOM | 963 | OG | SER | 106 | 79.744 | 54.756 | 20.763 | 1.00 | 38.89 | A_13 |
| ATOM | 965 | C | SER | 106 | 80.435 | 52.779 | 23.880 | 1.00 | 34.75 | A_13 |
| ATOM | 966 | O | SER | 106 | 81.652 | 52.884 | 24.042 | 1.00 | 33.01 | A_13 |
| ATOM | 967 | N | SER | 107 | 79.590 | 52.494 | 24.875 | 1.00 | 25.87 | A_13 |
| ATOM | 969 | CA | SER | 107 | 80.032 | 52.221 | 26.240 | 1.00 | 19.68 | A_13 |
| ATOM | 970 | CB | SER | 107 | 80.082 | 53.510 | 27.061 | 1.00 | 23.47 | A_13 |
| ATOM | 971 | OG | SER | 107 | 78.819 | 54.158 | 27.096 | 1.00 | 33.70 | A_13 |
| ATOM | 973 | C | SER | 107 | 79.100 | 51.200 | 26.892 | 1.00 | 13.60 | A_13 |
| ATOM | 974 | O | SER | 107 | 78.460 | 50.418 | 26.193 | 1.00 | 16.40 | A_13 |
| ATOM | 975 | N | SER | 108 | 79.028 | 51.205 | 28.221 | 1.00 | 17.31 | A_13 |
| ATOM | 977 | CA | SER | 108 | 78.188 | 50.259 | 28.949 | 1.00 | 20.12 | A_13 |
| ATOM | 978 | CB | SER | 108 | 78.745 | 50.009 | 30.364 | 1.00 | 22.63 | A_13 |
| ATOM | 979 | OG | SER | 108 | 78.444 | 51.061 | 31.271 | 1.00 | 27.69 | A_13 |
| ATOM | 981 | C | SER | 108 | 76.702 | 50.606 | 29.076 | 1.00 | 19.98 | A_13 |
| ATOM | 982 | O | SER | 108 | 75.921 | 49.785 | 29.562 | 1.00 | 35.96 | A_13 |
| ATOM | 983 | N | LYS | 109 | 76.311 | 51.820 | 28.713 | 1.00 | 16.24 | A_13 |
| ATOM | 985 | CA | LYS | 109 | 74.907 | 52.186 | 28.847 | 1.00 | 11.10 | A_13 |
| ATOM | 986 | CB | LYS | 109 | 74.740 | 53.688 | 28.690 | 1.00 | 12.41 | A_13 |
| ATOM | 987 | CG | LYS | 109 | 73.555 | 54.239 | 29.462 | 1.00 | 32.67 | A_13 |
| ATOM | 988 | CD | LYS | 109 | 73.353 | 55.732 | 29.258 | 1.00 | 25.94 | A_13 |
| ATOM | 989 | CE | LYS | 109 | 74.535 | 56.599 | 29.749 | 1.00 | 25.11 | A_13 |
| ATOM | 990 | NZ | LYS | 109 | 74.225 | 58.070 | 29.636 | 1.00 | 22.70 | A_13 |
| ATOM | 994 | C | LYS | 109 | 74.138 | 51.424 | 27.773 | 1.00 | 21.67 | A_13 |
| ATOM | 995 | O | LYS | 109 | 74.667 | 51.210 | 26.694 | 1.00 | 32.76 | A_13 |
| ATOM | 996 | N | GLY | 110 | 72.932 | 50.955 | 28.081 | 1.00 | 29.60 | A_13 |
| ATOM | 998 | CA | GLY | 110 | 72.156 | 50.206 | 27.096 | 1.00 | 10.31 | A_13 |
| ATOM | 999 | C | GLY | 110 | 72.965 | 49.043 | 26.542 | 1.00 | 20.08 | A_13 |
| ATOM | 1000 | O | GLY | 110 | 73.672 | 48.362 | 27.285 | 1.00 | 11.17 | A_13 |
| ATOM | 1001 | N | TYR | 111 | 72.924 | 48.859 | 25.227 | 1.00 | 12.05 | A_13 |
| ATOM | 1003 | CA | TYR | 111 | 73.665 | 47.791 | 24.583 | 1.00 | 13.45 | A_13 |
| ATOM | 1004 | CB | TYR | 111 | 72.713 | 46.871 | 23.806 | 1.00 | 21.16 | A_13 |
| ATOM | 1005 | CG | TYR | 111 | 71.776 | 46.101 | 24.716 | 1.00 | 12.28 | A_13 |
| ATOM | 1006 | CD1 | TYR | 111 | 70.455 | 46.510 | 24.906 | 1.00 | 14.85 | A_13 |
| ATOM | 1007 | CE1 | TYR | 111 | 69.618 | 45.837 | 25.795 | 1.00 | 19.08 | A_13 |
| ATOM | 1008 | CD2 | TYR | 111 | 72.232 | 44.995 | 25.435 | 1.00 | 21.86 | A_13 |
| ATOM | 1009 | CE2 | TYR | 111 | 71.405 | 44.314 | 26.324 | 1.00 | 10.00 | A_13 |
| ATOM | 1010 | CZ | TYR | 111 | 70.101 | 44.740 | 26.505 | 1.00 | 18.51 | A_13 |
| ATOM | 1011 | OH | TYR | 111 | 69.282 | 44.077 | 27.398 | 1.00 | 14.32 | A_13 |
| ATOM | 1013 | C | TYR | 111 | 74.779 | 48.335 | 23.695 | 1.00 | 16.73 | A_13 |
| ATOM | 1014 | O | TYR | 111 | 74.540 | 49.105 | 22.764 | 1.00 | 11.98 | A_13 |
| ATOM | 1015 | N | ASN | 112 | 76.008 | 47.930 | 23.999 | 1.00 | 11.80 | A_13 |
| ATOM | 1017 | CA | ASN | 112 | 77.184 | 48.357 | 23.240 | 1.00 | 16.37 | A_13 |
| ATOM | 1018 | CB | ASN | 112 | 78.453 | 47.867 | 23.927 | 1.00 | 27.52 | A_13 |
| ATOM | 1019 | CG | ASN | 112 | 79.701 | 48.460 | 23.324 | 1.00 | 20.16 | A_13 |
| ATOM | 1020 | OD1 | ASN | 112 | 80.327 | 47.861 | 22.447 | 1.00 | 20.99 | A_13 |
| ATOM | 1021 | ND2 | ASN | 112 | 80.082 | 49.640 | 23.801 | 1.00 | 15.12 | A_13 |

FIG. 5A-11

| ATOM | 1024 | C | ASN | 112 | 77.137 | 47.809 | 21.813 | 1.00 | 18.08 | A_13 |
|---|---|---|---|---|---|---|---|---|---|---|
| ATOM | 1025 | O | ASN | 112 | 77.288 | 46.606 | 21.592 | 1.00 | 12.69 | A_13 |
| ATOM | 1026 | N | LEU | 113 | 76.972 | 48.700 | 20.844 | 1.00 | 11.15 | A_13 |
| ATOM | 1028 | CA | LEU | 113 | 76.878 | 48.296 | 19.461 | 1.00 | 10.00 | A_13 |
| ATOM | 1029 | CB | LEU | 113 | 76.718 | 49.526 | 18.568 | 1.00 | 10.24 | A_13 |
| ATOM | 1030 | CG | LEU | 113 | 76.325 | 49.262 | 17.106 | 1.00 | 15.67 | A_13 |
| ATOM | 1031 | CD1 | LEU | 113 | 75.155 | 48.296 | 17.050 | 1.00 | 26.54 | A_13 |
| ATOM | 1032 | CD2 | LEU | 113 | 75.967 | 50.555 | 16.415 | 1.00 | 15.60 | A_13 |
| ATOM | 1033 | C | LEU | 113 | 78.037 | 47.403 | 18.986 | 1.00 | 25.17 | A_13 |
| ATOM | 1034 | O | LEU | 113 | 77.799 | 46.380 | 18.336 | 1.00 | 17.24 | A_13 |
| ATOM | 1035 | N | PHE | 114 | 79.274 | 47.759 | 19.327 | 1.00 | 28.89 | A_13 |
| ATOM | 1037 | CA | PHE | 114 | 80.442 | 46.974 | 18.910 | 1.00 | 19.15 | A_13 |
| ATOM | 1038 | CB | PHE | 114 | 81.753 | 47.579 | 19.434 | 1.00 | 14.60 | A_13 |
| ATOM | 1039 | CG | PHE | 114 | 82.923 | 46.627 | 19.374 | 1.00 | 18.53 | A_13 |
| ATOM | 1040 | CD1 | PHE | 114 | 83.419 | 46.175 | 18.144 | 1.00 | 26.13 | A_13 |
| ATOM | 1041 | CD2 | PHE | 114 | 83.514 | 46.162 | 20.547 | 1.00 | 17.22 | A_13 |
| ATOM | 1042 | CE1 | PHE | 114 | 84.475 | 45.271 | 18.086 | 1.00 | 10.43 | A_13 |
| ATOM | 1043 | CE2 | PHE | 114 | 84.571 | 45.259 | 20.502 | 1.00 | 16.51 | A_13 |
| ATOM | 1044 | CZ | PHE | 114 | 85.052 | 44.815 | 19.260 | 1.00 | 15.54 | A_13 |
| ATOM | 1045 | C | PHE | 114 | 80.359 | 45.508 | 19.306 | 1.00 | 10.00 | A_13 |
| ATOM | 1046 | O | PHE | 114 | 80.437 | 44.625 | 18.445 | 1.00 | 33.07 | A_13 |
| ATOM | 1047 | N | LEU | 115 | 80.206 | 45.249 | 20.600 | 1.00 | 12.18 | A_13 |
| ATOM | 1049 | CA | LEU | 115 | 80.113 | 43.877 | 21.103 | 1.00 | 10.59 | A_13 |
| ATOM | 1050 | CB | LEU | 115 | 79.874 | 43.895 | 22.616 | 1.00 | 14.14 | A_13 |
| ATOM | 1051 | CG | LEU | 115 | 81.082 | 43.937 | 23.578 | 1.00 | 34.39 | A_13 |
| ATOM | 1052 | CD1 | LEU | 115 | 82.337 | 44.354 | 22.863 | 1.00 | 14.93 | A_13 |
| ATOM | 1053 | CD2 | LEU | 115 | 80.815 | 44.836 | 24.793 | 1.00 | 13.42 | A_13 |
| ATOM | 1054 | C | LEU | 115 | 79.019 | 43.080 | 20.379 | 1.00 | 12.06 | A_13 |
| ATOM | 1055 | O | LEU | 115 | 79.298 | 42.109 | 19.675 | 1.00 | 13.35 | A_13 |
| ATOM | 1056 | N | VAL | 116 | 77.786 | 43.558 | 20.459 | 1.00 | 13.11 | A_13 |
| ATOM | 1058 | CA | VAL | 116 | 76.678 | 42.875 | 19.814 | 1.00 | 12.97 | A_13 |
| ATOM | 1059 | CB | VAL | 116 | 75.343 | 43.569 | 20.129 | 1.00 | 28.07 | A_13 |
| ATOM | 1060 | CG1 | VAL | 116 | 74.200 | 42.926 | 19.340 | 1.00 | 17.32 | A_13 |
| ATOM | 1061 | CG2 | VAL | 116 | 75.074 | 43.491 | 21.617 | 1.00 | 22.14 | A_13 |
| ATOM | 1062 | C | VAL | 116 | 76.862 | 42.724 | 18.313 | 1.00 | 10.00 | A_13 |
| ATOM | 1063 | O | VAL | 116 | 76.473 | 41.716 | 17.755 | 1.00 | 14.68 | A_13 |
| ATOM | 1064 | N | ALA | 117 | 77.481 | 43.706 | 17.667 | 1.00 | 10.80 | A_13 |
| ATOM | 1066 | CA | ALA | 117 | 77.726 | 43.662 | 16.224 | 1.00 | 18.28 | A_13 |
| ATOM | 1067 | CB | ALA | 117 | 78.223 | 45.014 | 15.727 | 1.00 | 14.94 | A_13 |
| ATOM | 1068 | C | ALA | 117 | 78.735 | 42.579 | 15.863 | 1.00 | 25.24 | A_13 |
| ATOM | 1069 | O | ALA | 117 | 78.562 | 41.872 | 14.861 | 1.00 | 18.50 | A_13 |
| ATOM | 1070 | N | ALA | 118 | 79.795 | 42.458 | 16.665 | 1.00 | 24.40 | A_13 |
| ATOM | 1072 | CA | ALA | 118 | 80.829 | 41.451 | 16.422 | 1.00 | 11.80 | A_13 |
| ATOM | 1073 | CB | ALA | 118 | 81.945 | 41.590 | 17.447 | 1.00 | 19.28 | A_13 |
| ATOM | 1074 | C | ALA | 118 | 80.178 | 40.056 | 16.496 | 1.00 | 10.00 | A_13 |
| ATOM | 1075 | O | ALA | 118 | 80.426 | 39.183 | 15.660 | 1.00 | 10.00 | A_13 |
| ATOM | 1076 | N | HIS | 119 | 79.309 | 39.875 | 17.487 | 1.00 | 19.01 | A_13 |
| ATOM | 1078 | CA | HIS | 119 | 78.587 | 38.624 | 17.674 | 1.00 | 14.36 | A_13 |
| ATOM | 1079 | CB | HIS | 119 | 77.725 | 38.751 | 18.924 | 1.00 | 10.00 | A_13 |
| ATOM | 1080 | CG | HIS | 119 | 76.796 | 37.602 | 19.166 | 1.00 | 10.00 | A_13 |
| ATOM | 1081 | CD2 | HIS | 119 | 75.691 | 37.187 | 18.498 | 1.00 | 14.94 | A_13 |
| ATOM | 1082 | ND1 | HIS | 119 | 76.905 | 36.783 | 20.263 | 1.00 | 20.37 | A_13 |
| ATOM | 1084 | CE1 | HIS | 119 | 75.917 | 35.909 | 20.270 | 1.00 | 17.53 | A_13 |
| ATOM | 1085 | NE2 | HIS | 119 | 75.161 | 36.134 | 19.208 | 1.00 | 17.55 | A_13 |
| ATOM | 1086 | C | HIS | 119 | 77.741 | 38.339 | 16.419 | 1.00 | 10.00 | A_13 |
| ATOM | 1087 | O | HIS | 119 | 77.779 | 37.245 | 15.856 | 1.00 | 10.64 | A_13 |
| ATOM | 1088 | N | GLU | 120 | 77.004 | 39.343 | 15.968 | 1.00 | 22.95 | A_13 |
| ATOM | 1090 | CA | GLU | 120 | 76.174 | 39.224 | 14.775 | 1.00 | 23.96 | A_13 |
| ATOM | 1091 | CB | GLU | 120 | 75.429 | 40.545 | 14.502 | 1.00 | 17.19 | A_13 |
| ATOM | 1092 | CG | GLU | 120 | 74.373 | 40.889 | 15.555 | 1.00 | 16.14 | A_13 |
| ATOM | 1093 | CD | GLU | 120 | 73.492 | 39.691 | 15.929 | 1.00 | 10.00 | A_13 |
| ATOM | 1094 | OE1 | GLU | 120 | 73.478 | 39.354 | 17.122 | 1.00 | 17.94 | A_13 |
| ATOM | 1095 | OE2 | GLU | 120 | 72.844 | 39.078 | 15.047 | 1.00 | 17.03 | A_13 |
| ATOM | 1096 | C | GLU | 120 | 76.992 | 38.832 | 13.549 | 1.00 | 11.45 | A_13 |
| ATOM | 1097 | O | GLU | 120 | 76.594 | 37.946 | 12.772 | 1.00 | 13.34 | A_13 |
| ATOM | 1098 | N | PHE | 121 | 78.127 | 39.498 | 13.353 | 1.00 | 10.00 | A_13 |
| ATOM | 1100 | CA | PHE | 121 | 78.959 | 39.187 | 12.216 | 1.00 | 14.70 | A_13 |
| ATOM | 1101 | CB | PHE | 121 | 80.040 | 40.245 | 12.039 | 1.00 | 10.00 | A_13 |
| ATOM | 1102 | CG | PHE | 121 | 79.481 | 41.623 | 11.792 | 1.00 | 21.57 | A_13 |
| ATOM | 1103 | CD1 | PHE | 121 | 80.235 | 42.764 | 12.069 | 1.00 | 16.73 | A_13 |
| ATOM | 1104 | CD2 | PHE | 121 | 78.164 | 41.788 | 11.331 | 1.00 | 13.91 | A_13 |
| ATOM | 1105 | CE1 | PHE | 121 | 79.682 | 44.054 | 11.891 | 1.00 | 11.69 | A_13 |
| ATOM | 1106 | CE2 | PHE | 121 | 77.615 | 43.066 | 11.152 | 1.00 | 18.93 | A_13 |
| ATOM | 1107 | CZ | PHE | 121 | 78.373 | 44.192 | 11.436 | 1.00 | 10.00 | A_13 |
| ATOM | 1108 | C | PHE | 121 | 79.505 | 37.756 | 12.283 | 1.00 | 17.14 | A_13 |
| ATOM | 1109 | O | PHE | 121 | 79.642 | 37.104 | 11.256 | 1.00 | 13.04 | A_13 |
| ATOM | 1110 | N | GLY | 122 | 79.738 | 37.245 | 13.490 | 1.00 | 16.60 | A_13 |

FIG. 5A-12

| | | | | | | | | | |
|---|---|---|---|---|---|---|---|---|---|
| ATOM | 1112 | CA | GLY | 122 | 80.202 | 35.872 | 13.627 | 1.00 19.45 | A_13 |
| ATOM | 1113 | C | GLY | 122 | 79.162 | 34.982 | 12.966 | 1.00 18.55 | A_13 |
| ATOM | 1114 | O | GLY | 122 | 79.500 | 33.988 | 12.306 | 1.00 10.03 | A_13 |
| ATOM | 1115 | N | HIS | 123 | 77.892 | 35.361 | 13.140 | 1.00 18.22 | A_13 |
| ATOM | 1117 | CA | HIS | 123 | 76.753 | 34.665 | 12.525 | 1.00 16.31 | A_13 |
| ATOM | 1118 | CB | HIS | 123 | 75.424 | 35.224 | 13.031 | 1.00 11.35 | A_13 |
| ATOM | 1119 | CG | HIS | 123 | 75.049 | 34.768 | 14.403 | 1.00 10.33 | A_13 |
| ATOM | 1120 | CD2 | HIS | 123 | 74.552 | 35.454 | 15.457 | 1.00 16.64 | A_13 |
| ATOM | 1121 | ND1 | HIS | 123 | 75.097 | 33.450 | 14.782 | 1.00 18.04 | A_13 |
| ATOM | 1123 | CE1 | HIS | 123 | 74.638 | 33.332 | 16.017 | 1.00 16.66 | A_13 |
| ATOM | 1124 | NE2 | HIS | 123 | 74.301 | 34.533 | 16.450 | 1.00 25.32 | A_13 |
| ATOM | 1125 | C | HIS | 123 | 76.771 | 34.853 | 10.997 | 1.00 13.66 | A_13 |
| ATOM | 1126 | O | HIS | 123 | 76.565 | 33.901 | 10.246 | 1.00 10.82 | A_13 |
| ATOM | 1127 | N | SER | 124 | 77.006 | 36.082 | 10.539 | 1.00 13.57 | A_13 |
| ATOM | 1129 | CA | SER | 124 | 77.030 | 36.368 | 9.099 | 1.00 12.03 | A_13 |
| ATOM | 1130 | CB | SER | 124 | 77.311 | 37.863 | 8.832 | 1.00 10.35 | A_13 |
| ATOM | 1131 | OG | SER | 124 | 76.399 | 38.706 | 9.510 | 1.00 14.26 | A_13 |
| ATOM | 1133 | C | SER | 124 | 78.117 | 35.548 | 8.422 | 1.00 21.45 | A_13 |
| ATOM | 1134 | O | SER | 124 | 78.079 | 35.333 | 7.210 | 1.00 10.00 | A_13 |
| ATOM | 1135 | N | LEU | 125 | 79.091 | 35.108 | 9.216 | 1.00 10.00 | A_13 |
| ATOM | 1137 | CA | LEU | 125 | 80.222 | 34.340 | 8.707 | 1.00 19.28 | A_13 |
| ATOM | 1138 | CB | LEU | 125 | 81.521 | 34.754 | 9.422 | 1.00 22.39 | A_13 |
| ATOM | 1139 | CG | LEU | 125 | 81.849 | 36.258 | 9.340 | 1.00 10.00 | A_13 |
| ATOM | 1140 | CD1 | LEU | 125 | 83.063 | 36.622 | 10.190 | 1.00 10.00 | A_13 |
| ATOM | 1141 | CD2 | LEU | 125 | 82.029 | 36.651 | 7.873 | 1.00 10.00 | A_13 |
| ATOM | 1142 | C | LEU | 125 | 79.986 | 32.851 | 8.843 | 1.00 10.00 | A_13 |
| ATOM | 1143 | O | LEU | 125 | 80.759 | 32.056 | 8.329 | 1.00 23.27 | A_13 |
| ATOM | 1144 | N | GLY | 126 | 78.932 | 32.477 | 9.563 | 1.00 22.87 | A_13 |
| ATOM | 1146 | CA | GLY | 126 | 78.604 | 31.070 | 9.720 | 1.00 17.27 | A_13 |
| ATOM | 1147 | C | GLY | 126 | 78.781 | 30.464 | 11.094 | 1.00 11.71 | A_13 |
| ATOM | 1148 | O | GLY | 126 | 78.784 | 29.244 | 11.236 | 1.00 24.16 | A_13 |
| ATOM | 1149 | N | LEU | 127 | 78.972 | 31.297 | 12.105 | 1.00 18.95 | A_13 |
| ATOM | 1151 | CA | LEU | 127 | 79.152 | 30.790 | 13.457 | 1.00 22.84 | A_13 |
| ATOM | 1152 | CB | LEU | 127 | 80.113 | 31.693 | 14.252 | 1.00 11.92 | A_13 |
| ATOM | 1153 | CG | LEU | 127 | 81.244 | 30.969 | 14.983 | 1.00 18.83 | A_13 |
| ATOM | 1154 | CD1 | LEU | 127 | 82.096 | 30.197 | 13.979 | 1.00 16.63 | A_13 |
| ATOM | 1155 | CD2 | LEU | 127 | 82.104 | 31.970 | 15.760 | 1.00 22.15 | A_13 |
| ATOM | 1156 | C | LEU | 127 | 77.802 | 30.699 | 14.163 | 1.00 21.02 | A_13 |
| ATOM | 1157 | O | LEU | 127 | 76.996 | 31.629 | 14.098 | 1.00 14.68 | A_13 |
| ATOM | 1158 | N | ASP | 128 | 77.563 | 29.572 | 14.828 | 1.00 18.87 | A_13 |
| ATOM | 1160 | CA | ASP | 128 | 76.336 | 29.345 | 15.571 | 1.00 16.46 | A_13 |
| ATOM | 1161 | CB | ASP | 128 | 75.996 | 27.855 | 15.540 | 1.00 17.60 | A_13 |
| ATOM | 1162 | CG | ASP | 128 | 74.577 | 27.552 | 15.996 | 1.00 23.55 | A_13 |
| ATOM | 1163 | OD1 | ASP | 128 | 73.796 | 28.488 | 16.258 | 1.00 10.00 | A_13 |
| ATOM | 1164 | OD2 | ASP | 128 | 74.236 | 26.355 | 16.087 | 1.00 32.36 | A_13 |
| ATOM | 1165 | C | ASP | 128 | 76.634 | 29.803 | 16.995 | 1.00 10.00 | A_13 |
| ATOM | 1166 | O | ASP | 128 | 77.650 | 30.420 | 17.244 | 1.00 29.54 | A_13 |
| ATOM | 1167 | N | HIS | 129 | 75.714 | 29.565 | 17.912 | 1.00 10.00 | A_13 |
| ATOM | 1169 | CA | HIS | 129 | 75.910 | 29.955 | 19.289 | 1.00 10.00 | A_13 |
| ATOM | 1170 | CB | HIS | 129 | 74.582 | 30.033 | 20.029 | 1.00 21.30 | A_13 |
| ATOM | 1171 | CG | HIS | 129 | 73.798 | 31.282 | 19.761 | 1.00 24.16 | A_13 |
| ATOM | 1172 | CD2 | HIS | 129 | 74.180 | 32.585 | 19.725 | 1.00 10.00 | A_13 |
| ATOM | 1173 | ND1 | HIS | 129 | 72.460 | 31.263 | 19.476 | 1.00 21.70 | A_13 |
| ATOM | 1175 | CE1 | HIS | 129 | 72.031 | 32.501 | 19.271 | 1.00 10.27 | A_13 |
| ATOM | 1176 | NE2 | HIS | 129 | 73.057 | 33.319 | 19.407 | 1.00 14.37 | A_13 |
| ATOM | 1177 | C | HIS | 129 | 76.780 | 28.947 | 19.992 | 1.00 30.04 | A_13 |
| ATOM | 1178 | O | HIS | 129 | 76.624 | 27.730 | 19.822 | 1.00 22.13 | A_13 |
| ATOM | 1179 | N | SER | 130 | 77.628 | 29.468 | 20.860 | 1.00 18.60 | A_13 |
| ATOM | 1181 | CA | SER | 130 | 78.534 | 28.662 | 21.636 | 1.00 10.79 | A_13 |
| ATOM | 1182 | CB | SER | 130 | 79.849 | 29.435 | 21.816 | 1.00 21.31 | A_13 |
| ATOM | 1183 | OG | SER | 130 | 80.782 | 28.731 | 22.616 | 1.00 16.34 | A_13 |
| ATOM | 1185 | C | SER | 130 | 77.898 | 28.368 | 22.987 | 1.00 31.13 | A_13 |
| ATOM | 1186 | O | SER | 130 | 76.962 | 29.060 | 23.440 | 1.00 15.87 | A_13 |
| ATOM | 1187 | N | LYS | 131 | 78.402 | 27.319 | 23.619 | 1.00 13.13 | A_13 |
| ATOM | 1189 | CA | LYS | 131 | 77.924 | 26.925 | 24.928 | 1.00 13.21 | A_13 |
| ATOM | 1190 | CB | LYS | 131 | 77.656 | 25.414 | 24.990 | 1.00 18.85 | A_13 |
| ATOM | 1191 | CG | LYS | 131 | 78.689 | 24.541 | 24.303 | 1.00 32.55 | A_13 |
| ATOM | 1192 | CD | LYS | 131 | 78.547 | 24.601 | 22.790 | 1.00 41.54 | A_13 |
| ATOM | 1193 | CE | LYS | 131 | 79.909 | 24.672 | 22.117 | 1.00 19.64 | A_13 |
| ATOM | 1194 | NZ | LYS | 131 | 80.747 | 25.799 | 22.617 | 1.00 13.47 | A_13 |
| ATOM | 1198 | C | LYS | 131 | 78.922 | 27.379 | 25.982 | 1.00 10.00 | A_13 |
| ATOM | 1199 | O | LYS | 131 | 78.666 | 27.260 | 27.185 | 1.00 13.35 | A_13 |
| ATOM | 1200 | N | ASP | 132 | 80.025 | 27.968 | 25.519 | 1.00 13.47 | A_13 |
| ATOM | 1202 | CA | ASP | 132 | 81.097 | 28.487 | 26.375 | 1.00 10.04 | A_13 |
| ATOM | 1203 | CB | ASP | 132 | 82.376 | 28.617 | 25.522 | 1.00 18.14 | A_13 |
| ATOM | 1204 | CG | ASP | 132 | 83.649 | 28.821 | 26.345 | 1.00 16.54 | A_13 |
| ATOM | 1205 | OD1 | ASP | 132 | 84.645 | 28.132 | 26.028 | 1.00 36.08 | A_13 |

FIG. 5A-13

| ATOM | 1206 | OD2 | ASP | 132 | 83.685 | 29.660 | 27.276 | 1.00 | 15.60 | A_13 |
|---|---|---|---|---|---|---|---|---|---|---|
| ATOM | 1207 | C | ASP | 132 | 80.603 | 29.875 | 26.836 | 1.00 | 18.74 | A_13 |
| ATOM | 1208 | O | ASP | 132 | 80.559 | 30.816 | 26.038 | 1.00 | 14.61 | A_13 |
| ATOM | 1209 | N | PRO | 133 | 80.305 | 30.039 | 28.142 | 1.00 | 15.61 | A_13 |
| ATOM | 1210 | CD | PRO | 133 | 80.617 | 29.127 | 29.251 | 1.00 | 21.19 | A_13 |
| ATOM | 1211 | CA | PRO | 133 | 79.818 | 31.320 | 28.662 | 1.00 | 10.00 | A_13 |
| ATOM | 1212 | CB | PRO | 133 | 79.542 | 31.007 | 30.135 | 1.00 | 10.00 | A_13 |
| ATOM | 1213 | CG | PRO | 133 | 80.633 | 30.063 | 30.450 | 1.00 | 30.94 | A_13 |
| ATOM | 1214 | C | PRO | 133 | 80.834 | 32.444 | 28.511 | 1.00 | 22.87 | A_13 |
| ATOM | 1215 | O | PRO | 133 | 80.526 | 33.574 | 28.742 | 1.00 | 21.65 | A_13 |
| ATOM | 1216 | N | GLY | 134 | 82.070 | 32.115 | 28.174 | 1.00 | 20.95 | A_13 |
| ATOM | 1218 | CA | GLY | 134 | 83.055 | 33.167 | 28.028 | 1.00 | 15.22 | A_13 |
| ATOM | 1219 | C | GLY | 134 | 83.182 | 33.578 | 26.581 | 1.00 | 34.54 | A_13 |
| ATOM | 1220 | O | GLY | 134 | 83.962 | 34.488 | 26.252 | 1.00 | 18.06 | A_13 |
| ATOM | 1221 | N | ALA | 135 | 82.490 | 32.846 | 25.706 | 1.00 | 21.09 | A_13 |
| ATOM | 1223 | CA | ALA | 135 | 82.547 | 33.110 | 24.263 | 1.00 | 27.50 | A_13 |
| ATOM | 1224 | CB | ALA | 135 | 82.131 | 31.858 | 23.453 | 1.00 | 10.00 | A_13 |
| ATOM | 1225 | C | ALA | 135 | 81.722 | 34.308 | 23.814 | 1.00 | 21.74 | A_13 |
| ATOM | 1226 | O | ALA | 135 | 80.641 | 34.556 | 24.328 | 1.00 | 13.84 | A_13 |
| ATOM | 1227 | N | LEU | 136 | 82.220 | 34.990 | 22.787 | 1.00 | 19.10 | A_13 |
| ATOM | 1229 | CA | LEU | 136 | 81.540 | 36.140 | 22.203 | 1.00 | 21.65 | A_13 |
| ATOM | 1230 | CB | LEU | 136 | 82.448 | 36.803 | 21.161 | 1.00 | 10.00 | A_13 |
| ATOM | 1231 | CG | LEU | 136 | 81.964 | 37.898 | 20.201 | 1.00 | 17.22 | A_13 |
| ATOM | 1232 | CD1 | LEU | 136 | 81.250 | 37.296 | 19.024 | 1.00 | 24.18 | A_13 |
| ATOM | 1233 | CD2 | LEU | 136 | 81.113 | 38.896 | 20.905 | 1.00 | 10.00 | A_13 |
| ATOM | 1234 | C | LEU | 136 | 80.250 | 35.632 | 21.558 | 1.00 | 19.32 | A_13 |
| ATOM | 1235 | O | LEU | 136 | 79.266 | 36.359 | 21.458 | 1.00 | 26.20 | A_13 |
| ATOM | 1236 | N | MET | 137 | 80.297 | 34.409 | 21.029 | 1.00 | 10.00 | A_13 |
| ATOM | 1238 | CA | MET | 137 | 79.123 | 33.791 | 20.423 | 1.00 | 10.02 | A_13 |
| ATOM | 1239 | CB | MET | 137 | 79.507 | 32.691 | 19.428 | 1.00 | 15.14 | A_13 |
| ATOM | 1240 | CG | MET | 137 | 80.181 | 33.223 | 18.169 | 1.00 | 16.42 | A_13 |
| ATOM | 1241 | SD | MET | 137 | 79.366 | 34.665 | 17.397 | 1.00 | 10.65 | A_13 |
| ATOM | 1242 | CE | MET | 137 | 77.848 | 34.005 | 16.975 | 1.00 | 10.87 | A_13 |
| ATOM | 1243 | C | MET | 137 | 78.122 | 33.256 | 21.447 | 1.00 | 12.70 | A_13 |
| ATOM | 1244 | O | MET | 137 | 77.187 | 32.539 | 21.087 | 1.00 | 10.00 | A_13 |
| ATOM | 1245 | N | PHE | 138 | 78.295 | 33.627 | 22.713 | 1.00 | 18.70 | A_13 |
| ATOM | 1247 | CA | PHE | 138 | 77.370 | 33.196 | 23.759 | 1.00 | 24.08 | A_13 |
| ATOM | 1248 | CB | PHE | 138 | 77.954 | 33.448 | 25.159 | 1.00 | 24.15 | A_13 |
| ATOM | 1249 | CG | PHE | 138 | 77.306 | 32.617 | 26.240 | 1.00 | 29.38 | A_13 |
| ATOM | 1250 | CD1 | PHE | 138 | 76.694 | 33.222 | 27.336 | 1.00 | 27.07 | A_13 |
| ATOM | 1251 | CD2 | PHE | 138 | 77.253 | 31.226 | 26.123 | 1.00 | 21.37 | A_13 |
| ATOM | 1252 | CE1 | PHE | 138 | 76.033 | 32.455 | 28.289 | 1.00 | 30.35 | A_13 |
| ATOM | 1253 | CE2 | PHE | 138 | 76.599 | 30.458 | 27.065 | 1.00 | 19.58 | A_13 |
| ATOM | 1254 | CZ | PHE | 138 | 75.986 | 31.070 | 28.154 | 1.00 | 17.69 | A_13 |
| ATOM | 1255 | C | PHE | 138 | 76.074 | 33.992 | 23.513 | 1.00 | 14.20 | A_13 |
| ATOM | 1256 | O | PHE | 138 | 76.115 | 35.105 | 23.014 | 1.00 | 10.27 | A_13 |
| ATOM | 1257 | N | PRO | 139 | 74.899 | 33.366 | 23.730 | 1.00 | 13.04 | A_13 |
| ATOM | 1258 | CD | PRO | 139 | 74.664 | 31.975 | 24.131 | 1.00 | 11.17 | A_13 |
| ATOM | 1259 | CA | PRO | 139 | 73.619 | 34.043 | 23.504 | 1.00 | 18.27 | A_13 |
| ATOM | 1260 | CB | PRO | 139 | 72.625 | 32.875 | 23.384 | 1.00 | 14.33 | A_13 |
| ATOM | 1261 | CG | PRO | 139 | 73.474 | 31.634 | 23.305 | 1.00 | 24.22 | A_13 |
| ATOM | 1262 | C | PRO | 139 | 73.162 | 35.018 | 24.584 | 1.00 | 16.51 | A_13 |
| ATOM | 1263 | O | PRO | 139 | 72.023 | 35.467 | 24.535 | 1.00 | 24.45 | A_13 |
| ATOM | 1264 | N | ILE | 140 | 74.034 | 35.375 | 25.524 | 1.00 | 23.16 | A_13 |
| ATOM | 1266 | CA | ILE | 140 | 73.652 | 36.290 | 26.604 | 1.00 | 25.00 | A_13 |
| ATOM | 1267 | CB | ILE | 140 | 73.688 | 35.559 | 27.966 | 1.00 | 12.10 | A_13 |
| ATOM | 1268 | CG2 | ILE | 140 | 73.336 | 36.519 | 29.085 | 1.00 | 12.62 | A_13 |
| ATOM | 1269 | CG1 | ILE | 140 | 72.738 | 34.341 | 27.904 | 1.00 | 22.67 | A_13 |
| ATOM | 1270 | CD1 | ILE | 140 | 72.827 | 33.353 | 29.073 | 1.00 | 27.73 | A_13 |
| ATOM | 1271 | C | ILE | 140 | 74.584 | 37.489 | 26.621 | 1.00 | 30.64 | A_13 |
| ATOM | 1272 | O | ILE | 140 | 75.778 | 37.317 | 26.682 | 1.00 | 23.16 | A_13 |
| ATOM | 1273 | N | TYR | 141 | 74.033 | 38.694 | 26.532 | 1.00 | 21.05 | A_13 |
| ATOM | 1275 | CA | TYR | 141 | 74.851 | 39.901 | 26.528 | 1.00 | 20.10 | A_13 |
| ATOM | 1276 | CB | TYR | 141 | 74.017 | 41.122 | 26.129 | 1.00 | 17.66 | A_13 |
| ATOM | 1277 | CG | TYR | 141 | 74.784 | 42.433 | 26.103 | 1.00 | 22.24 | A_13 |
| ATOM | 1278 | CD1 | TYR | 141 | 74.711 | 43.318 | 27.171 | 1.00 | 18.07 | A_13 |
| ATOM | 1279 | CE1 | TYR | 141 | 75.386 | 44.527 | 27.144 | 1.00 | 19.84 | A_13 |
| ATOM | 1280 | CD2 | TYR | 141 | 75.563 | 42.798 | 24.999 | 1.00 | 18.08 | A_13 |
| ATOM | 1281 | CE2 | TYR | 141 | 76.244 | 44.008 | 24.961 | 1.00 | 10.00 | A_13 |
| ATOM | 1282 | CZ | TYR | 141 | 76.149 | 44.867 | 26.038 | 1.00 | 25.17 | A_13 |
| ATOM | 1283 | OH | TYR | 141 | 76.814 | 46.070 | 26.043 | 1.00 | 30.78 | A_13 |
| ATOM | 1285 | C | TYR | 141 | 75.533 | 40.169 | 27.852 | 1.00 | 19.61 | A_13 |
| ATOM | 1286 | O | TYR | 141 | 74.910 | 40.146 | 28.913 | 1.00 | 16.08 | A_13 |
| ATOM | 1287 | N | THR | 142 | 76.817 | 40.476 | 27.772 | 1.00 | 26.26 | A_13 |
| ATOM | 1289 | CA | THR | 142 | 77.612 | 40.788 | 28.944 | 1.00 | 24.52 | A_13 |
| ATOM | 1290 | CB | THR | 142 | 78.498 | 39.568 | 29.362 | 1.00 | 10.00 | A_13 |
| ATOM | 1291 | OG1 | THR | 142 | 77.664 | 38.587 | 29.981 | 1.00 | 37.30 | A_13 |

FIG. 5A-14

| | | | | | | | | | |
|---|---|---|---|---|---|---|---|---|---|
| ATOM | 1293 | CG2 | THR | 142 | 79.543 | 39.961 | 30.390 | 1.00 14.88 | A_13 |
| ATOM | 1294 | C | THR | 142 | 78.467 | 41.976 | 28.580 | 1.00 25.46 | A_13 |
| ATOM | 1295 | O | THR | 142 | 78.980 | 42.058 | 27.464 | 1.00 10.00 | A_13 |
| ATOM | 1296 | N | TYR | 143 | 78.575 | 42.947 | 29.476 | 1.00 20.23 | A_13 |
| ATOM | 1298 | CA | TYR | 143 | 79.412 | 44.079 | 29.133 | 1.00 32.69 | A_13 |
| ATOM | 1299 | CB | TYR | 143 | 79.024 | 45.363 | 29.854 | 1.00 35.01 | A_13 |
| ATOM | 1300 | CG | TYR | 143 | 79.834 | 46.531 | 29.347 | 1.00 16.01 | A_13 |
| ATOM | 1301 | CD1 | TYR | 143 | 79.776 | 46.910 | 27.998 | 1.00 12.56 | A_13 |
| ATOM | 1302 | CE1 | TYR | 143 | 80.554 | 47.961 | 27.510 | 1.00 19.23 | A_13 |
| ATOM | 1303 | CD2 | TYR | 143 | 80.690 | 47.230 | 30.196 | 1.00 19.43 | A_13 |
| ATOM | 1304 | CE2 | TYR | 143 | 81.478 | 48.287 | 29.719 | 1.00 15.52 | A_13 |
| ATOM | 1305 | CZ | TYR | 143 | 81.403 | 48.643 | 28.376 | 1.00 12.56 | A_13 |
| ATOM | 1306 | OH | TYR | 143 | 82.193 | 49.654 | 27.892 | 1.00 18.85 | A_13 |
| ATOM | 1308 | C | TYR | 143 | 80.871 | 43.754 | 29.382 | 1.00 25.10 | A_13 |
| ATOM | 1309 | O | TYR | 143 | 81.373 | 43.846 | 30.503 | 1.00 28.90 | A_13 |
| ATOM | 1310 | N | THR | 144 | 81.539 | 43.375 | 28.303 | 1.00 35.25 | A_13 |
| ATOM | 1312 | CA | THR | 144 | 82.946 | 43.029 | 28.336 | 1.00 38.86 | A_13 |
| ATOM | 1313 | CB | THR | 144 | 83.158 | 41.568 | 27.873 | 1.00 23.22 | A_13 |
| ATOM | 1314 | OG1 | THR | 144 | 82.129 | 41.219 | 26.934 | 1.00 35.22 | A_13 |
| ATOM | 1316 | CG2 | THR | 144 | 83.105 | 40.616 | 29.082 | 1.00 17.53 | A_13 |
| ATOM | 1317 | C | THR | 144 | 83.720 | 44.017 | 27.488 | 1.00 21.63 | A_13 |
| ATOM | 1318 | O | THR | 144 | 84.434 | 43.651 | 26.556 | 1.00 37.44 | A_13 |
| ATOM | 1319 | N | GLY | 145 | 83.504 | 45.288 | 27.798 | 1.00 14.47 | A_13 |
| ATOM | 1321 | CA | GLY | 145 | 84.200 | 46.375 | 27.131 | 1.00 24.39 | A_13 |
| ATOM | 1322 | C | GLY | 145 | 84.119 | 46.536 | 25.628 | 1.00 41.65 | A_13 |
| ATOM | 1323 | O | GLY | 145 | 84.053 | 45.565 | 24.877 | 1.00 42.39 | A_13 |
| ATOM | 1324 | N | LYS | 146 | 84.122 | 47.792 | 25.195 | 1.00 33.04 | A_13 |
| ATOM | 1326 | CA | LYS | 146 | 84.059 | 48.103 | 23.778 | 1.00 29.29 | A_13 |
| ATOM | 1327 | CB | LYS | 146 | 83.260 | 49.392 | 23.539 | 1.00 26.47 | A_13 |
| ATOM | 1328 | CG | LYS | 146 | 83.087 | 49.721 | 22.059 | 1.00 33.24 | A_13 |
| ATOM | 1329 | CD | LYS | 146 | 82.812 | 51.194 | 21.833 | 1.00 13.70 | A_13 |
| ATOM | 1330 | CE | LYS | 146 | 82.620 | 51.497 | 20.343 | 1.00 18.35 | A_13 |
| ATOM | 1331 | NZ | LYS | 146 | 83.766 | 51.122 | 19.477 | 1.00 30.66 | A_13 |
| ATOM | 1335 | C | LYS | 146 | 85.491 | 48.297 | 23.308 | 1.00 41.61 | A_13 |
| ATOM | 1336 | O | LYS | 146 | 86.028 | 49.412 | 23.382 | 1.00 46.44 | A_13 |
| ATOM | 1337 | N | SER | 147 | 86.130 | 47.206 | 22.898 | 1.00 34.67 | A_13 |
| ATOM | 1339 | CA | SER | 147 | 87.509 | 47.258 | 22.416 | 1.00 30.76 | A_13 |
| ATOM | 1340 | CB | SER | 147 | 87.624 | 48.258 | 21.249 | 1.00 24.56 | A_13 |
| ATOM | 1341 | OG | SER | 147 | 86.638 | 48.002 | 20.257 | 1.00 31.81 | A_13 |
| ATOM | 1343 | C | SER | 147 | 88.464 | 47.626 | 23.567 | 1.00 33.60 | A_13 |
| ATOM | 1344 | O | SER | 147 | 88.789 | 48.806 | 23.789 | 1.00 39.96 | A_13 |
| ATOM | 1345 | N | HIS | 148 | 88.862 | 46.611 | 24.331 | 1.00 36.71 | A_13 |
| ATOM | 1347 | CA | HIS | 148 | 89.778 | 46.769 | 25.467 | 1.00 34.40 | A_13 |
| ATOM | 1348 | CB | HIS | 148 | 89.307 | 47.862 | 26.438 | 1.00 26.40 | A_13 |
| ATOM | 1349 | CG | HIS | 148 | 90.251 | 49.022 | 26.537 | 1.00 39.11 | A_13 |
| ATOM | 1350 | CD2 | HIS | 148 | 90.929 | 49.542 | 27.588 | 1.00 30.52 | A_13 |
| ATOM | 1351 | ND1 | HIS | 148 | 90.635 | 49.767 | 25.437 | 1.00 37.71 | A_13 |
| ATOM | 1353 | CE1 | HIS | 148 | 91.511 | 50.681 | 25.807 | 1.00 29.04 | A_13 |
| ATOM | 1354 | NE2 | HIS | 148 | 91.707 | 50.567 | 27.110 | 1.00 29.03 | A_13 |
| ATOM | 1356 | C | HIS | 148 | 89.949 | 45.436 | 26.190 | 1.00 39.41 | A_13 |
| ATOM | 1357 | O | HIS | 148 | 90.134 | 45.373 | 27.411 | 1.00 35.01 | A_13 |
| ATOM | 1358 | N | PHE | 149 | 89.840 | 44.386 | 25.383 | 1.00 25.35 | A_13 |
| ATOM | 1360 | CA | PHE | 149 | 89.996 | 42.966 | 25.721 | 1.00 30.54 | A_13 |
| ATOM | 1361 | CB | PHE | 149 | 88.788 | 42.423 | 26.495 | 1.00 33.34 | A_13 |
| ATOM | 1362 | CG | PHE | 149 | 88.951 | 42.440 | 27.996 | 1.00 31.37 | A_13 |
| ATOM | 1363 | CD1 | PHE | 149 | 89.387 | 41.302 | 28.673 | 1.00 30.46 | A_13 |
| ATOM | 1364 | CD2 | PHE | 149 | 88.624 | 43.575 | 28.740 | 1.00 40.67 | A_13 |
| ATOM | 1365 | CE1 | PHE | 149 | 89.492 | 41.293 | 30.075 | 1.00 18.92 | A_13 |
| ATOM | 1366 | CE2 | PHE | 149 | 88.728 | 43.574 | 30.136 | 1.00 23.23 | A_13 |
| ATOM | 1367 | CZ | PHE | 149 | 89.161 | 42.430 | 30.803 | 1.00 17.03 | A_13 |
| ATOM | 1368 | C | PHE | 149 | 90.026 | 42.366 | 24.295 | 1.00 41.76 | A_13 |
| ATOM | 1369 | O | PHE | 149 | 89.967 | 43.119 | 23.307 | 1.00 40.43 | A_13 |
| ATOM | 1370 | N | MET | 150 | 90.132 | 41.050 | 24.142 | 1.00 31.30 | A_13 |
| ATOM | 1372 | CA | MET | 150 | 90.152 | 40.531 | 22.779 | 1.00 20.65 | A_13 |
| ATOM | 1373 | CB | MET | 150 | 91.588 | 40.195 | 22.352 | 1.00 28.29 | A_13 |
| ATOM | 1374 | CG | MET | 150 | 92.494 | 41.436 | 22.188 | 1.00 34.71 | A_13 |
| ATOM | 1375 | SD | MET | 150 | 91.750 | 42.780 | 21.185 | 1.00 67.91 | A_13 |
| ATOM | 1376 | CE | MET | 150 | 92.512 | 42.498 | 19.518 | 1.00 22.43 | A_13 |
| ATOM | 1377 | C | MET | 150 | 89.201 | 39.370 | 22.497 | 1.00 21.51 | A_13 |
| ATOM | 1378 | O | MET | 150 | 88.498 | 38.901 | 23.391 | 1.00 25.37 | A_13 |
| ATOM | 1379 | N | LEU | 151 | 89.159 | 38.938 | 21.240 | 1.00 13.78 | A_13 |
| ATOM | 1381 | CA | LEU | 151 | 88.313 | 37.825 | 20.834 | 1.00 14.73 | A_13 |
| ATOM | 1382 | CB | LEU | 151 | 88.435 | 37.589 | 19.321 | 1.00 15.49 | A_13 |
| ATOM | 1383 | CG | LEU | 151 | 87.535 | 36.511 | 18.691 | 1.00 27.05 | A_13 |
| ATOM | 1384 | CD1 | LEU | 151 | 86.070 | 36.915 | 18.847 | 1.00 10.98 | A_13 |
| ATOM | 1385 | CD2 | LEU | 151 | 87.879 | 36.310 | 17.208 | 1.00 15.73 | A_13 |
| ATOM | 1386 | C | LEU | 151 | 88.732 | 36.563 | 21.600 | 1.00 25.01 | A_13 |

FIG. 5A-15

```
ATOM   1387  O    LEU  151      89.912  36.178  21.589  1.00 17.37       A_13
ATOM   1388  N    PRO  152      87.777  35.927  22.306  1.00 10.37       A_13
ATOM   1389  CD   PRO  152      86.425  36.450  22.575  1.00 15.35       A_13
ATOM   1390  CA   PRO  152      88.030  34.712  23.087  1.00 11.49       A_13
ATOM   1391  CB   PRO  152      86.658  34.412  23.702  1.00 15.98       A_13
ATOM   1392  CG   PRO  152      86.083  35.789  23.898  1.00 27.60       A_13
ATOM   1393  C    PRO  152      88.533  33.553  22.230  1.00 18.06       A_13
ATOM   1394  O    PRO  152      88.160  33.430  21.063  1.00 16.21       A_13
ATOM   1395  N    ASP  153      89.350  32.696  22.836  1.00 15.86       A_13
ATOM   1397  CA   ASP  153      89.933  31.526  22.185  1.00 20.25       A_13
ATOM   1398  CB   ASP  153      90.632  30.630  23.227  1.00 18.17       A_13
ATOM   1399  CG   ASP  153      91.843  31.301  23.908  1.00 24.01       A_13
ATOM   1400  OD1  ASP  153      92.517  32.159  23.284  1.00 14.96       A_13
ATOM   1401  OD2  ASP  153      92.131  30.937  25.077  1.00 20.20       A_13
ATOM   1402  C    ASP  153      88.887  30.678  21.452  1.00 24.64       A_13
ATOM   1403  O    ASP  153      89.113  30.221  20.330  1.00 13.51       A_13
ATOM   1404  N    ASP  154      87.757  30.453  22.114  1.00 24.11       A_13
ATOM   1406  CA   ASP  154      86.664  29.657  21.577  1.00 19.19       A_13
ATOM   1407  CB   ASP  154      85.527  29.632  22.587  1.00 18.27       A_13
ATOM   1408  CG   ASP  154      84.406  28.751  22.161  1.00 24.26       A_13
ATOM   1409  OD1  ASP  154      83.314  29.291  21.950  1.00 20.97       A_13
ATOM   1410  OD2  ASP  154      84.609  27.530  22.031  1.00 20.32       A_13
ATOM   1411  C    ASP  154      86.162  30.170  20.229  1.00 18.99       A_13
ATOM   1412  O    ASP  154      86.043  29.408  19.277  1.00 22.56       A_13
ATOM   1413  N    ASP  155      85.873  31.465  20.158  1.00 16.11       A_13
ATOM   1415  CA   ASP  155      85.407  32.078  18.917  1.00 25.30       A_13
ATOM   1416  CB   ASP  155      85.011  33.527  19.158  1.00 13.32       A_13
ATOM   1417  CG   ASP  155      83.975  33.655  20.249  1.00 11.19       A_13
ATOM   1418  OD1  ASP  155      84.347  34.136  21.332  1.00 12.26       A_13
ATOM   1419  OD2  ASP  155      82.810  33.255  20.029  1.00 10.00       A_13
ATOM   1420  C    ASP  155      86.461  31.992  17.828  1.00 13.98       A_13
ATOM   1421  O    ASP  155      86.141  31.656  16.687  1.00 14.08       A_13
ATOM   1422  N    VAL  156      87.713  32.310  18.160  1.00 16.49       A_13
ATOM   1424  CA   VAL  156      88.771  32.201  17.159  1.00 27.34       A_13
ATOM   1425  CB   VAL  156      90.145  32.826  17.625  1.00 23.59       A_13
ATOM   1426  CG1  VAL  156      90.327  32.750  19.119  1.00 13.94       A_13
ATOM   1427  CG2  VAL  156      91.312  32.153  16.919  1.00 21.70       A_13
ATOM   1428  C    VAL  156      88.874  30.738  16.657  1.00 16.95       A_13
ATOM   1429  O    VAL  156      88.946  30.506  15.448  1.00 13.79       A_13
ATOM   1430  N    GLN  157      88.762  29.763  17.561  1.00 19.45       A_13
ATOM   1432  CA   GLN  157      88.796  28.352  17.154  1.00 30.53       A_13
ATOM   1433  CB   GLN  157      88.579  27.422  18.353  1.00 23.08       A_13
ATOM   1434  CG   GLN  157      89.633  27.521  19.452  1.00 24.83       A_13
ATOM   1435  CD   GLN  157      90.950  26.872  19.089  1.00 20.26       A_13
ATOM   1436  OE1  GLN  157      91.743  27.422  18.316  1.00 25.80       A_13
ATOM   1437  NE2  GLN  157      91.204  25.702  19.673  1.00 38.67       A_13
ATOM   1440  C    GLN  157      87.667  28.136  16.148  1.00 14.16       A_13
ATOM   1441  O    GLN  157      87.869  27.541  15.096  1.00 14.11       A_13
ATOM   1442  N    GLY  158      86.505  28.709  16.437  1.00 19.16       A_13
ATOM   1444  CA   GLY  158      85.361  28.584  15.551  1.00 12.79       A_13
ATOM   1445  C    GLY  158      85.510  29.144  14.143  1.00 24.46       A_13
ATOM   1446  O    GLY  158      85.181  28.449  13.177  1.00 18.77       A_13
ATOM   1447  N    ILE  159      85.936  30.403  13.989  1.00 22.41       A_13
ATOM   1449  CA   ILE  159      86.091  30.946  12.628  1.00 31.18       A_13
ATOM   1450  CB   ILE  159      86.300  32.508  12.532  1.00 23.53       A_13
ATOM   1451  CG2  ILE  159      84.991  33.203  12.177  1.00 17.28       A_13
ATOM   1452  CG1  ILE  159      87.022  33.063  13.758  1.00 15.28       A_13
ATOM   1453  CD1  ILE  159      88.507  32.949  13.707  1.00 14.71       A_13
ATOM   1454  C    ILE  159      87.226  30.280  11.875  1.00 10.56       A_13
ATOM   1455  O    ILE  159      87.167  30.139  10.653  1.00 18.79       A_13
ATOM   1456  N    GLN  160      88.287  29.927  12.590  1.00 20.71       A_13
ATOM   1458  CA   GLN  160      89.411  29.294  11.943  1.00 10.00       A_13
ATOM   1459  CB   GLN  160      90.640  29.274  12.855  1.00 10.00       A_13
ATOM   1460  CG   GLN  160      91.114  30.690  13.182  1.00 13.93       A_13
ATOM   1461  CD   GLN  160      92.402  30.754  13.981  1.00 25.61       A_13
ATOM   1462  OE1  GLN  160      92.814  29.786  14.629  1.00 19.40       A_13
ATOM   1463  NE2  GLN  160      93.042  31.915  13.950  1.00 24.78       A_13
ATOM   1466  C    GLN  160      89.000  27.917  11.477  1.00 10.00       A_13
ATOM   1467  O    GLN  160      89.458  27.481  10.432  1.00 21.73       A_13
ATOM   1468  N    SER  161      88.068  27.268  12.186  1.00 10.00       A_13
ATOM   1470  CA   SER  161      87.610  25.946  11.760  1.00 11.63       A_13
ATOM   1471  CB   SER  161      86.688  25.292  12.800  1.00 18.40       A_13
ATOM   1472  OG   SER  161      85.365  25.795  12.759  1.00 15.44       A_13
ATOM   1474  C    SER  161      86.913  26.048  10.396  1.00 26.18       A_13
ATOM   1475  O    SER  161      86.839  25.065   9.654  1.00 13.96       A_13
ATOM   1476  N    LEU  162      86.428  27.247  10.070  1.00 19.36       A_13
ATOM   1478  CA   LEU  162      85.749  27.493   8.808  1.00 17.21       A_13
```

FIG. 5A-16

```
ATOM   1479  CB   LEU  162    84.584  28.477   9.007  1.00 14.37    A_13
ATOM   1480  CG   LEU  162    83.489  28.144  10.021  1.00 31.09    A_13
ATOM   1481  CD1  LEU  162    82.596  29.351  10.217  1.00 14.96    A_13
ATOM   1482  CD2  LEU  162    82.672  26.949   9.548  1.00 23.87    A_13
ATOM   1483  C    LEU  162    86.654  28.080   7.744  1.00 11.98    A_13
ATOM   1484  O    LEU  162    86.596  27.680   6.584  1.00 15.25    A_13
ATOM   1485  N    TYR  163    87.459  29.063   8.135  1.00 26.64    A_13
ATOM   1487  CA   TYR  163    88.320  29.796   7.204  1.00 18.28    A_13
ATOM   1488  CB   TYR  163    87.977  31.289   7.277  1.00 26.89    A_13
ATOM   1489  CG   TYR  163    86.519  31.600   7.039  1.00 18.80    A_13
ATOM   1490  CD1  TYR  163    86.027  31.744   5.749  1.00 10.00    A_13
ATOM   1491  CE1  TYR  163    84.680  31.936   5.515  1.00 12.83    A_13
ATOM   1492  CD2  TYR  163    85.622  31.672   8.099  1.00 16.58    A_13
ATOM   1493  CE2  TYR  163    84.266  31.867   7.873  1.00 12.32    A_13
ATOM   1494  CZ   TYR  163    83.807  31.991   6.576  1.00 11.77    A_13
ATOM   1495  OH   TYR  163    82.472  32.141   6.331  1.00 21.93    A_13
ATOM   1497  C    TYR  163    89.818  29.669   7.397  1.00 15.67    A_13
ATOM   1498  O    TYR  163    90.590  30.089   6.526  1.00 18.92    A_13
ATOM   1499  N    GLY  164    90.225  29.096   8.525  1.00 18.34    A_13
ATOM   1501  CA   GLY  164    91.636  28.966   8.826  1.00 10.61    A_13
ATOM   1502  C    GLY  164    92.149  30.215   9.525  1.00 15.63    A_13
ATOM   1503  O    GLY  164    91.334  31.139   9.775  1.00 21.42    A_13
ATOM   1504  OT   GLY  164    93.353  30.250   9.858  1.00 21.99    A_13
ATOM   3009  ZN   ZN   166    73.275  35.223  18.371  1.00 27.40    AION
ATOM   3010  ZN   ZN   167    65.511  41.122  10.564  1.00 27.86    AION
ATOM   3011  CA   CA   168    64.285  44.152  21.635  1.00 11.76    AION
ATOM   3012  CA   CA   165    73.319  39.377   1.854  1.00 40.73    AION
ATOM   3017  C5   WAY  169    67.400  35.999  20.267  1.00 38.86    A693
ATOM   3018  CF1  WAY  169    66.626  35.606  19.161  1.00 30.96    A693
ATOM   3019  CH   WAY  169    67.199  35.400  17.901  1.00 41.17    A693
ATOM   3020  C2   WAY  169    68.561  35.623  17.728  1.00 36.26    A693
ATOM   3021  C3   WAY  169    69.339  36.039  18.811  1.00 35.73    A693
ATOM   3022  C4   WAY  169    68.807  36.216  20.078  1.00 33.71    A693
ATOM   3023  N20  WAY  169    69.699  36.617  21.141  1.00 33.16    A693
ATOM   3024  CD   WAY  169    70.137  35.640  22.189  1.00 29.78    A693
ATOM   3025  C23  WAY  169    68.986  34.739  22.685  1.00 25.69    A693
ATOM   3026  C28  WAY  169    68.187  35.088  23.798  1.00 31.72    A693
ATOM   3027  C27  WAY  169    67.141  34.238  24.205  1.00 33.61    A693
ATOM   3028  CM   WAY  169    66.921  33.061  23.490  1.00 32.16    A693
ATOM   3029  N25  WAY  169    67.703  32.748  22.426  1.00 42.39    A693
ATOM   3030  C24  WAY  169    68.709  33.546  22.016  1.00 27.88    A693
ATOM   3031  S21  WAY  169    69.757  38.213  21.577  1.00 24.43    A693
ATOM   3032  C16  WAY  169    71.513  38.570  21.438  1.00 29.69    A693
ATOM   3033  C21  WAY  169    72.032  39.163  20.269  1.00 19.32    A693
ATOM   3034  C20  WAY  169    73.400  39.453  20.169  1.00 11.82    A693
ATOM   3035  C19  WAY  169    74.267  39.156  21.241  1.00 19.50    A693
ATOM   3036  C18  WAY  169    73.748  38.564  22.402  1.00 11.88    A693
ATOM   3037  C17  WAY  169    72.382  38.272  22.507  1.00 26.57    A693
ATOM   3038  O33  WAY  169    75.623  39.445  21.141  1.00 16.99    A693
ATOM   3039  C36  WAY  169    76.504  39.509  22.271  1.00 12.69    A693
ATOM   3040  O15  WAY  169    69.030  39.032  20.657  1.00 13.98    A693
ATOM   3041  O14  WAY  169    69.419  38.338  22.942  1.00 22.94    A693
ATOM   3042  C7   WAY  169    70.780  36.256  18.621  1.00 30.48    A693
ATOM   3043  N9   WAY  169    71.192  36.946  17.553  1.00 10.00    A693
ATOM   3044  O10  WAY  169    72.581  37.127  17.426  1.00 38.25    A693
ATOM   3045  O8   WAY  169    71.614  35.847  19.414  1.00 39.46    A693
ATOM   3046  C29  WAY  169    66.584  36.175  21.566  1.00 46.13    A693
ATOM   1505  CB   THR    7    40.443  57.305   5.225  1.00 21.20    B_13
ATOM   1506  OG1  THR    7    39.149  56.999   5.762  1.00 25.31    B_13
ATOM   1508  CG2  THR    7    41.017  56.087   4.541  1.00 23.15    B_13
ATOM   1509  C    THR    7    40.920  59.113   6.901  1.00 32.45    B_13
ATOM   1510  O    THR    7    41.453  59.582   7.908  1.00 36.97    B_13
ATOM   1513  N    THR    7    41.386  56.786   7.488  1.00 34.12    B_13
ATOM   1515  CA   THR    7    41.371  57.761   6.365  1.00 26.16    B_13
ATOM   1516  N    LEU    8    39.907  59.694   6.265  1.00 23.60    B_13
ATOM   1518  CA   LEU    8    39.387  60.984   6.649  1.00 22.66    B_13
ATOM   1519  CB   LEU    8    38.113  60.848   7.503  1.00 21.78    B_13
ATOM   1520  CG   LEU    8    36.860  61.484   6.863  1.00 27.13    B_13
ATOM   1521  CD1  LEU    8    36.996  63.016   6.705  1.00 19.05    B_13
ATOM   1522  CD2  LEU    8    36.622  60.854   5.510  1.00 19.23    B_13
ATOM   1523  C    LEU    8    40.432  61.896   7.298  1.00 27.16    B_13
ATOM   1524  O    LEU    8    41.077  62.667   6.597  1.00 46.24    B_13
ATOM   1525  N    LYS    9    40.615  61.804   8.618  1.00 27.84    B_13
ATOM   1527  CA   LYS    9    41.572  62.674   9.306  1.00 15.20    B_13
ATOM   1528  CB   LYS    9    41.147  64.143   9.148  1.00 32.32    B_13
ATOM   1529  CG   LYS    9    39.663  64.342   8.853  1.00 29.47    B_13
ATOM   1530  CD   LYS    9    38.788  64.243  10.084  1.00 28.34    B_13
```

FIG. 5A-17

| ATOM | 1531 | CE | LYS | 9 | 38.830 | 65.556 | 10.842 | 1.00 | 18.48 | B_13 |
|---|---|---|---|---|---|---|---|---|---|---|
| ATOM | 1532 | NZ | LYS | 9 | 38.732 | 66.725 | 9.888 | 1.00 | 33.19 | B_13 |
| ATOM | 1536 | C | LYS | 9 | 41.809 | 62.384 | 10.780 | 1.00 | 20.69 | B_13 |
| ATOM | 1537 | O | LYS | 9 | 41.268 | 61.428 | 11.334 | 1.00 | 25.62 | B_13 |
| ATOM | 1538 | N | TRP | 10 | 42.654 | 63.208 | 11.390 | 1.00 | 12.09 | B_13 |
| ATOM | 1540 | CA | TRP | 10 | 42.988 | 63.112 | 12.813 | 1.00 | 21.78 | B_13 |
| ATOM | 1541 | CB | TRP | 10 | 44.403 | 63.660 | 13.048 | 1.00 | 23.03 | B_13 |
| ATOM | 1542 | CG | TRP | 10 | 45.499 | 62.890 | 12.349 | 1.00 | 27.60 | B_13 |
| ATOM | 1543 | CD2 | TRP | 10 | 46.077 | 61.650 | 12.762 | 1.00 | 27.28 | B_13 |
| ATOM | 1544 | CE2 | TRP | 10 | 47.071 | 61.302 | 11.829 | 1.00 | 22.11 | B_13 |
| ATOM | 1545 | CE3 | TRP | 10 | 45.859 | 60.781 | 13.847 | 1.00 | 11.66 | B_13 |
| ATOM | 1546 | CD1 | TRP | 10 | 46.153 | 63.247 | 11.198 | 1.00 | 21.84 | B_13 |
| ATOM | 1547 | NE1 | TRP | 10 | 47.094 | 62.305 | 10.873 | 1.00 | 10.00 | B_13 |
| ATOM | 1549 | CZ2 | TRP | 10 | 47.847 | 60.143 | 11.929 | 1.00 | 25.24 | B_13 |
| ATOM | 1550 | CZ3 | TRP | 10 | 46.632 | 59.622 | 13.951 | 1.00 | 22.71 | B_13 |
| ATOM | 1551 | CH2 | TRP | 10 | 47.611 | 59.317 | 12.999 | 1.00 | 15.23 | B_13 |
| ATOM | 1552 | C | TRP | 10 | 41.987 | 63.915 | 13.679 | 1.00 | 30.88 | B_13 |
| ATOM | 1553 | O | TRP | 10 | 41.673 | 65.062 | 13.359 | 1.00 | 32.03 | B_13 |
| ATOM | 1554 | N | SER | 11 | 41.495 | 63.316 | 14.765 | 1.00 | 35.64 | B_13 |
| ATOM | 1556 | CA | SER | 11 | 40.548 | 63.981 | 15.665 | 1.00 | 30.37 | B_13 |
| ATOM | 1557 | CB | SER | 11 | 39.498 | 62.995 | 16.176 | 1.00 | 31.03 | B_13 |
| ATOM | 1558 | OG | SER | 11 | 38.485 | 62.815 | 15.202 | 1.00 | 41.11 | B_13 |
| ATOM | 1560 | C | SER | 11 | 41.206 | 64.691 | 16.840 | 1.00 | 20.70 | B_13 |
| ATOM | 1561 | O | SER | 11 | 40.558 | 65.002 | 17.838 | 1.00 | 36.52 | B_13 |
| ATOM | 1562 | N | LYS | 12 | 42.504 | 64.910 | 16.731 | 1.00 | 23.56 | B_13 |
| ATOM | 1564 | CA | LYS | 12 | 43.257 | 65.607 | 17.756 | 1.00 | 15.00 | B_13 |
| ATOM | 1565 | CB | LYS | 12 | 43.991 | 64.631 | 18.688 | 1.00 | 18.58 | B_13 |
| ATOM | 1566 | CG | LYS | 12 | 44.658 | 63.452 | 18.010 | 1.00 | 15.94 | B_13 |
| ATOM | 1567 | CD | LYS | 12 | 45.456 | 62.589 | 19.007 | 1.00 | 23.03 | B_13 |
| ATOM | 1568 | CE | LYS | 12 | 44.593 | 61.715 | 19.933 | 1.00 | 27.10 | B_13 |
| ATOM | 1569 | NZ | LYS | 12 | 44.075 | 62.402 | 21.157 | 1.00 | 34.75 | B_13 |
| ATOM | 1573 | C | LYS | 12 | 44.200 | 66.453 | 16.914 | 1.00 | 25.03 | B_13 |
| ATOM | 1574 | O | LYS | 12 | 44.567 | 66.039 | 15.808 | 1.00 | 25.20 | B_13 |
| ATOM | 1575 | N | MET | 13 | 44.536 | 67.647 | 17.401 | 1.00 | 18.44 | B_13 |
| ATOM | 1577 | CA | MET | 13 | 45.377 | 68.582 | 16.663 | 1.00 | 24.63 | B_13 |
| ATOM | 1578 | CB | MET | 13 | 44.864 | 70.015 | 16.880 | 1.00 | 13.15 | B_13 |
| ATOM | 1579 | CG | MET | 13 | 43.421 | 70.253 | 16.419 | 1.00 | 21.56 | B_13 |
| ATOM | 1580 | SD | MET | 13 | 43.167 | 70.131 | 14.616 | 1.00 | 31.39 | B_13 |
| ATOM | 1581 | CE | MET | 13 | 41.433 | 69.678 | 14.474 | 1.00 | 24.70 | B_13 |
| ATOM | 1582 | C | MET | 13 | 46.850 | 68.468 | 17.034 | 1.00 | 11.65 | B_13 |
| ATOM | 1583 | O | MET | 13 | 47.728 | 68.815 | 16.247 | 1.00 | 14.33 | B_13 |
| ATOM | 1584 | N | ASN | 14 | 47.103 | 67.985 | 18.242 | 1.00 | 16.99 | B_13 |
| ATOM | 1586 | CA | ASN | 14 | 48.448 | 67.793 | 18.760 | 1.00 | 24.42 | B_13 |
| ATOM | 1587 | CB | ASN | 14 | 48.437 | 68.006 | 20.268 | 1.00 | 17.84 | B_13 |
| ATOM | 1588 | CG | ASN | 14 | 47.896 | 69.356 | 20.633 | 1.00 | 35.10 | B_13 |
| ATOM | 1589 | OD1 | ASN | 14 | 48.614 | 70.346 | 20.560 | 1.00 | 34.88 | B_13 |
| ATOM | 1590 | ND2 | ASN | 14 | 46.610 | 69.424 | 20.955 | 1.00 | 32.98 | B_13 |
| ATOM | 1593 | C | ASN | 14 | 48.831 | 66.364 | 18.421 | 1.00 | 22.70 | B_13 |
| ATOM | 1594 | O | ASN | 14 | 48.278 | 65.405 | 18.976 | 1.00 | 26.03 | B_13 |
| ATOM | 1595 | N | LEU | 15 | 49.706 | 66.228 | 17.432 | 1.00 | 18.07 | B_13 |
| ATOM | 1597 | CA | LEU | 15 | 50.144 | 64.912 | 16.969 | 1.00 | 29.36 | B_13 |
| ATOM | 1598 | CB | LEU | 15 | 49.878 | 64.775 | 15.466 | 1.00 | 24.35 | B_13 |
| ATOM | 1599 | CG | LEU | 15 | 48.380 | 64.762 | 15.162 | 1.00 | 19.51 | B_13 |
| ATOM | 1600 | CD1 | LEU | 15 | 48.079 | 65.469 | 13.852 | 1.00 | 27.59 | B_13 |
| ATOM | 1601 | CD2 | LEU | 15 | 47.902 | 63.326 | 15.163 | 1.00 | 19.66 | B_13 |
| ATOM | 1602 | C | LEU | 15 | 51.613 | 64.704 | 17.257 | 1.00 | 28.48 | B_13 |
| ATOM | 1603 | O | LEU | 15 | 52.341 | 65.657 | 17.552 | 1.00 | 22.28 | B_13 |
| ATOM | 1604 | N | THR | 16 | 52.044 | 63.453 | 17.198 | 1.00 | 12.77 | B_13 |
| ATOM | 1606 | CA | THR | 16 | 53.433 | 63.158 | 17.446 | 1.00 | 16.59 | B_13 |
| ATOM | 1607 | CB | THR | 16 | 53.607 | 62.243 | 18.682 | 1.00 | 24.73 | B_13 |
| ATOM | 1608 | OG1 | THR | 16 | 52.912 | 61.005 | 18.481 | 1.00 | 12.79 | B_13 |
| ATOM | 1610 | CG2 | THR | 16 | 53.059 | 62.933 | 19.924 | 1.00 | 25.34 | B_13 |
| ATOM | 1611 | C | THR | 16 | 54.038 | 62.515 | 16.214 | 1.00 | 21.94 | B_13 |
| ATOM | 1612 | O | THR | 16 | 53.315 | 62.116 | 15.297 | 1.00 | 19.60 | B_13 |
| ATOM | 1613 | N | TYR | 17 | 55.365 | 62.453 | 16.184 | 1.00 | 18.25 | B_13 |
| ATOM | 1615 | CA | TYR | 17 | 56.092 | 61.810 | 15.097 | 1.00 | 19.54 | B_13 |
| ATOM | 1616 | CB | TYR | 17 | 56.300 | 62.753 | 13.910 | 1.00 | 16.87 | B_13 |
| ATOM | 1617 | CG | TYR | 17 | 57.277 | 63.892 | 14.116 | 1.00 | 27.90 | B_13 |
| ATOM | 1618 | CD1 | TYR | 17 | 56.839 | 65.135 | 14.587 | 1.00 | 13.93 | B_13 |
| ATOM | 1619 | CE1 | TYR | 17 | 57.700 | 66.221 | 14.652 | 1.00 | 17.08 | B_13 |
| ATOM | 1620 | CD2 | TYR | 17 | 58.613 | 63.764 | 13.723 | 1.00 | 14.99 | B_13 |
| ATOM | 1621 | CE2 | TYR | 17 | 59.479 | 64.841 | 13.777 | 1.00 | 25.98 | B_13 |
| ATOM | 1622 | CZ | TYR | 17 | 59.017 | 66.075 | 14.242 | 1.00 | 33.12 | B_13 |
| ATOM | 1623 | OH | TYR | 17 | 59.866 | 67.163 | 14.276 | 1.00 | 23.31 | B_13 |
| ATOM | 1625 | C | TYR | 17 | 57.417 | 61.318 | 15.650 | 1.00 | 18.57 | B_13 |
| ATOM | 1626 | O | TYR | 17 | 57.895 | 61.827 | 16.668 | 1.00 | 26.60 | B_13 |
| ATOM | 1627 | N | ARG | 18 | 57.973 | 60.286 | 15.030 | 1.00 | 13.01 | B_13 |

FIG. 5A-18

| | | | | | | | | | |
|---|---|---|---|---|---|---|---|---|---|
| ATOM | 1629 | CA | ARG | 18 | 59.245 | 59.750 | 15.492 | 1.00 18.74 | B_13 |
| ATOM | 1630 | CB | ARG | 18 | 59.033 | 58.589 | 16.473 | 1.00 11.96 | B_13 |
| ATOM | 1631 | CG | ARG | 18 | 60.320 | 57.911 | 16.970 | 1.00 15.06 | B_13 |
| ATOM | 1632 | CD | ARG | 18 | 60.012 | 56.596 | 17.690 | 1.00 11.72 | B_13 |
| ATOM | 1633 | NE | ARG | 18 | 61.165 | 55.689 | 17.752 | 1.00 10.00 | B_13 |
| ATOM | 1635 | CZ | ARG | 18 | 61.134 | 54.428 | 18.181 | 1.00 24.87 | B_13 |
| ATOM | 1636 | NH1 | ARG | 18 | 60.004 | 53.882 | 18.614 | 1.00 13.34 | B_13 |
| ATOM | 1639 | NH2 | ARG | 18 | 62.247 | 53.703 | 18.169 | 1.00 20.03 | B_13 |
| ATOM | 1642 | C | ARG | 18 | 60.076 | 59.309 | 14.307 | 1.00 13.14 | B_13 |
| ATOM | 1643 | O | ARG | 18 | 59.598 | 58.588 | 13.434 | 1.00 14.10 | B_13 |
| ATOM | 1644 | N | ILE | 19 | 61.304 | 59.813 | 14.252 | 1.00 15.55 | B_13 |
| ATOM | 1646 | CA | ILE | 19 | 62.238 | 59.476 | 13.193 | 1.00 10.41 | B_13 |
| ATOM | 1647 | CB | ILE | 19 | 63.307 | 60.603 | 13.054 | 1.00 17.20 | B_13 |
| ATOM | 1648 | CG2 | ILE | 19 | 64.273 | 60.307 | 11.903 | 1.00 16.57 | B_13 |
| ATOM | 1649 | CG1 | ILE | 19 | 62.613 | 61.952 | 12.836 | 1.00 15.47 | B_13 |
| ATOM | 1650 | CD1 | ILE | 19 | 63.543 | 63.110 | 12.783 | 1.00 14.99 | B_13 |
| ATOM | 1651 | C | ILE | 19 | 62.870 | 58.166 | 13.673 | 1.00 10.00 | B_13 |
| ATOM | 1652 | O | ILE | 19 | 63.829 | 58.179 | 14.434 | 1.00 10.00 | B_13 |
| ATOM | 1653 | N | VAL | 20 | 62.289 | 57.037 | 13.276 | 1.00 17.84 | B_13 |
| ATOM | 1655 | CA | VAL | 20 | 62.785 | 55.716 | 13.696 | 1.00 16.43 | B_13 |
| ATOM | 1656 | CB | VAL | 20 | 61.911 | 54.570 | 13.138 | 1.00 13.17 | B_13 |
| ATOM | 1657 | CG1 | VAL | 20 | 62.519 | 53.208 | 13.493 | 1.00 10.00 | B_13 |
| ATOM | 1658 | CG2 | VAL | 20 | 60.521 | 54.673 | 13.698 | 1.00 10.00 | B_13 |
| ATOM | 1659 | C | VAL | 20 | 64.268 | 55.449 | 13.387 | 1.00 16.02 | B_13 |
| ATOM | 1660 | O | VAL | 20 | 65.001 | 54.909 | 14.218 | 1.00 21.07 | B_13 |
| ATOM | 1661 | N | ASN | 21 | 64.698 | 55.762 | 12.177 | 1.00 10.00 | B_13 |
| ATOM | 1663 | CA | ASN | 21 | 66.098 | 55.571 | 11.830 | 1.00 22.13 | B_13 |
| ATOM | 1664 | CB | ASN | 21 | 66.392 | 54.128 | 11.386 | 1.00 19.75 | B_13 |
| ATOM | 1665 | CG | ASN | 21 | 65.549 | 53.673 | 10.212 | 1.00 17.63 | B_13 |
| ATOM | 1666 | OD1 | ASN | 21 | 65.329 | 52.477 | 10.042 | 1.00 31.82 | B_13 |
| ATOM | 1667 | ND2 | ASN | 21 | 65.109 | 54.602 | 9.375 | 1.00 11.42 | B_13 |
| ATOM | 1670 | C | ASN | 21 | 66.504 | 56.645 | 10.821 | 1.00 10.14 | B_13 |
| ATOM | 1671 | O | ASN | 21 | 65.639 | 57.377 | 10.340 | 1.00 11.74 | B_13 |
| ATOM | 1672 | N | TYR | 22 | 67.787 | 56.759 | 10.498 | 1.00 12.25 | B_13 |
| ATOM | 1674 | CA | TYR | 22 | 68.233 | 57.829 | 9.602 | 1.00 12.46 | B_13 |
| ATOM | 1675 | CB | TYR | 22 | 69.136 | 58.800 | 10.383 | 1.00 23.15 | B_13 |
| ATOM | 1676 | CG | TYR | 22 | 68.461 | 59.584 | 11.492 | 1.00 21.95 | B_13 |
| ATOM | 1677 | CD1 | TYR | 22 | 68.221 | 60.945 | 11.348 | 1.00 22.29 | B_13 |
| ATOM | 1678 | CE1 | TYR | 22 | 67.625 | 61.678 | 12.347 | 1.00 10.00 | B_13 |
| ATOM | 1679 | CD2 | TYR | 22 | 68.077 | 58.974 | 12.687 | 1.00 13.42 | B_13 |
| ATOM | 1680 | CE2 | TYR | 22 | 67.471 | 59.710 | 13.693 | 1.00 14.69 | B_13 |
| ATOM | 1681 | CZ | TYR | 22 | 67.254 | 61.064 | 13.505 | 1.00 12.89 | B_13 |
| ATOM | 1682 | OH | TYR | 22 | 66.660 | 61.829 | 14.466 | 1.00 16.56 | B_13 |
| ATOM | 1684 | C | TYR | 22 | 68.988 | 57.395 | 8.359 | 1.00 11.62 | B_13 |
| ATOM | 1685 | O | TYR | 22 | 69.793 | 56.478 | 8.407 | 1.00 16.23 | B_13 |
| ATOM | 1686 | N | THR | 23 | 68.792 | 58.111 | 7.261 | 1.00 10.39 | B_13 |
| ATOM | 1688 | CA | THR | 23 | 69.503 | 57.800 | 6.024 | 1.00 20.36 | B_13 |
| ATOM | 1689 | CB | THR | 23 | 68.909 | 58.582 | 4.829 | 1.00 16.21 | B_13 |
| ATOM | 1690 | OG1 | THR | 23 | 69.801 | 58.512 | 3.706 | 1.00 19.72 | B_13 |
| ATOM | 1692 | CG2 | THR | 23 | 68.663 | 60.039 | 5.206 | 1.00 16.62 | B_13 |
| ATOM | 1693 | C | THR | 23 | 70.990 | 58.153 | 6.163 | 1.00 17.35 | B_13 |
| ATOM | 1694 | O | THR | 23 | 71.377 | 58.958 | 7.024 | 1.00 13.88 | B_13 |
| ATOM | 1695 | N | PRO | 24 | 71.852 | 57.503 | 5.364 | 1.00 15.86 | B_13 |
| ATOM | 1696 | CD | PRO | 24 | 71.625 | 56.247 | 4.629 | 1.00 17.29 | B_13 |
| ATOM | 1697 | CA | PRO | 24 | 73.287 | 57.796 | 5.436 | 1.00 15.96 | B_13 |
| ATOM | 1698 | CB | PRO | 24 | 73.920 | 56.570 | 4.763 | 1.00 10.00 | B_13 |
| ATOM | 1699 | CG | PRO | 24 | 72.891 | 55.504 | 4.905 | 1.00 15.15 | B_13 |
| ATOM | 1700 | C | PRO | 24 | 73.635 | 59.069 | 4.668 | 1.00 27.08 | B_13 |
| ATOM | 1701 | O | PRO | 24 | 74.698 | 59.656 | 4.869 | 1.00 19.47 | B_13 |
| ATOM | 1702 | N | ASP | 25 | 72.728 | 59.489 | 3.794 | 1.00 16.99 | B_13 |
| ATOM | 1704 | CA | ASP | 25 | 72.927 | 60.663 | 2.958 | 1.00 10.00 | B_13 |
| ATOM | 1705 | CB | ASP | 25 | 71.792 | 60.758 | 1.953 | 1.00 11.53 | B_13 |
| ATOM | 1706 | CG | ASP | 25 | 71.665 | 59.521 | 1.105 | 1.00 33.88 | B_13 |
| ATOM | 1707 | OD1 | ASP | 25 | 70.570 | 59.311 | 0.556 | 1.00 22.66 | B_13 |
| ATOM | 1708 | OD2 | ASP | 25 | 72.653 | 58.762 | 0.980 | 1.00 29.59 | B_13 |
| ATOM | 1709 | C | ASP | 25 | 73.068 | 62.011 | 3.642 | 1.00 23.36 | B_13 |
| ATOM | 1710 | O | ASP | 25 | 73.694 | 62.916 | 3.093 | 1.00 20.32 | B_13 |
| ATOM | 1711 | N | MET | 26 | 72.480 | 62.158 | 4.826 | 1.00 18.44 | B_13 |
| ATOM | 1713 | CA | MET | 26 | 72.510 | 63.432 | 5.537 | 1.00 13.83 | B_13 |
| ATOM | 1714 | CB | MET | 26 | 71.154 | 64.151 | 5.368 | 1.00 10.00 | B_13 |
| ATOM | 1715 | CG | MET | 26 | 70.782 | 64.491 | 3.913 | 1.00 28.32 | B_13 |
| ATOM | 1716 | SD | MET | 26 | 69.016 | 64.786 | 3.599 | 1.00 12.18 | B_13 |
| ATOM | 1717 | CE | MET | 26 | 68.395 | 63.255 | 3.887 | 1.00 37.25 | B_13 |
| ATOM | 1718 | C | MET | 26 | 72.827 | 63.238 | 7.024 | 1.00 28.80 | B_13 |
| ATOM | 1719 | O | MET | 26 | 72.839 | 62.107 | 7.533 | 1.00 20.90 | B_13 |
| ATOM | 1720 | N | THR | 27 | 73.157 | 64.333 | 7.696 | 1.00 11.47 | B_13 |
| ATOM | 1722 | CA | THR | 27 | 73.456 | 64.292 | 9.121 | 1.00 13.94 | B_13 |

FIG. 5A-19

| | | | | | | | | | |
|---|---|---|---|---|---|---|---|---|---|
| ATOM | 1723 | CB | THR | 27 | 74.117 | 65.605 | 9.602 | 1.00 33.46 | B_13 |
| ATOM | 1724 | OG1 | THR | 27 | 73.209 | 66.702 | 9.415 | 1.00 10.00 | B_13 |
| ATOM | 1726 | CG2 | THR | 27 | 75.405 | 65.863 | 8.818 | 1.00 16.30 | B_13 |
| ATOM | 1727 | C | THR | 27 | 72.135 | 64.113 | 9.861 | 1.00 10.67 | B_13 |
| ATOM | 1728 | O | THR | 27 | 71.072 | 64.343 | 9.281 | 1.00 16.26 | B_13 |
| ATOM | 1729 | N | HIS | 28 | 72.193 | 63.691 | 11.124 | 1.00 18.13 | B_13 |
| ATOM | 1731 | CA | HIS | 28 | 70.986 | 63.514 | 11.915 | 1.00 10.00 | B_13 |
| ATOM | 1732 | CB | HIS | 28 | 71.322 | 63.033 | 13.333 | 1.00 10.00 | B_13 |
| ATOM | 1733 | CG | HIS | 28 | 71.793 | 61.608 | 13.401 | 1.00 22.65 | B_13 |
| ATOM | 1734 | CD2 | HIS | 28 | 72.893 | 61.003 | 12.889 | 1.00 22.73 | B_13 |
| ATOM | 1735 | ND1 | HIS | 28 | 71.103 | 60.627 | 14.080 | 1.00 19.90 | B_13 |
| ATOM | 1737 | CE1 | HIS | 28 | 71.755 | 59.481 | 13.985 | 1.00 16.52 | B_13 |
| ATOM | 1738 | NE2 | HIS | 28 | 72.843 | 59.681 | 13.268 | 1.00 20.38 | B_13 |
| ATOM | 1740 | C | HIS | 28 | 70.281 | 64.870 | 11.957 | 1.00 29.38 | B_13 |
| ATOM | 1741 | O | HIS | 28 | 69.074 | 64.941 | 11.742 | 1.00 17.20 | B_13 |
| ATOM | 1742 | N | SER | 29 | 71.056 | 65.944 | 12.153 | 1.00 23.96 | B_13 |
| ATOM | 1744 | CA | SER | 29 | 70.533 | 67.322 | 12.192 | 1.00 15.01 | B_13 |
| ATOM | 1745 | CB | SER | 29 | 71.661 | 68.334 | 12.438 | 1.00 14.05 | B_13 |
| ATOM | 1746 | OG | SER | 29 | 72.117 | 68.303 | 13.770 | 1.00 18.32 | B_13 |
| ATOM | 1748 | C | SER | 29 | 69.808 | 67.729 | 10.909 | 1.00 10.95 | B_13 |
| ATOM | 1749 | O | SER | 29 | 68.732 | 68.314 | 10.971 | 1.00 24.24 | B_13 |
| ATOM | 1750 | N | GLU | 30 | 70.415 | 67.449 | 9.757 | 1.00 10.96 | B_13 |
| ATOM | 1752 | CA | GLU | 30 | 69.820 | 67.786 | 8.470 | 1.00 10.00 | B_13 |
| ATOM | 1753 | CB | GLU | 30 | 70.715 | 67.330 | 7.309 | 1.00 10.12 | B_13 |
| ATOM | 1754 | CG | GLU | 30 | 71.967 | 68.143 | 7.042 | 1.00 22.31 | B_13 |
| ATOM | 1755 | CD | GLU | 30 | 72.823 | 67.529 | 5.930 | 1.00 10.15 | B_13 |
| ATOM | 1756 | OE1 | GLU | 30 | 72.533 | 67.753 | 4.749 | 1.00 31.98 | B_13 |
| ATOM | 1757 | OE2 | GLU | 30 | 73.796 | 66.817 | 6.223 | 1.00 29.59 | B_13 |
| ATOM | 1758 | C | GLU | 30 | 68.481 | 67.073 | 8.336 | 1.00 20.17 | B_13 |
| ATOM | 1759 | O | GLU | 30 | 67.493 | 67.685 | 7.943 | 1.00 14.31 | B_13 |
| ATOM | 1760 | N | VAL | 31 | 68.451 | 65.777 | 8.665 | 1.00 19.26 | B_13 |
| ATOM | 1762 | CA | VAL | 31 | 67.228 | 64.989 | 8.536 | 1.00 14.22 | B_13 |
| ATOM | 1763 | CB | VAL | 31 | 67.472 | 63.487 | 8.716 | 1.00 17.05 | B_13 |
| ATOM | 1764 | CG1 | VAL | 31 | 66.144 | 62.749 | 8.791 | 1.00 28.55 | B_13 |
| ATOM | 1765 | CG2 | VAL | 31 | 68.269 | 62.935 | 7.548 | 1.00 10.54 | B_13 |
| ATOM | 1766 | C | VAL | 31 | 66.138 | 65.458 | 9.477 | 1.00 12.36 | B_13 |
| ATOM | 1767 | O | VAL | 31 | 64.963 | 65.488 | 9.093 | 1.00 12.83 | B_13 |
| ATOM | 1768 | N | GLU | 32 | 66.530 | 65.805 | 10.703 | 1.00 20.46 | B_13 |
| ATOM | 1770 | CA | GLU | 32 | 65.596 | 66.306 | 11.710 | 1.00 16.04 | B_13 |
| ATOM | 1771 | CB | GLU | 32 | 66.269 | 66.365 | 13.094 | 1.00 14.71 | B_13 |
| ATOM | 1772 | CG | GLU | 32 | 66.512 | 64.985 | 13.741 | 1.00 23.30 | B_13 |
| ATOM | 1773 | CD | GLU | 32 | 67.724 | 64.930 | 14.700 | 1.00 21.41 | B_13 |
| ATOM | 1774 | OE1 | GLU | 32 | 68.229 | 63.823 | 15.003 | 1.00 15.79 | B_13 |
| ATOM | 1775 | OE2 | GLU | 32 | 68.183 | 65.985 | 15.157 | 1.00 13.71 | B_13 |
| ATOM | 1776 | C | GLU | 32 | 65.125 | 67.697 | 11.257 | 1.00 27.19 | B_13 |
| ATOM | 1777 | O | GLU | 32 | 63.951 | 68.042 | 11.383 | 1.00 19.82 | B_13 |
| ATOM | 1778 | N | LYS | 33 | 66.021 | 68.461 | 10.636 | 1.00 12.52 | B_13 |
| ATOM | 1780 | CA | LYS | 33 | 65.663 | 69.786 | 10.171 | 1.00 13.00 | B_13 |
| ATOM | 1781 | CB | LYS | 33 | 66.889 | 70.592 | 9.762 | 1.00 22.63 | B_13 |
| ATOM | 1782 | CG | LYS | 33 | 66.581 | 72.054 | 9.560 | 1.00 18.24 | B_13 |
| ATOM | 1783 | CD | LYS | 33 | 65.604 | 72.545 | 10.630 | 1.00 29.21 | B_13 |
| ATOM | 1784 | CE | LYS | 33 | 66.185 | 72.429 | 12.048 | 1.00 41.79 | B_13 |
| ATOM | 1785 | NZ | LYS | 33 | 65.181 | 71.939 | 13.054 | 1.00 20.17 | B_13 |
| ATOM | 1789 | C | LYS | 33 | 64.698 | 69.686 | 9.023 | 1.00 10.62 | B_13 |
| ATOM | 1790 | O | LYS | 33 | 63.734 | 70.437 | 8.971 | 1.00 22.94 | B_13 |
| ATOM | 1791 | N | ALA | 34 | 64.915 | 68.707 | 8.150 | 1.00 10.00 | B_13 |
| ATOM | 1793 | CA | ALA | 34 | 64.050 | 68.475 | 7.000 | 1.00 11.94 | B_13 |
| ATOM | 1794 | CB | ALA | 34 | 64.611 | 67.374 | 6.100 | 1.00 10.00 | B_13 |
| ATOM | 1795 | C | ALA | 34 | 62.640 | 68.115 | 7.423 | 1.00 10.00 | B_13 |
| ATOM | 1796 | O | ALA | 34 | 61.675 | 68.650 | 6.878 | 1.00 15.32 | B_13 |
| ATOM | 1797 | N | PHE | 35 | 62.510 | 67.208 | 8.387 | 1.00 21.32 | B_13 |
| ATOM | 1799 | CA | PHE | 35 | 61.187 | 66.789 | 8.852 | 1.00 18.32 | B_13 |
| ATOM | 1800 | CB | PHE | 35 | 61.267 | 65.451 | 9.614 | 1.00 25.48 | B_13 |
| ATOM | 1801 | CG | PHE | 35 | 61.620 | 64.260 | 8.735 | 1.00 14.33 | B_13 |
| ATOM | 1802 | CD1 | PHE | 35 | 61.149 | 64.171 | 7.427 | 1.00 17.91 | B_13 |
| ATOM | 1803 | CD2 | PHE | 35 | 62.436 | 63.240 | 9.217 | 1.00 18.05 | B_13 |
| ATOM | 1804 | CE1 | PHE | 35 | 61.486 | 63.086 | 6.610 | 1.00 18.49 | B_13 |
| ATOM | 1805 | CE2 | PHE | 35 | 62.778 | 62.158 | 8.413 | 1.00 15.01 | B_13 |
| ATOM | 1806 | CZ | PHE | 35 | 62.301 | 62.081 | 7.103 | 1.00 10.00 | B_13 |
| ATOM | 1807 | C | PHE | 35 | 60.428 | 67.862 | 9.658 | 1.00 18.68 | B_13 |
| ATOM | 1808 | O | PHE | 35 | 59.202 | 67.971 | 9.556 | 1.00 17.05 | B_13 |
| ATOM | 1809 | N | LYS | 36 | 61.160 | 68.664 | 10.425 | 1.00 16.30 | B_13 |
| ATOM | 1811 | CA | LYS | 36 | 60.579 | 69.749 | 11.229 | 1.00 19.34 | B_13 |
| ATOM | 1812 | CB | LYS | 36 | 61.676 | 70.420 | 12.052 | 1.00 24.61 | B_13 |
| ATOM | 1813 | CG | LYS | 36 | 61.200 | 71.293 | 13.191 | 1.00 18.38 | B_13 |
| ATOM | 1814 | CD | LYS | 36 | 62.408 | 71.795 | 13.962 | 1.00 19.34 | B_13 |
| ATOM | 1815 | CE | LYS | 36 | 62.067 | 72.267 | 15.356 | 1.00 21.80 | B_13 |

FIG. 5A-20

```
ATOM   1816  NZ   LYS   36    63.299  72.615  16.118  1.00  27.76   B_13
ATOM   1820  C    LYS   36    59.924  70.770  10.301  1.00  10.19   B_13
ATOM   1821  O    LYS   36    58.788  71.183  10.528  1.00  14.95   B_13
ATOM   1822  N    LYS   37    60.630  71.134   9.233  1.00  15.89   B_13
ATOM   1824  CA   LYS   37    60.126  72.076   8.230  1.00  19.95   B_13
ATOM   1825  CB   LYS   37    61.202  72.386   7.189  1.00  10.00   B_13
ATOM   1826  CG   LYS   37    62.209  73.439   7.569  1.00  13.18   B_13
ATOM   1827  CD   LYS   37    62.869  73.966   6.311  1.00  28.86   B_13
ATOM   1828  CE   LYS   37    61.825  74.460   5.281  1.00  31.44   B_13
ATOM   1829  NZ   LYS   37    60.878  75.512   5.772  1.00  26.23   B_13
ATOM   1833  C    LYS   37    58.939  71.482   7.472  1.00  25.64   B_13
ATOM   1834  O    LYS   37    57.968  72.177   7.161  1.00  24.39   B_13
ATOM   1835  N    ALA   38    59.060  70.205   7.128  1.00  17.12   B_13
ATOM   1837  CA   ALA   38    58.031  69.493   6.381  1.00  16.06   B_13
ATOM   1838  CB   ALA   38    58.459  68.038   6.154  1.00  12.19   B_13
ATOM   1839  C    ALA   38    56.692  69.557   7.094  1.00  11.12   B_13
ATOM   1840  O    ALA   38    55.648  69.736   6.458  1.00  31.10   B_13
ATOM   1841  N    PHE   39    56.732  69.393   8.417  1.00  21.01   B_13
ATOM   1843  CA   PHE   39    55.540  69.446   9.257  1.00  10.85   B_13
ATOM   1844  CB   PHE   39    55.841  68.833  10.639  1.00  14.45   B_13
ATOM   1845  CG   PHE   39    55.851  67.325  10.659  1.00  21.88   B_13
ATOM   1846  CD1  PHE   39    57.016  66.625  10.954  1.00  16.88   B_13
ATOM   1847  CD2  PHE   39    54.675  66.599  10.442  1.00  22.14   B_13
ATOM   1848  CE1  PHE   39    57.010  65.223  11.037  1.00  17.95   B_13
ATOM   1849  CE2  PHE   39    54.655  65.190  10.522  1.00  17.22   B_13
ATOM   1850  CZ   PHE   39    55.823  64.503  10.823  1.00  13.51   B_13
ATOM   1851  C    PHE   39    55.044  70.898   9.426  1.00  19.98   B_13
ATOM   1852  O    PHE   39    53.839  71.160   9.393  1.00  14.30   B_13
ATOM   1853  N    LYS   40    55.981  71.826   9.611  1.00  20.03   B_13
ATOM   1855  CA   LYS   40    55.681  73.245   9.795  1.00  18.64   B_13
ATOM   1856  CB   LYS   40    56.989  74.011  10.020  1.00  19.28   B_13
ATOM   1857  CG   LYS   40    57.064  75.392   9.440  1.00  26.34   B_13
ATOM   1858  CD   LYS   40    58.288  76.093   9.974  1.00  18.46   B_13
ATOM   1859  CE   LYS   40    58.021  76.673  11.339  1.00  20.86   B_13
ATOM   1860  NZ   LYS   40    57.053  77.814  11.232  1.00  27.28   B_13
ATOM   1864  C    LYS   40    54.899  73.790   8.612  1.00  20.57   B_13
ATOM   1865  O    LYS   40    54.034  74.654   8.756  1.00  22.54   B_13
ATOM   1866  N    VAL   41    55.216  73.251   7.445  1.00  17.15   B_13
ATOM   1868  CA   VAL   41    54.565  73.576   6.184  1.00  19.19   B_13
ATOM   1869  CB   VAL   41    55.095  72.566   5.086  1.00  17.28   B_13
ATOM   1870  CG1  VAL   41    53.987  72.064   4.160  1.00  10.00   B_13
ATOM   1871  CG2  VAL   41    56.224  73.191   4.293  1.00  19.38   B_13
ATOM   1872  C    VAL   41    53.026  73.472   6.354  1.00  20.38   B_13
ATOM   1873  O    VAL   41    52.268  74.280   5.810  1.00  28.57   B_13
ATOM   1874  N    TRP   42    52.587  72.511   7.163  1.00  23.10   B_13
ATOM   1876  CA   TRP   42    51.166  72.265   7.403  1.00  19.29   B_13
ATOM   1877  CB   TRP   42    50.912  70.757   7.487  1.00  22.19   B_13
ATOM   1878  CG   TRP   42    51.437  70.007   6.313  1.00  19.32   B_13
ATOM   1879  CD2  TRP   42    50.836  69.909   5.015  1.00  31.02   B_13
ATOM   1880  CE2  TRP   42    51.659  69.067   4.238  1.00  22.49   B_13
ATOM   1881  CE3  TRP   42    49.677  70.448   4.434  1.00  15.54   B_13
ATOM   1882  CD1  TRP   42    52.571  69.251   6.269  1.00  14.04   B_13
ATOM   1883  NE1  TRP   42    52.710  68.681   5.027  1.00  13.55   B_13
ATOM   1885  CZ2  TRP   42    51.360  68.752   2.912  1.00  18.87   B_13
ATOM   1886  CZ3  TRP   42    49.383  70.132   3.116  1.00  13.33   B_13
ATOM   1887  CH2  TRP   42    50.219  69.294   2.370  1.00  20.30   B_13
ATOM   1888  C    TRP   42    50.617  72.926   8.660  1.00  24.68   B_13
ATOM   1889  O    TRP   42    49.455  73.339   8.688  1.00  20.93   B_13
ATOM   1890  N    SER   43    51.432  72.987   9.710  1.00  20.63   B_13
ATOM   1892  CA   SER   43    51.007  73.601  10.968  1.00  22.47   B_13
ATOM   1893  CB   SER   43    51.955  73.231  12.116  1.00  10.00   B_13
ATOM   1894  OG   SER   43    53.265  73.716  11.891  1.00  33.50   B_13
ATOM   1896  C    SER   43    50.913  75.122  10.829  1.00  14.99   B_13
ATOM   1897  O    SER   43    50.224  75.784  11.595  1.00  11.58   B_13
ATOM   1898  N    ASP   44    51.613  75.667   9.843  1.00  26.20   B_13
ATOM   1900  CA   ASP   44    51.595  77.100   9.617  1.00  22.11   B_13
ATOM   1901  CB   ASP   44    52.620  77.485   8.549  1.00  11.09   B_13
ATOM   1902  CG   ASP   44    54.000  77.751   9.125  1.00  18.45   B_13
ATOM   1903  OD1  ASP   44    54.903  78.114   8.347  1.00  17.67   B_13
ATOM   1904  OD2  ASP   44    54.195  77.602  10.345  1.00  21.44   B_13
ATOM   1905  C    ASP   44    50.216  77.575   9.190  1.00  32.83   B_13
ATOM   1906  O    ASP   44    49.795  78.677   9.549  1.00  34.78   B_13
ATOM   1907  N    VAL   45    49.508  76.735   8.439  1.00  31.40   B_13
ATOM   1909  CA   VAL   45    48.191  77.094   7.932  1.00  14.00   B_13
ATOM   1910  CB   VAL   45    48.121  76.872   6.401  1.00  15.73   B_13
ATOM   1911  CG1  VAL   45    49.123  77.755   5.707  1.00  19.37   B_13
ATOM   1912  CG2  VAL   45    48.407  75.409   6.055  1.00  10.00   B_13
```

FIG. 5A-21

| ATOM | 1913 | C | VAL | 45 | 47.054 | 76.333 | 8.575 | 1.00 | 18.43 | B_13 |
|---|---|---|---|---|---|---|---|---|---|---|
| ATOM | 1914 | O | VAL | 45 | 45.954 | 76.304 | 8.026 | 1.00 | 26.09 | B_13 |
| ATOM | 1915 | N | THR | 46 | 47.295 | 75.754 | 9.747 | 1.00 | 18.49 | B_13 |
| ATOM | 1917 | CA | THR | 46 | 46.262 | 74.963 | 10.408 | 1.00 | 21.92 | B_13 |
| ATOM | 1918 | CB | THR | 46 | 46.222 | 73.529 | 9.751 | 1.00 | 27.61 | B_13 |
| ATOM | 1919 | OG1 | THR | 46 | 44.876 | 73.047 | 9.661 | 1.00 | 28.78 | B_13 |
| ATOM | 1921 | CG2 | THR | 46 | 47.054 | 72.550 | 10.522 | 1.00 | 10.65 | B_13 |
| ATOM | 1922 | C | THR | 46 | 46.505 | 74.931 | 11.932 | 1.00 | 18.41 | B_13 |
| ATOM | 1923 | O | THR | 46 | 47.554 | 75.363 | 12.411 | 1.00 | 18.63 | B_13 |
| ATOM | 1924 | N | PRO | 47 | 45.519 | 74.467 | 12.717 | 1.00 | 16.81 | B_13 |
| ATOM | 1925 | CD | PRO | 47 | 44.113 | 74.209 | 12.348 | 1.00 | 32.80 | B_13 |
| ATOM | 1926 | CA | PRO | 47 | 45.691 | 74.407 | 14.169 | 1.00 | 13.66 | B_13 |
| ATOM | 1927 | CB | PRO | 47 | 44.256 | 74.489 | 14.675 | 1.00 | 30.52 | B_13 |
| ATOM | 1928 | CG | PRO | 47 | 43.519 | 73.692 | 13.638 | 1.00 | 29.25 | B_13 |
| ATOM | 1929 | C | PRO | 47 | 46.346 | 73.105 | 14.622 | 1.00 | 28.40 | B_13 |
| ATOM | 1930 | O | PRO | 47 | 46.037 | 72.597 | 15.705 | 1.00 | 29.19 | B_13 |
| ATOM | 1931 | N | LEU | 48 | 47.220 | 72.547 | 13.784 | 1.00 | 27.10 | B_13 |
| ATOM | 1933 | CA | LEU | 48 | 47.915 | 71.302 | 14.124 | 1.00 | 21.49 | B_13 |
| ATOM | 1934 | CB | LEU | 48 | 48.087 | 70.418 | 12.885 | 1.00 | 16.21 | B_13 |
| ATOM | 1935 | CG | LEU | 48 | 46.924 | 69.476 | 12.538 | 1.00 | 15.14 | B_13 |
| ATOM | 1936 | CD1 | LEU | 48 | 45.618 | 70.049 | 13.000 | 1.00 | 26.83 | B_13 |
| ATOM | 1937 | CD2 | LEU | 48 | 46.894 | 69.206 | 11.035 | 1.00 | 32.93 | B_13 |
| ATOM | 1938 | C | LEU | 48 | 49.262 | 71.611 | 14.771 | 1.00 | 16.35 | B_13 |
| ATOM | 1939 | O | LEU | 48 | 49.885 | 72.648 | 14.498 | 1.00 | 26.65 | B_13 |
| ATOM | 1940 | N | ASN | 49 | 49.691 | 70.744 | 15.669 | 1.00 | 18.84 | B_13 |
| ATOM | 1942 | CA | ASN | 49 | 50.956 | 70.940 | 16.354 | 1.00 | 25.67 | B_13 |
| ATOM | 1943 | CB | ASN | 49 | 50.741 | 71.205 | 17.846 | 1.00 | 23.64 | B_13 |
| ATOM | 1944 | CG | ASN | 49 | 49.734 | 72.301 | 18.100 | 1.00 | 23.64 | B_13 |
| ATOM | 1945 | OD1 | ASN | 49 | 48.895 | 72.192 | 18.989 | 1.00 | 33.47 | B_13 |
| ATOM | 1946 | ND2 | ASN | 49 | 49.796 | 73.359 | 17.305 | 1.00 | 37.40 | B_13 |
| ATOM | 1949 | C | ASN | 49 | 51.695 | 69.643 | 16.195 | 1.00 | 22.08 | B_13 |
| ATOM | 1950 | O | ASN | 49 | 51.087 | 68.577 | 16.252 | 1.00 | 23.48 | B_13 |
| ATOM | 1951 | N | PHE | 50 | 52.994 | 69.723 | 15.951 | 1.00 | 25.59 | B_13 |
| ATOM | 1953 | CA | PHE | 50 | 53.762 | 68.510 | 15.806 | 1.00 | 19.57 | B_13 |
| ATOM | 1954 | CB | PHE | 50 | 54.258 | 68.343 | 14.380 | 1.00 | 12.47 | B_13 |
| ATOM | 1955 | CG | PHE | 50 | 53.161 | 68.024 | 13.432 | 1.00 | 14.47 | B_13 |
| ATOM | 1956 | CD1 | PHE | 50 | 52.665 | 68.989 | 12.581 | 1.00 | 17.81 | B_13 |
| ATOM | 1957 | CD2 | PHE | 50 | 52.566 | 66.770 | 13.445 | 1.00 | 14.44 | B_13 |
| ATOM | 1958 | CE1 | PHE | 50 | 51.585 | 68.705 | 11.754 | 1.00 | 23.43 | B_13 |
| ATOM | 1959 | CE2 | PHE | 50 | 51.488 | 66.482 | 12.624 | 1.00 | 20.62 | B_13 |
| ATOM | 1960 | CZ | PHE | 50 | 50.999 | 67.447 | 11.781 | 1.00 | 13.34 | B_13 |
| ATOM | 1961 | C | PHE | 50 | 54.858 | 68.419 | 16.826 | 1.00 | 23.56 | B_13 |
| ATOM | 1962 | O | PHE | 50 | 55.720 | 69.299 | 16.922 | 1.00 | 20.28 | B_13 |
| ATOM | 1963 | N | THR | 51 | 54.728 | 67.387 | 17.651 | 1.00 | 26.45 | B_13 |
| ATOM | 1965 | CA | THR | 51 | 55.650 | 67.090 | 18.725 | 1.00 | 29.37 | B_13 |
| ATOM | 1966 | CB | THR | 51 | 54.851 | 66.834 | 20.024 | 1.00 | 28.17 | B_13 |
| ATOM | 1967 | OG1 | THR | 51 | 53.946 | 65.738 | 19.824 | 1.00 | 40.86 | B_13 |
| ATOM | 1969 | CG2 | THR | 51 | 54.032 | 68.078 | 20.393 | 1.00 | 25.37 | B_13 |
| ATOM | 1970 | C | THR | 51 | 56.435 | 65.838 | 18.331 | 1.00 | 21.26 | B_13 |
| ATOM | 1971 | O | THR | 51 | 55.849 | 64.849 | 17.882 | 1.00 | 17.45 | B_13 |
| ATOM | 1972 | N | ARG | 52 | 57.755 | 65.889 | 18.477 | 1.00 | 15.17 | B_13 |
| ATOM | 1974 | CA | ARG | 52 | 58.604 | 64.752 | 18.126 | 1.00 | 20.79 | B_13 |
| ATOM | 1975 | CB | ARG | 52 | 59.868 | 65.241 | 17.429 | 1.00 | 20.81 | B_13 |
| ATOM | 1976 | CG | ARG | 52 | 60.871 | 64.160 | 17.110 | 1.00 | 19.06 | B_13 |
| ATOM | 1977 | CD | ARG | 52 | 62.208 | 64.808 | 16.880 | 1.00 | 22.17 | B_13 |
| ATOM | 1978 | NE | ARG | 52 | 63.293 | 63.848 | 16.904 | 1.00 | 18.57 | B_13 |
| ATOM | 1980 | CZ | ARG | 52 | 64.563 | 64.160 | 17.108 | 1.00 | 10.00 | B_13 |
| ATOM | 1981 | NH1 | ARG | 52 | 64.915 | 65.414 | 17.315 | 1.00 | 19.35 | B_13 |
| ATOM | 1984 | NH2 | ARG | 52 | 65.488 | 63.214 | 17.039 | 1.00 | 35.90 | B_13 |
| ATOM | 1987 | C | ARG | 52 | 58.995 | 63.903 | 19.328 | 1.00 | 22.29 | B_13 |
| ATOM | 1988 | O | ARG | 52 | 59.326 | 64.433 | 20.387 | 1.00 | 24.98 | B_13 |
| ATOM | 1989 | N | LEU | 53 | 59.013 | 62.586 | 19.140 | 1.00 | 19.90 | B_13 |
| ATOM | 1991 | CA | LEU | 53 | 59.378 | 61.660 | 20.203 | 1.00 | 27.02 | B_13 |
| ATOM | 1992 | CB | LEU | 53 | 58.279 | 60.625 | 20.434 | 1.00 | 16.80 | B_13 |
| ATOM | 1993 | CG | LEU | 53 | 56.859 | 61.138 | 20.639 | 1.00 | 23.45 | B_13 |
| ATOM | 1994 | CD1 | LEU | 53 | 55.943 | 59.943 | 20.884 | 1.00 | 24.07 | B_13 |
| ATOM | 1995 | CD2 | LEU | 53 | 56.801 | 62.143 | 21.785 | 1.00 | 21.02 | B_13 |
| ATOM | 1996 | C | LEU | 53 | 60.657 | 60.944 | 19.813 | 1.00 | 15.08 | B_13 |
| ATOM | 1997 | O | LEU | 53 | 60.822 | 60.539 | 18.671 | 1.00 | 13.89 | B_13 |
| ATOM | 1998 | N | HIS | 54 | 61.532 | 60.750 | 20.792 | 1.00 | 19.96 | B_13 |
| ATOM | 2000 | CA | HIS | 54 | 62.812 | 60.079 | 20.568 | 1.00 | 28.80 | B_13 |
| ATOM | 2001 | CB | HIS | 54 | 63.848 | 60.604 | 21.569 | 1.00 | 19.40 | B_13 |
| ATOM | 2002 | CG | HIS | 54 | 64.113 | 62.075 | 21.431 | 1.00 | 31.96 | B_13 |
| ATOM | 2003 | CD2 | HIS | 54 | 63.365 | 63.060 | 20.883 | 1.00 | 21.32 | B_13 |
| ATOM | 2004 | ND1 | HIS | 54 | 65.292 | 62.662 | 21.835 | 1.00 | 33.94 | B_13 |
| ATOM | 2006 | CE1 | HIS | 54 | 65.260 | 63.949 | 21.539 | 1.00 | 18.64 | B_13 |
| ATOM | 2007 | NE2 | HIS | 54 | 64.103 | 64.218 | 20.960 | 1.00 | 19.56 | B_13 |

FIG. 5A-22

```
ATOM   2009  C    HIS  54    62.695  58.555  20.647  1.00  13.04    B_13
ATOM   2010  O    HIS  54    63.620  57.850  20.282  1.00  19.90    B_13
ATOM   2011  N    ASP  55    61.586  58.076  21.219  1.00  17.27    B_13
ATOM   2013  CA   ASP  55    61.303  56.648  21.366  1.00  25.79    B_13
ATOM   2014  CB   ASP  55    62.099  56.038  22.533  1.00  29.40    B_13
ATOM   2015  CG   ASP  55    63.443  55.428  22.076  1.00  29.64    B_13
ATOM   2016  OD1  ASP  55    63.517  54.906  20.942  1.00  33.28    B_13
ATOM   2017  OD2  ASP  55    64.437  55.469  22.831  1.00  31.99    B_13
ATOM   2018  C    ASP  55    59.807  56.460  21.567  1.00  24.99    B_13
ATOM   2019  O    ASP  55    59.079  57.445  21.677  1.00  21.06    B_13
ATOM   2020  N    GLY  56    59.358  55.207  21.559  1.00  22.90    B_13
ATOM   2022  CA   GLY  56    57.954  54.877  21.737  1.00  21.80    B_13
ATOM   2023  C    GLY  56    57.155  54.926  20.447  1.00  14.48    B_13
ATOM   2024  O    GLY  56    57.720  55.108  19.379  1.00  19.38    B_13
ATOM   2025  N    ILE  57    55.841  54.742  20.545  1.00  11.78    B_13
ATOM   2027  CA   ILE  57    54.944  54.809  19.389  1.00  16.25    B_13
ATOM   2028  CB   ILE  57    53.737  53.804  19.510  1.00  22.94    B_13
ATOM   2029  CG2  ILE  57    52.442  54.417  18.955  1.00  24.79    B_13
ATOM   2030  CG1  ILE  57    54.025  52.505  18.744  1.00  25.63    B_13
ATOM   2031  CD1  ILE  57    53.586  52.520  17.240  1.00  17.48    B_13
ATOM   2032  C    ILE  57    54.410  56.238  19.301  1.00  18.78    B_13
ATOM   2033  O    ILE  57    53.866  56.777  20.270  1.00  11.40    B_13
ATOM   2034  N    ALA  58    54.598  56.842  18.140  1.00  14.67    B_13
ATOM   2036  CA   ALA  58    54.139  58.200  17.857  1.00  17.04    B_13
ATOM   2037  CB   ALA  58    55.270  59.015  17.245  1.00  10.00    B_13
ATOM   2038  C    ALA  58    53.048  58.009  16.825  1.00  25.41    B_13
ATOM   2039  O    ALA  58    52.956  56.940  16.243  1.00  22.59    B_13
ATOM   2040  N    ASP  59    52.211  59.020  16.609  1.00  13.36    B_13
ATOM   2042  CA   ASP  59    51.156  58.927  15.606  1.00  24.67    B_13
ATOM   2043  CB   ASP  59    50.348  60.237  15.545  1.00  10.00    B_13
ATOM   2044  CG   ASP  59    49.743  60.631  16.899  1.00  12.93    B_13
ATOM   2045  OD1  ASP  59    49.922  61.788  17.327  1.00  32.89    B_13
ATOM   2046  OD2  ASP  59    49.076  59.793  17.541  1.00  21.52    B_13
ATOM   2047  C    ASP  59    51.784  58.653  14.242  1.00  11.46    B_13
ATOM   2048  O    ASP  59    51.378  57.736  13.531  1.00  16.58    B_13
ATOM   2049  N    ILE  60    52.791  59.445  13.899  1.00  24.90    B_13
ATOM   2051  CA   ILE  60    53.494  59.346  12.624  1.00  12.17    B_13
ATOM   2052  CB   ILE  60    53.620  60.738  11.975  1.00  10.91    B_13
ATOM   2053  CG2  ILE  60    54.289  60.641  10.588  1.00  10.70    B_13
ATOM   2054  CG1  ILE  60    52.228  61.367  11.851  1.00  18.58    B_13
ATOM   2055  CD1  ILE  60    52.219  62.870  11.726  1.00  12.00    B_13
ATOM   2056  C    ILE  60    54.881  58.750  12.841  1.00  12.93    B_13
ATOM   2057  O    ILE  60    55.788  59.392  13.365  1.00  16.39    B_13
ATOM   2058  N    MET  61    55.015  57.485  12.483  1.00  19.08    B_13
ATOM   2060  CA   MET  61    56.275  56.784  12.617  1.00  16.97    B_13
ATOM   2061  CB   MET  61    56.011  55.328  13.035  1.00  23.79    B_13
ATOM   2062  CG   MET  61    55.313  55.172  14.422  1.00  12.37    B_13
ATOM   2063  SD   MET  61    56.389  55.360  15.913  1.00  31.01    B_13
ATOM   2064  CE   MET  61    57.204  53.749  15.861  1.00  14.93    B_13
ATOM   2065  C    MET  61    56.995  56.888  11.265  1.00  12.72    B_13
ATOM   2066  O    MET  61    56.438  56.538  10.216  1.00  15.31    B_13
ATOM   2067  N    ILE  62    58.170  57.518  11.294  1.00  16.64    B_13
ATOM   2069  CA   ILE  62    58.978  57.739  10.097  1.00  27.48    B_13
ATOM   2070  CB   ILE  62    59.557  59.181  10.060  1.00  10.00    B_13
ATOM   2071  CG2  ILE  62    60.191  59.462   8.717  1.00  18.65    B_13
ATOM   2072  CG1  ILE  62    58.460  60.203  10.342  1.00  18.51    B_13
ATOM   2073  CD1  ILE  62    58.983  61.499  10.931  1.00  16.23    B_13
ATOM   2074  C    ILE  62    60.155  56.787  10.046  1.00  15.06    B_13
ATOM   2075  O    ILE  62    60.873  56.606  11.033  1.00  10.73    B_13
ATOM   2076  N    SER  63    60.398  56.230   8.873  1.00  19.40    B_13
ATOM   2078  CA   SER  63    61.513  55.321   8.722  1.00  13.31    B_13
ATOM   2079  CB   SER  63    61.111  53.888   9.123  1.00  17.28    B_13
ATOM   2080  OG   SER  63    59.985  53.435   8.391  1.00  13.66    B_13
ATOM   2082  C    SER  63    62.086  55.339   7.315  1.00  19.86    B_13
ATOM   2083  O    SER  63    61.441  55.766   6.347  1.00  20.93    B_13
ATOM   2084  N    PHE  64    63.338  54.914   7.237  1.00  17.78    B_13
ATOM   2086  CA   PHE  64    64.072  54.823   5.989  1.00  18.81    B_13
ATOM   2087  CB   PHE  64    65.409  55.553   6.105  1.00  16.50    B_13
ATOM   2088  CG   PHE  64    65.278  57.054   6.171  1.00  22.54    B_13
ATOM   2089  CD1  PHE  64    65.321  57.817   5.013  1.00  20.48    B_13
ATOM   2090  CD2  PHE  64    65.155  57.708   7.395  1.00  24.76    B_13
ATOM   2091  CE1  PHE  64    65.246  59.207   5.071  1.00  13.94    B_13
ATOM   2092  CE2  PHE  64    65.079  59.105   7.461  1.00  14.29    B_13
ATOM   2093  CZ   PHE  64    65.128  59.847   6.298  1.00  10.16    B_13
ATOM   2094  C    PHE  64    64.293  53.336   5.823  1.00  10.30    B_13
ATOM   2095  O    PHE  64    64.571  52.637   6.799  1.00  14.11    B_13
ATOM   2096  N    GLY  65    64.121  52.842   4.610  1.00  13.58    B_13
```

FIG. 5A-23

```
ATOM   2098  CA   GLY   65      64.306  51.426   4.392  1.00 14.88      B_13
ATOM   2099  C    GLY   65      64.400  51.117   2.922  1.00 14.95      B_13
ATOM   2100  O    GLY   65      64.047  51.947   2.088  1.00 12.61      B_13
ATOM   2101  N    ILE   66      64.860  49.922   2.587  1.00 10.00      B_13
ATOM   2103  CA   ILE   66      64.995  49.555   1.187  1.00 19.70      B_13
ATOM   2104  CB   ILE   66      66.483  49.344   0.791  1.00 18.92      B_13
ATOM   2105  CG2  ILE   66      67.301  50.628   1.073  1.00 10.00      B_13
ATOM   2106  CG1  ILE   66      67.078  48.178   1.582  1.00 14.64      B_13
ATOM   2107  CD1  ILE   66      68.381  47.662   1.004  1.00 17.53      B_13
ATOM   2108  C    ILE   66      64.195  48.296   0.900  1.00 15.98      B_13
ATOM   2109  O    ILE   66      63.877  47.543   1.806  1.00 20.10      B_13
ATOM   2110  N    LYS   67      63.773  48.148  -0.349  1.00 18.78      B_13
ATOM   2112  CA   LYS   67      63.019  46.980  -0.787  1.00 14.73      B_13
ATOM   2113  CB   LYS   67      63.986  45.827  -1.073  1.00 22.08      B_13
ATOM   2114  CG   LYS   67      65.107  46.142  -2.066  1.00 15.53      B_13
ATOM   2115  CD   LYS   67      64.591  46.325  -3.487  1.00 16.76      B_13
ATOM   2116  CE   LYS   67      65.573  45.763  -4.523  1.00 21.90      B_13
ATOM   2117  NZ   LYS   67      66.975  46.257  -4.394  1.00 28.03      B_13
ATOM   2121  C    LYS   67      61.945  46.548   0.218  1.00 16.24      B_13
ATOM   2122  O    LYS   67      61.136  47.360   0.649  1.00 10.25      B_13
ATOM   2123  N    GLU   68      61.968  45.293   0.630  1.00 10.00      B_13
ATOM   2125  CA   GLU   68      60.986  44.787   1.570  1.00 10.00      B_13
ATOM   2126  CB   GLU   68      61.004  43.257   1.505  1.00 31.44      B_13
ATOM   2127  CG   GLU   68      59.733  42.550   1.696  1.00 27.13      B_13
ATOM   2128  CD   GLU   68      58.723  42.720   0.524  1.00 12.88      B_13
ATOM   2129  OE1  GLU   68      59.106  42.180  -0.613  1.00 14.05      B_13
ATOM   2130  OE2  GLU   68      57.681  43.274   0.753  1.00 38.61      B_13
ATOM   2131  C    GLU   68      61.402  45.292   2.954  1.00 32.89      B_13
ATOM   2132  O    GLU   68      62.541  45.099   3.390  1.00 19.77      B_13
ATOM   2133  N    HIS   69      60.467  45.918   3.659  1.00 15.43      B_13
ATOM   2135  CA   HIS   69      60.777  46.473   4.964  1.00 10.00      B_13
ATOM   2136  CB   HIS   69      61.173  47.928   4.802  1.00 15.60      B_13
ATOM   2137  CG   HIS   69      60.151  48.731   4.063  1.00 18.06      B_13
ATOM   2138  CD2  HIS   69      59.131  49.509   4.498  1.00 25.01      B_13
ATOM   2139  ND1  HIS   69      60.055  48.709   2.689  1.00 21.79      B_13
ATOM   2141  CE1  HIS   69      59.023  49.430   2.308  1.00 19.43      B_13
ATOM   2142  NE2  HIS   69      58.438  49.932   3.384  1.00 19.23      B_13
ATOM   2143  C    HIS   69      59.655  46.396   5.978  1.00 16.27      B_13
ATOM   2144  O    HIS   69      59.689  47.099   6.969  1.00 13.47      B_13
ATOM   2145  N    GLY   70      58.610  45.629   5.719  1.00 21.21      B_13
ATOM   2147  CA   GLY   70      57.567  45.520   6.720  1.00 15.93      B_13
ATOM   2148  C    GLY   70      56.147  45.784   6.287  1.00 13.13      B_13
ATOM   2149  O    GLY   70      55.283  45.986   7.147  1.00 12.19      B_13
ATOM   2150  N    ASP   71      55.891  45.805   4.983  1.00 10.00      B_13
ATOM   2152  CA   ASP   71      54.540  46.030   4.480  1.00 17.84      B_13
ATOM   2153  CB   ASP   71      54.086  47.490   4.636  1.00 21.86      B_13
ATOM   2154  CG   ASP   71      54.946  48.480   3.881  1.00 13.38      B_13
ATOM   2155  OD1  ASP   71      54.896  49.644   4.291  1.00 10.00      B_13
ATOM   2156  OD2  ASP   71      55.633  48.135   2.897  1.00 10.00      B_13
ATOM   2157  C    ASP   71      54.313  45.557   3.064  1.00 27.18      B_13
ATOM   2158  O    ASP   71      55.221  45.068   2.416  1.00 16.61      B_13
ATOM   2159  N    PHE  72      53.103  45.759   2.564  1.00 10.00      B_13
ATOM   2161  CA   PHE  72      52.788  45.317   1.213  1.00 19.60      B_13
ATOM   2162  CB   PHE  72      51.292  45.017   1.099  1.00 16.43      B_13
ATOM   2163  CG   PHE  72      50.849  43.779   1.851  1.00 27.69      B_13
ATOM   2164  CD1  PHE  72      51.399  42.532   1.561  1.00 22.33      B_13
ATOM   2165  CD2  PHE  72      49.848  43.855   2.823  1.00 27.58      B_13
ATOM   2166  CE1  PHE  72      50.955  41.383   2.225  1.00 22.03      B_13
ATOM   2167  CE2  PHE  72      49.403  42.709   3.486  1.00 21.82      B_13
ATOM   2168  CZ   PHE  72      49.957  41.473   3.184  1.00 10.00      B_13
ATOM   2169  C    PHE  72      53.225  46.313   0.130  1.00 18.56      B_13
ATOM   2170  O    PHE  72      52.840  46.190  -1.048  1.00 14.78      B_13
ATOM   2171  N    TYR  73      54.079  47.260   0.513  1.00 10.93      B_13
ATOM   2173  CA   TYR  73      54.558  48.295  -0.416  1.00 13.87      B_13
ATOM   2174  CB   TYR  73      53.943  49.649  -0.048  1.00 22.69      B_13
ATOM   2175  CG   TYR  73      52.439  49.581   0.007  1.00 16.43      B_13
ATOM   2176  CD1  TYR  73      51.774  49.385   1.219  1.00 18.21      B_13
ATOM   2177  CE1  TYR  73      50.386  49.219   1.257  1.00 35.13      B_13
ATOM   2178  CD2  TYR  73      51.683  49.618  -1.165  1.00 15.77      B_13
ATOM   2179  CE2  TYR  73      50.300  49.456  -1.133  1.00 39.16      B_13
ATOM   2180  CZ   TYR  73      49.663  49.258   0.080  1.00 28.27      B_13
ATOM   2181  OH   TYR  73      48.301  49.122   0.106  1.00 33.06      B_13
ATOM   2183  C    TYR  73      56.088  48.349  -0.425  1.00 18.05      B_13
ATOM   2184  O    TYR  73      56.721  49.339   0.003  1.00 10.00      B_13
ATOM   2185  N    PRO  74      56.702  47.287  -0.953  1.00 13.76      B_13
ATOM   2186  CD   PRO  74      56.063  46.221  -1.740  1.00 14.21      B_13
ATOM   2187  CA   PRO  74      58.158  47.183  -1.024  1.00 21.66      B_13
```

FIG. 5A-24

| | | | | | | | | | | |
|---|---|---|---|---|---|---|---|---|---|---|
| ATOM | 2188 | CB | PRO | 74 | 58.353 | 45.768 | -1.569 | 1.00 | 15.88 | B_13 |
| ATOM | 2189 | CG | PRO | 74 | 57.225 | 45.653 | -2.540 | 1.00 | 13.95 | B_13 |
| ATOM | 2190 | C | PRO | 74 | 58.747 | 48.226 | -1.959 | 1.00 | 27.68 | B_13 |
| ATOM | 2191 | O | PRO | 74 | 58.173 | 48.526 | -3.012 | 1.00 | 21.90 | B_13 |
| ATOM | 2192 | N | PHE | 75 | 59.883 | 48.794 | -1.562 | 1.00 | 20.91 | B_13 |
| ATOM | 2194 | CA | PHE | 75 | 60.554 | 49.773 | -2.395 | 1.00 | 15.84 | B_13 |
| ATOM | 2195 | CB | PHE | 75 | 61.498 | 50.637 | -1.548 | 1.00 | 11.67 | B_13 |
| ATOM | 2196 | CG | PHE | 75 | 60.765 | 51.589 | -0.641 | 1.00 | 14.42 | B_13 |
| ATOM | 2197 | CD1 | PHE | 75 | 59.831 | 52.484 | -1.162 | 1.00 | 16.56 | B_13 |
| ATOM | 2198 | CD2 | PHE | 75 | 60.976 | 51.574 | 0.726 | 1.00 | 10.00 | B_13 |
| ATOM | 2199 | CE1 | PHE | 75 | 59.119 | 53.345 | -0.327 | 1.00 | 11.14 | B_13 |
| ATOM | 2200 | CE2 | PHE | 75 | 60.274 | 52.423 | 1.558 | 1.00 | 10.28 | B_13 |
| ATOM | 2201 | CZ | PHE | 75 | 59.340 | 53.316 | 1.027 | 1.00 | 10.00 | B_13 |
| ATOM | 2202 | C | PHE | 75 | 61.236 | 49.068 | -3.573 | 1.00 | 14.23 | B_13 |
| ATOM | 2203 | O | PHE | 75 | 61.357 | 47.837 | -3.582 | 1.00 | 18.64 | B_13 |
| ATOM | 2204 | N | ASP | 76 | 61.742 | 49.845 | -4.526 | 1.00 | 12.83 | B_13 |
| ATOM | 2206 | CA | ASP | 76 | 62.330 | 49.287 | -5.740 | 1.00 | 20.69 | B_13 |
| ATOM | 2207 | CB | ASP | 76 | 61.394 | 49.644 | -6.911 | 1.00 | 14.28 | B_13 |
| ATOM | 2208 | CG | ASP | 76 | 61.212 | 51.144 | -7.080 | 1.00 | 14.37 | B_13 |
| ATOM | 2209 | OD1 | ASP | 76 | 61.361 | 51.882 | -6.095 | 1.00 | 22.32 | B_13 |
| ATOM | 2210 | OD2 | ASP | 76 | 60.941 | 51.597 | -8.202 | 1.00 | 15.92 | B_13 |
| ATOM | 2211 | C | ASP | 76 | 63.764 | 49.698 | -6.104 | 1.00 | 19.31 | B_13 |
| ATOM | 2212 | O | ASP | 76 | 64.056 | 49.864 | -7.278 | 1.00 | 18.67 | B_13 |
| ATOM | 2213 | N | GLY | 77 | 64.653 | 49.902 | -5.132 | 1.00 | 10.00 | B_13 |
| ATOM | 2215 | CA | GLY | 77 | 65.997 | 50.326 | -5.501 | 1.00 | 10.00 | B_13 |
| ATOM | 2216 | C | GLY | 77 | 65.989 | 51.790 | -5.970 | 1.00 | 16.22 | B_13 |
| ATOM | 2217 | O | GLY | 77 | 64.967 | 52.487 | -5.752 | 1.00 | 17.04 | B_13 |
| ATOM | 2218 | N | PRO | 78 | 67.080 | 52.305 | -6.589 | 1.00 | 12.53 | B_13 |
| ATOM | 2219 | CD | PRO | 78 | 68.319 | 51.564 | -6.856 | 1.00 | 12.24 | B_13 |
| ATOM | 2220 | CA | PRO | 78 | 67.207 | 53.691 | -7.086 | 1.00 | 11.81 | B_13 |
| ATOM | 2221 | CB | PRO | 78 | 68.546 | 53.678 | -7.816 | 1.00 | 10.00 | B_13 |
| ATOM | 2222 | CG | PRO | 78 | 69.316 | 52.693 | -7.066 | 1.00 | 12.78 | B_13 |
| ATOM | 2223 | C | PRO | 78 | 66.093 | 54.146 | -8.027 | 1.00 | 10.00 | B_13 |
| ATOM | 2224 | O | PRO | 78 | 65.621 | 53.381 | -8.853 | 1.00 | 27.46 | B_13 |
| ATOM | 2225 | N | SER | 79 | 65.641 | 55.386 | -7.852 | 1.00 | 19.14 | B_13 |
| ATOM | 2227 | CA | SER | 79 | 64.568 | 55.963 | -8.669 | 1.00 | 10.00 | B_13 |
| ATOM | 2228 | CB | SER | 79 | 64.970 | 56.033 | -10.148 | 1.00 | 20.11 | B_13 |
| ATOM | 2229 | OG | SER | 79 | 63.982 | 56.723 | -10.901 | 1.00 | 23.87 | B_13 |
| ATOM | 2231 | C | SER | 79 | 63.231 | 55.215 | -8.507 | 1.00 | 31.68 | B_13 |
| ATOM | 2232 | O | SER | 79 | 63.074 | 54.356 | -7.606 | 1.00 | 26.48 | B_13 |
| ATOM | 2233 | N | GLY | 80 | 62.250 | 55.589 | -9.327 | 1.00 | 10.00 | B_13 |
| ATOM | 2235 | CA | GLY | 80 | 60.940 | 54.969 | -9.260 | 1.00 | 10.07 | B_13 |
| ATOM | 2236 | C | GLY | 80 | 60.293 | 55.412 | -7.968 | 1.00 | 30.72 | B_13 |
| ATOM | 2237 | O | GLY | 80 | 60.347 | 56.600 | -7.643 | 1.00 | 20.65 | B_13 |
| ATOM | 2238 | N | LEU | 81 | 59.779 | 54.452 | -7.193 | 1.00 | 23.74 | B_13 |
| ATOM | 2240 | CA | LEU | 81 | 59.135 | 54.752 | -5.917 | 1.00 | 13.14 | B_13 |
| ATOM | 2241 | CB | LEU | 81 | 58.661 | 53.481 | -5.213 | 1.00 | 16.20 | B_13 |
| ATOM | 2242 | CG | LEU | 81 | 57.393 | 52.775 | -5.687 | 1.00 | 17.33 | B_13 |
| ATOM | 2243 | CD1 | LEU | 81 | 57.554 | 52.277 | -7.096 | 1.00 | 28.67 | B_13 |
| ATOM | 2244 | CD2 | LEU | 81 | 57.103 | 51.617 | -4.745 | 1.00 | 27.02 | B_13 |
| ATOM | 2245 | C | LEU | 81 | 60.122 | 55.466 | -5.019 | 1.00 | 14.51 | B_13 |
| ATOM | 2246 | O | LEU | 81 | 61.264 | 55.016 | -4.846 | 1.00 | 16.24 | B_13 |
| ATOM | 2247 | N | LEU | 82 | 59.692 | 56.590 | -4.470 | 1.00 | 11.33 | B_13 |
| ATOM | 2249 | CA | LEU | 82 | 60.540 | 57.381 | -3.594 | 1.00 | 17.52 | B_13 |
| ATOM | 2250 | CB | LEU | 82 | 60.442 | 58.861 | -3.986 | 1.00 | 18.51 | B_13 |
| ATOM | 2251 | CG | LEU | 82 | 61.355 | 59.499 | -5.044 | 1.00 | 15.37 | B_13 |
| ATOM | 2252 | CD1 | LEU | 82 | 61.800 | 58.504 | -6.104 | 1.00 | 17.05 | B_13 |
| ATOM | 2253 | CD2 | LEU | 82 | 60.639 | 60.744 | -5.659 | 1.00 | 16.87 | B_13 |
| ATOM | 2254 | C | LEU | 82 | 60.172 | 57.203 | -2.127 | 1.00 | 10.00 | B_13 |
| ATOM | 2255 | O | LEU | 82 | 61.045 | 57.056 | -1.275 | 1.00 | 19.90 | B_13 |
| ATOM | 2256 | N | ALA | 83 | 58.876 | 57.201 | -1.840 | 1.00 | 18.16 | B_13 |
| ATOM | 2258 | CA | ALA | 83 | 58.378 | 57.077 | -0.472 | 1.00 | 13.17 | B_13 |
| ATOM | 2259 | CB | ALA | 83 | 58.762 | 58.322 | 0.327 | 1.00 | 10.00 | B_13 |
| ATOM | 2260 | C | ALA | 83 | 56.846 | 56.925 | -0.500 | 1.00 | 10.00 | B_13 |
| ATOM | 2261 | O | ALA | 83 | 56.209 | 57.155 | -1.541 | 1.00 | 10.73 | B_13 |
| ATOM | 2262 | N | HIS | 84 | 56.268 | 56.619 | 0.662 | 1.00 | 10.00 | B_13 |
| ATOM | 2264 | CA | HIS | 84 | 54.811 | 56.472 | 0.810 | 1.00 | 23.81 | B_13 |
| ATOM | 2265 | CB | HIS | 84 | 54.270 | 55.188 | 0.157 | 1.00 | 30.45 | B_13 |
| ATOM | 2266 | CG | HIS | 84 | 54.848 | 53.925 | 0.711 | 1.00 | 17.68 | B_13 |
| ATOM | 2267 | CD2 | HIS | 84 | 54.856 | 53.415 | 1.964 | 1.00 | 10.00 | B_13 |
| ATOM | 2268 | ND1 | HIS | 84 | 55.525 | 53.025 | -0.076 | 1.00 | 14.94 | B_13 |
| ATOM | 2270 | CE1 | HIS | 84 | 55.933 | 52.015 | 0.666 | 1.00 | 29.72 | B_13 |
| ATOM | 2271 | NE2 | HIS | 84 | 55.543 | 52.224 | 1.912 | 1.00 | 13.81 | B_13 |
| ATOM | 2272 | C | HIS | 84 | 54.363 | 56.547 | 2.258 | 1.00 | 12.82 | B_13 |
| ATOM | 2273 | O | HIS | 84 | 55.099 | 56.148 | 3.166 | 1.00 | 20.02 | B_13 |
| ATOM | 2274 | N | ALA | 85 | 53.161 | 57.076 | 2.464 | 1.00 | 28.38 | B_13 |
| ATOM | 2276 | CA | ALA | 85 | 52.584 | 57.230 | 3.796 | 1.00 | 18.64 | B_13 |

FIG. 5A-25

| | | | | | | | | | | |
|---|---|---|---|---|---|---|---|---|---|---|
| ATOM | 2277 | CB | ALA | 85 | 52.638 | 58.705 | 4.223 | 1.00 | 13.89 | B_13 |
| ATOM | 2278 | C | ALA | 85 | 51.138 | 56.716 | 3.837 | 1.00 | 10.00 | B_13 |
| ATOM | 2279 | O | ALA | 85 | 50.434 | 56.728 | 2.828 | 1.00 | 10.00 | B_13 |
| ATOM | 2280 | N | PHE | 86 | 50.676 | 56.322 | 5.016 | 1.00 | 14.76 | B_13 |
| ATOM | 2282 | CA | PHE | 86 | 49.316 | 55.811 | 5.143 | 1.00 | 17.96 | B_13 |
| ATOM | 2283 | CB | PHE | 86 | 49.286 | 54.592 | 6.084 | 1.00 | 15.86 | B_13 |
| ATOM | 2284 | CG | PHE | 86 | 50.320 | 53.542 | 5.748 | 1.00 | 26.30 | B_13 |
| ATOM | 2285 | CD1 | PHE | 86 | 49.973 | 52.398 | 5.042 | 1.00 | 22.30 | B_13 |
| ATOM | 2286 | CD2 | PHE | 86 | 51.654 | 53.730 | 6.090 | 1.00 | 27.63 | B_13 |
| ATOM | 2287 | CE1 | PHE | 86 | 50.938 | 51.472 | 4.681 | 1.00 | 27.85 | B_13 |
| ATOM | 2288 | CE2 | PHE | 86 | 52.620 | 52.810 | 5.731 | 1.00 | 13.97 | B_13 |
| ATOM | 2289 | CZ | PHE | 86 | 52.266 | 51.683 | 5.027 | 1.00 | 23.08 | B_13 |
| ATOM | 2290 | C | PHE | 86 | 48.427 | 56.924 | 5.669 | 1.00 | 13.02 | B_13 |
| ATOM | 2291 | O | PHE | 86 | 48.870 | 57.747 | 6.466 | 1.00 | 15.02 | B_13 |
| ATOM | 2292 | N | PRO | 87 | 47.174 | 57.006 | 5.186 | 1.00 | 17.55 | B_13 |
| ATOM | 2293 | CD | PRO | 87 | 46.565 | 56.165 | 4.146 | 1.00 | 10.17 | B_13 |
| ATOM | 2294 | CA | PRO | 87 | 46.228 | 58.041 | 5.628 | 1.00 | 32.09 | B_13 |
| ATOM | 2295 | CB | PRO | 87 | 44.961 | 57.720 | 4.819 | 1.00 | 18.55 | B_13 |
| ATOM | 2296 | CG | PRO | 87 | 45.115 | 56.277 | 4.481 | 1.00 | 18.86 | B_13 |
| ATOM | 2297 | C | PRO | 87 | 45.995 | 57.955 | 7.139 | 1.00 | 25.18 | B_13 |
| ATOM | 2298 | O | PRO | 87 | 46.284 | 56.919 | 7.752 | 1.00 | 18.18 | B_13 |
| ATOM | 2299 | N | PRO | 88 | 45.462 | 59.032 | 7.760 | 1.00 | 11.49 | B_13 |
| ATOM | 2300 | CD | PRO | 88 | 45.015 | 60.303 | 7.164 | 1.00 | 10.00 | B_13 |
| ATOM | 2301 | CA | PRO | 88 | 45.217 | 59.034 | 9.202 | 1.00 | 19.03 | B_13 |
| ATOM | 2302 | CB | PRO | 88 | 44.399 | 60.302 | 9.402 | 1.00 | 14.16 | B_13 |
| ATOM | 2303 | CG | PRO | 88 | 44.939 | 61.196 | 8.357 | 1.00 | 16.39 | B_13 |
| ATOM | 2304 | C | PRO | 88 | 44.500 | 57.787 | 9.733 | 1.00 | 25.43 | B_13 |
| ATOM | 2305 | O | PRO | 88 | 43.670 | 57.165 | 9.044 | 1.00 | 15.90 | B_13 |
| ATOM | 2306 | N | GLY | 89 | 44.865 | 57.422 | 10.955 | 1.00 | 26.28 | B_13 |
| ATOM | 2308 | CA | GLY | 89 | 44.299 | 56.264 | 11.606 | 1.00 | 25.32 | B_13 |
| ATOM | 2309 | C | GLY | 89 | 45.343 | 55.713 | 12.546 | 1.00 | 34.38 | B_13 |
| ATOM | 2310 | O | GLY | 89 | 46.485 | 56.164 | 12.498 | 1.00 | 23.28 | B_13 |
| ATOM | 2311 | N | PRO | 90 | 44.977 | 54.774 | 13.437 | 1.00 | 13.87 | B_13 |
| ATOM | 2312 | CD | PRO | 90 | 43.613 | 54.259 | 13.631 | 1.00 | 16.36 | B_13 |
| ATOM | 2313 | CA | PRO | 90 | 45.898 | 54.164 | 14.398 | 1.00 | 10.34 | B_13 |
| ATOM | 2314 | CB | PRO | 90 | 44.963 | 53.360 | 15.300 | 1.00 | 15.93 | B_13 |
| ATOM | 2315 | CG | PRO | 90 | 43.870 | 52.975 | 14.373 | 1.00 | 23.25 | B_13 |
| ATOM | 2316 | C | PRO | 90 | 46.942 | 53.299 | 13.711 | 1.00 | 18.38 | B_13 |
| ATOM | 2317 | O | PRO | 90 | 46.875 | 53.064 | 12.505 | 1.00 | 26.81 | B_13 |
| ATOM | 2318 | N | ASN | 91 | 47.903 | 52.831 | 14.502 | 1.00 | 26.63 | B_13 |
| ATOM | 2320 | CA | ASN | 91 | 49.022 | 52.010 | 14.033 | 1.00 | 21.91 | B_13 |
| ATOM | 2321 | CB | ASN | 91 | 48.740 | 50.500 | 14.081 | 1.00 | 18.89 | B_13 |
| ATOM | 2322 | CG | ASN | 91 | 47.437 | 50.117 | 13.448 | 1.00 | 22.49 | B_13 |
| ATOM | 2323 | OD1 | ASN | 91 | 47.335 | 50.017 | 12.237 | 1.00 | 29.37 | B_13 |
| ATOM | 2324 | ND2 | ASN | 91 | 46.438 | 49.858 | 14.273 | 1.00 | 28.01 | B_13 |
| ATOM | 2327 | C | ASN | 91 | 49.656 | 52.438 | 12.721 | 1.00 | 20.07 | B_13 |
| ATOM | 2328 | O | ASN | 91 | 50.301 | 53.479 | 12.681 | 1.00 | 21.24 | B_13 |
| ATOM | 2329 | N | TYR | 92 | 49.423 | 51.716 | 11.633 | 1.00 | 20.15 | B_13 |
| ATOM | 2331 | CA | TYR | 92 | 50.052 | 52.081 | 10.367 | 1.00 | 18.70 | B_13 |
| ATOM | 2332 | CB | TYR | 92 | 49.905 | 50.953 | 9.344 | 1.00 | 14.48 | B_13 |
| ATOM | 2333 | CG | TYR | 92 | 50.906 | 49.821 | 9.567 | 1.00 | 24.41 | B_13 |
| ATOM | 2334 | CD1 | TYR | 92 | 52.266 | 50.003 | 9.287 | 1.00 | 27.39 | B_13 |
| ATOM | 2335 | CE1 | TYR | 92 | 53.198 | 48.979 | 9.471 | 1.00 | 18.14 | B_13 |
| ATOM | 2336 | CD2 | TYR | 92 | 50.499 | 48.571 | 10.044 | 1.00 | 28.07 | B_13 |
| ATOM | 2337 | CE2 | TYR | 92 | 51.427 | 47.529 | 10.230 | 1.00 | 36.50 | B_13 |
| ATOM | 2338 | CZ | TYR | 92 | 52.778 | 47.741 | 9.940 | 1.00 | 43.64 | B_13 |
| ATOM | 2339 | OH | TYR | 92 | 53.694 | 46.710 | 10.105 | 1.00 | 32.21 | B_13 |
| ATOM | 2341 | C | TYR | 92 | 49.633 | 53.431 | 9.797 | 1.00 | 21.78 | B_13 |
| ATOM | 2342 | O | TYR | 92 | 50.384 | 54.049 | 9.040 | 1.00 | 12.55 | B_13 |
| ATOM | 2343 | N | GLY | 93 | 48.464 | 53.916 | 10.198 | 1.00 | 15.83 | B_13 |
| ATOM | 2345 | CA | GLY | 93 | 48.015 | 55.216 | 9.732 | 1.00 | 11.69 | B_13 |
| ATOM | 2346 | C | GLY | 93 | 48.971 | 56.326 | 10.134 | 1.00 | 18.60 | B_13 |
| ATOM | 2347 | O | GLY | 93 | 49.561 | 56.300 | 11.227 | 1.00 | 22.00 | B_13 |
| ATOM | 2348 | N | GLY | 94 | 49.205 | 57.258 | 9.216 | 1.00 | 10.27 | B_13 |
| ATOM | 2350 | CA | GLY | 94 | 50.099 | 58.365 | 9.492 | 1.00 | 18.36 | B_13 |
| ATOM | 2351 | C | GLY | 94 | 51.567 | 58.061 | 9.234 | 1.00 | 15.54 | B_13 |
| ATOM | 2352 | O | GLY | 94 | 52.334 | 58.967 | 8.938 | 1.00 | 17.55 | B_13 |
| ATOM | 2353 | N | ASP | 95 | 51.977 | 56.801 | 9.351 | 1.00 | 17.69 | B_13 |
| ATOM | 2355 | CA | ASP | 95 | 53.386 | 56.457 | 9.134 | 1.00 | 19.67 | B_13 |
| ATOM | 2356 | CB | ASP | 95 | 53.637 | 54.986 | 9.444 | 1.00 | 15.96 | B_13 |
| ATOM | 2357 | CG | ASP | 95 | 53.346 | 54.634 | 10.900 | 1.00 | 25.37 | B_13 |
| ATOM | 2358 | OD1 | ASP | 95 | 53.627 | 53.484 | 11.297 | 1.00 | 16.05 | B_13 |
| ATOM | 2359 | OD2 | ASP | 95 | 52.835 | 55.488 | 11.656 | 1.00 | 14.66 | B_13 |
| ATOM | 2360 | C | ASP | 95 | 53.896 | 56.808 | 7.733 | 1.00 | 17.15 | B_13 |
| ATOM | 2361 | O | ASP | 95 | 53.162 | 56.711 | 6.746 | 1.00 | 19.09 | B_13 |
| ATOM | 2362 | N | ALA | 96 | 55.166 | 57.198 | 7.662 | 1.00 | 18.71 | B_13 |
| ATOM | 2364 | CA | ALA | 96 | 55.803 | 57.581 | 6.400 | 1.00 | 19.97 | B_13 |

FIG. 5A-26

```
ATOM   2365  CB   ALA   96      56.098  59.095   6.379  1.00  22.61      B_13
ATOM   2366  C    ALA   96      57.088  56.784   6.204  1.00  25.63      B_13
ATOM   2367  O    ALA   96      57.948  56.724   7.095  1.00  12.54      B_13
ATOM   2368  N    HIS   97      57.211  56.166   5.035  1.00  13.27      B_13
ATOM   2370  CA   HIS   97      58.375  55.357   4.730  1.00  25.28      B_13
ATOM   2371  CB   HIS   97      57.955  53.905   4.464  1.00  10.00      B_13
ATOM   2372  CG   HIS   97      57.264  53.257   5.624  1.00  12.02      B_13
ATOM   2373  CD2  HIS   97      57.214  53.603   6.929  1.00  10.00      B_13
ATOM   2374  ND1  HIS   97      56.516  52.104   5.499  1.00  12.91      B_13
ATOM   2375  CE1  HIS   97      56.038  51.770   6.688  1.00  10.00      B_13
ATOM   2376  NE2  HIS   97      56.445  52.664   7.571  1.00  10.64      B_13
ATOM   2378  C    HIS   97      59.069  55.959   3.520  1.00  13.82      B_13
ATOM   2379  O    HIS   97      58.415  56.273   2.517  1.00  12.27      B_13
ATOM   2380  N    PHE   98      60.379  56.154   3.647  1.00  10.67      B_13
ATOM   2382  CA   PHE   98      61.224  56.718   2.595  1.00  15.67      B_13
ATOM   2383  CB   PHE   98      61.970  57.938   3.156  1.00  10.76      B_13
ATOM   2384  CG   PHE   98      61.055  59.025   3.627  1.00  17.93      B_13
ATOM   2385  CD1  PHE   98      60.730  60.082   2.786  1.00  18.92      B_13
ATOM   2386  CD2  PHE   98      60.476  58.974   4.893  1.00  14.14      B_13
ATOM   2387  CE1  PHE   98      59.833  61.066   3.201  1.00  22.42      B_13
ATOM   2388  CE2  PHE   98      59.574  59.962   5.315  1.00  10.00      B_13
ATOM   2389  CZ   PHE   98      59.257  61.002   4.469  1.00  10.00      B_13
ATOM   2390  C    PHE   98      62.218  55.669   2.064  1.00  26.64      B_13
ATOM   2391  O    PHE   98      62.882  54.969   2.851  1.00  13.27      B_13
ATOM   2392  N    ASP   99      62.331  55.577   0.738  1.00  12.24      B_13
ATOM   2394  CA   ASP   99      63.229  54.612   0.102  1.00  10.00      B_13
ATOM   2395  CB   ASP   99      62.884  54.471  -1.385  1.00  10.00      B_13
ATOM   2396  CG   ASP   99      63.615  53.311  -2.067  1.00  22.86      B_13
ATOM   2397  OD1  ASP   99      63.170  52.890  -3.160  1.00  11.60      B_13
ATOM   2398  OD2  ASP   99      64.624  52.806  -1.528  1.00  21.20      B_13
ATOM   2399  C    ASP   99      64.677  55.046   0.264  1.00  12.66      B_13
ATOM   2400  O    ASP   99      65.121  56.010  -0.366  1.00  18.37      B_13
ATOM   2401  N    ASP  100      65.439  54.289   1.046  1.00  12.86      B_13
ATOM   2403  CA   ASP  100      66.833  54.642   1.260  1.00  14.46      B_13
ATOM   2404  CB   ASP  100      67.308  54.271   2.660  1.00  17.70      B_13
ATOM   2405  CG   ASP  100      68.006  55.437   3.358  1.00  16.15      B_13
ATOM   2406  OD1  ASP  100      68.091  55.447   4.602  1.00  15.74      B_13
ATOM   2407  OD2  ASP  100      68.470  56.354   2.655  1.00  27.08      B_13
ATOM   2408  C    ASP  100      67.793  54.171   0.179  1.00  13.66      B_13
ATOM   2409  O    ASP  100      68.961  53.932   0.416  1.00  19.54      B_13
ATOM   2410  N    ASP  101      67.254  53.954  -1.010  1.00  12.83      B_13
ATOM   2412  CA   ASP  101      68.074  53.590  -2.164  1.00  10.00      B_13
ATOM   2413  CB   ASP  101      67.471  52.413  -2.933  1.00  10.00      B_13
ATOM   2414  CG   ASP  101      67.997  51.065  -2.449  1.00  16.87      B_13
ATOM   2415  OD1  ASP  101      67.232  50.089  -2.458  1.00  19.89      B_13
ATOM   2416  OD2  ASP  101      69.184  50.968  -2.066  1.00  18.51      B_13
ATOM   2417  C    ASP  101      68.108  54.858  -3.029  1.00  26.72      B_13
ATOM   2418  O    ASP  101      68.602  54.853  -4.172  1.00  12.11      B_13
ATOM   2419  N    GLU  102      67.500  55.922  -2.496  1.00  13.76      B_13
ATOM   2421  CA   GLU  102      67.462  57.217  -3.161  1.00  12.54      B_13
ATOM   2422  CB   GLU  102      66.135  57.958  -2.916  1.00  13.01      B_13
ATOM   2423  CG   GLU  102      64.873  57.257  -3.381  1.00  15.50      B_13
ATOM   2424  CD   GLU  102      64.973  56.707  -4.791  1.00  29.02      B_13
ATOM   2425  OE1  GLU  102      65.640  57.307  -5.665  1.00  12.78      B_13
ATOM   2426  OE2  GLU  102      64.399  55.635  -5.021  1.00  12.36      B_13
ATOM   2427  C    GLU  102      68.544  58.040  -2.505  1.00  14.96      B_13
ATOM   2428  O    GLU  102      68.939  57.760  -1.371  1.00  10.00      B_13
ATOM   2429  N    THR  103      69.030  59.039  -3.228  1.00  19.38      B_13
ATOM   2431  CA   THR  103      70.021  59.957  -2.693  1.00  16.49      B_13
ATOM   2432  CB   THR  103      70.973  60.490  -3.801  1.00  19.31      B_13
ATOM   2433  OG1  THR  103      71.661  59.384  -4.399  1.00  25.44      B_13
ATOM   2435  CG2  THR  103      72.006  61.462  -3.212  1.00  10.75      B_13
ATOM   2436  C    THR  103      69.180  61.104  -2.141  1.00  12.91      B_13
ATOM   2437  O    THR  103      68.414  61.727  -2.867  1.00  13.59      B_13
ATOM   2438  N    TRP  104      69.252  61.322  -0.842  1.00  20.60      B_13
ATOM   2440  CA   TRP  104      68.497  62.388  -0.237  1.00  13.62      B_13
ATOM   2441  CB   TRP  104      67.852  61.902   1.063  1.00  22.66      B_13
ATOM   2442  CG   TRP  104      66.837  60.808   0.870  1.00  22.99      B_13
ATOM   2443  CD2  TRP  104      65.505  60.953   0.347  1.00  27.35      B_13
ATOM   2444  CE2  TRP  104      64.936  59.654   0.287  1.00  12.61      B_13
ATOM   2445  CE3  TRP  104      64.741  62.054  -0.079  1.00  11.89      B_13
ATOM   2446  CD1  TRP  104      67.013  59.473   1.108  1.00  17.89      B_13
ATOM   2447  NE1  TRP  104      65.876  58.775   0.755  1.00  14.24      B_13
ATOM   2449  CZ2  TRP  104      63.632  59.429  -0.186  1.00  10.00      B_13
ATOM   2450  CZ3  TRP  104      63.445  61.832  -0.549  1.00  22.21      B_13
ATOM   2451  CH2  TRP  104      62.904  60.527  -0.598  1.00  23.31      B_13
ATOM   2452  C    TRP  104      69.416  63.570   0.033  1.00  16.43      B_13
```

FIG. 5A-27

| | | | | | | | | | |
|---|---|---|---|---|---|---|---|---|---|
| ATOM | 2453 | O | TRP | 104 | 70.520 | 63.380 | 0.526 | 1.00 11.13 | B_13 |
| ATOM | 2454 | N | THR | 105 | 68.960 | 64.775 | -0.322 | 1.00 19.48 | B_13 |
| ATOM | 2456 | CA | THR | 105 | 69.716 | 66.015 | -0.097 | 1.00 10.40 | B_13 |
| ATOM | 2457 | CB | THR | 105 | 70.153 | 66.749 | -1.398 | 1.00 10.00 | B_13 |
| ATOM | 2458 | OG1 | THR | 105 | 69.305 | 66.401 | -2.501 | 1.00 18.53 | B_13 |
| ATOM | 2460 | CG2 | THR | 105 | 71.596 | 66.464 | -1.709 | 1.00 34.62 | B_13 |
| ATOM | 2461 | C | THR | 105 | 68.904 | 67.062 | 0.641 | 1.00 20.82 | B_13 |
| ATOM | 2462 | O | THR | 105 | 67.686 | 66.952 | 0.768 | 1.00 15.93 | B_13 |
| ATOM | 2463 | N | SER | 106 | 69.621 | 68.073 | 1.125 | 1.00 38.37 | B_13 |
| ATOM | 2465 | CA | SER | 106 | 69.029 | 69.222 | 1.791 | 1.00 20.77 | B_13 |
| ATOM | 2466 | CB | SER | 106 | 69.979 | 69.778 | 2.862 | 1.00 17.95 | B_13 |
| ATOM | 2467 | OG | SER | 106 | 70.281 | 68.825 | 3.864 | 1.00 29.88 | B_13 |
| ATOM | 2469 | C | SER | 106 | 68.889 | 70.245 | 0.657 | 1.00 19.23 | B_13 |
| ATOM | 2470 | O | SER | 106 | 68.202 | 71.260 | 0.782 | 1.00 21.34 | B_13 |
| ATOM | 2471 | N | SER | 107 | 69.577 | 69.981 | -0.450 | 1.00 18.73 | B_13 |
| ATOM | 2473 | CA | SER | 107 | 69.533 | 70.884 | -1.592 | 1.00 20.92 | B_13 |
| ATOM | 2474 | CB | SER | 107 | 70.945 | 71.380 | -1.927 | 1.00 19.84 | B_13 |
| ATOM | 2475 | OG | SER | 107 | 71.556 | 71.957 | -0.788 | 1.00 27.31 | B_13 |
| ATOM | 2477 | C | SER | 107 | 68.848 | 70.284 | -2.828 | 1.00 18.68 | B_13 |
| ATOM | 2478 | O | SER | 107 | 67.660 | 69.953 | -2.771 | 1.00 21.51 | B_13 |
| ATOM | 2479 | N | SER | 108 | 69.623 | 70.038 | -3.888 | 1.00 18.53 | B_13 |
| ATOM | 2481 | CA | SER | 108 | 69.091 | 69.544 | -5.152 | 1.00 16.21 | B_13 |
| ATOM | 2482 | CB | SER | 108 | 69.285 | 70.632 | -6.205 | 1.00 29.10 | B_13 |
| ATOM | 2483 | OG | SER | 108 | 70.665 | 70.969 | -6.271 | 1.00 21.47 | B_13 |
| ATOM | 2485 | C | SER | 108 | 69.645 | 68.260 | -5.745 | 1.00 17.68 | B_13 |
| ATOM | 2486 | O | SER | 108 | 68.964 | 67.618 | -6.541 | 1.00 19.67 | B_13 |
| ATOM | 2487 | N | LYS | 109 | 70.895 | 67.919 | -5.448 | 1.00 11.70 | B_13 |
| ATOM | 2489 | CA | LYS | 109 | 71.468 | 66.721 | -6.047 | 1.00 10.00 | B_13 |
| ATOM | 2490 | CB | LYS | 109 | 72.994 | 66.748 | -5.989 | 1.00 18.86 | B_13 |
| ATOM | 2491 | CG | LYS | 109 | 73.657 | 65.833 | -7.013 | 1.00 16.33 | B_13 |
| ATOM | 2492 | CD | LYS | 109 | 75.143 | 65.726 | -6.740 | 1.00 11.58 | B_13 |
| ATOM | 2493 | CE | LYS | 109 | 75.787 | 64.655 | -7.606 | 1.00 27.43 | B_13 |
| ATOM | 2494 | NZ | LYS | 109 | 77.218 | 64.492 | -7.251 | 1.00 35.03 | B_13 |
| ATOM | 2498 | C | LYS | 109 | 70.916 | 65.428 | -5.444 | 1.00 29.39 | B_13 |
| ATOM | 2499 | O | LYS | 109 | 71.432 | 64.905 | -4.449 | 1.00 29.95 | B_13 |
| ATOM | 2500 | N | GLY | 110 | 69.852 | 64.922 | -6.055 | 1.00 14.77 | B_13 |
| ATOM | 2502 | CA | GLY | 110 | 69.227 | 63.705 | -5.576 | 1.00 24.08 | B_13 |
| ATOM | 2503 | C | GLY | 110 | 67.793 | 64.105 | -5.342 | 1.00 20.25 | B_13 |
| ATOM | 2504 | O | GLY | 110 | 67.203 | 64.737 | -6.198 | 1.00 16.21 | B_13 |
| ATOM | 2505 | N | TYR | 111 | 67.248 | 63.772 | -4.182 | 1.00 10.00 | B_13 |
| ATOM | 2507 | CA | TYR | 111 | 65.879 | 64.130 | -3.845 | 1.00 24.52 | B_13 |
| ATOM | 2508 | CB | TYR | 111 | 65.030 | 62.868 | -3.688 | 1.00 22.46 | B_13 |
| ATOM | 2509 | CG | TYR | 111 | 64.676 | 62.244 | -4.999 | 1.00 10.83 | B_13 |
| ATOM | 2510 | CD1 | TYR | 111 | 65.380 | 61.155 | -5.483 | 1.00 25.38 | B_13 |
| ATOM | 2511 | CE1 | TYR | 111 | 65.068 | 60.592 | -6.720 | 1.00 18.68 | B_13 |
| ATOM | 2512 | CD2 | TYR | 111 | 63.646 | 62.769 | -5.776 | 1.00 16.02 | B_13 |
| ATOM | 2513 | CE2 | TYR | 111 | 63.328 | 62.223 | -7.013 | 1.00 31.72 | B_13 |
| ATOM | 2514 | CZ | TYR | 111 | 64.041 | 61.131 | -7.473 | 1.00 23.68 | B_13 |
| ATOM | 2515 | OH | TYR | 111 | 63.711 | 60.550 | -8.666 | 1.00 20.96 | B_13 |
| ATOM | 2517 | C | TYR | 111 | 65.856 | 64.944 | -2.553 | 1.00 22.83 | B_13 |
| ATOM | 2518 | O | TYR | 111 | 66.410 | 64.518 | -1.538 | 1.00 11.66 | B_13 |
| ATOM | 2519 | N | ASN | 112 | 65.278 | 66.140 | -2.611 | 1.00 17.47 | B_13 |
| ATOM | 2521 | CA | ASN | 112 | 65.180 | 67.006 | -1.431 | 1.00 15.77 | B_13 |
| ATOM | 2522 | CB | ASN | 112 | 64.658 | 68.401 | -1.817 | 1.00 15.93 | B_13 |
| ATOM | 2523 | CG | ASN | 112 | 64.694 | 69.384 | -0.657 | 1.00 10.00 | B_13 |
| ATOM | 2524 | OD1 | ASN | 112 | 63.757 | 69.465 | 0.132 | 1.00 15.33 | B_13 |
| ATOM | 2525 | ND2 | ASN | 112 | 65.754 | 70.180 | -0.586 | 1.00 13.70 | B_13 |
| ATOM | 2528 | C | ASN | 112 | 64.214 | 66.329 | -0.472 | 1.00 17.73 | B_13 |
| ATOM | 2529 | O | ASN | 112 | 63.007 | 66.243 | -0.737 | 1.00 12.61 | B_13 |
| ATOM | 2530 | N | LEU | 113 | 64.755 | 65.830 | 0.630 | 1.00 16.28 | B_13 |
| ATOM | 2532 | CA | LEU | 113 | 63.962 | 65.121 | 1.619 | 1.00 15.93 | B_13 |
| ATOM | 2533 | CB | LEU | 113 | 64.841 | 64.703 | 2.804 | 1.00 11.93 | B_13 |
| ATOM | 2534 | CG | LEU | 113 | 64.719 | 63.352 | 3.521 | 1.00 17.15 | B_13 |
| ATOM | 2535 | CD1 | LEU | 113 | 65.002 | 63.640 | 4.987 | 1.00 10.00 | B_13 |
| ATOM | 2536 | CD2 | LEU | 113 | 63.370 | 62.667 | 3.362 | 1.00 16.08 | B_13 |
| ATOM | 2537 | C | LEU | 113 | 62.802 | 65.994 | 2.085 | 1.00 14.61 | B_13 |
| ATOM | 2538 | O | LEU | 113 | 61.673 | 65.528 | 2.161 | 1.00 17.98 | B_13 |
| ATOM | 2539 | N | PHE | 114 | 63.073 | 67.267 | 2.346 | 1.00 16.81 | B_13 |
| ATOM | 2541 | CA | PHE | 114 | 62.056 | 68.212 | 2.791 | 1.00 15.65 | B_13 |
| ATOM | 2542 | CB | PHE | 114 | 62.638 | 69.630 | 2.888 | 1.00 22.16 | B_13 |
| ATOM | 2543 | CG | PHE | 114 | 61.596 | 70.714 | 2.882 | 1.00 12.27 | B_13 |
| ATOM | 2544 | CD1 | PHE | 114 | 60.804 | 70.952 | 4.004 | 1.00 19.93 | B_13 |
| ATOM | 2545 | CD2 | PHE | 114 | 61.378 | 71.470 | 1.746 | 1.00 13.56 | B_13 |
| ATOM | 2546 | CE1 | PHE | 114 | 59.813 | 71.932 | 3.984 | 1.00 17.08 | B_13 |
| ATOM | 2547 | CE2 | PHE | 114 | 60.398 | 72.441 | 1.726 | 1.00 13.79 | B_13 |
| ATOM | 2548 | CZ | PHE | 114 | 59.615 | 72.666 | 2.848 | 1.00 10.70 | B_13 |
| ATOM | 2549 | C | PHE | 114 | 60.860 | 68.220 | 1.842 | 1.00 19.55 | B_13 |

FIG. 5A-28

| | | | | | | | | | |
|---|---|---|---|---|---|---|---|---|---|
| ATOM | 2550 | O | PHE | 114 | 59.714 | 68.156 | 2.285 | 1.00 15.97 | B_13 |
| ATOM | 2551 | N | LEU | 115 | 61.135 | 68.309 | 0.543 | 1.00 13.35 | B_13 |
| ATOM | 2553 | CA | LEU | 115 | 60.096 | 68.323 | -0.485 | 1.00 17.91 | B_13 |
| ATOM | 2554 | CB | LEU | 115 | 60.741 | 68.462 | -1.868 | 1.00 24.65 | B_13 |
| ATOM | 2555 | CG | LEU | 115 | 60.501 | 69.739 | -2.679 | 1.00 22.70 | B_13 |
| ATOM | 2556 | CD1 | LEU | 115 | 61.033 | 70.939 | -1.943 | 1.00 17.98 | B_13 |
| ATOM | 2557 | CD2 | LEU | 115 | 61.148 | 69.624 | -4.048 | 1.00 28.50 | B_13 |
| ATOM | 2558 | C | LEU | 115 | 59.235 | 67.042 | -0.443 | 1.00 21.61 | B_13 |
| ATOM | 2559 | O | LEU | 115 | 58.002 | 67.093 | -0.344 | 1.00 13.99 | B_13 |
| ATOM | 2560 | N | VAL | 116 | 59.898 | 65.895 | -0.511 | 1.00 11.14 | B_13 |
| ATOM | 2562 | CA | VAL | 116 | 59.199 | 64.616 | -0.482 | 1.00 22.27 | B_13 |
| ATOM | 2563 | CB | VAL | 116 | 60.163 | 63.421 | -0.772 | 1.00 17.40 | B_13 |
| ATOM | 2564 | CG1 | VAL | 116 | 59.437 | 62.086 | -0.629 | 1.00 23.09 | B_13 |
| ATOM | 2565 | CG2 | VAL | 116 | 60.741 | 63.534 | -2.169 | 1.00 12.16 | B_13 |
| ATOM | 2566 | C | VAL | 116 | 58.502 | 64.414 | 0.864 | 1.00 10.00 | B_13 |
| ATOM | 2567 | O | VAL | 116 | 57.368 | 63.950 | 0.911 | 1.00 16.18 | B_13 |
| ATOM | 2568 | N | ALA | 117 | 59.153 | 64.803 | 1.954 | 1.00 10.00 | B_13 |
| ATOM | 2570 | CA | ALA | 117 | 58.585 | 64.640 | 3.297 | 1.00 19.50 | B_13 |
| ATOM | 2571 | CB | ALA | 117 | 59.608 | 64.995 | 4.352 | 1.00 11.81 | B_13 |
| ATOM | 2572 | C | ALA | 117 | 57.309 | 65.455 | 3.505 | 1.00 30.87 | B_13 |
| ATOM | 2573 | O | ALA | 117 | 56.327 | 64.955 | 4.053 | 1.00 10.00 | B_13 |
| ATOM | 2574 | N | ALA | 118 | 57.322 | 66.714 | 3.087 | 1.00 24.62 | B_13 |
| ATOM | 2576 | CA | ALA | 118 | 56.140 | 67.553 | 3.222 | 1.00 20.76 | B_13 |
| ATOM | 2577 | CB | ALA | 118 | 56.407 | 68.917 | 2.654 | 1.00 16.19 | B_13 |
| ATOM | 2578 | C | ALA | 118 | 54.968 | 66.894 | 2.485 | 1.00 20.54 | B_13 |
| ATOM | 2579 | O | ALA | 118 | 53.843 | 66.889 | 2.981 | 1.00 22.12 | B_13 |
| ATOM | 2580 | N | HIS | 119 | 55.255 | 66.315 | 1.321 | 1.00 10.00 | B_13 |
| ATOM | 2582 | CA | HIS | 119 | 54.259 | 65.647 | 0.489 | 1.00 17.27 | B_13 |
| ATOM | 2583 | CB | HIS | 119 | 54.909 | 65.263 | -0.860 | 1.00 11.16 | B_13 |
| ATOM | 2584 | CG | HIS | 119 | 54.006 | 64.530 | -1.813 | 1.00 26.59 | B_13 |
| ATOM | 2585 | CD2 | HIS | 119 | 53.377 | 63.335 | -1.706 | 1.00 16.63 | B_13 |
| ATOM | 2586 | ND1 | HIS | 119 | 53.723 | 64.995 | -3.085 | 1.00 12.44 | B_13 |
| ATOM | 2588 | CE1 | HIS | 119 | 52.961 | 64.124 | -3.715 | 1.00 14.58 | B_13 |
| ATOM | 2589 | NE2 | HIS | 119 | 52.734 | 63.101 | -2.901 | 1.00 26.44 | B_13 |
| ATOM | 2590 | C | HIS | 119 | 53.722 | 64.419 | 1.227 | 1.00 17.00 | B_13 |
| ATOM | 2591 | O | HIS | 119 | 52.510 | 64.218 | 1.331 | 1.00 17.01 | B_13 |
| ATOM | 2592 | N | GLU | 120 | 54.626 | 63.607 | 1.751 | 1.00 10.31 | B_13 |
| ATOM | 2594 | CA | GLU | 120 | 54.231 | 62.401 | 2.466 | 1.00 12.32 | B_13 |
| ATOM | 2595 | CB | GLU | 120 | 55.463 | 61.627 | 2.961 | 1.00 15.34 | B_13 |
| ATOM | 2596 | CG | GLU | 120 | 56.354 | 61.078 | 1.848 | 1.00 10.00 | B_13 |
| ATOM | 2597 | CD | GLU | 120 | 55.574 | 60.260 | 0.867 | 1.00 18.64 | B_13 |
| ATOM | 2598 | OE1 | GLU | 120 | 55.598 | 60.565 | -0.348 | 1.00 18.08 | B_13 |
| ATOM | 2599 | OE2 | GLU | 120 | 54.920 | 59.308 | 1.320 | 1.00 14.49 | B_13 |
| ATOM | 2600 | C | GLU | 120 | 53.347 | 62.777 | 3.635 | 1.00 12.41 | B_13 |
| ATOM | 2601 | O | GLU | 120 | 52.323 | 62.130 | 3.888 | 1.00 26.62 | B_13 |
| ATOM | 2602 | N | PHE | 121 | 53.750 | 63.813 | 4.359 | 1.00 10.29 | B_13 |
| ATOM | 2604 | CA | PHE | 121 | 52.993 | 64.286 | 5.506 | 1.00 14.37 | B_13 |
| ATOM | 2605 | CB | PHE | 121 | 53.780 | 65.344 | 6.270 | 1.00 20.10 | B_13 |
| ATOM | 2606 | CG | PHE | 121 | 55.057 | 64.827 | 6.852 | 1.00 24.55 | B_13 |
| ATOM | 2607 | CD1 | PHE | 121 | 56.037 | 65.700 | 7.292 | 1.00 10.00 | B_13 |
| ATOM | 2608 | CD2 | PHE | 121 | 55.292 | 63.454 | 6.936 | 1.00 23.62 | B_13 |
| ATOM | 2609 | CE1 | PHE | 121 | 57.247 | 65.212 | 7.813 | 1.00 18.59 | B_13 |
| ATOM | 2610 | CE2 | PHE | 121 | 56.488 | 62.954 | 7.448 | 1.00 15.21 | B_13 |
| ATOM | 2611 | CZ | PHE | 121 | 57.472 | 63.834 | 7.888 | 1.00 25.40 | B_13 |
| ATOM | 2612 | C | PHE | 121 | 51.607 | 64.791 | 5.110 | 1.00 16.63 | B_13 |
| ATOM | 2613 | O | PHE | 121 | 50.676 | 64.760 | 5.921 | 1.00 26.80 | B_13 |
| ATOM | 2614 | N | GLY | 122 | 51.471 | 65.238 | 3.864 | 1.00 11.98 | B_13 |
| ATOM | 2616 | CA | GLY | 122 | 50.175 | 65.664 | 3.380 | 1.00 12.95 | B_13 |
| ATOM | 2617 | C | GLY | 122 | 49.284 | 64.427 | 3.381 | 1.00 13.71 | B_13 |
| ATOM | 2618 | O | GLY | 122 | 48.113 | 64.483 | 3.753 | 1.00 13.74 | B_13 |
| ATOM | 2619 | N | HIS | 123 | 49.859 | 63.284 | 3.016 | 1.00 16.90 | B_13 |
| ATOM | 2621 | CA | HIS | 123 | 49.126 | 62.009 | 3.008 | 1.00 24.90 | B_13 |
| ATOM | 2622 | CB | HIS | 123 | 49.918 | 60.918 | 2.279 | 1.00 18.28 | B_13 |
| ATOM | 2623 | CG | HIS | 123 | 49.945 | 61.084 | 0.794 | 1.00 21.62 | B_13 |
| ATOM | 2624 | CD2 | HIS | 123 | 50.889 | 60.764 | -0.119 | 1.00 13.04 | B_13 |
| ATOM | 2625 | ND1 | HIS | 123 | 48.887 | 61.618 | 0.093 | 1.00 17.18 | B_13 |
| ATOM | 2627 | CE1 | HIS | 123 | 49.176 | 61.621 | -1.195 | 1.00 16.02 | B_13 |
| ATOM | 2628 | NE2 | HIS | 123 | 50.386 | 61.108 | -1.353 | 1.00 15.58 | B_13 |
| ATOM | 2629 | C | HIS | 123 | 48.864 | 61.562 | 4.446 | 1.00 19.74 | B_13 |
| ATOM | 2630 | O | HIS | 123 | 47.744 | 61.179 | 4.785 | 1.00 15.41 | B_13 |
| ATOM | 2631 | N | SER | 124 | 49.904 | 61.627 | 5.284 | 1.00 13.32 | B_13 |
| ATOM | 2633 | CA | SER | 124 | 49.813 | 61.270 | 6.695 | 1.00 27.50 | B_13 |
| ATOM | 2634 | CB | SER | 124 | 51.131 | 61.582 | 7.425 | 1.00 18.63 | B_13 |
| ATOM | 2635 | OG | SER | 124 | 52.221 | 60.837 | 6.925 | 1.00 13.32 | B_13 |
| ATOM | 2637 | C | SER | 124 | 48.703 | 62.102 | 7.335 | 1.00 13.76 | B_13 |
| ATOM | 2638 | O | SER | 124 | 48.061 | 61.677 | 8.306 | 1.00 20.65 | B_13 |
| ATOM | 2639 | N | LEU | 125 | 48.481 | 63.300 | 6.814 | 1.00 13.33 | B_13 |

FIG. 5A-29

```
ATOM   2641  CA   LEU   125     47.439  64.133   7.387  1.00 24.62    B_13
ATOM   2642  CB   LEU   125     47.893  65.592   7.436  1.00 20.76    B_13
ATOM   2643  CG   LEU   125     49.076  65.849   8.383  1.00 14.66    B_13
ATOM   2644  CD1  LEU   125     49.739  67.159   8.064  1.00 16.16    B_13
ATOM   2645  CD2  LEU   125     48.610  65.811   9.822  1.00 16.44    B_13
ATOM   2646  C    LEU   125     46.058  63.966   6.724  1.00 24.77    B_13
ATOM   2647  O    LEU   125     45.066  64.528   7.195  1.00 15.63    B_13
ATOM   2648  N    GLY   126     45.988  63.192   5.644  1.00 17.38    B_13
ATOM   2650  CA   GLY   126     44.700  62.968   5.001  1.00 22.41    B_13
ATOM   2651  C    GLY   126     44.453  63.487   3.603  1.00 13.20    B_13
ATOM   2652  O    GLY   126     43.349  63.366   3.096  1.00 20.86    B_13
ATOM   2653  N    LEU   127     45.452  64.079   2.972  1.00 12.39    B_13
ATOM   2655  CA   LEU   127     45.267  64.592   1.617  1.00 11.56    B_13
ATOM   2656  CB   LEU   127     45.965  65.947   1.467  1.00 19.19    B_13
ATOM   2657  CG   LEU   127     45.300  67.206   2.039  1.00 14.42    B_13
ATOM   2658  CD1  LEU   127     44.875  67.030   3.496  1.00 32.31    B_13
ATOM   2659  CD2  LEU   127     46.288  68.374   1.912  1.00 25.45    B_13
ATOM   2660  C    LEU   127     45.770  63.619   0.550  1.00 26.54    B_13
ATOM   2661  O    LEU   127     46.920  63.156   0.601  1.00 18.76    B_13
ATOM   2662  N    ASP   128     44.908  63.285  -0.407  1.00 28.54    B_13
ATOM   2664  CA   ASP   128     45.292  62.376  -1.480  1.00 10.89    B_13
ATOM   2665  CB   ASP   128     44.059  61.762  -2.136  1.00 15.95    B_13
ATOM   2666  CG   ASP   128     44.351  60.430  -2.794  1.00 23.44    B_13
ATOM   2667  OD1  ASP   128     43.377  59.735  -3.164  1.00 41.43    B_13
ATOM   2668  OD2  ASP   128     45.541  60.059  -2.918  1.00 18.12    B_13
ATOM   2669  C    ASP   128     46.060  63.203  -2.502  1.00 25.34    B_13
ATOM   2670  O    ASP   128     46.489  64.308  -2.213  1.00 16.36    B_13
ATOM   2671  N    HIS   129     46.283  62.645  -3.682  1.00 17.53    B_13
ATOM   2673  CA   HIS   129     47.001  63.366  -4.718  1.00 26.87    B_13
ATOM   2674  CB   HIS   129     47.495  62.398  -5.794  1.00 10.00    B_13
ATOM   2675  CG   HIS   129     48.729  61.645  -5.400  1.00 19.64    B_13
ATOM   2676  CD2  HIS   129     49.769  61.996  -4.609  1.00 19.96    B_13
ATOM   2677  ND1  HIS   129     49.012  60.373  -5.859  1.00 23.97    B_13
ATOM   2679  CE1  HIS   129     50.170  59.977  -5.372  1.00 17.95    B_13
ATOM   2680  NE2  HIS   129     50.658  60.944  -4.605  1.00 13.79    B_13
ATOM   2681  C    HIS   129     46.153  64.457  -5.360  1.00 39.97    B_13
ATOM   2682  O    HIS   129     45.011  64.220  -5.757  1.00 25.97    B_13
ATOM   2683  N    SER   130     46.743  65.640  -5.481  1.00 21.04    B_13
ATOM   2685  CA   SER   130     46.090  66.776  -6.109  1.00 16.72    B_13
ATOM   2686  CB   SER   130     46.847  68.058  -5.757  1.00 20.97    B_13
ATOM   2687  OG   SER   130     46.358  69.154  -6.502  1.00 25.52    B_13
ATOM   2689  C    SER   130     46.098  66.582  -7.622  1.00 24.66    B_13
ATOM   2690  O    SER   130     46.779  65.694  -8.145  1.00 29.24    B_13
ATOM   2691  N    LYS   131     45.315  67.403  -8.315  1.00 26.96    B_13
ATOM   2693  CA   LYS   131     45.253  67.358  -9.769  1.00 20.25    B_13
ATOM   2694  CB   LYS   131     43.796  67.379 -10.247  1.00 33.22    B_13
ATOM   2695  CG   LYS   131     43.159  68.775 -10.302  1.00 32.85    B_13
ATOM   2696  CD   LYS   131     43.335  69.436 -11.675  1.00 15.99    B_13
ATOM   2697  CE   LYS   131     43.023  70.919 -11.601  1.00 30.34    B_13
ATOM   2698  NZ   LYS   131     43.879  71.647 -10.600  1.00 30.44    B_13
ATOM   2702  C    LYS   131     45.998  68.602 -10.249  1.00 15.31    B_13
ATOM   2703  O    LYS   131     46.414  68.698 -11.402  1.00 30.72    B_13
ATOM   2704  N    ASP   132     46.191  69.536  -9.323  1.00 23.41    B_13
ATOM   2706  CA   ASP   132     46.869  70.798  -9.581  1.00 22.69    B_13
ATOM   2707  CB   ASP   132     46.641  71.726  -8.379  1.00 24.86    B_13
ATOM   2708  CG   ASP   132     46.819  73.200  -8.712  1.00 24.93    B_13
ATOM   2709  OD1  ASP   132     46.007  74.009  -8.208  1.00 29.71    B_13
ATOM   2710  OD2  ASP   132     47.766  73.555  -9.448  1.00 28.82    B_13
ATOM   2711  C    ASP   132     48.358  70.497  -9.728  1.00 14.97    B_13
ATOM   2712  O    ASP   132     49.047  70.235  -8.742  1.00 19.64    B_13
ATOM   2713  N    PRO   133     48.874  70.538 -10.964  1.00 16.94    B_13
ATOM   2714  CD   PRO   133     48.209  70.971 -12.199  1.00 21.42    B_13
ATOM   2715  CA   PRO   133     50.293  70.264 -11.215  1.00 19.34    B_13
ATOM   2716  CB   PRO   133     50.457  70.636 -12.690  1.00 20.48    B_13
ATOM   2717  CG   PRO   133     49.347  71.636 -12.929  1.00 21.80    B_13
ATOM   2718  C    PRO   133     51.237  71.059 -10.322  1.00 17.45    B_13
ATOM   2719  O    PRO   133     52.319  70.590 -10.006  1.00 23.30    B_13
ATOM   2720  N    GLY   134     50.799  72.246  -9.904  1.00 32.46    B_13
ATOM   2722  CA   GLY   134     51.610  73.104  -9.051  1.00 19.44    B_13
ATOM   2723  C    GLY   134     51.306  72.958  -7.569  1.00 22.33    B_13
ATOM   2724  O    GLY   134     51.556  73.877  -6.795  1.00 21.92    B_13
ATOM   2725  N    ALA   135     50.698  71.836  -7.190  1.00 34.71    B_13
ATOM   2727  CA   ALA   135     50.355  71.580  -5.794  1.00 18.35    B_13
ATOM   2728  CB   ALA   135     48.948  70.987  -5.690  1.00 14.30    B_13
ATOM   2729  C    ALA   135     51.370  70.616  -5.210  1.00 10.00    B_13
ATOM   2730  O    ALA   135     51.739  69.647  -5.858  1.00 17.52    B_13
ATOM   2731  N    LEU   136     51.727  70.842  -3.952  1.00 21.29    B_13
```

FIG. 5A-30

| | | | | | | | | | | |
|---|---|---|---|---|---|---|---|---|---|---|
| ATOM | 2733 | CA | LEU | 136 | 52.692 | 70.015 | -3.230 | 1.00 | 14.62 | B_13 |
| ATOM | 2734 | CB | LEU | 136 | 52.738 | 70.458 | -1.763 | 1.00 | 18.54 | B_13 |
| ATOM | 2735 | CG | LEU | 136 | 54.007 | 70.308 | -0.921 | 1.00 | 34.11 | B_13 |
| ATOM | 2736 | CD1 | LEU | 136 | 53.587 | 69.907 | 0.485 | 1.00 | 14.76 | B_13 |
| ATOM | 2737 | CD2 | LEU | 136 | 54.969 | 69.296 | -1.508 | 1.00 | 11.64 | B_13 |
| ATOM | 2738 | C | LEU | 136 | 52.232 | 68.564 | -3.287 | 1.00 | 13.50 | B_13 |
| ATOM | 2739 | O | LEU | 136 | 53.033 | 67.640 | -3.238 | 1.00 | 19.04 | B_13 |
| ATOM | 2740 | N | MET | 137 | 50.921 | 68.364 | -3.281 | 1.00 | 17.54 | B_13 |
| ATOM | 2742 | CA | MET | 137 | 50.360 | 67.019 | -3.324 | 1.00 | 25.11 | B_13 |
| ATOM | 2743 | CB | MET | 137 | 49.010 | 66.981 | -2.599 | 1.00 | 19.80 | B_13 |
| ATOM | 2744 | CG | MET | 137 | 49.083 | 67.312 | -1.117 | 1.00 | 15.35 | B_13 |
| ATOM | 2745 | SD | MET | 137 | 50.354 | 66.361 | -0.262 | 1.00 | 11.22 | B_13 |
| ATOM | 2746 | CE | MET | 137 | 49.882 | 64.680 | -0.764 | 1.00 | 13.90 | B_13 |
| ATOM | 2747 | C | MET | 137 | 50.254 | 66.387 | -4.721 | 1.00 | 28.08 | B_13 |
| ATOM | 2748 | O | MET | 137 | 49.730 | 65.268 | -4.863 | 1.00 | 12.18 | B_13 |
| ATOM | 2749 | N | PHE | 138 | 50.771 | 67.070 | -5.743 | 1.00 | 10.00 | B_13 |
| ATOM | 2751 | CA | PHE | 138 | 50.751 | 66.528 | -7.097 | 1.00 | 12.27 | B_13 |
| ATOM | 2752 | CB | PHE | 138 | 51.327 | 67.523 | -8.094 | 1.00 | 19.38 | B_13 |
| ATOM | 2753 | CG | PHE | 138 | 51.051 | 67.175 | -9.534 | 1.00 | 25.74 | B_13 |
| ATOM | 2754 | CD1 | PHE | 138 | 52.090 | 67.077 | -10.448 | 1.00 | 19.74 | B_13 |
| ATOM | 2755 | CD2 | PHE | 138 | 49.747 | 67.007 | -9.990 | 1.00 | 24.46 | B_13 |
| ATOM | 2756 | CE1 | PHE | 138 | 51.843 | 66.824 | -11.786 | 1.00 | 19.54 | B_13 |
| ATOM | 2757 | CE2 | PHE | 138 | 49.495 | 66.750 | -11.335 | 1.00 | 24.12 | B_13 |
| ATOM | 2758 | CZ | PHE | 138 | 50.544 | 66.664 | -12.230 | 1.00 | 18.15 | B_13 |
| ATOM | 2759 | C | PHE | 138 | 51.619 | 65.269 | -7.068 | 1.00 | 25.93 | B_13 |
| ATOM | 2760 | O | PHE | 138 | 52.658 | 65.226 | -6.414 | 1.00 | 12.50 | B_13 |
| ATOM | 2761 | N | PRO | 139 | 51.166 | 64.194 | -7.714 | 1.00 | 25.17 | B_13 |
| ATOM | 2762 | CD | PRO | 139 | 49.870 | 64.004 | -8.392 | 1.00 | 10.00 | B_13 |
| ATOM | 2763 | CA | PRO | 139 | 51.950 | 62.956 | -7.713 | 1.00 | 18.48 | B_13 |
| ATOM | 2764 | CB | PRO | 139 | 50.981 | 61.946 | -8.339 | 1.00 | 15.96 | B_13 |
| ATOM | 2765 | CG | PRO | 139 | 50.140 | 62.798 | -9.250 | 1.00 | 18.82 | B_13 |
| ATOM | 2766 | C | PRO | 139 | 53.299 | 62.950 | -8.430 | 1.00 | 17.22 | B_13 |
| ATOM | 2767 | O | PRO | 139 | 53.849 | 61.876 | -8.661 | 1.00 | 36.93 | B_13 |
| ATOM | 2768 | N | ILE | 140 | 53.844 | 64.114 | -8.767 | 1.00 | 24.48 | B_13 |
| ATOM | 2770 | CA | ILE | 140 | 55.118 | 64.155 | -9.477 | 1.00 | 20.03 | B_13 |
| ATOM | 2771 | CB | ILE | 140 | 54.996 | 64.807 | -10.892 | 1.00 | 18.71 | B_13 |
| ATOM | 2772 | CG2 | ILE | 140 | 56.334 | 64.709 | -11.639 | 1.00 | 23.96 | B_13 |
| ATOM | 2773 | CG1 | ILE | 140 | 53.932 | 64.113 | -11.724 | 1.00 | 24.68 | B_13 |
| ATOM | 2774 | CD1 | ILE | 140 | 53.861 | 64.669 | -13.125 | 1.00 | 25.83 | B_13 |
| ATOM | 2775 | C | ILE | 140 | 56.109 | 64.992 | -8.700 | 1.00 | 27.87 | B_13 |
| ATOM | 2776 | O | ILE | 140 | 55.758 | 66.043 | -8.248 | 1.00 | 22.39 | B_13 |
| ATOM | 2777 | N | TYR | 141 | 57.332 | 64.512 | -8.535 | 1.00 | 12.36 | B_13 |
| ATOM | 2779 | CA | TYR | 141 | 58.350 | 65.281 | -7.834 | 1.00 | 21.85 | B_13 |
| ATOM | 2780 | CB | TYR | 141 | 59.418 | 64.353 | -7.266 | 1.00 | 15.16 | B_13 |
| ATOM | 2781 | CG | TYR | 141 | 60.592 | 65.096 | -6.672 | 1.00 | 15.65 | B_13 |
| ATOM | 2782 | CD1 | TYR | 141 | 61.755 | 65.306 | -7.407 | 1.00 | 18.56 | B_13 |
| ATOM | 2783 | CE1 | TYR | 141 | 62.836 | 65.967 | -6.859 | 1.00 | 10.00 | B_13 |
| ATOM | 2784 | CD2 | TYR | 141 | 60.546 | 65.576 | -5.366 | 1.00 | 11.42 | B_13 |
| ATOM | 2785 | CE2 | TYR | 141 | 61.626 | 66.236 | -4.814 | 1.00 | 13.45 | B_13 |
| ATOM | 2786 | CZ | TYR | 141 | 62.770 | 66.429 | -5.567 | 1.00 | 10.00 | B_13 |
| ATOM | 2787 | OH | TYR | 141 | 63.841 | 67.109 | -5.016 | 1.00 | 18.97 | B_13 |
| ATOM | 2789 | C | TYR | 141 | 59.042 | 66.270 | -8.776 | 1.00 | 19.52 | B_13 |
| ATOM | 2790 | O | TYR | 141 | 59.709 | 65.859 | -9.727 | 1.00 | 21.37 | B_13 |
| ATOM | 2791 | N | THR | 142 | 58.932 | 67.556 | -8.465 | 1.00 | 23.99 | B_13 |
| ATOM | 2793 | CA | THR | 142 | 59.573 | 68.616 | -9.238 | 1.00 | 19.53 | B_13 |
| ATOM | 2794 | CB | THR | 142 | 58.515 | 69.578 | -9.807 | 1.00 | 10.00 | B_13 |
| ATOM | 2795 | OG1 | THR | 142 | 57.704 | 68.880 | -10.756 | 1.00 | 37.02 | B_13 |
| ATOM | 2797 | CG2 | THR | 142 | 59.151 | 70.757 | -10.457 | 1.00 | 34.35 | B_13 |
| ATOM | 2798 | C | THR | 142 | 60.483 | 69.332 | -8.235 | 1.00 | 19.89 | B_13 |
| ATOM | 2799 | O | THR | 142 | 60.120 | 69.513 | -7.076 | 1.00 | 25.67 | B_13 |
| ATOM | 2800 | N | TYR | 143 | 61.699 | 69.677 | -8.643 | 1.00 | 30.64 | B_13 |
| ATOM | 2802 | CA | TYR | 143 | 62.609 | 70.344 | -7.707 | 1.00 | 32.54 | B_13 |
| ATOM | 2803 | CB | TYR | 143 | 64.091 | 70.190 | -8.108 | 1.00 | 26.34 | B_13 |
| ATOM | 2804 | CG | TYR | 143 | 65.008 | 71.048 | -7.244 | 1.00 | 10.69 | B_13 |
| ATOM | 2805 | CD1 | TYR | 143 | 65.066 | 70.866 | -5.852 | 1.00 | 16.37 | B_13 |
| ATOM | 2806 | CE1 | TYR | 143 | 65.801 | 71.738 | -5.035 | 1.00 | 26.03 | B_13 |
| ATOM | 2807 | CD2 | TYR | 143 | 65.714 | 72.114 | -7.795 | 1.00 | 17.36 | B_13 |
| ATOM | 2808 | CE2 | TYR | 143 | 66.451 | 73.006 | -6.981 | 1.00 | 15.32 | B_13 |
| ATOM | 2809 | CZ | TYR | 143 | 66.489 | 72.810 | -5.610 | 1.00 | 10.00 | B_13 |
| ATOM | 2810 | OH | TYR | 143 | 67.184 | 73.665 | -4.790 | 1.00 | 27.84 | B_13 |
| ATOM | 2812 | C | TYR | 143 | 62.330 | 71.815 | -7.456 | 1.00 | 24.77 | B_13 |
| ATOM | 2813 | O | TYR | 143 | 62.201 | 72.611 | -8.399 | 1.00 | 26.19 | B_13 |
| ATOM | 2814 | N | THR | 144 | 62.292 | 72.160 | -6.170 | 1.00 | 22.23 | B_13 |
| ATOM | 2816 | CA | THR | 144 | 62.103 | 73.533 | -5.727 | 1.00 | 33.68 | B_13 |
| ATOM | 2817 | CB | THR | 144 | 60.668 | 73.814 | -5.189 | 1.00 | 28.06 | B_13 |
| ATOM | 2818 | OG1 | THR | 144 | 60.277 | 72.812 | -4.241 | 1.00 | 38.14 | B_13 |
| ATOM | 2820 | CG2 | THR | 144 | 59.681 | 73.857 | -6.346 | 1.00 | 48.73 | B_13 |

FIG. 5A-31

| | | | | | | | | | | |
|---|---|---|---|---|---|---|---|---|---|---|
| ATOM | 2821 | C | THR | 144 | 63.178 | 73.893 | -4.695 | 1.00 | 35.52 | B_13 |
| ATOM | 2822 | O | THR | 144 | 64.207 | 74.465 | -5.064 | 1.00 | 39.57 | B_13 |
| ATOM | 2823 | N | GLY | 145 | 62.967 | 73.552 | -3.422 | 1.00 | 35.95 | B_13 |
| ATOM | 2825 | CA | GLY | 145 | 63.967 | 73.872 | -2.407 | 1.00 | 35.01 | B_13 |
| ATOM | 2826 | C | GLY | 145 | 63.509 | 74.025 | -0.965 | 1.00 | 26.81 | B_13 |
| ATOM | 2827 | O | GLY | 145 | 62.566 | 74.773 | -0.670 | 1.00 | 40.81 | B_13 |
| ATOM | 2828 | N | LYS | 146 | 64.302 | 73.439 | -0.066 | 1.00 | 27.13 | B_13 |
| ATOM | 2830 | CA | LYS | 146 | 64.071 | 73.423 | 1.389 | 1.00 | 23.89 | B_13 |
| ATOM | 2831 | CB | LYS | 146 | 65.163 | 72.548 | 2.049 | 1.00 | 29.08 | B_13 |
| ATOM | 2832 | CG | LYS | 146 | 64.992 | 72.209 | 3.524 | 1.00 | 19.99 | B_13 |
| ATOM | 2833 | CD | LYS | 146 | 66.079 | 71.224 | 3.913 | 1.00 | 20.44 | B_13 |
| ATOM | 2834 | CE | LYS | 146 | 66.181 | 71.010 | 5.402 | 1.00 | 24.16 | B_13 |
| ATOM | 2835 | NZ | LYS | 146 | 67.250 | 69.987 | 5.727 | 1.00 | 23.37 | B_13 |
| ATOM | 2839 | C | LYS | 146 | 63.926 | 74.778 | 2.124 | 1.00 | 18.98 | B_13 |
| ATOM | 2840 | O | LYS | 146 | 63.900 | 74.831 | 3.353 | 1.00 | 28.15 | B_13 |
| ATOM | 2841 | N | SER | 147 | 63.826 | 75.871 | 1.382 | 1.00 | 35.50 | B_13 |
| ATOM | 2843 | CA | SER | 147 | 63.661 | 77.185 | 1.992 | 1.00 | 31.59 | B_13 |
| ATOM | 2844 | CB | SER | 147 | 64.988 | 77.673 | 2.594 | 1.00 | 27.05 | B_13 |
| ATOM | 2845 | OG | SER | 147 | 65.996 | 77.756 | 1.586 | 1.00 | 48.28 | B_13 |
| ATOM | 2847 | C | SER | 147 | 63.203 | 78.131 | 0.902 | 1.00 | 27.12 | B_13 |
| ATOM | 2848 | O | SER | 147 | 62.743 | 79.251 | 1.168 | 1.00 | 33.75 | B_13 |
| ATOM | 2849 | N | HIS | 148 | 63.248 | 77.644 | -0.332 | 1.00 | 25.13 | B_13 |
| ATOM | 2851 | CA | HIS | 148 | 62.872 | 78.465 | -1.463 | 1.00 | 23.42 | B_13 |
| ATOM | 2852 | CB | HIS | 148 | 63.704 | 78.076 | -2.678 | 1.00 | 17.40 | B_13 |
| ATOM | 2853 | CG | HIS | 148 | 65.174 | 78.020 | -2.398 | 1.00 | 45.97 | B_13 |
| ATOM | 2854 | CD2 | HIS | 148 | 66.204 | 77.524 | -3.121 | 1.00 | 27.24 | B_13 |
| ATOM | 2855 | ND1 | HIS | 148 | 65.724 | 78.476 | -1.213 | 1.00 | 43.49 | B_13 |
| ATOM | 2857 | CE1 | HIS | 148 | 67.024 | 78.253 | -1.218 | 1.00 | 30.28 | B_13 |
| ATOM | 2858 | NE2 | HIS | 148 | 67.342 | 77.676 | -2.366 | 1.00 | 45.28 | B_13 |
| ATOM | 2860 | C | HIS | 148 | 61.381 | 78.433 | -1.796 | 1.00 | 47.15 | B_13 |
| ATOM | 2861 | O | HIS | 148 | 60.936 | 79.166 | -2.704 | 1.00 | 40.97 | B_13 |
| ATOM | 2862 | N | PHE | 149 | 60.601 | 77.636 | -1.053 | 1.00 | 48.76 | B_13 |
| ATOM | 2864 | CA | PHE | 149 | 59.170 | 77.557 | -1.347 | 1.00 | 32.44 | B_13 |
| ATOM | 2865 | CB | PHE | 149 | 58.856 | 76.364 | -2.269 | 1.00 | 27.77 | B_13 |
| ATOM | 2866 | CG | PHE | 149 | 58.415 | 76.781 | -3.657 | 1.00 | 24.63 | B_13 |
| ATOM | 2867 | CD1 | PHE | 149 | 57.826 | 75.874 | -4.520 | 1.00 | 25.66 | B_13 |
| ATOM | 2868 | CD2 | PHE | 149 | 58.550 | 78.106 | -4.072 | 1.00 | 30.89 | B_13 |
| ATOM | 2869 | CE1 | PHE | 149 | 57.376 | 76.277 | -5.767 | 1.00 | 17.10 | B_13 |
| ATOM | 2870 | CE2 | PHE | 149 | 58.104 | 78.520 | -5.311 | 1.00 | 18.57 | B_13 |
| ATOM | 2871 | CZ | PHE | 149 | 57.513 | 77.608 | -6.166 | 1.00 | 30.20 | B_13 |
| ATOM | 2872 | C | PHE | 149 | 58.061 | 77.791 | -0.308 | 1.00 | 27.40 | B_13 |
| ATOM | 2873 | O | PHE | 149 | 58.299 | 77.971 | 0.892 | 1.00 | 29.69 | B_13 |
| ATOM | 2874 | N | MET | 150 | 56.836 | 77.729 | -0.822 | 1.00 | 28.66 | B_13 |
| ATOM | 2876 | CA | MET | 150 | 55.621 | 78.027 | -0.094 | 1.00 | 20.63 | B_13 |
| ATOM | 2877 | CB | MET | 150 | 55.251 | 79.431 | -0.503 | 1.00 | 25.60 | B_13 |
| ATOM | 2878 | CG | MET | 150 | 55.599 | 79.691 | -1.989 | 1.00 | 23.95 | B_13 |
| ATOM | 2879 | SD | MET | 150 | 57.336 | 80.086 | -2.296 | 1.00 | 76.68 | B_13 |
| ATOM | 2880 | CE | MET | 150 | 57.209 | 81.473 | -3.385 | 1.00 | 21.07 | B_13 |
| ATOM | 2881 | C | MET | 150 | 54.436 | 77.118 | -0.450 | 1.00 | 30.58 | B_13 |
| ATOM | 2882 | O | MET | 150 | 54.104 | 76.948 | -1.628 | 1.00 | 16.91 | B_13 |
| ATOM | 2883 | N | LEU | 151 | 53.727 | 76.664 | 0.581 | 1.00 | 36.94 | B_13 |
| ATOM | 2885 | CA | LEU | 151 | 52.576 | 75.772 | 0.431 | 1.00 | 25.68 | B_13 |
| ATOM | 2886 | CB | LEU | 151 | 51.968 | 75.474 | 1.807 | 1.00 | 23.46 | B_13 |
| ATOM | 2887 | CG | LEU | 151 | 51.087 | 74.232 | 1.927 | 1.00 | 24.21 | B_13 |
| ATOM | 2888 | CD1 | LEU | 151 | 51.936 | 72.998 | 1.657 | 1.00 | 21.54 | B_13 |
| ATOM | 2889 | CD2 | LEU | 151 | 50.487 | 74.150 | 3.314 | 1.00 | 19.89 | B_13 |
| ATOM | 2890 | C | LEU | 151 | 51.498 | 76.322 | -0.491 | 1.00 | 17.09 | B_13 |
| ATOM | 2891 | O | LEU | 151 | 50.795 | 77.267 | -0.136 | 1.00 | 35.38 | B_13 |
| ATOM | 2892 | N | PRO | 152 | 51.338 | 75.727 | -1.686 | 1.00 | 16.90 | B_13 |
| ATOM | 2893 | CD | PRO | 152 | 52.154 | 74.643 | -2.255 | 1.00 | 25.80 | B_13 |
| ATOM | 2894 | CA | PRO | 152 | 50.334 | 76.170 | -2.653 | 1.00 | 29.65 | B_13 |
| ATOM | 2895 | CB | PRO | 152 | 50.447 | 75.110 | -3.749 | 1.00 | 24.68 | B_13 |
| ATOM | 2896 | CG | PRO | 152 | 51.892 | 74.791 | -3.722 | 1.00 | 14.34 | B_13 |
| ATOM | 2897 | C | PRO | 152 | 48.910 | 76.261 | -2.087 | 1.00 | 10.00 | B_13 |
| ATOM | 2898 | O | PRO | 152 | 48.543 | 75.505 | -1.184 | 1.00 | 20.25 | B_13 |
| ATOM | 2899 | N | ASP | 153 | 48.117 | 77.180 | -2.639 | 1.00 | 19.53 | B_13 |
| ATOM | 2901 | CA | ASP | 153 | 46.723 | 77.387 | -2.226 | 1.00 | 15.90 | B_13 |
| ATOM | 2902 | CB | ASP | 153 | 45.986 | 78.304 | -3.213 | 1.00 | 22.34 | B_13 |
| ATOM | 2903 | CG | ASP | 153 | 46.418 | 79.741 | -3.115 | 1.00 | 28.86 | B_13 |
| ATOM | 2904 | OD1 | ASP | 153 | 47.016 | 80.115 | -2.074 | 1.00 | 35.34 | B_13 |
| ATOM | 2905 | OD2 | ASP | 153 | 46.142 | 80.494 | -4.084 | 1.00 | 30.09 | B_13 |
| ATOM | 2906 | C | ASP | 153 | 45.953 | 76.084 | -2.169 | 1.00 | 27.31 | B_13 |
| ATOM | 2907 | O | ASP | 153 | 45.309 | 75.783 | -1.167 | 1.00 | 23.50 | B_13 |
| ATOM | 2908 | N | ASP | 154 | 46.000 | 75.339 | -3.276 | 1.00 | 25.51 | B_13 |
| ATOM | 2910 | CA | ASP | 154 | 45.316 | 74.063 | -3.392 | 1.00 | 20.91 | B_13 |
| ATOM | 2911 | CB | ASP | 154 | 45.745 | 73.364 | -4.682 | 1.00 | 14.23 | B_13 |
| ATOM | 2912 | CG | ASP | 154 | 45.033 | 72.062 | -4.885 | 1.00 | 22.95 | B_13 |

FIG. 5A-32

| | | | | | | | | | |
|---|---|---|---|---|---|---|---|---|---|
| ATOM | 2913 | OD1 | ASP | 154 | 45.590 | 71.026 | -4.516 | 1.00 17.80 | B_13 |
| ATOM | 2914 | OD2 | ASP | 154 | 43.904 | 72.076 | -5.388 | 1.00 19.14 | B_13 |
| ATOM | 2915 | C | ASP | 154 | 45.551 | 73.155 | -2.173 | 1.00 26.95 | B_13 |
| ATOM | 2916 | O | ASP | 154 | 44.629 | 72.491 | -1.696 | 1.00 22.92 | B_13 |
| ATOM | 2917 | N | ASP | 155 | 46.776 | 73.155 | -1.654 | 1.00 23.56 | B_13 |
| ATOM | 2919 | CA | ASP | 155 | 47.110 | 72.338 | -0.490 | 1.00 28.69 | B_13 |
| ATOM | 2920 | CB | ASP | 155 | 48.618 | 72.118 | -0.388 | 1.00 12.87 | B_13 |
| ATOM | 2921 | CG | ASP | 155 | 49.208 | 71.566 | -1.676 | 1.00 24.35 | B_13 |
| ATOM | 2922 | OD1 | ASP | 155 | 49.705 | 72.369 | -2.500 | 1.00 27.89 | B_13 |
| ATOM | 2923 | OD2 | ASP | 155 | 49.152 | 70.335 | -1.875 | 1.00 16.96 | B_13 |
| ATOM | 2924 | C | ASP | 155 | 46.582 | 72.976 | 0.781 | 1.00 25.41 | B_13 |
| ATOM | 2925 | O | ASP | 155 | 46.055 | 72.275 | 1.656 | 1.00 13.36 | B_13 |
| ATOM | 2926 | N | VAL | 156 | 46.733 | 74.296 | 0.891 | 1.00 16.99 | B_13 |
| ATOM | 2928 | CA | VAL | 156 | 46.222 | 75.021 | 2.053 | 1.00 22.26 | B_13 |
| ATOM | 2929 | CB | VAL | 156 | 46.340 | 76.571 | 1.901 | 1.00 25.69 | B_13 |
| ATOM | 2930 | CG1 | VAL | 156 | 45.811 | 77.249 | 3.158 | 1.00 14.95 | B_13 |
| ATOM | 2931 | CG2 | VAL | 156 | 47.768 | 77.007 | 1.641 | 1.00 17.52 | B_13 |
| ATOM | 2932 | C | VAL | 156 | 44.727 | 74.705 | 2.129 | 1.00 10.00 | B_13 |
| ATOM | 2933 | O | VAL | 156 | 44.224 | 74.234 | 3.145 | 1.00 22.47 | B_13 |
| ATOM | 2934 | N | GLN | 157 | 44.033 | 74.980 | 1.029 | 1.00 16.19 | B_13 |
| ATOM | 2936 | CA | GLN | 157 | 42.604 | 74.758 | 0.930 | 1.00 17.97 | B_13 |
| ATOM | 2937 | CB | GLN | 157 | 42.108 | 75.039 | -0.497 | 1.00 17.10 | B_13 |
| ATOM | 2938 | CG | GLN | 157 | 40.804 | 75.852 | -0.547 | 1.00 26.00 | B_13 |
| ATOM | 2939 | CD | GLN | 157 | 40.949 | 77.284 | -0.005 | 1.00 25.84 | B_13 |
| ATOM | 2940 | OE1 | GLN | 157 | 41.218 | 77.505 | 1.177 | 1.00 39.61 | B_13 |
| ATOM | 2941 | NE2 | GLN | 157 | 40.744 | 78.255 | -0.875 | 1.00 32.22 | B_13 |
| ATOM | 2944 | C | GLN | 157 | 42.347 | 73.324 | 1.309 | 1.00 18.69 | B_13 |
| ATOM | 2945 | O | GLN | 157 | 41.368 | 73.155 | 1.982 | 1.00 10.00 | B_13 |
| ATOM | 2946 | N | GLY | 158 | 43.272 | 72.460 | 0.903 | 1.00 31.05 | B_13 |
| ATOM | 2948 | CA | GLY | 158 | 43.156 | 71.053 | 1.205 | 1.00 21.69 | B_13 |
| ATOM | 2949 | C | GLY | 158 | 43.129 | 70.738 | 2.684 | 1.00 13.51 | B_13 |
| ATOM | 2950 | O | GLY | 158 | 42.108 | 70.263 | 3.182 | 1.00 14.91 | B_13 |
| ATOM | 2951 | N | ILE | 159 | 44.224 | 71.006 | 3.398 | 1.00 19.34 | B_13 |
| ATOM | 2953 | CA | ILE | 159 | 44.268 | 70.686 | 4.827 | 1.00 19.14 | B_13 |
| ATOM | 2954 | CB | ILE | 159 | 45.669 | 70.880 | 5.503 | 1.00 12.57 | B_13 |
| ATOM | 2955 | CG2 | ILE | 159 | 46.268 | 69.542 | 5.960 | 1.00 19.22 | B_13 |
| ATOM | 2956 | CG1 | ILE | 159 | 46.603 | 71.702 | 4.633 | 1.00 31.62 | B_13 |
| ATOM | 2957 | CD1 | ILE | 159 | 46.426 | 73.177 | 4.824 | 1.00 25.87 | B_13 |
| ATOM | 2958 | C | ILE | 159 | 43.235 | 71.461 | 5.610 | 1.00 21.87 | B_13 |
| ATOM | 2959 | O | ILE | 159 | 42.691 | 70.952 | 6.592 | 1.00 21.02 | B_13 |
| ATOM | 2960 | N | GLN | 160 | 42.959 | 72.689 | 5.186 | 1.00 12.08 | B_13 |
| ATOM | 2962 | CA | GLN | 160 | 41.967 | 73.483 | 5.874 | 1.00 11.43 | B_13 |
| ATOM | 2963 | CB | GLN | 160 | 41.949 | 74.916 | 5.346 | 1.00 29.25 | B_13 |
| ATOM | 2964 | CG | GLN | 160 | 43.158 | 75.737 | 5.827 | 1.00 22.01 | B_13 |
| ATOM | 2965 | CD | GLN | 160 | 43.098 | 77.199 | 5.416 | 1.00 18.77 | B_13 |
| ATOM | 2966 | OE1 | GLN | 160 | 42.260 | 77.593 | 4.607 | 1.00 36.02 | B_13 |
| ATOM | 2967 | NE2 | GLN | 160 | 43.997 | 78.004 | 5.965 | 1.00 28.49 | B_13 |
| ATOM | 2970 | C | GLN | 160 | 40.596 | 72.820 | 5.772 | 1.00 22.28 | B_13 |
| ATOM | 2971 | O | GLN | 160 | 39.855 | 72.786 | 6.754 | 1.00 14.16 | B_13 |
| ATOM | 2972 | N | SER | 161 | 40.304 | 72.183 | 4.634 | 1.00 32.89 | B_13 |
| ATOM | 2974 | CA | SER | 161 | 39.005 | 71.537 | 4.474 | 1.00 29.25 | B_13 |
| ATOM | 2975 | CB | SER | 161 | 38.847 | 70.901 | 3.085 | 1.00 19.70 | B_13 |
| ATOM | 2976 | OG | SER | 161 | 39.594 | 69.706 | 2.946 | 1.00 24.88 | B_13 |
| ATOM | 2978 | C | SER | 161 | 38.831 | 70.503 | 5.566 | 1.00 22.08 | B_13 |
| ATOM | 2979 | O | SER | 161 | 37.745 | 70.340 | 6.118 | 1.00 26.26 | B_13 |
| ATOM | 2980 | N | LEU | 162 | 39.931 | 69.852 | 5.919 | 1.00 19.14 | B_13 |
| ATOM | 2982 | CA | LEU | 162 | 39.913 | 68.829 | 6.953 | 1.00 29.17 | B_13 |
| ATOM | 2983 | CB | LEU | 162 | 41.081 | 67.852 | 6.767 | 1.00 12.08 | B_13 |
| ATOM | 2984 | CG | LEU | 162 | 40.982 | 66.666 | 5.812 | 1.00 20.09 | B_13 |
| ATOM | 2985 | CD1 | LEU | 162 | 40.661 | 67.184 | 4.478 | 1.00 24.51 | B_13 |
| ATOM | 2986 | CD2 | LEU | 162 | 42.299 | 65.884 | 5.794 | 1.00 27.00 | B_13 |
| ATOM | 2987 | C | LEU | 162 | 39.965 | 69.392 | 8.364 | 1.00 24.75 | B_13 |
| ATOM | 2988 | O | LEU | 162 | 39.047 | 69.191 | 9.162 | 1.00 22.04 | B_13 |
| ATOM | 2989 | N | TYR | 163 | 41.015 | 70.151 | 8.652 | 1.00 20.72 | B_13 |
| ATOM | 2991 | CA | TYR | 163 | 41.211 | 70.689 | 9.980 | 1.00 10.00 | B_13 |
| ATOM | 2992 | CB | TYR | 163 | 42.695 | 70.595 | 10.343 | 1.00 10.95 | B_13 |
| ATOM | 2993 | CG | TYR | 163 | 43.221 | 69.167 | 10.209 | 1.00 10.00 | B_13 |
| ATOM | 2994 | CD1 | TYR | 163 | 43.114 | 68.261 | 11.264 | 1.00 37.53 | B_13 |
| ATOM | 2995 | CE1 | TYR | 163 | 43.452 | 66.913 | 11.103 | 1.00 26.00 | B_13 |
| ATOM | 2996 | CD2 | TYR | 163 | 43.703 | 68.689 | 8.990 | 1.00 23.78 | B_13 |
| ATOM | 2997 | CE2 | TYR | 163 | 44.048 | 67.342 | 8.822 | 1.00 17.88 | B_13 |
| ATOM | 2998 | CZ | TYR | 163 | 43.914 | 66.461 | 9.879 | 1.00 24.28 | B_13 |
| ATOM | 2999 | OH | TYR | 163 | 44.210 | 65.121 | 9.711 | 1.00 13.27 | B_13 |
| ATOM | 3001 | C | TYR | 163 | 40.634 | 72.085 | 10.187 | 1.00 26.45 | B_13 |
| ATOM | 3002 | O | TYR | 163 | 39.975 | 72.327 | 11.190 | 1.00 31.25 | B_13 |
| ATOM | 3003 | N | GLY | 164 | 40.819 | 72.975 | 9.219 | 1.00 29.43 | B_13 |
| ATOM | 3005 | CA | GLY | 164 | 40.291 | 74.324 | 9.340 | 1.00 30.64 | B_13 |

FIG. 5A-33

| ATOM | 3006 | C | GLY | 164 | 41.402 | 75.344 | 9.424 | 1.00 | 30.89 | B_13 |
|---|---|---|---|---|---|---|---|---|---|---|
| ATOM | 3007 | O | GLY | 164 | 41.101 | 76.564 | 9.368 | 1.00 | 26.89 | B_13 |
| ATOM | 3008 | OT | GLY | 164 | 42.570 | 74.911 | 9.560 | 1.00 | 27.71 | B_13 |
| ATOM | 3013 | ZN | ZN | 166 | 51.961 | 60.891 | -2.865 | 1.00 | 28.31 | BION |
| ATOM | 3014 | ZN | ZN | 167 | 56.468 | 50.981 | 3.458 | 1.00 | 26.20 | BION |
| ATOM | 3015 | CA | CA | 168 | 63.096 | 53.752 | -5.445 | 1.00 | 14.89 | BION |
| ATOM | 3016 | CA | CA | 165 | 50.705 | 55.618 | 13.085 | 1.00 | 15.79 | BION |
| ATOM | 3047 | C5 | WAY | 169 | 54.585 | 56.119 | -6.288 | 1.00 | 40.09 | B693 |
| ATOM | 3048 | CF1 | WAY | 169 | 54.019 | 54.934 | -5.802 | 1.00 | 21.52 | B693 |
| ATOM | 3049 | CH | WAY | 169 | 53.271 | 54.923 | -4.624 | 1.00 | 32.32 | B693 |
| ATOM | 3050 | C2 | WAY | 169 | 53.100 | 56.104 | -3.898 | 1.00 | 21.39 | B693 |
| ATOM | 3051 | C3 | WAY | 169 | 53.667 | 57.286 | -4.369 | 1.00 | 18.26 | B693 |
| ATOM | 3052 | C4 | WAY | 169 | 54.402 | 57.308 | -5.540 | 1.00 | 20.63 | B693 |
| ATOM | 3053 | N20 | WAY | 169 | 54.933 | 58.531 | -5.964 | 1.00 | 22.15 | B693 |
| ATOM | 3054 | CD | WAY | 169 | 54.297 | 59.340 | -7.031 | 1.00 | 30.92 | B693 |
| ATOM | 3055 | C23 | WAY | 169 | 53.576 | 58.491 | -8.087 | 1.00 | 20.75 | B693 |
| ATOM | 3056 | C28 | WAY | 169 | 54.224 | 58.114 | -9.279 | 1.00 | 34.14 | B693 |
| ATOM | 3057 | C27 | WAY | 169 | 53.539 | 57.335 | -10.228 | 1.00 | 33.99 | B693 |
| ATOM | 3058 | CM | WAY | 169 | 52.209 | 56.944 | -9.968 | 1.00 | 23.49 | B693 |
| ATOM | 3059 | N25 | WAY | 169 | 51.602 | 57.318 | -8.814 | 1.00 | 23.61 | B693 |
| ATOM | 3060 | C24 | WAY | 169 | 52.246 | 58.071 | -7.880 | 1.00 | 20.52 | B693 |
| ATOM | 3061 | S21 | WAY | 169 | 56.531 | 58.783 | -5.660 | 1.00 | 20.46 | B693 |
| ATOM | 3062 | C16 | WAY | 169 | 56.457 | 60.446 | -5.010 | 1.00 | 39.00 | B693 |
| ATOM | 3063 | C21 | WAY | 169 | 56.700 | 60.669 | -3.634 | 1.00 | 28.79 | B693 |
| ATOM | 3064 | C20 | WAY | 169 | 56.656 | 61.967 | -3.109 | 1.00 | 12.65 | B693 |
| ATOM | 3065 | C19 | WAY | 169 | 56.373 | 63.058 | -3.946 | 1.00 | 15.68 | B693 |
| ATOM | 3066 | C18 | WAY | 169 | 56.126 | 62.828 | -5.319 | 1.00 | 12.08 | B693 |
| ATOM | 3067 | C17 | WAY | 169 | 56.169 | 61.538 | -5.852 | 1.00 | 15.19 | B693 |
| ATOM | 3068 | O33 | WAY | 169 | 56.337 | 64.360 | -3.424 | 1.00 | 16.79 | B693 |
| ATOM | 3069 | C36 | WAY | 169 | 56.982 | 65.456 | -4.084 | 1.00 | 20.80 | B693 |
| ATOM | 3070 | O15 | WAY | 169 | 56.973 | 57.923 | -4.580 | 1.00 | 21.90 | B693 |
| ATOM | 3071 | O14 | WAY | 169 | 57.259 | 58.799 | -6.913 | 1.00 | 10.86 | B693 |
| ATOM | 3072 | C7 | WAY | 169 | 53.486 | 58.556 | -3.613 | 1.00 | 10.00 | B693 |
| ATOM | 3073 | N9 | WAY | 169 | 53.741 | 58.606 | -2.303 | 1.00 | 10.00 | B693 |
| ATOM | 3074 | O10 | WAY | 169 | 53.539 | 59.846 | -1.659 | 1.00 | 23.73 | B693 |
| ATOM | 3075 | O8 | WAY | 169 | 53.107 | 59.569 | -4.154 | 1.00 | 15.89 | B693 |
| ATOM | 3076 | C29 | WAY | 169 | 55.383 | 55.968 | -7.606 | 1.00 | 28.30 | B693 |
| ATOM | 1 | OH2 | WAT | 301 | 67.399 | 53.332 | 19.612 | 1.00 | 10.00 | SOLV |
| ATOM | 2 | OH2 | WAT | 302 | 61.288 | 46.506 | 17.898 | 1.00 | 10.00 | SOLV |
| ATOM | 3 | OH2 | WAT | 303 | 79.538 | 50.433 | 20.115 | 1.00 | 10.00 | SOLV |
| ATOM | 4 | OH2 | WAT | 304 | 80.982 | 25.236 | 19.076 | 1.00 | 26.37 | SOLV |
| ATOM | 5 | OH2 | WAT | 305 | 82.461 | 30.767 | 19.346 | 1.00 | 13.02 | SOLV |
| ATOM | 6 | OH2 | WAT | 306 | 67.759 | 41.912 | 4.887 | 1.00 | 17.30 | SOLV |
| ATOM | 7 | OH2 | WAT | 307 | 60.785 | 41.727 | 10.585 | 1.00 | 20.42 | SOLV |
| ATOM | 8 | OH2 | WAT | 308 | 89.638 | 33.523 | 25.640 | 1.00 | 33.45 | SOLV |
| ATOM | 9 | OH2 | WAT | 309 | 77.721 | 51.975 | 4.391 | 1.00 | 13.91 | SOLV |
| ATOM | 10 | OH2 | WAT | 310 | 96.022 | 34.702 | 6.692 | 1.00 | 25.50 | SOLV |
| ATOM | 11 | OH2 | WAT | 311 | 71.292 | 38.746 | 26.741 | 1.00 | 13.06 | SOLV |
| ATOM | 12 | OH2 | WAT | 312 | 85.939 | 49.781 | 3.498 | 1.00 | 12.04 | SOLV |
| ATOM | 13 | OH2 | WAT | 313 | 58.101 | 41.127 | 10.261 | 1.00 | 40.97 | SOLV |
| ATOM | 14 | OH2 | WAT | 314 | 86.373 | 42.692 | 0.747 | 1.00 | 17.24 | SOLV |
| ATOM | 15 | OH2 | WAT | 315 | 78.257 | 39.885 | 24.626 | 1.00 | 18.57 | SOLV |
| ATOM | 16 | OH2 | WAT | 316 | 68.341 | 48.572 | 25.558 | 1.00 | 18.33 | SOLV |
| ATOM | 17 | OH2 | WAT | 317 | 79.806 | 29.147 | 18.371 | 1.00 | 10.00 | SOLV |
| ATOM | 18 | OH2 | WAT | 318 | 87.119 | 44.480 | 23.137 | 1.00 | 46.31 | SOLV |
| ATOM | 19 | OH2 | WAT | 319 | 55.885 | 39.688 | 11.459 | 1.00 | 21.26 | SOLV |
| ATOM | 20 | OH2 | WAT | 320 | 73.250 | 41.084 | 0.386 | 1.00 | 18.49 | SOLV |
| ATOM | 21 | OH2 | WAT | 321 | 72.079 | 46.488 | -6.835 | 1.00 | 27.48 | SOLV |
| ATOM | 22 | OH2 | WAT | 322 | 71.923 | 37.638 | -3.750 | 1.00 | 29.19 | SOLV |
| ATOM | 23 | OH2 | WAT | 323 | 74.998 | 28.451 | 2.684 | 1.00 | 34.60 | SOLV |
| ATOM | 24 | OH2 | WAT | 324 | 87.769 | 44.123 | 9.214 | 1.00 | 15.60 | SOLV |
| ATOM | 25 | OH2 | WAT | 325 | 86.113 | 24.382 | 16.709 | 1.00 | 25.17 | SOLV |
| ATOM | 26 | OH2 | WAT | 326 | 81.205 | 57.603 | 0.529 | 1.00 | 34.27 | SOLV |
| ATOM | 27 | OH2 | WAT | 327 | 75.163 | 62.739 | 12.391 | 1.00 | 16.47 | SOLV |
| ATOM | 28 | OH2 | WAT | 328 | 65.604 | 44.690 | 2.830 | 1.00 | 26.64 | SOLV |
| ATOM | 29 | OH2 | WAT | 329 | 61.899 | 45.512 | 29.269 | 1.00 | 15.82 | SOLV |
| ATOM | 30 | OH2 | WAT | 330 | 58.763 | 41.730 | 8.338 | 1.00 | 27.95 | SOLV |
| ATOM | 31 | OH2 | WAT | 331 | 69.823 | 44.729 | 6.258 | 1.00 | 13.37 | SOLV |
| ATOM | 32 | OH2 | WAT | 332 | 79.220 | 61.263 | 12.781 | 1.00 | 28.84 | SOLV |
| ATOM | 33 | OH2 | WAT | 333 | 78.105 | 37.095 | 27.911 | 1.00 | 34.48 | SOLV |
| ATOM | 34 | OH2 | WAT | 334 | 75.939 | 25.608 | 12.364 | 1.00 | 35.21 | SOLV |
| ATOM | 35 | OH2 | WAT | 335 | 90.256 | 42.668 | 16.539 | 1.00 | 45.05 | SOLV |
| ATOM | 36 | OH2 | WAT | 336 | 86.761 | 51.457 | 13.881 | 1.00 | 25.26 | SOLV |
| ATOM | 37 | OH2 | WAT | 337 | 67.479 | 42.004 | -5.009 | 1.00 | 33.30 | SOLV |
| ATOM | 38 | OH2 | WAT | 338 | 82.018 | 50.963 | 8.823 | 1.00 | 19.80 | SOLV |
| ATOM | 39 | OH2 | WAT | 339 | 80.278 | 32.895 | -1.126 | 1.00 | 30.16 | SOLV |
| ATOM | 40 | OH2 | WAT | 340 | 71.683 | 50.944 | 31.567 | 1.00 | 29.62 | SOLV |

FIG. 5A-34

```
ATOM     41  OH2 WAT   341      61.633  49.360  10.951  1.00 15.47      SOLV
ATOM     42  OH2 WAT   342      89.589  43.811   5.959  1.00 18.08      SOLV
ATOM     43  OH2 WAT   343      70.742  35.952  14.932  1.00 34.03      SOLV
ATOM     44  OH2 WAT   344      89.836  28.590  26.657  1.00 18.11      SOLV
ATOM     45  OH2 WAT   345      70.822  32.764   1.461  1.00 22.35      SOLV
ATOM     46  OH2 WAT   346      63.056  34.653   0.491  1.00 29.51      SOLV
ATOM     47  OH2 WAT   347      58.054  46.282   2.363  1.00 10.00      SOLV
ATOM     48  OH2 WAT   348      67.914  58.660  -6.267  1.00 18.30      SOLV
ATOM     49  OH2 WAT   349      70.170  56.725   0.575  1.00 11.89      SOLV
ATOM     50  OH2 WAT   350      55.922  73.897   0.623  1.00 18.86      SOLV
ATOM     51  OH2 WAT   351      73.489  53.195   2.061  1.00 24.35      SOLV
ATOM     52  OH2 WAT   352      58.033  50.530  19.075  1.00 25.52      SOLV
ATOM     53  OH2 WAT   353      63.245  57.302  17.340  1.00 13.88      SOLV
ATOM     54  OH2 WAT   354      58.442  71.334  -5.670  1.00 17.51      SOLV
ATOM     55  OH2 WAT   355      62.535  61.154  16.706  1.00 12.38      SOLV
ATOM     56  OH2 WAT   356      66.949  51.163 -10.284  1.00 17.92      SOLV
ATOM     57  OH2 WAT   357      57.588  54.191   9.850  1.00 17.88      SOLV
ATOM     58  OH2 WAT   358      64.836  48.085   4.627  1.00 17.80      SOLV
ATOM     59  OH2 WAT   359      66.445  61.785  19.640  1.00 24.12      SOLV
ATOM     60  OH2 WAT   360      55.740  42.557   0.533  1.00 27.32      SOLV
ATOM     61  OH2 WAT   361      74.075  57.146  13.179  1.00 18.01      SOLV
ATOM     62  OH2 WAT   362      46.987  69.315  -2.545  1.00 11.87      SOLV
ATOM     63  OH2 WAT   363      53.842  52.266  -2.612  1.00 25.20      SOLV
ATOM     64  OH2 WAT   364      33.425  65.313  -4.686  1.00 28.97      SOLV
ATOM     65  OH2 WAT   365      45.633  51.173  10.502  1.00 31.97      SOLV
ATOM     66  OH2 WAT   366      39.040  71.050  -0.722  1.00 20.81      SOLV
ATOM     67  OH2 WAT   367      54.517  67.335  -6.251  1.00 46.24      SOLV
ATOM     68  OH2 WAT   368      45.083  67.138  20.314  1.00 29.47      SOLV
ATOM     69  OH2 WAT   369      65.758  67.669  -6.655  1.00 14.69      SOLV
ATOM     70  OH2 WAT   370      44.943  78.174  12.948  1.00 23.88      SOLV
ATOM     71  OH2 WAT   371      37.141  57.403   1.723  1.00 23.72      SOLV
ATOM     72  OH2 WAT   372      62.407  66.806  13.368  1.00 13.36      SOLV
ATOM     73  OH2 WAT   373      50.776  47.263   5.661  1.00 38.22      SOLV
ATOM     74  OH2 WAT   374      56.697  47.264  11.752  1.00 24.75      SOLV
ATOM     75  OH2 WAT   375      42.566  60.884  15.739  1.00 16.25      SOLV
ATOM     76  OH2 WAT   376      59.299  74.342  13.838  1.00 31.27      SOLV
ATOM     77  OH2 WAT   377      72.976  63.691  -0.667  1.00 20.36      SOLV
ATOM     78  OH2 WAT   378      72.876  60.516  -6.752  1.00 34.24      SOLV
ATOM     79  OH2 WAT   379      63.998  68.760  16.371  1.00 19.04      SOLV
ATOM     80  OH2 WAT   380      44.947  66.728  -2.566  1.00 29.51      SOLV
ATOM     81  OH2 WAT   381      57.690  61.926  -9.414  1.00 29.01      SOLV
ATOM     82  OH2 WAT   382      44.595  80.810   5.831  1.00 27.43      SOLV
ATOM     83  OH2 WAT   383      78.065  36.583  24.121  1.00 14.08      SOLV
ATOM     84  OH2 WAT   384      42.289  64.651  -0.868  1.00 25.57      SOLV
ATOM     85  OH2 WAT   385      59.851  68.458 -12.381  1.00 30.18      SOLV
ATOM     86  OH2 WAT   386      53.784  72.644  -4.782  1.00 22.35      SOLV
ATOM     87  OH2 WAT   387      72.793  27.922   8.925  1.00 32.13      SOLV
ATOM     88  OH2 WAT   388      57.224  68.062  -6.072  1.00 17.87      SOLV
ATOM     89  OH2 WAT   389      45.210  44.988   4.285  1.00 25.10      SOLV
ATOM     90  OH2 WAT   390      49.413  53.782   1.546  1.00 21.68      SOLV
ATOM     91  OH2 WAT   391      45.232  59.677   1.393  1.00 19.25      SOLV
ATOM     92  OH2 WAT   392      42.551  59.954   5.056  1.00 27.30      SOLV
ATOM     93  OH2 WAT   393      58.412  43.750   3.948  1.00 58.70      SOLV
ATOM     94  OH2 WAT   394      56.942  54.199  -2.588  1.00 31.14      SOLV
ATOM     95  OH2 WAT   395      55.216  51.994   9.824  1.00 13.25      SOLV
ATOM     96  OH2 WAT   396      51.642  54.651  14.874  1.00 10.00      SOLV
ATOM     97  OH2 WAT   397      48.690  56.156  13.991  1.00 28.59      SOLV
ATOM     98  OH2 WAT   398      74.412  37.913   0.396  1.00 12.55      SOLV
ATOM     99  OH2 WAT   399      81.920  53.968  18.267  1.00 14.05      SOLV
ATOM    100  OH2 WAT   400      70.413  41.780   1.170  1.00 16.68      SOLV
ATOM    101  OH2 WAT   401      71.098  53.544   2.407  1.00 27.63      SOLV
ATOM    102  OH2 WAT   402      94.383  32.979   9.497  1.00 27.97      SOLV
ATOM    103  OH2 WAT   403      70.765  66.069  16.389  1.00 38.09      SOLV
ATOM    104  OH2 WAT   404      78.651  34.890  29.495  1.00 48.60      SOLV
ATOM    105  OH2 WAT   405      80.289  39.811  24.727  1.00 20.74      SOLV
ATOM    106  OH2 WAT   406      63.627  47.414   7.301  1.00 40.21      SOLV
ATOM    107  OH2 WAT   407      74.679  30.772  11.524  1.00 37.03      SOLV
ATOM    108  OH2 WAT   408      80.240  36.041  26.681  1.00 27.42      SOLV
ATOM    109  OH2 WAT   409      84.971  25.909  18.426  1.00 24.96      SOLV
ATOM    110  OH2 WAT   410      57.832  41.294   5.792  1.00 71.90      SOLV
ATOM    111  OH2 WAT   411      55.484  68.139  -9.086  1.00 48.47      SOLV
ATOM    112  OH2 WAT   412      65.535  68.260   2.400  1.00 26.24      SOLV
ATOM    113  OH2 WAT   413      80.085  42.291  -3.144  1.00 26.49      SOLV
ATOM    114  OH2 WAT   414      82.088  37.456  27.733  1.00 42.54      SOLV
ATOM    115  OH2 WAT   415      61.020  53.195  21.566  1.00 38.16      SOLV
ATOM    116  OH2 WAT   416      55.968  70.365  -5.096  1.00 28.42      SOLV
ATOM    117  OH2 WAT   417      51.619  57.620  -0.487  1.00 41.81      SOLV
```

FIG. 5A-35

```
ATOM    118  OH2 WAT   418      40.651  66.108   2.086  1.00 40.11      SOLV
ATOM    119  OH2 WAT   419      58.453  49.818   7.926  1.00 38.96      SOLV
ATOM    120  OH2 WAT   420      53.768  51.716  13.623  1.00 43.62      SOLV
ATOM    121  OH2 WAT   421      76.068  60.373  21.292  1.00 39.30      SOLV
ATOM    122  OH2 WAT   422      56.186  50.034  17.422  1.00 37.47      SOLV
END
```

Compound C
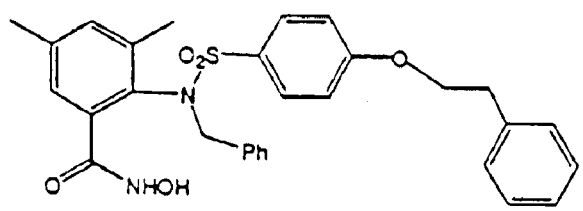
Compound D
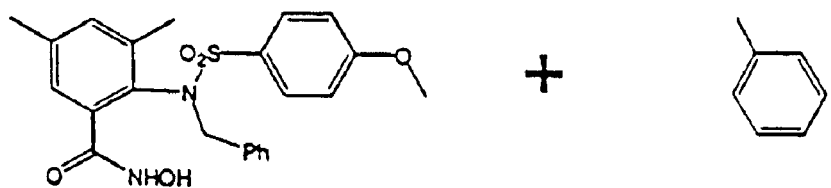
FIG. 7

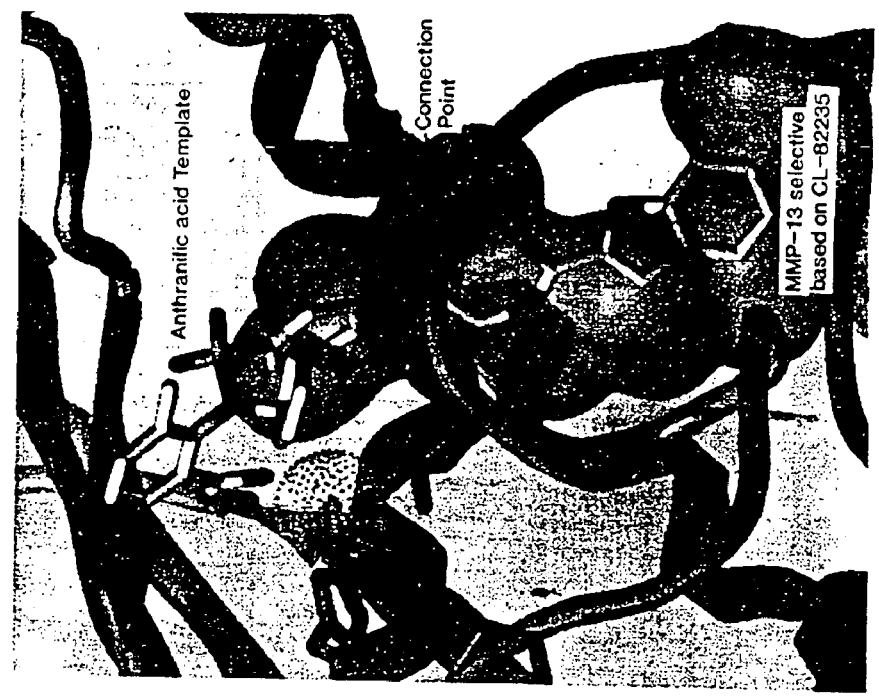
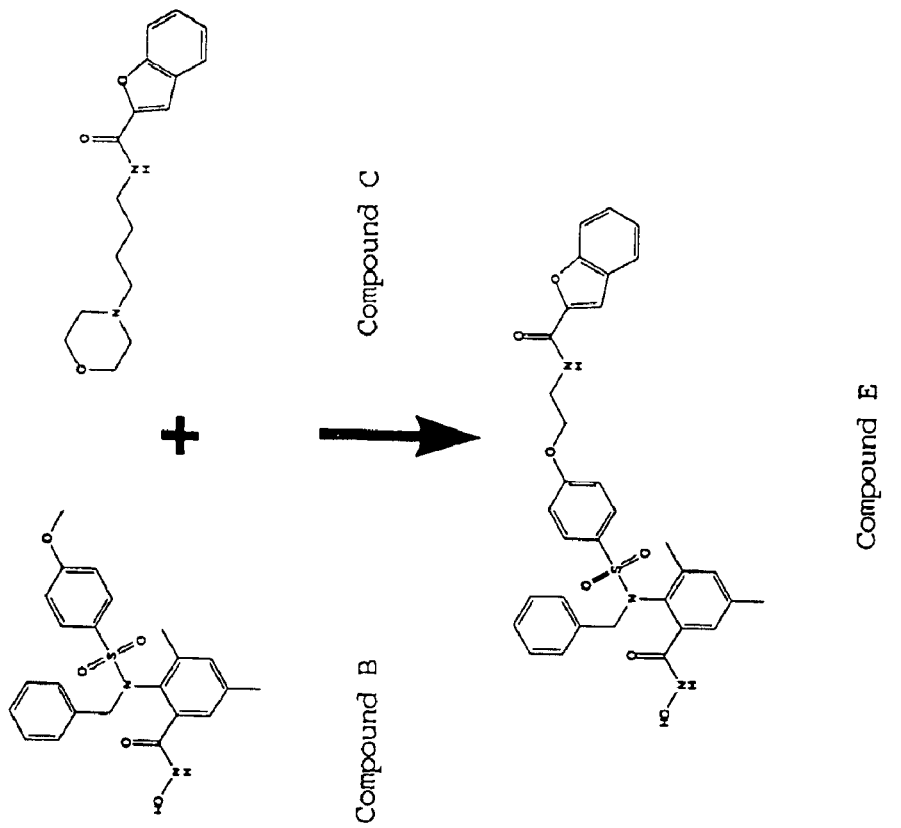
FIG. 8

SEQUENCE LISTING

<160> NUMBER OF SEQ ID NOS: 4

<210> SEQ ID NO 1
<211> LENGTH: 164
<212> TYPE: PRT
<213> ORGANISM: human MMP-13 - catalytic fragment

<400> SEQUENCE: 1

-continued

Tyr Asn Val Phe Pro Arg Thr Leu Lys Trp Ser Lys Met Asn Leu Thr
1               5                   10                  15

Tyr Arg Ile Val Asn Tyr Thr Pro Asp Met Thr His Ser Glu Val Glu
            20                  25                  30

Lys Ala Phe Lys Lys Ala Phe Lys Val Trp Ser Asp Val Thr Pro Leu
        35                  40                  45

Asn Phe Thr Arg Leu His Asp Gly Ile Ala Asp Ile Met Ile Ser Phe
    50                  55                  60

Gly Ile Lys Glu His Gly Asp Phe Tyr Pro Phe Asp Gly Pro Ser Gly
65              70                  75                  80

Leu Leu Ala His Ala Phe Pro Pro Gly Pro Asn Tyr Gly Gly Asp Ala
            85                  90                  95

His Phe Asp Asp Asp Glu Thr Trp Thr Ser Ser Lys Gly Tyr Asn
            100                 105                 110

Leu Phe Leu Val Ala Ala His Glu Phe Gly His Ser Leu Gly Leu Asp
        115                 120                 125

His Ser Lys Asp Pro Gly Ala Leu Met Phe Pro Ile Tyr Thr Tyr Thr
    130                 135                 140

Gly Lys Ser His Phe Met Leu Pro Asp Asp Asp Val Gln Gly Ile Gln
145                 150                 155                 160

Ser Leu Tyr Gly

<210> SEQ ID NO 2
<211> LENGTH: 174
<212> TYPE: PRT
<213> ORGANISM: human MMP-13 - entire protein

<400> SEQUENCE: 2

Val Gly Glu Tyr Asn Val Phe Pro Arg Thr Leu Lys Trp Ser Lys Met
1               5                   10                  15

Asn Leu Thr Tyr Arg Ile Val Asn Tyr Thr Pro Asp Met Thr His Ser
            20                  25                  30

Glu Val Glu Lys Ala Phe Lys Lys Ala Phe Lys Val Trp Ser Asp Val
        35                  40                  45

Thr Pro Leu Asn Phe Thr Arg Leu His Asp Gly Ile Ala Asp Ile Met
    50                  55                  60

Ile Ser Phe Gly Ile Lys Glu His Gly Asp Phe Tyr Pro Phe Asp Gly
65              70                  75                  80

Pro Ser Gly Leu Leu Ala His Ala Phe Pro Pro Gly Pro Asn Tyr Gly
            85                  90                  95

Gly Asp Ala His Phe Asp Asp Asp Glu Thr Trp Thr Ser Ser Ser Lys
            100                 105                 110

Gly Tyr Asn Leu Phe Leu Val Ala Ala His Glu Phe Gly His Ser Leu
        115                 120                 125

Gly Leu Asp His Ser Lys Asp Pro Gly Ala Leu Met Phe Pro Ile Tyr
    130                 135                 140

Thr Tyr Thr Gly Lys Ser His Phe Met Leu Pro Asp Asp Asp Val Gln
145                 150                 155                 160

Gly Ile Gln Ser Leu Tyr Gly Pro Gly Asp Glu Asp Pro Asn
                165                 170

<210> SEQ ID NO 3
<211> LENGTH: 164
<212> TYPE: PRT
<213> ORGANISM: human MMP-1

-continued

```
<400> SEQUENCE: 3

Val Leu Thr Glu Gly Asn Pro Arg Trp Glu Gln Thr His Leu Thr Tyr
1               5                   10                  15

Arg Ile Glu Asn Tyr Thr Pro Asp Leu Pro Arg Ala Asp Val Asp His
            20                  25                  30

Ala Ile Glu Lys Ala Phe Gln Leu Trp Ser Asn Val Thr Pro Leu Thr
        35                  40                  45

Phe Thr Lys Val Ser Glu Gly Gln Ala Asp Ile Met Ile Ser Phe Val
    50                  55                  60

Arg Gly Asp His Arg Asp Asn Ser Pro Phe Asp Gly Pro Gly Gly Asn
65                  70                  75                  80

Leu Ala His Ala Phe Gln Pro Gly Pro Gly Ile Gly Gly Asp Ala His
                85                  90                  95

Phe Asp Glu Asp Glu Arg Trp Thr Asn Asn Phe Arg Glu Tyr Asn Leu
            100                 105                 110

His Arg Val Ala Ala His Glu Leu Gly His Ser Leu Gly Leu Ser His
        115                 120                 125

Ser Thr Asp Ile Gly Ala Leu Met Tyr Pro Ser Tyr Thr Phe Ser Gly
    130                 135                 140

Asp Val Gln Leu Ala Gln Asp Asp Ile Asp Gly Ile Gln Ala Ile Tyr
145                 150                 155                 160

Gly Arg Ser Gln

<210> SEQ ID NO 4
<211> LENGTH: 158
<212> TYPE: PRT
<213> ORGANISM: human MMP-8

<400> SEQUENCE: 4

Asn Pro Lys Trp Glu Arg Thr Asn Leu Thr Tyr Arg Ile Arg Asn Tyr
1               5                   10                  15

Thr Pro Gln Leu Ser Glu Ala Glu Val Glu Arg Ala Ile Lys Asp Ala
            20                  25                  30

Phe Glu Leu Trp Ser Val Ala Ser Pro Leu Ile Phe Thr Arg Ile Ser
        35                  40                  45

Gln Gly Glu Ala Asp Ile Asn Ile Ala Phe Tyr Gln Arg Asp His Gly
    50                  55                  60

Asp Asn Ser Pro Phe Asp Gly Pro Asn Gly Ile Leu Ala His Ala Phe
65                  70                  75                  80

Gln Pro Gly Gln Gly Ile Gly Gly Asp Ala His Phe Asp Ala Glu Glu
                85                  90                  95

Thr Trp Thr Asn Thr Ser Ala Asn Tyr Asn Leu Phe Leu Val Ala Ala
            100                 105                 110

His Glu Phe Gly His Ser Leu Gly Leu Ala His Ser Ser Asp Pro Gly
        115                 120                 125

Ala Leu Met Tyr Pro Asn Tyr Ala Phe Arg Glu Thr Ser Asn Tyr Ser
    130                 135                 140

Leu Pro Gln Asp Asp Ile Asp Gly Ile Gln Ala Ile Tyr Gly
145                 150                 155
```

METHODS FOR DESIGNING AGENTS THAT INTERACT WITH MMP-13

FIELD OF THE INVENTION

The present invention relates to the three dimensional structure of human collagenase 3 (MMP-13), as well as to (i) methods of using the MMP-13 structure to rationally design or identify compounds or molecules that inhibit or activate MMP-13 activity, and (ii) compounds identified using said methods.

BACKGROUND OF THE INVENTION

Human collagenase-3 (MMP-13) is a member of the matrix metalloproteinase (MMP) family which includes the collagenases, stromelysins and gelatinases. The MMPs are involved in the degradation of the extracellular matrix and are associated with normal tissue remodeling processes such as pregnancy, wound healing, and angiogenesis. MMP expression and activity is highly controlled because of the degradative nature of these enzymes, where an apparent loss in MMP regulation results in the pathological destruction of connective tissue and the ensuing disease state. Accordingly, MMPs are a highly active set of targets for the design of therapeutic agents for the disease areas of arthritis and oncology (for reviews, see Woessner, J. F., *FASEB* 1991; Ries, C., and Petrides, E., *Biol. Chem. Hoppe-Seyler* 1995; Browner, M. F., *Perspect. Drug Discovery Des.* 1995; Morphy, et al., *Curr. Med. Chem.* 1995; and Zask, et al., *Curr. Pharm. Des.* 1996).

MMP-13 was identified on the basis of differential expression in normal breast tissues and in breast carcinoma. In addition, its expression has been reported in squamous cell carcinomas of the larynx, head and neck, in HCS-2/8 human chondrosarcoma cells, during fetal ossification, and in articular cartilage of arthritic patients.

There have been a number of X-ray and NMR structures solved for the catalytic domain of MMPs complexed with a variety of inhibitors (see e.g., Bode, et al., *EMBO J.* 1994; Gooley, et al., *Nat. Struct. Biol.* 1994; Lovejoy, et al., *Science* 1994; Lovejoy, et al., *Ann. N.Y. Acad. Sci.* 1994; Lovejoy, et al., *Biochemistry* 1994; Spurlino, et al., *Proteins: Struct. Funct., Genet.* 1994; Stams, et al., *Nat. Struct. Biol.* 1994; Becker, et al., *Protein Sci.* 1995; Gonnella, et al., *Proc. Natl. Acad. Sci. U.S.A.* 1995; Van Doren, et al., *Protein Sci.* 1995; Botos, et al., *Proc. Natl. Acad. Sci. USA* 1996; Broutin, et al., *Acta Crystallogr., Sect. D: Biol. Crystallogr.* 1996; Gooley, et al., *J. Biomol. NMR* 1996; Betz, et al., *Eur. J. Biochem.* 1997; Gonnella, et al., *Bioorg. Med. Chem.* 1997; and Moy, et al., *Biochemistry* 1998). There is a close similarity in the overall three-dimensional fold for these proteins consistent with the relatively high sequence homology (>40%). Despite this similarity in the MMP structures, there is a distinct substrate specificity between these enzymes indicative of specific biological roles for the various MMPs and a corresponding association with unique disease processes. One example of this potential specificity is the over-expression of MMP-13 in breast carcinoma and MMP-1 in papillary carcinomas. Therefore, the current paradigm in the development of MMP inhibitors is to design specificity into the structures of the small molecule instead of developing a broad spectrum MMP inhibitor (Birkedal-Hansen, et al., *Crit. Rev. Oral Biol. Med.* 1993; and Rockwell, et al., *J. Am. Chem. Soc.* 1996). The rationale behind this approach is that an inhibitor specific for the MMP uniquely associated with a disease process may potentially minimize toxic side effects. Therefore, extensive structural information for the various MMPs is critical for a structure-based approach in designing inhibitor selectivity (Birkedal-Hansen, et al., *Crit. Rev. Oral Biol. Med.* 1993; Rockwell, et al., *J. Am. Chem. Soc.* 1996; Ghose, et al., *J. Am. Chem. Soc.* 1995; Hajduk, et al., *J. Am. Chem. Soc.* 1997; and Olejniczak, et al., *J. Am. Chem. Soc.* 1997).

This concept has been facilitated by the extensive structural data available for the MMPs where a significant difference in the size and shape of the S1' pocket has been observed (Moy, et al., *Biochemistry* 1998; Bode, et al., *EMBO J.* 1994; Gooley, et al., *Nat. Struct. Biol.* 1994; Lovejoy, et al., *Ann. N.Y. Acad. Sci.* 1994; Lovejoy, et al., *Biochemistry* 1994; Lovejoy, et al., *Science* 1994; Spurlino, et al., *Proteins: Struct., Funct., Genet.* 1994; Stams, et al., *Nat. Struct. Biol.* 1994; Becker, et al., *Protein Sci.* 1995; Gonnella, et al., *Proc. Natl. Acad. Sci. U.S.A.* 1995; Van Doren, et al., *Protein Sci.* 1995; Botos, et al., *Proc. Natl. Acad. Sci. U.S.A.* 1996; Broutin, et al., *Acta Crystallogr., Sect. D: Biol. Crystallogr.* 1996; Gooley, et al., *J. Biomol. NMR* 1996; Betz, et al., *Eur. J. Biochem.* 1997; and Gonnella, et al., *Bioorg. Med. Chem.* 1997). This structural difference across the MMP family provides an obvious approach for designing specificity into potent MMP inhibitors by designing compounds that appropriately fill the available space in the S1' pocket while taking advantage of sequence differences. A number of examples have been previously reported using this approach where some selectivity between MMPs has been achieved by incorporating a biphenyl into the S1' pocket (see e.g., Hajduk, et al., *J. Am. Chem. Soc.* 1997; and Olejniczak, et al., *J. Am. Chem. Soc.* 1997).

The inventors have determined both the solution and crystal structures of MMP-13, and, using rational drug design methods, have designed a novel, potent inhibitor that is highly selective for MMP-13.

SUMMARY OF THE INVENTION

The present invention relates to the three dimensional structure of human collagenase 3 (MMP-13), and more specifically, to the crystal and solution structures of MMP-13 complexed with the inhibitor N-Hydroxy-2-[(4-methoxy-benzenesulfonyl)-pyridin-3-ylmethyl-amino]-3-methyl-benzamide (hereinafter referred to as "Compound A"), as determined using crystallography, spectroscopy and various computer modeling techniques. Particularly, the invention is directed to an MMP-13 active site comprised of the three dimensional structures of various binding pockets located both to the right (S1', S2', S3') and left (S1, S2, S3) of the catalytic zinc of MMP-13, and most particularly is directed to the three dimensional structure of an MMP-13 active site comprising the catalytic zinc and the S1' binding pocket, which is critical to the design and selection of inhibitors with increased potency and specificity for MMP-13, or conversely, for the design and selection of inhibitors of matrix metalloproteinases that are specific against MMP-13.

Accordingly, the present invention discloses a solution comprising a biologically active catalytic fragment of human collagenase-3 (MMP-13) complexed with Compound A, as well as a crystallized catalytic fragment of MMP-13 complexed with Compound A. The three dimensional structure of the catalytic fragment of MMP-13 is provided by the relative atomic structural coordinates of FIGS. 4 and 4A-1 to 4A-32, as obtained from spectroscopy data, and FIGS. 5 and 5A-1 to 5A-35, as obtained from crystallography data. Also provided is an active site of MMP-13, characterized by a catalytic zinc, a beta strand, a Ca$^{2+}$ binding loop, an alpha helix and a random coil region, wherein the beta strand of said active site preferably comprises residues N14, L15, T16, Y17, R18, I19, and V20 according to FIG. 1, the Ca$^{2+}$ binding loop comprises residues F75, D76, G77, P78, and S79 according to FIG. 1, the alpha helix comprises residues N112, L113, F114, L115, V116, A117, A118, H119, E120, F121, G122, and H123 according to FIG. 1, and the random coil region comprises residues P139, I140, and Y141 according to FIG. 1. Said active site is further characterized by a three dimensional structure comprising the relative structural coordinates of the catalytic zinc and amino acid residues N14, L15, T16, Y17, R18, I19, V20, F75, D76, G77, P78, S79, N112, L113, F114, L115, V116, A117, A118, H119, E120, F121, G122, H123, P139, I140, and Y141 according to the solution or crystal coordinates of FIGS. 4 and 4A-1 to 4A-32 or FIGS. 5 and 5A-1 to 5A-35, respectively, in each case, ± a root mean square deviation from the catalytic zinc and conserved backbone atoms of said amino acids of not more than 1.5 Å.

In an alternate embodiment of the invention, an active site of MMP-13 is characterized by a three dimensional structure comprising the relative structural coordinates of the catalytic zinc and amino acid residues L81, L82, L115, V116, H119, L136 and I140 according to the solution or crystal coordinates of FIG. 4 or 5, respectively, in each case, ± a root mean square deviation from the catalytic zinc and conserved backbone atoms of said amino acids of not more than 1.5 Å.

The solution or crystal structural coordinates of MMP-13 or portions thereof as provided by this invention may be stored in a machine-readable form on a machine-readable storage medium, e.g. a computer hard drive, diskette, DAT tape, etc., for display as a three-dimensional shape or for other uses involving computer-assisted manipulation of, or computation based on, the structural coordinates or the three-dimensional structures they define. By way of example, the data defining the three dimensional structure of MMP-13 or an MMP-13 complex of the present invention, or of a portion of MMP-13 or an MMP-13 complex as disclosed herein, may be stored in a machine-readable storage medium, and may be displayed as a graphical three-dimensional representation of the relevant structural coordinates, typically using a computer capable of reading the data from said storage medium and programmed with instructions for creating the representation from such data.

Accordingly, the present invention provides a machine, such as a computer, programmed in memory with the coordinates of the MMP-13 molecule or molecular complex, or portions thereof (such as, by way of example, the coordinates of the MMP-13 catalytic zinc with adjacent S1', S2' and/or S3' binding pockets), together with a program capable of converting the coordinates into a three dimensional graphical representation of the structural coordinates on a display connected to the machine. A machine having a memory containing such data aids in the rational design or selection of inhibitors or activators of MMP-13 activity, including the evaluation of ability of a particular chemical entity to favorably associate with MMP-13 or an MMP-13 complex as disclosed herein, as well as in the modeling of compounds, proteins, complexes, etc. related by structural or sequence homology to MMP-13.

The present invention is additionally directed to a method of determining the three dimensional structure of a molecule or molecular complex whose structure is unknown, comprising the steps of first obtaining crystals or a solution of the molecule or molecular complex whose structure is unknown, and then generating X-ray diffraction data from the crystallized molecule or molecular complex and/or generating NMR data from the solution of the molecule or molecular complex. The generated diffraction or spectroscopy data from the molecule or molecular complex can then be compared with the known three dimensional structure of MMP-13 as disclosed herein, and the three dimensional structure of the unknown molecule or molecular complex conformed to the known MMP-13 structure using standard techniques such as molecular replacement analysis, 2D, 3D and 4D isotope filtering, editing and triple resonance NMR techniques, and computer homology modeling. Alternatively, a three dimensional model of the unknown molecule may be generated by generating a sequence alignment between MMP-13 and the unknown molecule, based on any or all of amino acid sequence identity, secondary structure elements or tertiary folds, and then generating by computer modeling a three dimensional structure for the molecule using the three dimensional structure of, and sequence alignment with, MMP-13.

The present invention further provides a method for identifying a potential inhibitor or activator of MMP-13, comprising the steps of using a three dimensional structure of MMP-13 as defined by the relative structural coordinates of amino acids encoding MMP-13 to design or select a potential inhibitor or activator, and synthesizing or obtaining said potential inhibitor or activator. The inhibitor or activator may be selected by screening an appropriate database, may designed de novo by analyzing the steric configurations and charge potentials of an empty MMP-13 active site in conjunction with the appropriate software programs, or may be designed using characteristics of known inhibitors or activators to MMP-13 or other collagenases in order to create "hybrid" activators or inhibitors. The method of the present invention is preferably used to design or select inhibitors of MMP-13 activity.

Alternatively, the present invention provides a method for identifying a potential inhibitor or activator that is selective for one or more members of the matrix metalloproteinase family except MMP-13, comprising the steps of (i) using the three dimensional structures of MMP-13 and the desired target matrix metalloproteinase(s) as defined by the relative structural coordinates of amino acids encoding MMP-13 and the target matrix metalloproteinase(s) in order to design or select such a potential inhibitor or activator, and (ii) synthesizing or obtaining said potential inhibitor or activator. In this case, the potential inhibitor or activator is designed to incorporate chemical or steric features favorable for association with an active site of the desired matrix metalloproteinase(s) and unfavorable for association with an MMP-13 active site, preferably where said active site comprises the MMP-13 S1' pocket. The inhibitor or activator may be selected by screening an appropriate database, may designed de novo by analyzing the steric configurations and charge potentials of empty MMP-13/matrix metalloproteinase active sites in conjunction with the appropriate software programs, or may be designed using characteristics of known inhibitors or activators to MMP-13 or other collagenases in order to create "hybrid" activators or inhibitors.

Also provided by the present invention are the inhibitors and activators designed or selected using the methods disclosed herein.

BRIEF DESCRIPTION OF THE FIGURES

FIG. 1 depicts the amino acid sequence encoding the catalytic fragment of human MMP-13 (Seq ID No. 1).

FIG. 2 depicts the sequence based alignment between (A) MMP-13 (Seq ID No. 2) and MMP-8 (Seq ID No. 4) and (B)

MMP-13 (Seq ID No. 2) and MMP-1 (Seq ID No. 3) used for the MMP-13 homology model.

Figure 3:
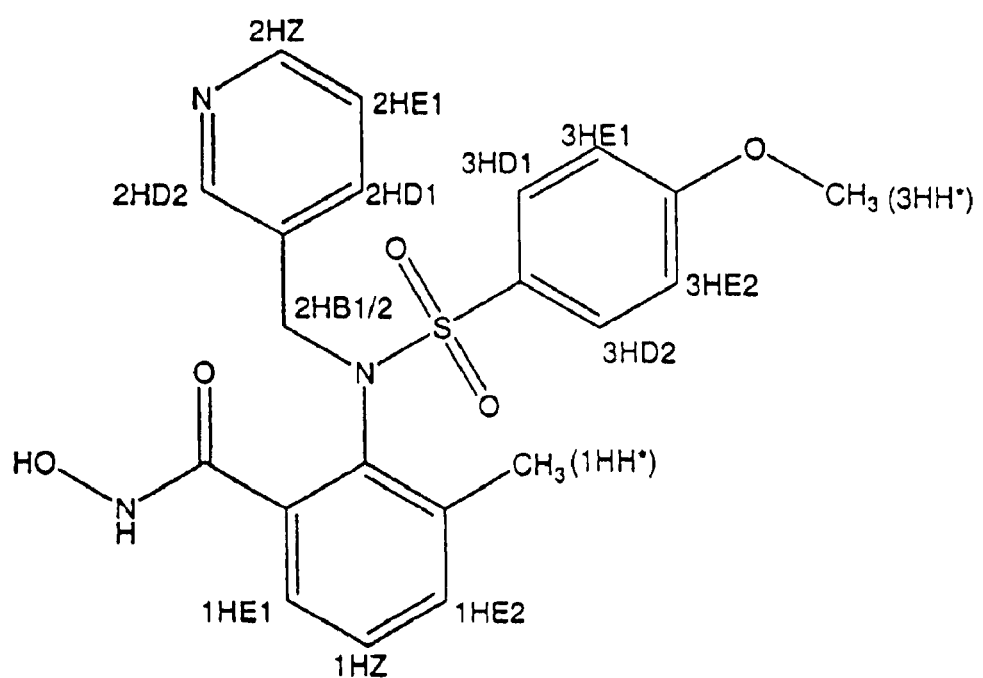

FIG. 3 is an illustration of the sulfonamide derivative of the hydroxamic inhibitor N-Hydroxy-2-[(4-methoxy-benzenesulfonyl)-pyridin-3-ylmethyl-amino]-3-methyl-benzamide (Compound A), with the corresponding proton labels.

FIGS. 4 and 4A-1 to 4A-32 lists the atomic structure coordinates for the restrained minimized mean structure of MMP-13 complexed with Compound A as derived by NMR spectroscopy. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location (Å). All non-protein atoms (Compound A, zinc and calcium) are listed as HETATM instead of atoms using PDB conventions.

FIGS. 5 and 5A-1 to 5A-35 lists the atomic structure coordinates for MMP-13 as derived by X-ray diffraction of a crystallized MMP-13: Compound A complex. Figure headings are as noted above, except "Occ" indicates the occupancy factor, and "B" indicates the "B-value", which is a measure of how mobile the atom is in the atomic structure (Å$^2$). "MOL" indicates the segment identification used to uniquely identify each molecule in the crystal.

Figure 6:
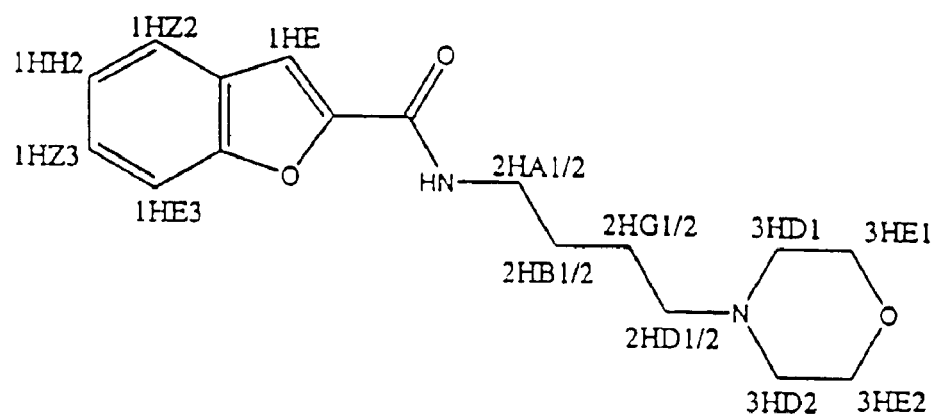

FIG. 6 is an illustration of the Compound B inhibitor, with the corresponding proton labels.

FIG. 7 is a design scheme dividing 2-[Benzyl-(4-phenethyloxy-benzenesulfonyl)-amino]-N-hydroxy-3,5-dimethyl-benzamide (hereinafter referred to as "Compound C") into two components corresponding to its potency component (2-[Benzyl-(4-methoxy-benzenesulfonyl)-amino]-N-hydroxy-3,5-dimethyl-benzamide, hereinafter referred to as "Compound D") and its selectivity component, thereby providing the basis for the design of a hybrid inhibitor with Compound B.

FIG. 8 is a design scheme showing the flow from Compound B and Compound C to the hybrid inhibitor benzofuran-2-carboxylic acid (2-{4-[benzyl-(2-hydroxycarbamoyl-4,6-dimethyl-phenyl)-sulfamoyl]-phenoxy}-ethyl)-amide (hereinafter referred to as "Compound E"). FIG. 8 illustrates an expanded view of the NMR MMP-13: Compound B complex overlayed with the MMP-13: Compound D model, demonstrating the approach to forming the hybrid inhibitor Compound E. The MMP-13 active site is shown as a grid surface with Compound B and Compound D shown as liquorice bonds. The view is looking at the S1' pocket.

DETAILED DESCRIPTION OF THE INVENTION

As used herein, the following terms and phrases shall have the meanings set forth below:

"Compound A" is N-Hydroxy-2-[(4-methoxy-benzenesulfonyl)-pyridin-3-ylmethyl-amino]-3-methyl-benzamide, as shown in FIG. 3. "Compound B" is the compound having the chemical structure shown in FIG. 6. "Compound C" is 2-[Benzyl-(4-phenethyloxy-benzenesulfonyl)-amino]-N-hydroxy-3,5-dimethyl-benzamide, also shown in FIG. 7. "Compound D" is 2-[Benzyl-(4-methoxy-benzenesulfonyl)-amino]-N-hydroxy-3,5-dimethyl-benzamide, also shown in FIG. 7. "Compound E" is Benzofuran-2-carboxylic acid (2-{4-[benzyl-(2-hydroxycarbamoyl-4,6-dimethyl-phenyl)-sulfamoyl]-phenoxy}-ethyl)-amide, as shown in FIG. 8.

"Compound F" is 2-(Benzyl-4-(3-phenyl-propoxy)-benzenesulfonyl]-amino)-N-hydroxy-3,5-dimethyl-benzamide.

Unless otherwise noted, "MMP-13" includes both human collagenase 3 as encoded by the amino acid sequence of FIG. 1 (including conservative substitutions thereof), as well as "MMP-13 analogues", defined herein as proteins comprising an MMP-13 like active site as defined by the present invention, including, but not limited to, an active site characterized by a three dimensional structure comprising the relative structural coordinates of the catalytic zinc and amino acid residues L81, L82, L115, V116, H119, L136 and I140 according to the solution or crystal coordinates of FIGS. 4 and 4A-1 to 4A-32 or FIGS. 5 and 5A-1 to 5A-35, respectively, in each case, of: a root mean square deviation from the catalytic zinc and conserved backbone atoms of said amino acids of not more than 1.5 Å, or more preferably, not more than 1.0 Å, or most preferably, not more than 0.5 Å. Alternatively, an MMP-13 analogue of the present invention is a protein which comprises an MMP-13 like active site characterized by a catalytic zinc, a beta strand, a Ca$^{2+}$ binding loop, an alpha helix and a random coil region, or, more particularly, comprising an active site characterized by a three dimensional structure comprising the relative structural coordinates of the catalytic zinc and of amino acid residues N14, L15, T16, Y17, R18, I19, V20, F75, D76, G77, P78, S79, N112, L113, F114, L115, V116, A117, A118, H119, E120, F121, G122, H123, P139, I140, and Y141 according to FIGS. 4 and 4A-1 to 4A-32 or FIGS. 5 and 5A-1 to 5A-35, or more preferably, where said three dimensional structure further comprises the relative structural coordinates of amino acid residues G80, L81, L82, A83, H84, A85, K109, G110, Y111, S124, L125, G126, L127, D128, H129, S130, K131, D132, P133, G134, A135, L136, M137, F138, T142, Y143, T144, and G145 according to FIGS. 4 and 4A-1 to 4A-32 or FIGS. 5 and 5A-1 to 5A-35, or most preferably, where said three dimensional structure still further comprises the relative structural coordinates of F149 and P152 according to FIGS. 4 and 4A-1 to 4A-32 or FIGS. 5 and 5A-1 to 5A-35, in each case, ± a root mean square deviation from the catalytic zinc and the conserved backbone atoms (N, Ca, C, and O) of said amino acids of not more than 1.5 Å (or more preferably, not more than 1.0 Å, or most preferably, not more than 0.5 Å).

Unless otherwise indicated, "protein" or "molecule" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original sets provided in FIGS. 4 and 4A-1 to 4A-32 or FIGS. 5 and 5A-1 to 5A-35 by mathematical manipulation, such as by inversion or integer additions or subtractions. As such, it is recognized that the structural coordinates of the present invention are relative, and are in no way specifically limited by the actual x, y, z coordinates of FIGS. 4 and 4A-1 to 4A-32 or FIGS. 5 and 5A-1 to 5A-35. Further, it is recognized that the structural coordinates taken from FIGS. 5 and 5A-1 to 5A-35 may be from either molecule of MMP-13 catalytic fragment in the MMP-13: Compound A crystal (i.e., from A-13 or B-13).

An "agent" shall include a protein, polypeptide, peptide, nucleic acid, including DNA or RNA, molecule, compound, antibiotic or drug.

"Root mean square deviation" is the square root of the arithmetic mean of the squares of the deviations from the mean, and is a way of expressing deviation or variation from the structural coordinates described herein.

It will be obvious to the skilled practitioner that the numbering of the amino acid residues in the various isoforms of MMP-13 or in MMP-13 analogues covered by the present invention may be different than that set forth herein, or may contain certain conservative amino acid substitutions that yield the same three dimensional structures as those defined by FIGS. 4 and 4A-1 to 4A-32 or FIGS. 5 and 5A-1 to 5A-35 herein. Corresponding amino acids and conservative substitutions in other isoforms or analogues are easily identified by visual inspection of the relevant amino acid sequences or by using commercially available homology software programs. "Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic), and includes substitutions having an inconsequential effect on the three dimensional structure of MMP-13 with respect to the use of said structure for the identification and design of MMP-13 activators or inhibitors, for molecular replacement analyses and/or for homology modeling.

An "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound, antibiotic or drug). As such, the active site may include both the actual site of substrate cleavage or collagenase activity, as well as certain or all binding sites or pockets adjacent to the site of substrate cleavage that nonetheless may affect MMP-13 activity upon interaction or association with an agent, either by direct interference with the site of substrate cleavage or by indirectly affecting the steric conformation or charge potential of the MMP-13 molecule. The catalytic center of the MMP-13 molecule is characterized by a zinc atom chelated by $H_{119}$, H123 and H129. MMP-13 binding sites or pockets located to the right of the catalytic zinc include S1', S2' and S3'. Binding sites or pockets to the left of the catalytic zinc include S1, S2 and S3.

The present invention relates to the three dimensional structure of human collagenase 3 (MMP-13) or an MMP-13 analogue, and more specifically, to the crystal and solution structures of MMP-13 complexed with an inhibitor, referred to herein as "Compound A", as determined using crystallography, spectroscopy and various computer modeling techniques. The three dimensional solution and crystal structures of the MMP-13: Compound A complex (as disclosed herein at FIGS. 4 and 4A-1 to 4A-32 or FIGS. 5 and 5A-1 to 5A-35, respectively) and the uncomplexed MMP-13 catalytic fragment (which may be computationally derived from the structural coordinates of FIGS. 4 and 4A-1 to 4A-32 or FIGS. 5 and 5A-1 to 5A-35) are useful for a number of applications, including, but not limited to, the visualization, identification and characterization of MMP-13 active sites, including the MMP-13 catalytic zinc chelated by H119, H123 and H129, as well as the various MMP-13 binding pockets adjacent to the catalytic zinc of the MMP-13 molecule. The active site structures may then be used to predict the orientation and binding affinity of a designed or selected activator or inhibitor of the MMP-13 protein. Accordingly, the invention is particularly directed to the three dimensional structure of an MMP-13 active site, including but not limited to the S1', S2', S3', S1, S2 and/or S3 binding pockets, taken separately or together with the catalytic zinc of the MMP-13 molecule.

The present invention provides a solution comprising a biologically active catalytic fragment of human collagenase-3 (MMP-13) complexed with Compound A. In a particular embodiment, the catalytic fragment of MMP-13 comprises the amino acid residues of FIG. 1, or conservative substitutions thereof. Preferably, the solution provided for herein comprises MMP-13 complexed with Compound A in a 1:1 molar ratio, and more preferably comprises 1 mM MMP-13 in an equimolar complex with Compound A, in a buffer comprising 10 mM deuterated Tris-Base, 100 mM NaCl, 5 mM $CaCl_2$, 0.1 mM $ZnCl_2$, 2 mM $NaN_3$, and 10 mM deuterated DTT in either 90% $H_2O$/10% $D_2O$ or 100% $D_2O$, at a preferred pH of 6.5. The concentration of MMP-13: Compound A in the solution should be high enough to yield a good signal-to-noise ratio in the NMR spectrum, but not so high as to result in precipitation or aggregation of the protein. Further, the MMP-13 of the solution may be either $^{15}N$ enriched or $^{15}N$, $^{13}C$ enriched. As exemplified below, NMR spectra from the solution of the present invention are preferably obtained at a temperature of 35° C.

The secondary structure of the catalytic fragment used in the solution of the present invention comprises three alpha helices and a mixed parallel and anti-parallel beta sheet comprising five beta strands, configured in the order $\beta_I$, $\alpha_A$, $\beta_{II}$, $\beta_{III}$, $\beta_{IV}$, $\alpha_B$, and $\beta_C$. The three alpha helices correspond to residues 28–44 ($\alpha_A$), 112–123 ($\alpha_B$) and 153–163 ($\alpha_C$) of FIG. 1, and the five beta strands correspond to residues 83–86 ($\beta_I$), 95–100 ($\beta_{II}$) 59–66 ($\beta_{III}$), 14–20 ($\beta_{IV}$), and 49–53 ($\beta_V$) of FIG. 1, respectively. While the solution of the present invention comprises MMP-13 in a 1:1 molar ratio with Compound A, it is understood that one of ordinary skill in the art may devise additional solutions using alternate inhibitors or ligands in the appropriate molar concentrations, thereby preventing the auto-degradation of MMP-13 and creating a solution of sufficient stability and concentration to obtain a usable NMR spectrum.

The protein used in the solution of the present invention includes MMP-13, as well as MMP-13 analogues, where said protein comprises an active site characterized by the three dimensional structure comprising the relative structural coordinates of the catalytic zinc and amino acid residues L81, L82, L115, V116, H119, L136 and I140 (or conservative substitutions thereof) according to the solution coordinates of FIGS. 4 and 4A-1 to 4A-32, ± a root mean square deviation from the catalytic zinc and the conserved backbone atoms of said amino acids of not more than 1.5 Å, or more preferably, not more than 1.0 Å, or most preferably, not more than 0.5 Å. These residues comprise the residues most closely associated with Compound A in the MMP-13: Compound A complex, as determined from the observed NOES between MMP-13 and Compound A (Table 1).

Alternatively, a protein used in the solution of the present invention comprises an active site characterized by a catalytic zinc, a beta strand (comprising amino acid residues N14, L15, T16, Y17, R18, I19, and V20 or conservative substitutions thereof), a $Ca^{2+}$ binding loop (comprising amino acid residues F75, D76, G77, P78, and S79 or conservative substitutions thereof), an alpha helix (comprising amino acid residues N112, L113, F114, L115, V116, A117, A118, H119, E120, F121, G122, and H123 or conservative substitutions thereof) and a random coil region (comprising amino acid residues P139, I140, and Y141 or conservative substitutions thereof), or, more particularly, characterized by a three dimensional structure comprising the relative structural coordinates of the catalytic zinc and the amino acid residues N14, L15, T16, Y17, R18, I19, V20, F75, D76, G77, P78, S79, N112, L113, F114, L115, V116, A117, A118, H119, E120, F121, G122, H123, P139, I140, and Y141 according to FIGS. 4 and 4A-1 to 4A-32, or more preferably, where said three dimensional structure further comprises the relative structural coordinates of amino acid residues G80, L81, L82, A83, H84, A85, K109, G110, Y111, S124, L125, G126, L127, D128, H129, S130, K131, D132, P133, G134, A135, L136, M137, F138, T142, Y143, T144, and G145 according to FIGS. 4 and 4A-1 to 4A-32 (incorporating an S1' pocket in the active site), or most preferably, where said three dimensional structure still further comprises the relative structural coordinates of F149 and P152 according to FIGS. 4 and 4A-1 to 4A-32 (further defining a hydrophobic area at the bottom of the S1' pocket), including, in each case, conservative substitutions of said amino acids and, in each case, ± a root mean square deviation from the catalytic zinc and the conserved backbone atoms (N, Cα, C, and O) of said amino acids of not more than 1.5 Å (or more preferably, not more than 1.0 Å, or most preferably, not more than 0.5 Å). Finally, in the most preferred embodiment, the protein used in the solution of the present invention comprises the complete structural coordinates according to FIGS. 4 and 4A-1 to 4A-32, ± a root mean square deviation from the conserved backbone atoms of said amino acids (or conservative substitutions thereof) of not more than 1.5 Å (or more preferably, not more than 1.0 Å, and most preferably, not more than 0.5 Å).

Also provided by the present invention is a crystallized catalytic fragment of MMP-13 complexed with Compound A. The crystal of the present invention effectively diffracts X-rays for the determination of the structural coordinates of the MMP-13: Compound A complex, and is characterized as being in orthorhombic form with space group P21212, and having unit cell parameters of a=108.3 Å, b=79.8 Å, and c=36.1 Å. Further, the crystal complex of the present invention consists of two molecules of MMP-13: Compound A complex in the asymmetric crystal unit.

In a preferred embodiment, the MMP-13 of the crystal complex of the present invention comprises the amino acid residues of FIG. 1 (or conservative substitutions thereof), and is characterized by a secondary structure comprising three alpha helices and a mixed parallel and anti-parallel beta sheet comprising five beta strands, configured in the order $\beta_I$, $\alpha_A$, $\beta_{II}$, $\beta_{III}$, $\beta_{IV}$, $\beta_{IV}$, $\beta_V$, $\alpha_B$, and $\alpha_C$. Further, the three alpha helices preferably correspond to residues 28–44 ($\alpha_A$), 112–123 ($\alpha_B$) and 153–163 ($\alpha_C$) of FIG. 1, and the five beta strands correspond to residues 83–86 ($\beta_I$), 95–100 ($\beta_{II}$), 59–66 ($\beta_{III}$), 14–20 ($\beta_{IV}$), and 49–53 ($\beta_V$) of FIG. 1, respectively.

The protein used in the crystal or crystal complex of the present invention includes MMP-13, as well as MMP-13 analogues, where said protein comprises an active site characterized by the three dimensional structure comprising the relative structural coordinates of the catalytic zinc and amino acid residues L81, L82, L115, V116, H119, L136 and I140 (or conservative substitutions thereof) according to the crystal coordinates of FIGS. 5 and 5A-1 to 5A-35, ± a root mean square deviation from the catalytic zinc and the conserved backbone atoms of said amino acids of not more than 1.5 Å, or more preferably, not more than 1.0 Å, or most preferably, not more than 0.5 Å.

Alternatively, a protein used in the crystal or crystal complex of the present invention comprises an active site characterized by a catalytic zinc, a beta strand (comprising amino acid residues N14, L15, T16, Y17, R18, I19, and V20 or conservative substitutions thereof), a $Ca^{2+}$ binding loop (comprising amino acid residues F75, D76, G77, P78, and S79 or conservative substitutions thereof), an alpha helix (comprising amino acid residues N112, L113, F114, L115, V116, A117, A118, H119, E120, F121, G122, and H123 or conservative substitutions thereof) and a random coil region (comprising amino acid residues P139, I140, and Y141 or conservative substitutions thereof), or, more particularly, characterized by a three dimensional structure comprising the relative structural coordinates of the catalytic zinc and amino acid residues N14, L15, T16, Y17, R18, I19, V20, F75, D76, G77, P78, S79, N112, L113, F114, L115, V116, A117, A118, H119, E120, F121, G122, H123, P139, I140, and Y141 according to FIGS. 5 and 5A-1 to 5A-35, or more preferably, where said three dimensional structure further comprises the relative structural coordinates of amino acid residues G80, L81, L82, A83, H84, A85, K109, G110, Y111, S124, L125, G126, L127, D128, H129, S130, K131, D132, P133, G134, A135, L136, M137, F138, T142, Y143, T144, and G145 according to FIGS. 5 and 5A-1 to 5A-35 (incorporating an S1' pocket in the active site), or most preferably, where said three dimensional structure still further comprises the relative structural coordinates of F149 and P152 according to FIGS. 5 and 5A-1 to 5A-35 (further defining a hydrophobic area at the bottom of the S1' pocket), in each case, including conservative substitutions of the said amino acids and, in each case, ± a root mean square deviation from the catalytic zinc and the conserved backbone atoms of said amino acids of not more than 1.5 Å (or more preferably, not more than 1.0 Å, or most preferably, not more than 0.5 Å).

Finally, in the most preferred embodiment, the protein used in the crystal of the present invention comprises the complete structural coordinates according to FIGS. 5 and 5A-1 to 5A-35, ± a root mean square deviation from the conserved backbone atoms of said amino acids (or conservative substitutions thereof) of not more than 1.5 Å (or more preferably, not more than 1.0 Å, and most preferably, not more than 0.5 Å).

Molecular modeling methods known in the art may be used to identify an active site or binding pocket of the MMP-13 molecule, MMP-13 molecular complex, or an MMP-13 analogue. Specifically, the structural coordinates provided by the present invention may be used to characterize a three dimensional model of the MMP-13 molecule, molecular complex or MMP-13 analogue. From such a model, putative active sites may be computationally visualized, identified and characterized based on the surface structure of the molecule, surface charge, steric arrangement, the presence of reactive amino acids, regions of hydrophobicity or hydrophilicity, etc. Such putative active sites may be further refined using chemical shift perturbations of spectra generated from various and distinct MMP-13 complexes, competitive and non-competitive inhibition experiments, and/or by the generation and characterization of MMP-13 mutants to identify critical residues or characteristics of the active site.

The identification of putative active sites of a molecule or molecular complex is of great importance, as most often the biological activity of a molecule or molecular complex results from the interaction between an agent and one or more active sites of the molecule or molecular complex. Accordingly, the active sites of a molecule or molecular complex are the best targets to use in the design or selection of activators or inhibitors that affect the activity of the molecule or molecular complex.

The present invention is directed to an active site of MMP-13 or an MMP-13 analogue, that, as a result of its shape, reactivity, charge potential, etc., favorably interacts or associates with another agent (including, without limitation, a protein, polypeptide, peptide, nucleic acid, including DNA or RNA, molecule, compound, antibiotic or drug). As such, the active site of the present invention includes both the actual site of substrate cleavage or collagenase activity (the catalytic zinc chelated by H119, H123, and H129), as well as binding sites or pockets adjacent to the site of substrate cleavage (i.e., S1', S2', S3', S1, S2, and/or S3) that may nonetheless affect MMP-13 activity upon interaction or association with an agent, either by direct interference with the site of substrate cleavage or by indirectly affecting the steric conformation or charge potential of the MMP-13 molecule. Accordingly, the present invention is directed to an active site of the MMP-13 molecule characterized by a zinc atom chelated by H119, H123 and H129, and preferably the S1' binding pocket to the right of the catalytic zinc.

In an alternate embodiment, the active site of the present invention is characterized by the three dimensional structure comprising the relative structural coordinates of the catalytic zinc and amino acid residues L81, L82, L115, V116, H119, L136 and I140 (or conservative substitutions thereof) according to the solution or crystal coordinates of FIGS. 4 and 4A-1 to 4A-32 or FIGS. 5 and 5A-1 to 5A-35, respectively, in each case, ± a root mean square deviation from the catalytic zinc and the conserved backbone atoms of said amino acids of not more than 1.5 Å, or more preferably, not more than 1.0 Å, or most preferably, not more than 0.5 Å.

Alternatively, the active site of the present invention is characterized by a catalytic zinc, a beta strand (comprising amino acid residues N14, L15, T16, Y17, R18, I19, and V20 or conservative substitutions thereof), a $Ca^{2+}$ binding loop (comprising amino acid residues F75, D76, G77, P78, and S79 or conservative substitutions thereof), an alpha helix (comprising amino acid residues N112, L113, F114, L115, V116, A117, A118, H119, E120, F121, G122, and H123 or conservative substitutions thereof) and a random coil region (comprising amino acid residues P139, I140, and Y141 or conservative substitutions thereof), or, more particularly, is characterized by a three dimensional structure comprising the relative solution or crystal structural coordinates of the catalytic zinc and amino acid residues N14, L15, T16, Y17, R18, I19, V20, F75, D76, G77, P78, S79, N112, L113, F114, L115, V116, A117, A118, H119, E120, F121, G122, H123, P139, I140, and Y141 according to FIGS. 4 and 4A-1 to 4A-32 or FIGS. 5 and 5A-1 to 5A-35, respectively, or more preferably, where said three dimensional structure further comprises the relative solution or crystal structural coordinates of amino acid residues G80, L81, L82, A83, H84, A85, K109, G110, Y111, S124, L125, G126, L127, D128, H129, S130, K131, D132, P133, G134, A135, L136, M137, F138, T142, Y143, T144, and G145 according to FIGS. 4 and 4A-1 to 4A-32 or FIGS. 5 and 5A-1 to 5A-35, or most preferably, where said three dimensional structure still further comprises the relative solution or crystal structural coordinates of F149 and P152 according to FIGS. 4 and 4A-1 to 4A-32 or FIGS. 5 and 5A-1 to 5A-35, in each case, including conservative substitutions of said amino acids, and in each case, ± a root mean square deviation from the catalytic zinc and the conserved backbone atoms of said amino acids of not more than 1.5 Å (or more preferably, not more than 1.0 Å, or most preferably, not more than 0.5 Å).

In order to use the structural coordinates generated for a crystal or solution structure of the present invention as set forth in FIGS. 4 and 4A-1 to 4A-32 or FIGS. 5 and 5A-1 to 5A-35, respectively, it is often necessary to display the relevant coordinates as, or convert them to, a three dimensional shape or graphical representation, or to otherwise manipulate them. For example, a three dimensional representation of the structural coordinates is often used in rational drug design, molecular replacement analysis, homology modeling, and mutation analysis. This is typically accomplished using any of a wide variety of commercially available software programs capable of generating three dimensional graphical representations of molecules or portions thereof from a set of structural coordinates. Examples of said commercially available software programs include, without limitation, the following: GRID (Oxford University, Oxford, UK); MCSS (Molecular Simulations, San Diego, Calif.); AUTODOCK (Scripps Research Institute, La Jolla, Calif.); DOCK (University of California, San Francisco, Calif.); Flo99 (Thistlesoft, Morris Township, N.J.); Ludi (Molecular Simulations, San Diego, Calif.); QUANTA (Molecular Simulations, San Diego, Calif.); Insight (Molecular Simulations, San Diego, Calif.); SYBYL (TRIPOS, Inc., St. Louis. MO); and LEAPFROG (TRIPOS, Inc., St. Louis, Mo.).

For storage, transfer and use with such programs, a machine, such as a computer, is provided for that produces a three dimensional representation of the MMP-13 molecule, a portion thereof (such as an active site or a binding site), a MMP-13 molecular complex, or an MMP-13 analogue. The machine of the present invention comprises a machine-readable data storage medium comprising a data storage material encoded with machine-readable data. Machine-readable storage media comprising data storage material include conventional computer hard drives, floppy disks, DAT tape, CD-ROM, and other magnetic, magneto-optical, optical, floptical and other media which may be adapted for use with a computer. The machine of the present invention also comprises a working memory for storing instructions for processing the machine-readable data, as well as a central processing unit (CPU) coupled to the working memory and to the machine-readable data storage medium for the purpose of processing the machine-readable data into the desired three dimensional representation. Finally, the machine of the present invention further comprises a display connected to the CPU so that the three dimensional representation may be visualized by the user. Accordingly, when used with a machine programmed with instructions for using said data, e.g., a computer loaded with one or more programs of the sort identified above, the machine provided for herein is capable of displaying a graphical three-dimensional representation of any of the molecules or molecular complexes, or portions of molecules of molecular complexes, described herein.

In one embodiment of the invention, the machine-readable data comprises the relative structural coordinates of the catalytic zinc and amino acid residues L81, L82, L115, V116, $H_{119}$, L136 and I140 according to FIGS. 4 and 4A-1 to 4A-32 or FIGS. 5 and 5A-1 to 5A-35, in each case, including conservative substitutions thereof, and in each case, ± a root mean square deviation from the catalytic zinc and the conserved backbone atoms of said amino acids of not more than 1.5 Å (or more preferably, not more than 1.0 Å, and most preferably, not more than 0.5 Å), wherein said structural coordinates characterize an active site of MMP-13 or an MMP-13 analogue.

In an alternate preferred embodiment, the machine-readable data comprises the structural coordinates of the catalytic zinc and amino acid residues N14, L15, T16, Y17, R18, I19, V20, F75, D76, G77, P78, S79, N112, L113, F114, L115, V116, A117, A118, H119, E120, F121, G122, H123, P139, I140, and Y141 according to FIGS. 4 and 4A-1 to 4A-32 or FIGS. 5 and 5A-1 to 5A-35, in each case, including conservative substitutions thereof, and in each case, ± a root mean square deviation from the catalytic zinc and the conserved backbone atoms of said amino acids of not more than 1.5 Å (or more preferably, not more than 1.0 Å, and most preferably, not more than 0.5 Å). In an even more preferred embodiment, the machine-readable data further comprises the relative structural coordinates of amino acid residues G80, L81, L82, A83, H84, A85, K109, G110, Y111, S124, L125, G126, L127, D128, H129, S130, K131, D132, P133, G134, A135, L136, M137, F138, T142, Y143, T144, and G145 according to FIGS. 4 and 4A-1 to 4A-32 or FIGS. 5 and 5A-1 to 5A-35, or most preferably, still further comprises the relative structural coordinates of F149 and P152 according to FIGS. 4 and 4A-1 to 4A-32 or FIGS. 5 and 5A-1 to 5A-35, in each case, including conservative substitutions of said amino acids, and in each case, ± a root mean square deviation from the catalytic zinc and the conserved backbone atoms of said amino acids of not more than 1.5 Å (or more preferably, not more than 1.0 Å, or most preferably, not more than 0.5 Å).

Finally, it is most preferred that the machine-readable data comprise the relative structural coordinates of all residues constituting the MMP-13 catalytic fragment according to FIGS. 4 and 4A-1 to 4A-32 or FIGS. 5 and 5A-1 to 5A-35, in each case, ± a root mean square deviation from the conserved backbone atoms of said amino acids of not more than 1.5 Å. In each case, the noted embodiments comprise conservative substitutions of the noted residues resulting in same structural coordinates within the stated root mean square deviation.

The structural coordinates of the present invention permit the use of various molecular design and analysis techniques in order to (i) solve the three dimensional structures of related molecules, molecular complexes or MMP-13 analogues, and (ii) to design, select, and synthesize chemical agents capable of favorably associating or interacting with an active site of an MMP-13 molecule or MMP-13 analogue, wherein said chemical agents potentially act as activators or inhibitors of MMP-13 or of an MMP-13 analogue.

More specifically, the present invention provides a method for determining the molecular structure of a molecule or molecular complex whose structure is unknown, comprising the steps of obtaining crystals or a solution of the molecule or molecular complex whose structure is unknown, and then generating x-ray diffraction data from the crystallized molecule or molecular complex, and/or generating NMR data from the solution of the molecule or molecular complex. The x-ray diffraction data from the molecule or molecular complex whose structure is unknown is then compared to the x-ray diffraction data obtained from the MMP-13: Compound A crystal of the present invention. Alternatively, the NMR data from the molecule or molecular structure whose structure is unknown is then compared with the NMR data obtained from the MMP-13: Compound A solution of the present invention. Then, molecular replacement analysis is used to conform the three dimensional structure determined from the MMP-13: Compound A crystal of solution of the present invention to the x-ray diffraction data from the unknown molecule or molecular complex, or, alternatively, 2), 3D and 4D isotope filtering, editing and triple resonance NMR techniques are used to conform the three dimensional structure determined from the MMP-13: Compound A solution of the present invention to the NMR data from the solution molecule or molecular complex.

Molecular replacement analysis uses a molecule having a known structure as a starting point to model the structure of an unknown crystalline sample. This technique is based on the principle that two molecules which have similar structures, orientations and positions will diffract x-rays similarly. A corresponding approach to molecular replacement is applicable to modeling an unknown solution structure using NMR technology. The NMR spectra and resulting analysis of the NMR data for two similar structures will be essentially identical for regions of the proteins that are structurally conserved, where the NMR analysis consists of obtaining the NMR resonance assignments and the structural constraint assignments, which may contain hydrogen bond, distance, dihedral angle, coupling constant, chemical shift and dipolar coupling constant constraints. The observed differences in the NMR spectra of the two structures will highlight the differences between the two structures and identify the corresponding differences in the structural constraints. The structure determination process for the unknown structure is then based on modifying the NMR constraints from the known structure to be consistent with the observed spectral differences between the NMR spectra.

Accordingly, in one non-limiting embodiment of the invention, the resonance assignments for the MMP-13: Compound A complex provide the starting point for resonance assignments of MMP-13 in a new MMP-13: "unsolved agent" complex. Chemical shift perturbances in two dimensional 15N/$^1$H spectra can be observed and compared between the MMP-13: Compound A complex and the new MMP-13: agent complex. In this way, the affected residues may be correlated with the three dimensional structure of MMP-13 as provided by the relevant residues of FIGS. 4 and 4A-1 to 4A-32. This effectively identifies the region of the MMP-13: agent complex that has incurred a structural change relative to the MMP-13: Compound A complex. The $^1$H, $^{15}$N, $^{13}$C and $^{13}$CO NMR resonance assignments corresponding to both the sequential backbone and side-chain amino acid assignments of MMP-13 may then be obtained and the three dimensional structure of the new MMP-13: agent complex may be generated using standard 2D, 3D and 4D triple resonance NMR techniques and NMR assignment methodology, using the MMP-13: Compound A structure, resonance assignments and structural constraints as a reference. Various computer fitting analyses of the new agent with the three dimensional model of MMP-13 may be performed in order to generate an initial three dimensional model of the new agent complexed with MMP-13, and the resulting three dimensional model may be refined using standard experimental constraints and energy minimization techniques in order to position and orient the new agent in association with the three dimensional structure of MMP-13.

The present invention further provides that the structural coordinates of the present invention may be used with standard homology modeling techniques in order to determine the unknown three-dimensional structure of a molecule or molecular complex. Homology modeling involves constructing a model of an unknown structure using structural coordinates of one or more related protein molecules, molecular complexes or parts thereof (i.e., active sites). Homology modeling may be conducted by fitting common or homologous portions of the protein whose three dimensional structure is to be solved to the three dimensional structure of homologous structural elements in the known molecule, specifically using the relevant (i.e., homologous)

structural coordinates provided by FIGS. 4 and 4A-1 to 4A-32 and/or FIGS. 5 and 5A-1 to 5A-35 herein. Homology may be determined using amino acid sequence identity, homologous secondary structure elements, and/or homologous tertiary folds. Homology modeling can include rebuilding part or all of a three dimensional structure with replacement of amino acids (or other components) by those of the related structure to be solved.

Accordingly, a three dimensional structure for the unknown molecule or molecular complex may be generated using the three dimensional structure of the MMP-13: Compound A complex of the present invention, refined using a number of techniques well known in the art, and then used in the same fashion as the structural coordinates of the present invention, for instance, in applications involving molecular replacement analysis, homology modeling, and rational drug design.

Determination of the three dimensional structure of MMP-13 and its catalytic active site as disclosed herein is critical to the rational identification and/or design of therapeutic agents that may act as inhibitors or activators of MMP-13 enzymatic activity. Alternatively, using conventional drug assay techniques, the only way to identify such an agent is to screen thousands of test compounds, either in culture or by administration to suitable animal models in a laboratory setting, until an agent having the desired inhibitory or activating effect on a target compound is identified. Necessarily, such conventional screening methods are expensive, time consuming, and do not elucidate the method of action of the identified agent on the target compound.

However, advancing X-ray, spectroscopic and computer modeling technologies allow researchers to visualize the three dimensional structure of a targeted compound. Using such a three dimensional structure, researchers identify putative binding sites and then identify or design agents to interact with these binding sites. These agents are then screened for an activating or inhibitory effect upon the target molecule. In this manner, not only are the number of agents to be screened for the desired activity greatly reduced, but the mechanism of action on the target compound is better understood.

Accordingly, the present invention further provides a method for identifying a potential inhibitor or activator of MMP-13, comprising the steps of using a three dimensional structure of MMP-13 as defined by the relative structural coordinates of amino acids encoding MMP-13 to design or select a potential inhibitor or activator, and synthesizing or obtaining said potential inhibitor or activator. The inhibitor or activator may be selected by screening an appropriate database, may designed de novo by analyzing the steric configurations and charge potentials of an empty MMP-13 active site in conjunction with the appropriate software programs, or may be designed using characteristics of known inhibitors or activators to MMP-13 or other collagenases in order to create "hybrid" activators or inhibitors. The method of the present invention is preferably used to design or select inhibitors of MMP-13 activity.

An agent that interacts or associates with an active site of MMP-13 or an MMP-13 analogue may be identified by determining an active site of MMP-13 or of the MMP-13 analogue from a three dimensional model of the MMP-13 or MMP-13 analogue, and performing computer fitting analyses to identify an agent which interacts or associates with said active site. Computer fitting analyses utilize various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. The degree of association may be determined computationally by any number of commercially available software programs, or may be determined experimentally using standard binding assays.

Three dimensional models of the putative active site may be generated using any one of a number of methods known in the art, and include, but are not limited to, homology modeling as well as computer analysis of raw structural coordinate data generated using crystallographic or spectroscopy techniques. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. MO) and LEAPFROG (TRIPOS, Inc., St. Louis, Mo.).

In a preferred method of the present invention, the identified active site of MMP-13 or the MMP-13 analogue comprises a catalytic zinc, a beta strand, a $Ca^{2+}$ binding loop, an alpha helix and a random coil region. More preferably, the identified active site comprises a catalytic zinc, a beta strand comprising residues N14, L15, T16, Y17, R18, I19, and V20 according to FIG. 1 (or conservative substitutions thereof), a $Ca^{2+}$ binding loop comprising residues F75, D76, G77, P78, and S79 according to FIG. 1 (or conservative substitutions thereof), an alpha helix comprising residues N112, L113, F114, L115, V116, A117, A118, H119, E120, F121, G122, and H123 according to FIG. 1 (or conservative substitutions thereof), and a random coil region comprising residues P139, I140, and Y141 according to FIG. 1 (or conservative substitutions thereof).

More specifically, the identified active site of the present method comprises the relative structural coordinates of the catalytic zinc and amino acid residues N14, L15, T16, Y17, R18, I19, V20, F75, D76, G77, P78, S79, N112, L113, F114, L115, V116, A117, A118, $H_{119}$, E120, F121, G122, H123, P139, I140, and Y141 according to FIGS. 4 and 4A-1 to 4A-32 or FIGS. 5 and 5A-1 to 5A-35, in each case, including conservative substitutions of said amino acids, and in each case, ± a root mean square deviation from the catalytic zinc and the conserved backbone atoms of said amino acids of not more than 1.5 Å(or more preferably, not more than 1.0 Å, or most preferably, not more than 0.5 Å. In an alternate preferred embodiment, the identified active site further comprises the relative structural coordinates of amino acid residues G80, L81, L82, A83, H84, A85, K109, G110, Y111, S124, L125, G126, L127, D128, H129, S130, K131, D132, P133, G134, A135, L136, M137, F138, T142, Y143, T144, and G145 according to FIG. 4 or 5, in each case, including conservative substitutions of said amino acids, and in each case, of: a root mean square deviation from the conserved backbone atoms of said amino acids of not more than 1.5 Å (or more preferably, not more than 1.0 Å, or most preferably, not more than 0.5 Å). In yet a third preferred embodiment, the identified active site of the present method further comprises the relative structural coordinates of amino acid residues F149 and P152 according to FIGS. 4 and 4A-1 to 4A-32 or FIGS. 5 and 5A-1 to 5A-35, in each case, including conservative substitutions of said amino acids, and in each case, ± a root mean square deviation from the conserved backbone atoms of said amino acids of not more than 1.5 Å (or more preferably, not more than 1.0 Å, or most preferably, not more than 0.5 Å). Embodiments comprising conservative substitutions of the noted amino acids result in the same structural coordinates of the corresponding residues in FIGS. 4 and 4A-1 to 4A-32 or FIGS. 5 and 5A-1 to 5A-35 within the stated root mean square deviation.

The effect of such an agent identified by computer fitting analyses on MMP-13 (or MMP-13 analogue) activity may be further evaluated computationally, or experimentally by contacting the identified agent with MMP-13 (or an MMP-13 analogue) and measuring the effect of the agent on the enzyme's activity. Depending upon the action of the agent on the active site of MMP-13, the agent may act either as an inhibitor or activator of MMP-13 activity. Standard enzymatic assays may be performed and the results analyzed to determine whether the agent is an inhibitor of MMP-13 activity (i.e., the agent may reduce or prevent binding affinity between MMP-13 and the relevant substrate, and thereby reduce the level or rate of MMP-13 activity compared to baseline), or an activator of MMP-13 activity (i.e., the agent may increase binding affinity between MMP-13 and the relevant substrate, and thereby increase the level or rate of MMP-13 activity compared to baseline). Further tests may be performed to evaluate the selectivity of the identified agent to MMP-13 with regard to the other metalloproteinases.

Agents designed or selected to interact with MMP-13 must be capable of both physically and structurally associating with MMP-13 via various covalent and/or non-covalent molecular interactions, and of assuming a three dimensional configuration and orientation that complements the relevant active site of the MMP-13 molecule.

Accordingly, using these criteria, the structural coordinates of the MMP-13: Compound A complex as disclosed herein, and/or structural coordinates derived therefrom using molecular replacement analysis or homology modeling, agents may be designed to increase either or both of the potency and selectivity of known inhibitors or activators, either by modifying the structure of known inhibitors or activators or by designing new agents de novo via computational inspection of the three dimensional configuration and electrostatic potential of an MMP-13 active site.

Accordingly, in one embodiment of the invention, the structural coordinates of FIGS. 4 and 4A-1 to 4A-32 or FIGS. 5 and 5A-1 to 5A-35 of the present invention, or structural coordinates derived there from using molecular replacement or homology modeling techniques as discussed above, are used to screen a database for agents that may act as potential inhibitors or activators of MMP-13 activity (or the activity of MMP-13 analogues). Specifically, the obtained structural coordinates of the present invention are read into a software package and the three dimensional structure is analyzed graphically. A number of computational software packages may be used for the analysis of structural coordinates, including, but not limited to, Sybyl (Tripos Associates), QUANTA and XPLOR (Brunger, A. T. (1993) *XPLOR Version* 3.1 Manual, Yale University, New Haven, Conn.). Additional software programs check for the correctness of the coordinates with regard to features such as bond and atom types. If necessary, the three dimensional structure is modified and then energy minimized using the appropriate software until all of the structural parameters are at their equilibrium/optimal values. The energy minimized structure is superimposed against the original structure to make sure there are no significant deviations between the original and the energy minimized coordinates. The energy minimized coordinates of MMP-3 complexed with a "solved" inhibitor or activator are then analyzed and the interactions between the solved ligand and MMP-13 are identified. The final MMP-13 structure is modified by graphically removing the solved inhibitor or activator so that only MMP-13 and a few residues of the solved agent are left for analysis of the binding site cavity. QSAR and SAR analysis and/or conformational analysis may be carried out to determine how other inhibitors or activators compare to the solved inhibitor or activator. The solved agent may be docked into the uncomplexed structure's binding site to be used as a template for data base searching, using software to create excluded volume and distance restrained queries for the searches.

The energy minimized coordinates of MMP-13 complexed with a "solved" inhibitor or activator are then analyzed and the interactions between the solved ligand and MMP-13 are identified. The final MMP-13 structure is modified by graphically removing the solved inhibitor or activator so that only MMP-13 and a few residues of the solved agent are left for analysis of the binding site cavity. QSAR and SAR analysis and/or conformational analysis may be carried out to determine how other inhibitors or activators compare to the solved inhibitor or activator. The solved agent may be docked into the uncomplexed structure's binding site to be used as a template for data base searching, using software to create excluded volume and distance restrained queries for the searches. Structures qualifying as hits are then screened for activity using standard assays and other methods known in the art.

Further, once the specific interaction is determined between the solved inhibitor or activator, docking studies with different inhibitors or activators allow for the generation of initial models of new inhibitors or activators in complex with MMP-13. The integrity of these new models may be evaluated a number of ways, including constrained conformational analysis using molecular dynamics methods (i.e., where both MMP-13 and the complexed activator or inhibitor are allowed to sample different three dimensional conformational states until the most favorable state is reached or found to exist between the protein and the complexed agent). The final structure as proposed by the molecular dynamics analysis is analyzed visually to make sure that the model is in accord with known experimental SAR based on measured binding affinities. Once models are obtained of the original solved agent bound to MMP-13 and computer models of other molecules bound to MMP-13, strategies are determined for designing modifications into the activators or inhibitors to improve their activity and/or enhance their selectivity.

Once an MMP-13 binding agent has been optimally selected or designed, as described above, substitutions may then be made in some of its atoms or side groups in order to improve or modify its selectivity and binding properties. Generally, initial substitutions are conservative, i.e., the replacement group will have approximately the same size, shape, hydrophobicity and charge as the original group. Such substituted chemical compounds may then be analyzed for efficiency of fit to MMP-13 by the same computer methods described in detail above.

Alternatively, the present invention provides a method for identifying potential inhibitor or activator that is selective for one or more members of the matrix metalloproteinase family except MMP-13, comprising the steps of (i) using the three dimensional structures of MMP-13 and the desired target matrix metalloproteinase(s) as defined by the relative structural coordinates of amino acids encoding MMP-13 and the target matrix metalloproteinase(s) in order to design or select such a potential inhibitor or activator, and (ii) synthesizing or obtaining said potential inhibitor or activator. In this case, the potential inhibitor or activator is designed to incorporate chemical or steric features favorable for association with an active site of the desired matrix metalloproteinase(s) and unfavorable for association with an MMP-13 active site, preferably where said active site comprises the MMP-13 S1' pocket. The inhibitor or activator may be selected by screening an appropriate database, may designed de novo by analyzing the steric configurations and charge potentials of empty MMP-13/matrix metalloproteinase active sites in conjunction with the appropriate software programs, or may be designed using characteristics of known inhibitors or activators to MMP-13 or other collagenases in order to create "hybrid" activators or inhibitors.

Various molecular analysis and rational drug design techniques are further disclosed in U.S. Pat. Nos. 5,834,228, 5,939,528, and 5,856,116, as well as in PCT Application No. PCT/US98/16879, published as WO 99/09148, the contents of which are hereby incorporated by reference.

The present invention may be better understood by reference to the following non-limiting Examples. The following Examples are presented in order to more fully illustrate the preferred embodiments of the invention, and should in no way be construed as limiting the scope of the present invention.

EXAMPLE 1

$^{1}$H, $^{15}$N and $^{13}$CO Assignments and Secondary Structure Determination of MMP-13 Complexed with Compound A Methods and Results: The uniform $^{15}$N and $^{13}$C— labeled 165 amino-acid catalytic fragment of human collagenase-3 (MMP-13) was expressed in *E. coli* strain BL21 (DE3) containing the plasmid pProMMP-13 according to a published method (Freije et al., *J. Biol. Chem.* 1994). MMP-13 was purified as previously described (Moy et al., *J. Biomol.* 1997) with minor modifications. N-terminal amino acid sequencing was performed to confirm the protein's identity while the uniform $^{15}$N and $^{13}$C labeling of MMP-13 was confirmed by MALDI-TOF mass spectrometry (PerSeptive Biosystems). The sulfonamide derivative of the hydroxamic acid compound, N-Hydroxy-2-[(4-methoxy-benzenesulfonyl)-pyridin-3-ylmethyl-amino]-3-methyl-benzamide, was prepared from 2-amino-3-methyl-benzoic acid methyl ester and p-methoxybenzenesulfonyl chloride followed by alkylation with 3-picolyl chloride, hydrolysis (LiOH/THF) to afford the carboxylic acid and conversion to the hydroxamic acid (oxalyl chloride/DMF/NH2OH). Formation of the HCl salt yielded Compound A as shown in FIG. 3.

The NMR samples contained 1 mM of MMP-13 determined spectrophotometrically in a equimolar complex with Compound A in a buffer containing 10 mM deuterated Tris-Base, 100 mM NaCl, 5 mM $CaCl_2$, 0.1 mM $ZnCl_2$, 2 mM $NaN_3$, 10 mM deuterated DTT, in either 90% $H_2O$/10% $D_2O$ or 100% $D_2O$ at pH 6.5. All NMR spectra were recorded at 35° C. on a Bruker AMX-2 600 spectrometer equipped with a triple-resonance gradient probe.

Spectra were processed using the NMRPipe software package (Delaglio et al., *J. Biomol. NMR* 1995) and analyzed with PIPP (Garrett et al., *J. Magn. Reson.* 1991), NMRPipe and PEAK-SORT, an in-house software package. The assignments of the $^{1}$H, $^{15}$N, $^{13}$CO, and $^{13}$C resonances were based on the following experiments: CBCA(CO)NH, CBCANH, C(CO)NH, HC(CO)NH, HBHA(CO)NH, HNCO, HCACO, HNHA, HNCA, HCCH-COSY and HCCH-TOCSY (for reviews, see Bax et al., *Methods Enzmmol.* 1994; and Clore & Gronenborn, *Methods Enzymol.* 1994). The accuracy of the MMP-13 NMR assignments was further confirmed by sequential NOEs in the $^{15}$N-edited NOESY-HSQC spectra.

Prior to analysis of the MMP-13 NMR structure, the structure determination of the inhibitor-free catalytic fragment of MMP-1 has been reported (Moy et al., *Biochemistry* 1998; Moy et al., *J. Biomol. NMR* 1997)(30 simulated annealing structures deposited with Protein Data Bank, Accession No. 1AYK; restrained minimized mean structure deposited with Protein Data Bank, Accession No. 2AYK). Because the MMPs are highly autocatalytic, the NMR analysis of the inhibitor-free MMP-1 was accomplished by establishing buffer conditions where the enzyme was still active but the rate of self-cleavage of the enzyme had been diminished. This was achieved by the addition of DTT which significantly diminished self-aggregation of the enzyme and by lowering the pH of the sample to 6.5, just above the pH where the enzyme was known to be inactivated because of the loss of the catalytic zinc. Under these conditions, an MMP-1 NMR sample was typically stable for 1–2 months. Unfortunately this was not the case for MMP-13, the protein rapidly degraded within a few hours which required the use of an inhibitor to assign the MMP-13 NMR resonances.

The secondary structure of the MMP-13: Compound A complex is based on characteristic NOE data involving the NH, Hα and Hβ protons from $^{15}$N-edited NOESY-HSQC and $^{13}$C-edited NOESY-HMQC spectra, $^{3}$JHNα coupling constants from HNHA, slowly exchanging NH protons and $^{13}$Cα and $^{13}$C secondary chemical shifts (for reviews, see Wishart & Sykes, *Methods Enzymol.* 1994; and Wuthrich, *NMR of Proteins and Nucleic Acids*, John Wiley & Sons, New York 1986). It was determined that the MMP-13 NMR structure in the complex is composed of three α-helices corresponding to residues 28–44 ($a_α$), 112–123 ($a_β$) and 153–163 ($a_C$) and a mixed parallel and anti-parallel α-sheet consisting of 5 strands corresponding to residues 83–86 ($β_1$), 95–100 ($β_2$), 59–66 ($β_3$), 14–20 ($β_4$) and 49–53 ($β_5$). This is essentially identical to the secondary structure observed for other MMP structures.

There were three distinct regions in the MMP-13: Compound A spectra where the resonance assignments are incomplete. These correspond to residues G70–Y73, P87–N91 and T144–H148. Residues T144–H148 correspond to part of the dynamic loop region previously seen in the MMP-1 structure (Moy et al., *J. Biomol. NMR* 1997). This suggests a similar dynamic profile for this region in the MMP-13 structure even in the presence of a high-affinity inhibitor ($IC_{50}$=33 nM). Residues P87 to N91 contain a cluster of prolines which disrupt the sequential assignment process because of the missing NH. Residues G70 to Y73 correspond to a loop region in the vicinity of the structural zinc which was readily assigned in the MMP-1 structure. The backbone and side-chain $^{1}$H, $^{15}$N, $^{13}$C, and $^{13}$CO assignments are essentially complete for the remainder of the protein.

EXAMPLE 2

High Resolution Solution Structure of the Catalytic Fragment of MMP-13 Complexed with Compound A Materials and Methods:

Preparation of Compound A: The sulfonamide derivative of the hydroxamic acid compound, Compound A, was prepared according to the procedure noted in Example 1 to yield the compound of FIG. 3.

Expression of recombinant $^{15}$N and $^{13}$C/$^{15}$N-labeled MMP-13: A 169-residue C-terminally truncated human collagenase-3 (MMP-13) was expressed in *E. coli*. The coding sequence of a C-terminally truncated procollagenase was amplified by PCR from the plasmid pNot3a, that contains the entire coding sequence of MMP-13 (Frieje, et al., *J. Biol. Chem.* 1994). The PCR primers contained the appropriate restriction sites for ease of cloning. The construct codes for a truncated proMMP-13 with an N-terminal methionine added and a C-terminal proline at residue 169 of the native proMMP-13 sequence. The PCR amplified DNA fragment was the cloned into pET-21a (+) at the Nde I/Sal I sites, resulting in a recombinant plasmid designated as pProMMP-13. *E. coli* bacteria, BL21 (DE3), containing the plasmid pProMMP-13, were grown in LB broth supplemented with 100 μg/ml ampicilin. An overnight culture was diluted 1:20 and grown at 37° C. to an $A_{600}$ of 0.6–0.8 with vigorous shaking. Isopropyl β-D-galactoside (IPTG) was added to a final concentration of 1 mM and cultures were shaken for 3 h at 37° C. The cells were harvested by centrifugation (7000×g for 15 min) at 4° C., washed with PBS, and frozen at −70° C. until further use.

Uniform $^{15}$N and $^{13}$C-labeled ProMMP-13 was obtained by growing BL21(DE3) *E. coli* in defined media containing 2.0 g/l [$^{13}$C6, 98%+]D-glucose and 1.0 g/l [$^{15}$N, 98%+] ammonium chloride as the sole carbon and nitrogen sources, respectively. In addition, the defined media contained M9 salts (Sambrook, et al., *Molecular Cloning: A Laboratory Manual*, Cold Spring Harbor Laboratory Press, New York, N.Y. 1989), trace elements, vitamins and 100 μg/ml ampicilin. Conditions for induction and growth were the same as above.

Purification of recombinant $^{15}$N and $^{13}$C MMP-13: MMP-13 was purified according to Moy et al., *J. Biomol. NMR* 1997, with modifications as follows. Frozen cell pellets were thawed on ice. Cells were resuspended by homogenization in lysis buffer (0.1 M Tricine, pH 8.0, 10 mM EDTA, 2 mM DTT, 0.5 mM PMSF). Cells were lysed by French Press (2×) followed by treatment with lysozyme (1 mg/ml; final) at room temperature for 30 min. The lysate was centrifuged at 45,000×g for 30 minutes. The pellet was washed twice with 50 mM Tricine pH 7.5, 0.2 M NaCl$_2$, 0.5% Triton X-100, resuspended in fresh urea buffer (20 mM Tricine, pH 7.5, 8 M urea, 0.2% NaN$_3$, 2 mM DTT) and incubated at room temperature for 1 hour. The urea solubilized protein was centrifuged at 45,000×g for 30 min and the resultant supernatant was filtered and applied to a Hitrap-Q Sepharose (Pharmacia Biotech) anion exchange column equilibrated in 6 M urea buffer. The column was washed with urea buffer and eluted with a 0–0.25 M NaCl linear gradient. Fractions containing proMMP-13 were detected by SDS-PAGE, pooled and quickly diluted into 5-fold excess of renaturing buffer (50 mM Tricine, pH 7.5, 0.4 M NaCl, 10 mM CaCl$_2$, 0.1 mM ZnOAc$_2$, 0.02% NaN$_3$). After 2 days of dialysis against 25 volumes of renaturing buffer (with three changes), refolded proMMP-13 was concentrated to about 4–10 mg/ml in a Millipore Biomax 5 concentrator. ProMMP-13 was activated to MMP-13CAT (catalytic domain) by an overnight incubation at 37° C. in the presence of 1 mM p-aminophenylmercuric acetate (APMA).

The activated protein is then applied onto a Superdex-75 16/60 gel filtration column equilibrated in 2.5 mM Tris-HCl, pH 7.5, 5 mM CaCl$_2$, 0.4 M NaCl, 2 mM DTT, 0.02% NaN$_3$ and 0.05 mM ZnOAc$_2$. The protein is eluted and fractions containing MMP-13CAT were identified by SDS-PAGE. Peak fractions were pooled and the protein was concentrated in a Millipore Biomax concentrator to about 5 mg/ml and stored at −70° C. N-terminal amino acid sequencing was performed to confirm the protein's identity. The uniform $^{15}$N and $^{13}$C labeling of MMP-13-CAT was confirmed by MALDI-TOF mass spectrometry (PerSeptive Biosystems).

NMR Sample Preparation: The MMP-13: Compound A NMR sample contained 1 mM $^{15}$N-or $^{15}$N/$^{13}$C-labeled MMP-13 with Compound A in a 1:1 ratio. The sample was prepared by repeated buffer exchange using 20–30 ml solution containing 10 mM deuterated Tris-Base, 100 mM NaCl, 5 mM CaCl$_2$, 0.1 mM ZnCl$_2$, 2 mM NaN$_3$, 10 mM deuterated DTT, and 0.2 mM Compound A in either 90% H$_2$O/ 10% D$_2$O or 100% D$_2$O. Buffer exchange was carried out on a Millipore Ultrafree-15 Centrifugal Filter Unit. Excess Compound A was removed by additional buffer exchanges where Compound A was removed from the buffer.

NMR Data Collection: All spectra were recorded at 35° C. on a Bruker AMX-2 600 spectrometer using a gradient enhanced triple-resonance $^1$H/$^{13}$C/$^{15}$N probe. For spectra recorded in H$_2$O, water suppression was achieved with the WATERGATE sequence and water-flip back pulses (Piotto, et al., *J. Biomol. NMR* 1992; Grzesiek and Bax, *J. Am. Chem. Soc.* 1993). Quadrature detection in the indirectly detected dimensions were recorded with States-TPPI hypercomplex phase increment (Marion, et al., *J. Magn. Reson.* 1989). Spectra were collected with appropriate refocusing delays to allow for 0,0 or −90,180 phase correction.

The resonance assignments and bound conformation of Compound A in the MMP-1: Compound A complex were based on the 2D $^{12}$C/$^2$C-filtered NOESY (Petros, et al., *FEBS Lett.* 1992; Gemmecker, et al., *J. Magn. Reson.* 1992), 2D $^{12}$C/$^{12}$C-filtered TOCSY (Petros, et al., *FEBS Lett.* 1992; Gemmecker, et al., *J. Magn. Reson.* 1992) and $^{12}$C/$^{12}$C-filtered COSY experiments (Ikura and Bax, *J. Magn. Reson.* 1992).

The MMP-13: Compound A structure is based on the following series of spectra: HNHA (Vuister and Bax, *J. Am. Chem. Soc.* 1993), HNHB (Archer, et al., *J. Magn. Reson.* 1992), 3D long-range $^{13}$C—13C correlation (Bax and Popchapsky, *J. Magn. Reson.* 1992), coupled CT-HCACO (Powers, et al., *J. Magn. Reson.* 1991; Vuister, et al., *J. Am. Chem. Soc.* 1992), HACAHB-COSY (Grzesiek, et al., *J. Amer. Chem. Soc.* 1995), 3D $^5$N-(Mario, et al., *Biochemistry* 1989; Zuiderweg and Fesik, *Biochemistry* 1989) and $^{13}$C-edited NOESY (Zuiderweg, et al., *J. Magn. Reson.* 1990; Ikura, et al., *J. Magn. Reson.* 1990), and 3D $^{13}$C-edited/$^{12}$C-filtered NOESY (Lee, et al., *FEBS Lett.* 1994). experiments. The $^{15}$N-edited NOESY, $^{13}$C-edited NOESY and 3D $^{13}$C-edited/$^{12}$C-filtered NOESY experiments were collected with 100 msec, 120 msec and 110 msec mixing times, respectively. The acquisition parameters for each of the experiments used in determining the solution structure of MMP-13 complexed with Compound A were as reported previously (Moy, et al., *Biochemistry*, 1998).

Spectra were processed using the NMRPRPipe software package (Delaglio, et al., *J. Biomol. NMR*, 1995) and analyzed with PIPP (Garrett, et al., *J. Magn. Reson.*, 1991) on a Sun Sparc Workstation. When appropriate, data processing included a solvent filter, zero-padding data to a power of two, linear predicting back one data point of indirectly acquired data to obtain zero phase corrections, linear prediction of additional points for the indirectly acquired dimensions to increase resolution. Linear prediction by the means of the mirror image technique was used only for constant-time experiments (Zhu and Bax, J. Magn. Reson., 1992). In all cases data was processed with a skewed sine-bell apodization function and one zero-filling was used in all dimensions.

Interproton Distance Restraints: The NOEs assigned from 3D $^{13}$C-edited/$^{12}$C-filtered NOESY and 3D $^{15}$N-edited NOESY experiments were classified into strong, medium, and weak corresponding to interproton distance restraints of 1.8–2.7 Å (1.8–2.9 Å for NOEs involving NH protons), 1.8–3.3 Å (1.8–3.5 Å for NOEs involving NH protons), and 1.8–5.0 Å, respectively (Williamson, et al., *J. Mol. Biol.*, 1985; Clore, et al., *EMBO J.*, 1986). Upper distance limits for distances involving methyl protons and non-stereospecifically assigned methylene protons were corrected appropriately for center averaging (Wuthrich, et al.,*J. Mol. Biol.*, 1983).

Torsion Angle Restraints and Stereospecific Assignments. The β-methylene stereospecific assignments and $\chi_1$ torsion angle restraints were obtained primarily from a qualitative estimate of the magnitude of $^3J_{\alpha\beta}$ coupling constants from the HACAHB-COSY experiment (Grzesiek, et al., *J. Am. Chem. Soc.*, 1992) and $^3J_{N\beta}$ coupling constants from the HNHB experiment (Archer, et al., *J. Man. Reson.*, 1991). Further support for the assignments was obtained from approximate distance restraints for intraresidue NOEs involving NH, CαH, and CβH protons (Powers, et al., *Biochemistry*, 1993).

The φ and ψ torsion angle restraints were obtained from $^3J_{NH\alpha}$ coupling constants measured from the relative intensity of Hα crosspeaks to the NH diagonal in the HNHA experiment (Vuister and Bax, J. Am. Chem. Soc. 1993), from a qualitative estimate of the magnitude of $^3J_{\alpha\beta}$ coupling constants from the HACAHB-COSY experiment (Grzesiek, et al.,*J. Am. Chem. Soc.,* 1992) and from approximate distance restraints for intraresidue and sequential NOEs involving NH, CαH, and CβH protons by means of the conformational grid search program STEREOSEARCH (Nilges, et al., *Biopolymers* 1990), as described previously (Kraulis, et al., *Biochemistry* 1989). $^1J_{c\alpha H\alpha}$ coupling constants obtained from a coupled 3D CT-HCACO spectrum were used to ascertain the presence of non-glycine residues with positive f backbone torsion angles (Vuister, et al,*J. Am. Chem. Soc.* 1992). The presence of a $^1J_{c\alpha H\alpha}$ coupling constant greater then 130 Hz allowed for a minimum φ restraint of -2° to -178°.

The Ile and Leu χ2 torsion angle restraints and the stereospecific assignments for leucine methyl groups were determined from $^3J_{C\alpha C\delta}$ coupling constants obtained from the relative intensity of Cα and Cδ cross peaks in a 3D long-range $^{13}$C-$^{13}$C NMR correlation spectrum (Bax, et al., *J. Am. Chem. Soc.* 1992), in conjunction with the relative intensities of intraresidue NOEs (Powers, et al., *Biochemistry* 1993). Stereospecific assignments for valine methyl groups were determined based on the relative intensity of intraresidue NH-CγH and CαH-CγH NOEs as described by Zuiderweg et al. (1985) (Zuiderweg, et al., *Biopolymers* 1985). The minimum ranges employed for the φ, ψ, and χ torsion angle restraints were ±30°, ±50°, and ±20°, respectively (Kraulis, et al., *Biochemistry* 1989).

Structure Calculations: The structures were calculated using the hybrid distance geometry-dynamical simulated annealing method of Nilges et al. (1988) (Protein Eng.) with minor modifications (Clore, et al., *Biochemistry* 1990) using the program XPLOR (Brunger, *X-Plor Version* 3.1 *Manual*, Yale University, New Haven, Conn.), adapted to incorporate pseudopotentials for $^3J_{NH\alpha}$ coupling constants (Garrett, et al., *J. Magn. Reson. Ser. B* 1994), secondary $^{13}$Cα/$^{13}$Cβchemical shift restraints (Kuszewski, et al., *J. Magn. Reson. Ser B* 1995) and a conformational database potential (Kuszewski, et al., *Protein Sci.* 1996; Kuszewski, et al., *J. Magn. Reson.* 1997). The target function that is minimized during restrained minimization and simulated annealing comprises only quadratic harmonic terms for covalent geometry, $^3J_{NH\alpha}$ coupling constants and secondary $^{13}$Cα/$^{13}$Cβ chemical shift restraints, square-well quadratic potentials for the experimental distance and torsion angle restraints, and a quartic van der Waals term for non-bonded contacts. All peptide bonds were constrained to be planar and trans. There were no hydrogen-bonding, electrostatic, or 6–12 Lennard-Jones empirical potential energy terms in the target function.

To prevent the Zn and Ca ions from being expelled during the high-temperature simulated annealing stages of the refinement protocol, a minimal number of distance restraints between the His sidechain and Zn and between backbone atoms and Cα were included in the XPLOR distance restraint file based on the observed coordination in the X-ray structures (Lovejoy, et al., *Science* 1994; Lovejoy, et al., *Biochemistry* 1994; Spurlino, et al., *Proteins: Struct., Funct., Genet.* 1994; Borkakoti, et al., *Nat. Struct. Biol.* 1994).

The starting MMP-13: Compound A complex structure for the simulated-annealing protocol was obtained by manually docking Compound A into a homology model for MMP-13. The initial orientation of Compound A in the MMP-13 active site was based on the previously reported MMP-1: CGS-27023A structure (Moy, et al., *Biochemistry* 1999).

Homology modeling methods were utilized to generate a three dimensional model of MMP-13. The linear amino acid sequence corresponding to the catalytic domain of MMP-13 was aligned (SYBYL) with the catalytic domains of MMP-1, MMP-7 and MMP-8 based on the availability of their x-ray crystallographic structures (Bode, et al., *EMBO J.* 1994; Spurlino., *Proteins: Struct., Funct., Genet.* 1994; Betz, et al., *Eur. J. Biochem.* 1997; Lovejoy, et al., *Nat. Struct. Biol.* 1999; Borkakoti, et al., *Nat. Struct. Biol.* 1994; Browner, et al., *Biochemistry* 1995). The alignments of MMP-13 with MMP-1 and MMP-8 demonstrated the highest homology where the computed identities are 58.9% and 61.4%, respectively (FIG. 2).

The X-ray structure of MMP-8 was selected to be used as the template for homology modeling the structure of MMP-13. This decision was based mainly on the sequence alignment shown in FIG. 2B where no insertions (labeled "###") are found in the critical specificity loop (Labeled Underlined and Boldface). In FIG. 2A, the region labeled "###" in the specificity loop shows that there is an "insertion" of 2 additional amino acid residues compared to the sequence length of MMP-1. Based on our analysis of the alignments, MMP-8 would allow for a more accurate modeling of the inhibitor binding pockets since no predictions have to be made within this loop region.

COMPOSER (SYBYL) was used to construct the initial homology model of MMP-13. The only insertion was a serine (labeled '**'in FIG. 2B) at position 32 of MMP-13. The insertion of S32 occurs within a coiled region which is at the entrance of a long alpha helix and about 17 angstroms from the S' specificity loop. The model of MMP-13 was then energy minimized utilizing a set of nested refinement procedures (Chen, et al., *J. Biomol. Struct. Dyn.* 1995), but where the protein backbone heavy atoms were constrained as close as possible to their original positions.

The MMP-13: Compound A model was then subjected to a 1000 steps of CHARMM minimization with the 5 intramolecular NOE restraints and the 47 distance restraints observed between MMP-13 and Compound A where the coordinates for MMP-13 were kept fixed. This approach approximated the positioning of Compound A in the active site of MMP-13 without distorting the MMP-13 structure. The final structure was exported as a PDB file and used as the starting point for XPLOR simulated annealing protocol where all the residues in the structure were free to move. Since the initial stage of the simulated annealing protocol corresponds to high-temperature dynamics (1500 K) with a relatively weak XPLOR NOE force constant (Ries and Petrides, *Biol. Chem. Hoppe-Seyler* 1995), the initial MMP-13: Compound A structure does not bias the structure determination process since the structure is effectively free to explore the available conformational space. Additionally, each iteration of the simulated annealing process begins with a random trajectory for the molecular dynamics. The fact that these trajectories differ by upwards of 10 Å assures a distinct exploration of conformational space for the ensemble of MMP-13: Compound A structures determined from the simulated annealing protocol.

Results and Discussion

Compound A Resonance Assignments and Bound Conformation: The primary structure of Compound A along with the proton naming convention is shown in FIG. 3. The NMR assignments for Compound A in the MMP-13 complex followed established protocols using 2D $^{12}$C-filtering experiments (Petros, et al., *FEBS Lett.* 1992; Gemmecker, et al., *J. Magn. Reson.* 1992; Ikura and Bax, *J. Am. Chem. Soc.* 1992) since the NMR sample was composed of $^{13}$C/$^{15}$N labeled MMP-13 and unlabeled Compound A. Thus, traditional 2D-NOESY, COSY and TOCSY spectra of Compound A in the presence of MMP-13 yielded straightforward assignments for Compound A along with assignments for free Compound A (data not shown). The only notable difference in the assignments for free and bound Compound A is the observation of two distinct resonances for 2HB1/2 in the complex (4.91 ppm; 4.67 ppm). The missing resonance in the free Compound A may simply be obscured by water. Also, an observation that the 4 protons on the p-methoxyphenyl ring are degenerate suggests rapid ring flips when complexed to MMP-13. This was also seen with CGS-27023A complexed with both MMP-1 and stromelysin (Gonnella, et al., *Bioorg. Med. Chem.* 1997; Moy, et al., *Biochemistry* 1998; Moy, et al., *Biochemistry* 1999).

Compound A does not adopt a preferred conformation in the absence of MMP-13 as evident by the lack of structural NOEs. Only a minimal number of intramolecular NOEs were observed for Compound A in the MMP-13 complex which were relevant to the bound conformation of Compound A (data not shown). The minimal number of structural NOEs is a result of the Compound A conformation, structure and chemical shift degeneracy. A number of the observed NOEs correspond to a sequential interaction which have no effect on the overall conformation of the inhibitor and were not used in the refinement of Compound A or the complex. The structural intramolecular NOEs observed are primarily between 1HH* and the pyridine ring and between 2HB1/2 and both the p-methoxyphenyl and aryl ring. These NOEs are consistent with the "splayed" conformation previously observed for CGS-27023A bound to both MMP-1 and stromelysin, but the bound conformation of Compound A is predominately determined from the intermolecular NOEs between Compound A and MMP-13 (Table 1).

Structure Determination: The NMR structure determination methodology is an iterative procedure where the current state of the structure is used to analyze the ambiguous NOE data. In essence, the structure is used as a distance filter to sort through the ambiguous NOE list where the first structure is determined from unambiguous data. For the refinement of MMP-13, the initial structure was a homology model based on the MMP-8 X-ray structure. This was justified by the overall similarity in previously reported MMP structures and from the secondary structure assignments by NMR for MMP-13. The regular secondary structure elements of MMP-13 were identified from a qualitative analysis of sequential and inter-strand NOEs, NH exchange rates, $^3$JHNα coupling constants (Clore, et at., *Crit. Rev. Biochem. Mol. Biol.* 1989) and the $^{13}$Cα and $^{13}$C secondary chemical shifts (Spera and Bax, *J. Am. Chem. Soc.* 1991). The deduced secondary structure is essentially identical to the inhibitor-free MMP-1 NMR structures previously reported.

The final 30 simulated annealing structures calculated for residues 7–164 were based on 3279 experimental NMR restraints, consisting of 2561 approximate interproton distance restraints, 51 distance restraints between MMP-13 and Compound A, 88 distance restraints for 44 backbone hydrogen bonds, 391 torsion angle restraints, 103 $^3$J$_{NH\alpha}$ restraints 123 Cα restraints and 108 Cβ restraints. Stereospecific assignments were obtained for 81 of the 100 residues with β-methylene protons, for the methyl groups of 5 of the 6 Val residues, and for the methyl groups of 12 of the 13 Leu residues. In addition, 12 out of the 12 Phe residues and 7 out of the 8 Tyr residues were well defined making it possible to assign NOE restraints to only one of the pair of CδH and CεH protons and to assign a χ2 torsion angle restraint. Similarly, χ2 torsion angle restraints were assigned for the three Trp residues. The atomic rms distribution of the 30 simulated annealing structures about the mean coordinate positions for residues 7–164 is 0.43±0.06 Å for the backbone atoms, 0.81±0.09 Å for all atoms, and 0.47±0.04 Å for all atoms excluding disordered surface side chains. The mean standard deviation for the φ and ψ backbone torsion angles of residues 7–164 are 6.2±11.3° and 7.1±11.8°, respectively. The high quality of the MMP-13 NMR structure is also evident by the results of PROCHECK analysis and by a calculated, large negative value for the Lennard-Jones-van der Waals energy (−695±11 kcal mol-1). For the PROCHECK statistics, an overall G-factor of 0.16±0.16, a hydrogen bond energy of 0.82±0.05 and only 7.8±1.0 bad contacts per 100 residues are consistent with a good quality structure comparable to ~1 Å X-ray structure.

The high quality of the MMP-13 NMR structure is also evident by the very small deviations from idealized covalent geometry, by the absence of interproton distance and torsion angle violations greater than 0.1 Å and 1°, respectively and by the fact that most of the backbone torsion angles for non-glycine residues lie within expected regions of the Ramachandran plot (not shown). 91.5% of the residues lie within the most favored region of the Ramachandran φ, ψ plot and 7.8% in the additionally allowed regions. $^1$JCαHα coupling constants from the coupled CT-HCACO experiment indicated that all non-glycine residues have negative φ torsion angles.

The quality of the NMR data to properly define the complex is also supported by the well-defined coordinates for Compound A and the active site residues, where the atomic rms distribution is 0.47±0.08 Å and 0.18±0.03 Å for the heavy atoms of Compound A and MMP-13 backbone atoms, respectively.

Description of the MMP-13: Compound A Structure: The overall fold of MMP-13 is essentially identical to previously reported MMP structures (Bode, et al., *EMBO J.* 1994; Gooley, et al., *Nat. Struct. Biol.* 1994; Lovejoy, et al., *Science* 1994; Lovejoy, et al., *Ann. N.Y. Acad. Sci.* 1994; Lovejoy, et al., *Biochemistry* 1994; Spurlino, et al., *Proteins: Struct. Funct., Genet.* 1994; Stams, et al., *Nat. Struct. Biol.* 1994; Becker, et al., *Protein Sci.* 1995; Gonnella, et al., *Proc. Natl. Acad. Sci. U.S.A.* 1995; Van Doren, et al., *Protein Sci.* 1995; Botos, et al., *Proc. Natl. Acad. Sci. USA* 1996; Broutin, et al., *Acta Crystallogr., Sect. D: Biol. Crystallogr.* 1996; Gooley, et al., *J. Biomol. NMR* 1996; Betz, et al., *Eur. J. Biochem.* 1997; Gonnella, et al., *Bioorg. Med. Chem.* 1997; Moy, et al., *Biochemistry* 1998 and Moy, et al., *Biochemistry* 1999). The MMP-13 NMR structure is composed of three α-helices corresponding to residues 28–44 ($\alpha_A$), 112–123 ($\alpha_B$) and 153–163 ($\alpha_C$) and a mixed parallel and anti-parallel b-sheet consisting of 5 strands corresponding to residues =83–86 ($\beta_1$), 95–100 ($\beta_2$), 59–66 ($\beta_3$), 14–20 ($\beta_4$) and 49–53 ($\beta_5$). The active site of MMP-13 is bordered by β-strand IV, the $Ca^{+2}$ binding loop, helix B and a random coil region from residues P139–Y141. The catalytic zinc is chelated by H119, H123, and H129 while the structural zinc is chelated by H69, H84 and H97. The calcium ion is chelated in a loop region consisting of residues D75 to G79. An interesting feature of the MMP active-site structure is an apparent kink in the backbone that occurs between the $Ca^2$ binding loop and β-strand IV. In the case of MMP-13, this results in the NHs of both L82 and A83 facing toward the active site of the enzyme. An important feature of substrate and inhibitor binding to the MMPs are hydrogen bonding interactions with β-strand IV which is facilitated by this unusual kink conformation (Lovejoy, et al., *Science* 1994; Lovejoy, et al., *Biochemistry* 1994; Spurlino, et al., *Proteins: Struct., Funct., Genet.* 1994; and Borkakoti, et al., *Nat. Struct. Biol.* 1994).

The interaction of Compound A in the active site of MMP-13 was determined by 5 intramolecular NOEs for Compound A and by a total of 47 intermolecular distance restraints between MMP-13 and Compound A. The key MMP-13 residues involved in the interaction with the inhibitor correspond to three distinct MMP-13 regions: residues L81, L82 and A83 from β-strand IV; residues L115, V116, and H119 from α-helix II; and L136, I140 and Y141 from the active site loop which comprise the S1' and S2' pockets of MMP-13. A unique feature of the MMP-13 structure is the large S1' pocket which nearly reaches the surface of the protein.

Compound A binds to the right-side of the catalytic Zn where the p-methoxyphenyl of Compound A sits in the S1' pocket of the MMP-13 active site. This positioning is evident from the observed NOEs from 3HH*, 3HE1/2 and 3HD1/2 to L115, V116, H119, L136, and Y141. The aryl group primarily interacts with the side-chain of L81 as evident by the strong NOEs between 1HH*, 1HE2 and 1HZ and the L81 spin-system. Finally, the pyridine ring is essentially solvent exposed but interacts with the side-chain of I140. These interactions position Compound A such that the hydroxamic acid moiety of Compound A chelates to the "right" of the catalytic zinc and the sulfonyl oxygens are in hydrogen-bonding distance to the backbone NH of L82.

It is interesting to note that the active site loop is highly dynamic in both the inhibitor-free and CGS-27023A structures based on $S^2$ order-parameters (Moy, et al., *J. Biomol. NMR* 1997). This region in the MMP-13: Compound A structure appears to be significantly less mobile by the observation that most of the residues in this loop region were easily observable in the $^1H$-$^{15}N$ HSQC spectra and readily assigned. One possible explanation for this difference is the hydrophobic interaction between the pyridine ring of Compound A and the side-chain for Ile-140. In MMP-1, I140 is replaced by a serine which essentially eliminates this beneficial interaction.

Another unique feature of the MMP-13 NMR structure is the apparent dynamic nature of residues H69 to Y73. These residues are completely disordered due to the lack of any assignment information and the resulting absence of any constraint information presumably a result of the flexible nature of these residues. Residues H69 to Y73 occur between the $Ca^{+2}$ binding loop and the structural zinc where the corresponding region in the previously solved MMP-1 NMR structures is well defined. There is no apparent explanation for this change in mobility between the two NMR structures but it may contribute to the observed difference in the physical behavior of MMP-1 and MMP-13. Under identical conditions, inhibitor-free MMP-I is stable for upwards of two months whereas inhibitor-free MMP-13 degrades immediately.

Comparison of the MMP-13: Compound A and MMP-1: CGS-27023A Structures: The high-resolution NMR structure for the MMP-13: Compound A complex was effectively and efficiently determined by using a homology model based on the MMP-1 NMR structure as an initial structure to analyze ambiguous NOESY data. This result is evident of the high structural and sequence similarity between members of the MMP family and consistent with the previously observed best-fit superposition of the backbone atoms for MMP-1, stromelysin, matrilysin and neutrophil collagenase (Moy, et al., *Biochemistry* 1998; Moy, et al., *Biochemistry* 1999).

The strong similarity between the various MMP structures creates an initial difficulty in designing specific MMP inhibitors. This is exemplified by the high sequence similarity among the MMPs in the active site. Comparison of the sequence similarity between MMP-13 and MMP-1 illustrates this difficulty. There are only a few significant residue differences between the two enzymes where these modifications results in a significant change in the local environment of the active site. The R114 to V115 modification results in a conversion from a hydrophilic to a hydrophobic environment at the base of the S1' pocket between MMP-1 and MMP-13, respectively. Similarly, the N80 to L81 substitution places a bulkier hydrophobic residue in the S2' pocket for MMP-13 compared to a more hydrophilic environment for MMP-1. Similarly in the active loop region, I140 a bulky hydrophobic residue in MMP-13 replaces the smaller hydrophilic S139 residue in MMP-1. Clearly, it is feasible to incorporate substituents into a small molecule to take advantage of these spatial distinct environmental changes between MMP-1 and MMP-13. Nevertheless, when these sequence and environmental differences are averaged across the MMP family it becomes less discriminating and extremely difficult to design an inhibitor to a specific MMP subtype based strictly on the small sequence differences.

Conversely, the most distinct structural difference between the MMPs and readily amenable to incorporating specificity in drug design is the relative size and shape of the S1' pocket. This is clearly evident by comparison of the defined S1', pockets for MMP-13 and MMP-1. The large difference in size in the S1' pockets between the MMP-13 and MMP-1 NMR structures is striking. The S1' pocket for MMP-13 nearly reaches the outer surface of the protein and is greater then twice the size of MMP-1. The additional size of the MMP-13 S1' pocket relative to MMP-1 is best illustrated by the filling capacity of the two inhibitors. In the MMP-1: CGS-27023A NMR structure, the p-methoxyphenyl effectively fills the available S1' pocket for MMP-1. Conversely, in the MMP-13: Compound A complex the p-methoxyphenyl only partially fills the available space within the MMP-13 S1' pocket. The size of the MMP-13 pocket is actually similar in size to stromelysin where the design of stromelysin inhibitors has taken advantage of this deeper S1' pocket by using a biphenyl substituent in another series instead of the p-methoxyphenyl in Compound A to bind into the S1' pocket (Hajduk, et al., *J. Am. Chem. Soc.* 1997; Olejniczak, et al., *J. Am. Chem. Soc.* 1997). Thus, the NMR structures for MMP-13 and MMP-I suggest that a ready approach to designing specificity between these MMPs is to take advantage of the significantly different sized S1' pockets. The high mobility of the MMP-1 active site presents a potential caveat to this analysis of the static images of the MMP-1 and MMP-13 structures. It is probable that the MMP-1 active site is capable of accommodating a S1' substituent larger then implied from its current structure due to its increased mobility in both free and inhibited structures.

Examination of the binding mode of Compound A in the MMP-13: Compound A complex suggests a conformation generally similar to CGS-27023A in the MMP-1: CGS-27023A NMR structure previously reported (30 simulated annealing structures deposited with Protein Data Bank, Accession No. 4AYK; restrained minimized mean structure deposited with Protein Data Bank, Accession No. 3AYK). Compound A and CGS-27023A are structurally very similar with the only difference being the nature of the substituent binding in the S2' pocket where an aryl group in Compound A replaces the isopropyl group in CGS-27023A. The strong resemblance between the binding mode of Compound A and CGS-27023A is apparent from the nearly identical intermolecular NOE patterns observed between the inhibitors and the proteins. The key MMP-13 residues involved in the interaction with Compound A correspond to L81, L82 and A83 from β-strand IV; residues L15, V116, and H119 from α-helix II; and L136, I140 and Y141 from the active site loop. Similarly, the MMP-1 residues involved in the interaction with CGS-27023A correspond to residues N80, L81, A82 and H83 from β-strand IV; residues R114, V115, H118 and E119 from α-helix II; and L135, P138, Y137, S139 and Y140 from the dynamic flexible loop.

As stated previously, there are three distinct residue changes between MMP-13 and MMP-1 in the active site. The R114 to L115 change between MMP-1 and MMP-13, respectively, has a significant impact on the environment at the base of the S1' pocket but since Compound A only partially fills the MMP-13 S1' pocket this change should not effect the binding conformation of Compound A relative to CGS-27023A. Conversely, the N80 to L81 substitution directly interacts with the inhibitors in the S2' pocket and may result in an effective change in the binding mode of the inhibitors. To complicate the analysis, the only change in the inhibitors are the substituents that bind the S2' pocket. For the MMP-1: CGS-27023A complex, the isopropyl group interacts with both the sidechains of N80 and H83 where the aryl group from Compound A only interacts with L81 in MMP-13. Additionally, CGS-27023A is in hydrogen-bonding distance to both L81 and A82, whereas Compound A appears to form a bifurcated hydrogen bond with L82. This analysis suggests that CGS-27023A binds closer to β-strand IV since the S2' pocket is more accessible in MMP-1 due to the absence of the bulky L81 side-chain and the presence of the aryl group in Compound A. A direct comparison of the bound conformations suggest only a subtle difference in the relative orientation of the inhibitors. The S139 to I140 difference between MMP-1 and MMP-13, respectively, appears to be related to a mobility change as opposed to a structural change. In the MMP-1: CGS-27023A structure the pyridine ring position is essentially undefined and solvent exposed this compares to the MMP-13: Compound A structure where the pyridine ring binds with the side-chain of I140. Clearly, Ile is a bulkier more hydrophobic group relative to Ser which would provide a beneficial hydrophobic interactions with the pyridine ring. The more interesting observation is the apparent decrease in mobility for the active loop in the MMP-13 structure which may be related the pyridine ring I140 interaction. This appears to be consistent with previously inhibited MMP X-ray structures (Spurlino, et al., *Proteins: Struct. Funct. Genet.* 1994) where the inhibitor may extend the formation of a β-sheet between b-strand IV and the active loop region which results in low B-factors in the X-ray structure. This may suggest that the mobility of the active loop region is easily removed with any positive interaction with the inhibitor.

There are apparently some interesting differences between the mode of binding for the two inhibitors in the MMP-13: Compound A and MMP-1: CGS-27023A NMR structures. The more striking observation is the overall similarity between the two structures. Despite some significant sequence differences and a large difference in the size and shape of the S1' pocket either inhibitor structure would accurately predict the other structure. This observation seems to indicate that the major contributing factors to inhibitors binding the MMPs is the fit in the S1' pocket and the binding of the hydroxamic acid to the catalytic zinc. The interaction in the S2' pocket appears to have a more subtle impact on inhibitor binding and selectivity since both Compound A and CGS-27023A are low nanomolar inhibitors of MMP-13 and MMP-1, respectively. Therefore, the high-resolution solution structure of the MMP-13: Compound A in conjunction with the previously reported MMP-1 NMR structures suggest that taking advantage of the significant differences in the size and shape of the S1' pocket is a reasonable approach for developing specific MMP inhibitors.

The studies described herein present the high-resolution solution structure of MMP-13 complexed with a sulfonamide derivative of a hydroxamic acid compound (Compound A). The overall fold of MMP-13 is similar to previously reported MMPs structures. The major difference is the large S1' pocket which nearly reaches the surface of the protein. The structure was based on a total of 3279 constraints including 47 distance restraints between MMP-13 and Compound A from X-filtered NOESY experiments. The inhibitor was found to bind to the "right" side of the catalytic Zn such that the p-methoxyphenyl ring sits in the S1' pocket, the aryl moiety interacts with L81 of βIV, the pyridine ring interacts with I140 of the active site loop, hydrogen bond interactions exist between the sulfonamide oxygens with residue L82 and the hydroxamic acid chelates the catalytic Zn. This inhibitor binds MMP-13 similarly to the MMP-1: CGS-27023A complex suggesting that appropriately filling the S1' pocket may play a key role in developing selective MMP inhibitors.

TABLE 1

Observed NOEs Between Compound A and MMP-13

| Compound A | MMP-13 | NOE Class | Compound A | MMP-1 | NOE Class |
|---|---|---|---|---|---|
| 1HH* | L81 Hγ | W | 3HH* | Y141 Hα | M |
| 1HH* | L81 Hδ1# | W | 3HH* | Y141 Hβ1 | W |
| 1HH* | L81 Hδ2# | M | 3HH* | Y141 Hβ2 | W |
| 1HH* | L81 Hα | S | 3HH* | Y141 Hδ2 | W |
| 1HE2 | L81 Hδ1# | W | 3HE2 | L82 Hδ1# | W |
| 1HE2 | L81 Hδ2# | M | 3HE1 | A83 Hβ# | W |
| 1HZ | L81 Hδ1# | W | 3HE1 | H116 Hα | W |
| 1HZ | L81 Hδ2# | M | 3HE1 | H116 Hγ1# | M |
| 2HZ | I140 Hγ2# | W | 3HE2 | H116 Hγ2# | W |
| 2HE1 | I140 Hδ1# | W | 3HE2 | I140 Hγ2# | W |
| 3HH* | L82 Hδ1# | W | 3HE2 | Y141 Hα | W |
| 3HH* | L115 Hβ# | W | 3HE2 | Y141 Hβ1 | W |
| 3HH* | L115 Hγ | W | 3HE2 | Y141 Hβ2 | W |
| 3HH* | L115 Hδ1# | W | 3HD2 | L82 Hδ1# | W |
| 3HH* | L115 Hδ2# | W | 3HD1 | A83 Hβ# | W |
| 3HH* | V116 Hα | W | 3HD1 | V116 Hγ1# | W |
| 3HH* | V116 Hγ1# | W | 3HD2 | V116 Hγ2# | W |
| 3HH* | V116 Hγ2# | M | 3HD2 | I140 Hα | W |
| 3HH* | H119 Hα | W | 3HD2 | I140 Hγ2# | W |
| 3HH* | H119 Hδ2 | W | 3HD2 | Y141 Hα | W |
| 3HH* | H119 Hβ1 | W | 3HD2 | Y141 Hβ1 | W |
| 3HH* | H119 Hβ2 | W | 3HD2 | Y141 Hβ2 | W |
| 3HH* | L136 Hδ1# | W | 3HD2 | Y141 HN | W |
| 3HH* | L136 Hδ2# | W | | | |

EXAMPLE 3

Structure Based Design of a Novel, Potent, and Selective Inhibitor for MMP-13

The matrix metalloproteinases (MMPs) comprise a family of zinc containing enzymes that cleave a broad range of substrates including collagens, fibronectin and gelatins where the substrate preference various for individual MMPs. The design of MMP inhibitors has been initially based upon imitation of the binding interaction of natural protein substrates to MMPs where structural information of MMPs complexed with peptide substrates has been determined by x-ray crystallography and NMR spectroscopy. This structural information has provided a general description of the MMPs active site.

The active site for the MMPs is composed of a catalytic zinc chelated by three histidines where three substrate binding pockets are located to both the right (S1', S2', S3') and left (S1, S2, S3) of the catalytic zinc. The substrate binding pockets were identified by the interactions of side chains from the peptide substrate with the MMPs. The primary effort in MMP inhibitor design has focused on compounds that chelate the catalytic zinc while primarily binding in the S1' and S2' pockets. This has evolved from the observation that the structural characteristics of the S1' pocket (size, shape, amino acid composition) incurs the greatest variability between the individual MMPs and this provides an obvious approach in designing selective and specific MMP inhibitors. Nevertheless, there has also been success in utilizing the binding pockets to the left of the catalytic zinc in addition to or in combination with the right handed binding pockets in the design of inhibitors.

The underlying challenge in designing MMP inhibitors is the reasonably high sequence and structural homology observed between the individual members of the MMP family making it intrinsically difficult to design an inhibitor that will function against a single MMP in the absence of structural information. The problem with a non-specific MMP inhibitor as a drug is the high likelihood of serious side-effects because of the large number of enzymes in the MMP family and their corresponding diversity in targets and function. Accordingly, the detailed structural information provided herein is a critical component of an inhibitor design program targeting a particular MMP enzyme.

Materials and Methods:

Synthesis of Compound D and Compound E: The sulfonamide derived from 2-amino-3,5-dimethyl-benzoic acid methyl ester and p-methoxybenzenesulfonyl chloride was N-alkylated with benzyl bromide and the ester group of the resulting intermediate was hydrolyzed (LiOH/THF) to afford the carboxylic acid. The corresponding hydroxamic acid was formed by preparation of the acid chloride (oxalyl chloride/DMF) followed by reaction with hydroxylamine. Compound E was synthesized by reaction of 2-amino-3,5-dimethyl-benzoic acid methyl ester and p-fluorobenzenesulfonyl chloride followed by N-alkylation with benzyl bromide. Hydrolysis of the methyl ester (LiOH/THF) followed by displacement of fluorine with the alkoxide of benzofuran-2-carboxylic acid (2-hydroxy-ethyl)-amide gave, after conversion to the hydroxamic acid and formation of the HCl salt as described above, Compound E.

NMR Sample Preparation: Uniformly (>95%) $^{15}$N— and $^{15}$N/$^{13}$C-labeled human recombinant MMP-13 was expressed in $E.\ coli$ and purified as described previously. 1 mM $^{13}$C/$^{15}$N— and $^{15}$N— MMP-13 NMR samples were prepared by concentration and buffer exchange using Millipore Ultrafree –10 centrifugal filters into a buffer containing 10 mM deuterated Tris-base, 100 mM NaCl, 5 mM CaCl$_2$, 0.1 mM ZnCl$_2$, 2 mM NaN$_3$, 10 mM deuterated DTT in 90% H$_2$O/10% D$_{2O}$ or 100% D2O. The 10:1 Compound B: MMP-13 samples were prepared by addition of Compound B into either a 1 mM $^{13}$C/$^{15}$N- or $^{15}$N-MMP-13 sample followed by pH readjustment. The sample to explore the potential of competitive inhibition between Compound B and Compound A was prepared by first adding 1 mM of Compound A to a 1 mM $^{15}$N-MMP-13 sample followed by the addition of 10 mM Compound B. The initial MMP-13: Compound A sample was made by buffer exchange of $^{15}$N— MMP-13 into the buffer containing 0.1 mM Compound A followed by additional buffer exchanges to remove excess Compound A. Finally, 10 mM of Compound B was added to the 1 mM $^{15}$N— MMP-13: Compound A sample followed by pH readjustment.

NMR Data Collection: All spectra were recorded at 35° C. on a Bruker AMX-2 600 spectrometer using a gradient enhanced triple-resonance $^1$H/$^{13}$C/$^{15}$N probe. For spectra recorded in H$_2$O, water suppression was achieved with the WATERGATE sequence and water-flip back pulses (Piotto, et al., $J.\ Biomol.\ NMR$ 1992; Grzesiek and Bax, J. Am. Chem. Soc. 1993). Quadrature detection in the indirectly detected dimensions were recorded with States-TPPI hypercomplex phase increment (Marion, et al., $J.\ Magn.\ Reson.$ 1989). Spectra were collected with appropriate refocusing delays to allow for 0,0 or –90,180 phase correction.

The resonance assignments and bound conformation of Compound A in the MMP-1: Compound A complex were based on the 2D $^{12}$C/$^{12}$C-filtered NOESY (Petros, et al., $FEBS\ Lett.$ 1992; Gemmecker, et al., $J.\ Magn.\ Reson.$ 1992), 2D $^{12}$C/$^{12}$C-filtered TOCSY (Petros, et al., $FEBS\ Lett.$ 1992; Gemmecker, et al., $J.\ Magn.\ Reson.$ 1992) and $^{12}$C/$^{12}$C-filtered COSY experiments (Ikura and Bax, J. Am. Chem. Soc. 1992).

The assignments of the $^1$H, $^{15}$N, and $^{13}$C resonances of MMP-13 in the MMP-13: Compound B complex were based on the previous assignments for the MMP-13: Compound A complex in combination with a minimal set of experiments: 2D $^1$H-$^{15}$N HSQC, 3D $^{15}$N— edited NOESY (Marion, et al. *Biochemistry* 1989; Zuiderweg and Fesik, Biochemistry 1989), CBCA(CO)NH (Grzesiek and Bax, J. Am. Chem. Soc. 1992), C(CO)NH (Grzesiek, et al., *J. Magn. Reson., Ser. B* 1993), HNHA (Vuister and Bax, J. Am. Chem. Soc. 1993) and HNCA (Kay, et al., *J. Magn.*

Reson. 1990). The acquisition parameters for each of the experiments used in determining the solution structure of the MMP-13: Compound B complex were as reported previously (Moy, et al., *Biochemistry* 1996).

The MMP-13: Compound B structure is based on observed NOEs from the 3D $^{15}$N-edited NOESY (Marion, et al. *Biochemistry* 1989; Zuiderweg and Fesik, Biochemistry 1989) and 3D $^{13}$C-edited/$^{12}$C-filtered NOESY (Vuister and Bax, J. Am. Chem. Soc. 1993; Lee, et al., *FEBS Lett.* 1994). The 3D $^{15}$N-edited NOESY and 3D $^{13}$C-edited/$^{12}$C-filtered NOESY experiments were collected with 100 msec and 110 msec mixing times, respectively.

Molecular Analysis and Design: The minimized models of Compound B and Compound D complexed to MMP-13 were prepared as previously described (Chen, et al., *J. Biomol. Struct. Dyn.* 1995; Chen, et al., *Biochemistry* (in press) 1998). Using molecular dynamics methods (Sybyl v6.4 from Tripos Inc), protein regions within 5 Å from Compound B were sampled along with the inhibitor, whereas everything else remained rigid during the simulations. Upon energy convergence, the last 50 frames from the final 100 picoseconds run was averaged and this averaged structure underwent a final minimization. The final protein-Compound B model appeared to have optimized possible polar and van der waals interactions. The identical procedure was applied to the complex of MMP-13 and Compound D. Since the two complexes used identical MMP-13 structures, the proteins were overlapped to depict the positions of the two inhibitors within the active site. Graphics analysis of the inhibitors showed that the methylene carbon of Compound B containing the 2HB1/2 protons (FIG. 6) overlapped identically with the methoxy carbon from Compound D. This analysis indicated the optimal or minimal linkage length of connecting the benzofuran moiety to the methoxy region of Compound D. The final design scheme is shown in FIG. 8 for the hybrid inhibitor. The homology model of MMP-9 was constructed using the COMPOSER program (Tripos INC, Sybyl v.6.4).

High-throughput Screening Analysis: Compound B was identified as an initial lead from the analysis of the MMP-13 high-throughput screen (HTS). A total of 58079 compounds were screened for their ability to inhibit MMP-13 enzymatic activity where 385 compounds were shown to have ≧40% inhibition at 10 µg/ml dosage. Compound B was shown to exhibit weak inhibition of MMP-13 (89% at the 10 µg/ml), but more intriguing was the observation of a complete lack of activity against other MMPs (MMP-1, MMP-9 and TACE). The primary structure of Compound B along with the proton naming convention is shown in FIG. 6.

The resulting HTS hits were further examined by cluster analysis. The hits were clustered based on structural similarities where the properties of these compounds were compared against the properties of the set of orally available drugs. The properties used to profile the HTS hits consists of: total number of non-hydrogen atoms, number of heteroatoms, number of hydrogen-bond donors and acceptors, calculated logP and molecular weight. This profile analysis provides an initial means to predict the likelihood that an HTS hit may have drug-like characteristics such as bioavailability and in-vivo stability. The profile of Compound B indicates that the compound has properties similar to orally available drugs suggesting that it would be an ideal candidate for optimization of its enzyme potency and selectivity.

A common feature of known MMP inhibitor structures is the presence of a Zn-chelator that plays a fundamental role in its activity. In most cases Zn chelation occurs from the presence of a hydroxamic acid in the structure of the small molecule. As apparent from the structure of Compound B, the compound does not contain an obvious substituent that would chelate Zn. Thus, the unique structure of Compound B suggested a potential novel mechanism for inhibition of MMP-13 further strengthening the choice of Compound B as an initial lead candidate. Therefore, the identification of Compound B as a candidate to optimize its activity and selectivity was based on three unique observations: its intrinsic MMP-13 selectivity, its structural profile similar to known bioavailable drugs and finally its apparent novel structure.

NMR Structure of the MMP-13—Compound B Complex: The NMR binding studies provided critical information pertaining to the mechanism of Compound B inhibition of MMP-13 and the method for designing increase potency. The major question presented when Compound B was identified from HTS was its unknown MMP-13 binding site and its method for inducing MMP-13 inhibition. Previous work on the NMR structure of MMP-13 complexed with Compound A and MMP-1 complexed with CGS-27023A provided the framework and methodology to analysis Compound B bound to MMP-13 (Moy, et al., *Biochemistry Submitted* 1999; Moy, et al., *Biochemistry* 1999).

The Compound B MMP-13 binding site was initially identified from chemical shift perturbation in the $^1$H-$^{15}$N HSQC spectra. The observed perturbations were mapped onto a GRASP surface (not shown). It is apparent that the major effect of Compound B on the chemical shifts of MMP-13 occurs in the proximity of the S1' pocket suggesting that Compound B sits in this pocket. From the NMR and X-ray structures of MMP-13, it was determined that the S1' pocket for MMP-13 is very deep and linear in shape while nearly reaching the surface of the protein. In fact, a number of residues at the surface of MMP-13 near the base of the S1' pocket show significant chemical shift perturbation in the presence of Compound B. Since Compound B is a linear molecule, docking studies would place the inhibitor stretched throughout the linear S1' pocket of MMP-13. The only question remaining was whether to place the morpholine or the benzofuran moiety of Compound B at one end of the pocket, adjacent to the catalytic zinc or the opposite end, distant from the zinc atom. Property analysis of the enzymes S1' pocket depicts that the end adjacent to the zinc is relatively polar whereas the opposite end is hydrophobic. This analysis lead us to dock Compound B with the morpholine ring adjacent to the catalytic zinc atom with the benzofuran moiety siting in a hydrophobic pocket formed by L115, L136, F149 and P152 at the base of the S1' pocket. To further verify the proposed binding of Compound B in the S1' pocket of MMP-13, a simple competition experiment with Compound A was conducted. The $^1$H-$^{15}$N HSQC experiment for the MMP-13: Compound B complex was collected in the presence of Compound A. The presence of Compound A displaced all of Compound B as evident by the distinct differences in the $^1$H-$^{15}$N HSQC spectra which further suggests that both compounds bind in the S1' pocket.

The relative orientation and binding of Compound B with MMP-13 was further confirmed by the observation of intermolecular NOEs between Compound B and MMP-13 from the 3D $^{13}$C-edited/$^{12}$C-filtered NOESY experiment. The NOESY spectra was collected in the presence of a ten-fold excess of Compound B because of the weak affinity of Compound B with MMP-13. Nevertheless, a total of 16 NOEs were observed between Compound B and L81, L115, V116, Y141, T142 and Y143 which support the initial positioning of Compound B in the MMP-13 S1' pocket. An expanded 2D plane from the 3D $^{13}$C-edited/$^{12}$C-filtered NOESY experiment (not shown) demonstrated examples of some key intermolecular NOEs between Compound B benzofuran group resonances and L115 δ and Compound B resonances proximal to the morpholine ring and L82 δ. The complex of Compound B with MMP-13 was subjected to energy refinement using the NMR results as constraints (Moy, et al., *Biochemistry* 1999; Chen, et al., *J. Biomol. Struct. Dyn.* 1995). The modeling results depict the morpholine oxygen forming a hydrogen bond with the backbone amide group of Leu-82 and the benzofuran group packs deep in the S1' pocket with the peptide bond linker portion forming hydrogen bonds with protein backbone groups. The complex shows no apparent interactions between the inhibitor and the catalytic zinc justifying the ligands micromolar potency.

Structures of MMP-1, MMP-9 and MMP-13: The recent NMR solution structures of MMP-1 and MMP-13 were used as starting points for molecular modeling and analysis (Moy, et al., *Biochemistry Submitted* 1999; Moy, et al., *Biochemistry* 1998; Moy, et al., *Biochemistry* 1999). A homology model for MMP-9 was developed based on its strong homology to MMP-1 (54% identity around the catalytic domain). Based on the homology model, the catalytic site of MMP-9 is similar to the corresponding sites in MMP-1 and MMP-13. All three structures were used as starting points for analysis and synthetic design.

Comparative analysis of the MMP structures shows that residue positions 115 and 144, in addition to the length of the specificity loop, determines the size and shape of the S1' pockets. Alignment of the NMR structures for MMP-1 and MMP-13 shows that MMP-13 contains two additional insertions in the specificity loop. The homology model of MMP-9 indicates no additional insertions so its length is identical to MMP-1.

Residue positions 115 and 144 are important in establishing the relative length of the S1' pockets for the MMPs where the larger the side chain at these positions results in a smaller S1' pocket. Since residue 115 is spatially closer to the catalytic zinc than residue 144, a larger side chain for residue 115 will have a greater impact on defining a smaller S1' pocket compared to residue 144. MMP-1 has the largest side chain at position 115, thus its S1' pocket is the smallest. MMP-9 has an Arg at position 144 resulting in its S1' pocket being longer compared to MMP-1. Conversely, MMP-13 has short side chains at both positions 115 and 144. The short side chains combined with an increased length of its specificity loop result in MMP-13 having the largest S1' pocket.

To summarize, the size of the MMP S1' pockets are as follows: MMP-13>MMP-9>MMP-1 where this structural feature plays a critical role in the design strategy for developing a potent and specific MMP-13 inhibitor.

Design Strategy: A strategy utilizing NMR and molecular modeling was applied towards the design and synthesis of an MMP-13 selective inhibitor lead. The basic approach behind the design strategy is to optimize the affinity of the chemical lead Compound B while maintaining its inherent MMP-13 selectivity. This can be achieved by taking advantage of the distinct structural feature of MMP-13, its deep linear S1' pocket, while combining overlapping structural features of Compound B with other potent inhibitors. Compound C is an example of a potent and selective inhibitor for MMP-9 and MMP-13 (See Table 2). Based on the NMR solution structure of MMP-13 complexed with Compound A (FIGS. 4 and 4A-1 to 4A-32), structurally similar, inhibitors were positioned into the active site of MMP-13.

FIG. 7 shows the critical regions of Compound C, which can be broken down into two components, Compound D which represents the zinc chelating portion of the compound that contributes to the binding potency and the toluene group (1A) which contributes to enhanced ligand selectivity against MMP-1. The strategy was to design a new inhibitor based on replacing the toluene group (1A) with a component of Compound B critical for binding within the extended S1' pocket of MMP-13. The overlay of the NMR solution structure for Compound B with the model for Compound D is shown in FIG. 8. The close similarity between the positioning of the two structures made it readily apparent that it would be possible to generate a hybrid of the two structures combining the potent Compound D with the selective component of Compound B (FIG. 8. These results were then used to design the proposed hybrid inhibitor Compound E. The assay data in Table 2 clearly shows that the new inhibitor, Compound E, has better potency compared to Compound C in addition to improved selectivity towards MMP-13. Thus, the combination of NMR spectroscopy with molecular modeling techniques resulted in the design of a novel, potent and selective MMP-13 inhibitor (Compound E) which has an IC50 of 17 nM for MMP-13 and showed >5800, 56 and >500 fold selectivity against MMP-1, MMP-9 and TACE, respectively. To the best of our knowledge, this represents the first example of a potent MMP-13 inhibitor that has been shown to be selective against MMP-9.

TABLE 2

| | IC50 and Selectivity Data | | | | | | |
|---|---|---|---|---|---|---|---|
| Compound | MMP-1 | MMP-9 | MMP-13 | TACE | S-1[a] | S-9[a] | S-TACE[a] |
| C | 750 nM | 46 nM | 75 nM | 470 nM | 10.0 x | 0.6 x | 6.3 x |
| D | 82 nM | 21 nM | 15 nM | 240 nM | 5.5 x | 1.4 x | 16 x |
| E | NA | 945 nM | 17 nM | 19% | >5800 x | 56 x | >500 x |
| F | 1025 nM | 71 nM | 301 nM | 664 nM | 3.4 x | 0.2 x | 2.2 x |

[a]Selectivity data presented as a ratio of the MMP or TACE IC50 with MMP-13

EXAMPLE 4

The X-ray crystal structure of the MMP-13: Compound A complex was determined using the following procedure:

Gene/expression system/production: The cDNA coding for human MMP-13 proenzyme had 85 residues of the PRO domain, followed by 165 residues of the catalytic domain (CAT). The gene was carried on a pET-21a expression plasmid, under the control of a bacteriophage T7 promoter. The expression host was *Escherichia coli* BL21(DE3), which had a chromosomal copy of T7 RNA polymerase under lac control. Cells were grown in nutrient broth, and synthesis of PRO-CAT was induced by isopropyl-β-thiogalactoside. The protein accumulated to 5–10% of total cellular protein, essentially all of which was aggregated into inclusion bodies.

For potential MAD experiments, the plasmid was transferred into a methionine auxotroph host. PRO-CAT with selenomethionine substitution was produced by induction in a defined medium, with methionine replaced by selenomethionine.

Purification and refolding of PRO-CAT: Frozen cells were disrupted mechanically, and inclusion bodies were isolated by centrifugation. PRO-CAT was solubilized with urea containing dithiothreitol to disrupt any disulfide bridges. PRO-CAT was partially purified by anion-exchange chromatography, in urea, on Q Sepharose. The protein was diluted to about 400 μg/ml in a solution of sodium chloride, calcium chloride, and zinc acetate, buffered with tricine-HCl. Refolding proceeded over 3–4 days, during dialysis, with multiple buffer changes. PRO-CAT was then concentrated for activation and release of CAT.

Activation of PRO-CAT: The presently-accepted view of MMPs holds that the proenzyme form is maintained in an inactive state through the coordination of one cysteine from the PRO domain into the active-site zinc. If this cysteine is displaced, the enzyme becomes active. In our protocol, aminophenyl mercuric acetate was added to the protein solution to form a mercurial adduct with the cysteine. Progress of activation was monitored by SDS polyacrylamide gel eletrophoresis. Results indicated that the CAT domain accumulated and the PRO domain was degraded to small peptides.

Purification of MMP-13 (CAT)—Size Exclusion: Following activation and PRO cleavage, MMP-13 was isolated by size-exclusion chromatography through SuperDex 75 in a solution of sodium chloride, calcium chloride, and zinc acetate, buffered with tris-HCl.

Purification of MMP-13—Affinity: MMP-13 was further purified by affinity chromatography on an immobilized hydroxamate inhibitor. The affinity matrix was prepared by coupling an hydroxamate inhibitor to Sepharose through the amino group of the piperazine ring. MMP-13 can be absorbed to the matrix and desorbed by displacement using another inhibitor of choice.

Characterization of MMP-13: Protein preparations for crystallization trials were validated by several techniques. Routinely, SDS-PAGE showed a predominant species whose migration was consistent with a molecular weight of around 19,000. MALDITOF mass spectroscopy demonstrates a single species consistent with the expected size of 18,588 amu. (MMP-13 prepared with selenomethionine showed essentially complete replacement). N-terminal sequencing demonstrated that the protein begins with YNVF, as expected for correct cleavage between PRO and CAT. Retention volume in analytical size-exclusion chromatography was consistent with a monomeric protein: no detectable aggregation was observed. The final protein was enzymatically active on a fluorogenic peptide substrate, and degraded denatured collagen.

Crystallization of MMP-13 complex with Compound A: The MMP-13 protein solution was buffered with 10 mM tris-HCL buffer, pH 7.5, and 0.25 M NaCl. The concentration of protein used for crystallization was 20.0 mg/ml. The inhibitor solution was added to a protein solution with a mole ratio (protein:inhibitor) of 1:2, and was mixed for more than 1 hour.

Crystallization conditions were screened by the hanging-drop vapor diffusion method (Mcpherson, A., *Methods Biochem. Anal.* 1976). A successful procedure for growing crystals of this complex at room temperature was identified, and crystals were obtained. Specifically, a solution was prepared from 3 μl of protein solution and 3 μl of precipitant solution, which consisted of 26% PEG4000, 0.1 M ammonium sulfate, and 0.1 M sodium chloride. A drop of this solution was suspended on a microscope coverslip glass which had been coated with silicone to prevent drop spreading. The reservoir solutions consisted of 0.6 ml precipitant solution. Equilibration was performed at room temperature by vapor diffusion. Crystals began appearing after three days. After two weeks, these crystals stopped growing. The X-ray data which have been processed show that the MMP-13 complex was crystallized in two forms. One crystal form is C-centered orthorhombic; it belonged to space group C2221, and had a cell dimension of a=36.3 Å, b=134.4 Å, and c=134.8 Å. This crystal had high mosaicity; therefore, it would be of little use when working on the structure of the complex. The second crystal form is primitive orthorhombic, from space group P21212, with a cell constant of a=108.3 Å, b=79.8 Å, and c=36.1 Å. This crystal had low mosaicity, but it was very small in most cases.

In order to obtain a big single crystal for X-ray data collections, the seeding technique (Thaller, C., et al., *J. Mol. Biol.* 1981) was applied. This was accomplished by using both the microseeding and the macroseeding methods. Small seed crystals were transferred to a 20% PEG4000 precipitant solution on a depression slide. A single washed crystal was injected into a hanging-drop solution, which was composed of 3 μl of MMP-13 complex solution and 3 μl of precipitant solution. The reservoir solutions consisted of 0.6 ml precipitant solution at pH 8.0. This procedure successfully produced bigger crystals with a maximum edge dimension of up to 0.35×0.1×0.1 mm$^3$. These crystals diffracted X-ray at a resolution of 2.0 Å.

X-Ray Data Collection: X-ray diffraction data from 30.0–2.0 Å resolution for the MMP-13: Compound A complex crystal (P21212 form) was collected by using an RAXIS IIc Image Plate area detector which used graphite monochromatic CuKa radiation from a Rigaku RU200 rotating anode generator (operating at 50 kV, 100 mA) at a low temperature of 100 K. The oscillation angle for each plate was 1 degree, and exposure time was 20 minutes per 'image'. The processing of X-ray diffraction data was accomplished using the HKL programs (Otwinowski, Z. and Minor, W., *Methods in Enzymology* 276:307–26). The R-merges for full and partial reflections were 4.0% and 6.04% respectively. 18,782 unique reflections (81% complete at 2.0 Å resolutions) were collected.

Structure Determination and Refinement: The MMP-13 complex crystal structure has been determined by a combination of crystallographic modeling and the Molecular Replacement method using models of MMP-13 derived from the MMP-1 and MMP-8 structures. The homology between MMP-13 and MMP-8 is 56% by sequence, and at least 70% by structure. Crystals of the MMP-13 complex have two molecules in the asymmetric unit, i.e., the unit is a dimer. Conventional molecular replacement was not effective for determination of this dimer structure by using a monomer model. There are two reasons for this: (1) the high symmetry of the crystal structure; and (2) the conformations and the configurations of the side chain and the main chain in flexible loops of MMP-13 and MMP-8.

Firstly, the crystal structure of the MMP-13 complex is highly symmetrical. The P21212 crystal has four symmetry operations, and there are eight molecules in a unit cell. A second crystal form, belonging to space group C222, and having eight symmetry operations in a unit cell, has been identified. In this crystal, there are 16 monomers per cell in the dimer structure, and 32 monomers per cell in the tetramer structure. Therefore, the rotation search and especial translation search become more difficult. Secondly, even though the MMP family's catalytic domain structure is highly conserved, the conformations and the configurations of the side chain and the main chain in flexible loops of MMP-13 and MMP-8 may not be the same. In particular, the similarity between the two structures may not be sufficient to permit the determination of the dimer structure using a monomer as the searching model.

Many attempts at a rotation and translation search were made by using the X-ray data and models of either a monomer of MMP-8 or a dimer of MMP-1. Some rotation solutions were obtained, but no final translation solution has been found by using the monomer model. Accordingly, to determine this structure, it was proposed that a dimer model be constructed first; the molecular replacement method was then applied to solve the structure.

The key idea of this proposal was crystal packing. To construct a dimer, the orientations of each monomer were determined on the basis of a rotation search. The positions of each monomer were located on the basis of the molecular packing in unit cell. Many dimer models have been constructed and applied as the 'model' for searching the rotation and translation using program AMORE (Collaborative Computational Project, Number 4 (CCP4) (1994), *Acta Cryst.* D50:760–763). One dimer model was found to be correct, and finally resulted in the MMP-13 3-D crystal structure using the molecular replacement method. The MMP-13 complex structure was confirmed by observing the most important and significant fact that the positions of the two zinc ions and the two calcium ions could be identified from the difference (Fo-Fc) maps with five-sigma cut, where Fo was observed structure factor and Fc was the calculated structure factor of the dimer model without zinc and calcium atoms.

These ions were located in the exact positions where they were observed in other MMP family members. The molecule fits the (2Fo-Fc) electron densities very well, both in main chain and in side chain. The molecule fits the 2Fo-Fc electron density quite well. All of these MMP molecules are conserved in the core structure region, especially the position of the central helix and the catalytic zinc. The MMP-13 dimer structure was further confirmed by applying the molecular replacement programs XPLOR (Brunger, A. T., *XPLOR Version* 3.1 Manual, Yale University, New Haven Conn.) and MERLOT (Fitzgerald, P., MERLOT, version 2.4 (Nov. 10, 1991). All of them worked very well, and produced results which were in agreement with the MMP-13 structure.

Structure Refinement: The structure refinement was carried out by the program XPLOR. The initial dimer model included 320 amino acid residues without zinc and calcium ions. The dimer model was refined against 2.0 Å X-ray data, collected on an RAXIS IIc area detector at a temperature of 100 K. The progress of the refinement was evaluated from the quality of the protein molecular conformations and the electron density maps, and the values of the crystallographic R-factor. The initial R-factor was 52%. After rigid-body minimization, conjugated-gradient minimization, a heating stage, a slow-cooling stage in the range from 4000K to 300K, energy minimization, B-factor refinement, and positional refinement, the R-factor lowered to 0.32. Electron-density maps with coefficients of (2Fo-Fc) and (Fo-Fc), as well as the phases, were calculated. The difference map shows four zinc ions and four calcium ions in the dimer structure with five-sigma cut. Some side chain loops and a few main loops were rebuilt on the interactive graphics system. The rebuilt dimer plus the zinc and calcium ions, as the new model, was refined. The R-factor was down to 26.6%. At this stage, a model of inhibitor Compound A was positioned in the active-site region based on the difference electron density.

The complex structure was refined by repeating the above steps, with the R-factor down to 20%. The water molecules were modeled as oxygen atoms. Their initial positions were located by searching the peaks in the (Fo-Fc) difference maps. These positions were then checked by calculating the distance between 'water' and the oxygen and nitrogen of the protein. Together with the protein (complex) atoms, these 'water' molecules were refined against the X-ray data. Once the temperature factor of water was higher than 50, this water was omitted. 120 water molecules near the protein were found, and five water molecules were identified in the active site of each monomer. The (2Fo-Fc) maps were used to adjust the solvent model and to aid in the placement of new solvent molecules, as well as to check and correct the whole model. The r.m.s. deviations of Ca atoms for bond angles and bond distances from ideal geometry were 1.60 and 0.012 Å. The final crystallographic R-factor was 22%, at a resolution of 2.0 Å.

All publications mentioned herein above, whether to issued patents, pending applications, published articles, protein structure deposits, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for designing an agent that interacts with MMP-13, comprising:
   providing a composition including MMP-13:
   generating a three dimensional model of MMP-13; and
   utilizing the three dimensional model to design an agent that interacts with MMP-13,
   wherein the three dimensional model of MMP-13 includes relative structural coordinates of a plurality of atoms of MMP-13, and the relative structural coordinates are selected according to:
      FIGS. 4 and 4A-1 to 4A-32, ± a root mean square deviation from the backbone atoms of amino acids of not more than 1.5 Å; or
      FIGS. 5 and 5A-1 to 5A-35, ± a root mean square deviation from the backbone atoms of amino acids of not more than 1.5 Å.

2. The method of claim 1, wherein the relative structural coordinates include relative structural coordinates of an atom of an active site of MMP-13.

3. The method of claim 1, wherein the relative structural coordinates include relative structural coordinates of an atom selected from the group consisting of atoms belonging to residues N14, L15, T16, Y17, R18, I19, V20, F75, D76, G77, P78, S79, N112, L113, F114, L115, V116, A117, A118, H119, E120, F121, G122, H123, P139, I140, Y141, and catalytic zinc.

4. The method of claim 1, wherein relative structural coordinates include relative structural coordinates of an atom selected from the group consisting of the atoms belonging to residues N14, L15, T16, Y17, R18, I19, V20, F75, D76, G77, P78, S79, G80, L81, L82, A83, H84, A85, K109, G110, Y111, N112, L113, F114, L115, V116, A117, A118, H119, E120, F121, G122, H123, S124, L125, G126, L127, D128, H129, S130, K131, D132, P133, G134, A135, L136, M137, F138, P139, I140, Y141, T142, Y143, T144, G145, F149, P152, and catalytic zinc.

5. The method of claim 1, wherein the three dimensional model includes an agent.

6. The method of claim 5, wherein utilizing the three dimensional model includes altering the chemical structure of the agent.

7. The method of claim 1, wherein the relative structural coordinates include coordinates according to FIGS. 4 and 4A-1 to 4A-32, ± a root mean square deviation from the backbone atoms of amino acids of not more than 1.5 Å.

8. The method of claim 1, wherein the relative structural coordinates include coordinates according to FIGS. 5 and 5A-1 to 5A-35, ± a root mean square deviation from the backbone atoms of amino acids of not more than 1.5 Å.

9. The method of claim 1, wherein the composition includes a crystal including MMP-13 or the composition includes an isotopically labeled MMP-13.

10. The method of claim 1, further comprising determining the relative structural coordinates of atoms of MMP-13 from the composition.

11. The method of claim 1, wherein utilizing the three dimensional includes designing an agent that interacts more strongly with MMP-13 than with another MMP.

12. The method of claim 1, further comprising synthesizing or obtaining an agent.

13. The method of claim 12, further comprising contacting the agent with MMP-13 to determine the interaction between the agent and MMP-13.

14. The method of claim 13, wherein the agent is an agent designed by the method.

15. The method of claim 1, wherein utilizing the three dimensional model includes comparing MMP-13 to another MMP.

16. The method of claim 1, wherein utilizing the three dimensional model includes determining the fit of an agent with an active site of MMP-13.

17. The method of claim 1, wherein utilizing the three dimensional model includes identifying residues of MMP-13 that can influence the interaction of an agent with MMP-13.

18. A method for designing an agent that interacts with MMP-13, comprising:
   generating a three dimensional model of MMP-13 including relative structural coordinates of a plurality of atoms of an active site of MMP-13 and relative structural coordinates of a first agent that interacts with MMP-13;
   utilizing the three dimensional model to design a second agent that interacts with MMP-13, wherein utilizing includes altering the relative structural coordinates of the first agent;
   synthesizing or obtaining the second agent; and
   determining the interaction of MMP-13 with the second agent,
   wherein the relative structural coordinates of MMP-13 are selected according to:
      FIGS. 4 and 4A-1 to 4A-32, ± a root mean square deviation from the backbone atoms of amino acids of not more than 1.5 Å; or
      FIGS. 5 and 5A-1 to 5A-35, ± a root mean square deviation from the backbone atoms of amino acids of not more than 1.5 Å.

19. The method of claim 18, wherein the relative structural coordinates of MMP-13 include relative structural coordinates of an atom of MMP-13 selected from the group consisting of atoms belonging to residues N14, L15, T16, Y17, R18, I19, V20, F75, D76, G77, P78, S79, N112, L113, F114, L115, V116, A117, A118, H119, E120, F121, G122, H123, P139, I140, Y141, and catalytic zinc.

20. The method of claim 18, wherein the relative structural coordinates of MMP-13 include relative structural coordinates of an atom of MMP-13 selected from the group consisting of the atoms belonging to residues N14, L15, T16, Y17, R18, I19, V20, F75, D76, G77, P78, S79, G80, L81, L82, A83, H84, A85, K109, G110, Y111, N112, L113, F114, L115, V116, A117, A118, H119, E120, F121, G122, H123, S124, L125, G126, L127, D128, H129, S130, K131, D132, P133, G134, A135, L136, M137, F138, P139, I140, Y141, T142, Y143, T144, G145, F149, P152, and catalytic zinc.

21. The method of claim 18, wherein altering the relative structural coordinates of the first agent includes adding, removing, or changing the position of an atom of the first agent.

22. The method of claim 18, further comprising comparing the model including relative structural coordinates of the first agent to a model including the second agent.

23. A method for designing an agent that interacts with MMP-13, comprising:
   generating a three dimensional model of MMP-13;
   utilizing the three dimensional model to design an agent that interacts with MMP-13; and
   synthesizing or obtaining the agent,
   wherein the three dimensional model of MMP-13 includes relative structural coordinates of a plurality of atoms of MMP-13, and the relative structural coordinates are selected according to:
      FIGS. 4 and 4A-1 to 4A-32, ± a root mean square deviation from the backbone atoms of amino acids of not more than 1.5 Å; or FIGS. 5 and 5A-1 to 5A-35, ± a root mean square deviation from the backbone atoms of amino acids of not more than 1.5 Å.

24. The method of claim 23, wherein the relative structural coordinates include relative structural coordinates of an atom of an active site of MMP-13.

25. The method of claim 23, wherein the relative structural coordinates include relative structural coordinates of an atom selected from the group consisting of atoms belonging to residues N14, L15, T16, Y17, R18, I19, V20, F75, D76, G77, P78, S79, N112, L113, F114, L115, V116, A117, A118, H119, E120, F121, G122, H123, P139, I140, Y141, and catalytic zinc.

26. The method of claim 23, wherein relative structural coordinates include relative structural coordinates of an atom selected from the group consisting of the atoms belonging to residues N14, L15, T16, Y17, R18, I19, V20, F75, D76, G77, P78, S79, G80, L81, L82, A83, H84, A85, K109, G110, Y111, N112, L113, F114, L115, V116, A117, A118, H119, E120, F121, G122, H123, S124, L125, G126, L127, D128, H129, S130, K131, D132, P133, G134, A135, L136, M137, F138, P139, I140, Y141, T142, Y143, T144, G145, F149, P152, and catalytic zinc.

27. The method of claim 23, wherein the three dimensional model includes the agent.

28. The method of claim 27, wherein utilizing the three dimensional model includes altering the chemical structure of the agent.

29. The method of claim 23, wherein the relative structural coordinates include coordinates according to FIGS. 4 and 4A-1 to 4A-32, ± a root mean square deviation from the backbone atoms of amino acids of not more than 1.5 Å.

30. The method of claim 23, wherein the relative structural coordinates include coordinates according to FIGS. 5 and 5A-1 to 5A-35, ± a root mean square deviation from the backbone atoms of amino acids of not more than 1.5 Å.

31. The method of claim 23, further comprising providing a composition including MMP-13.

32. The method of claim 31, wherein the composition includes a crystal including MMP-13 or the composition includes an isotopically labeled MMP-13.

33. The method of claim 31, further comprising determining the relative structural coordinates of atoms of MMP-13 from the composition.

34. The method of claim 23, wherein utilizing the three dimensional includes designing an agent that interacts more strongly with MMP-13 than with another MMP.

35. The method of claim 34, further comprising contacting the agent with MMP-13 to determine the interaction between the agent and MMP-13.

36. The method of claim 35, wherein the agent is an agent designed by the method.

37. The method of claim 23, wherein utilizing the three dimensional model includes comparing MMP-13 to another MMP.

38. The method of claim 23, wherein utilizing the three dimensional model includes determining the fit of an agent with an active site of MMP-13.

39. The method of claim 23, wherein utilizing the three dimensional model includes identifying residues of MMP-13 that can influence the interaction of an agent with MMP-13.

* * * * *